United States Patent
Burnett et al.

(10) Patent No.: US 10,391,275 B2
(45) Date of Patent: Aug. 27, 2019

(54) SYSTEMS, DEVICES AND METHODS FOR DRAINING AND ANALYZING BODILY FLUIDS

(71) Applicant: Potrero Medical, Inc., Hayward, CA (US)

(72) Inventors: Daniel R. Burnett, San Francisco, CA (US); Rich Keenan, Livermore, CA (US); Dimitri Sokolov, Castro Valley, CA (US); Stephen Boyd, San Francisco, CA (US); Martin Williams, San Francisco, CA (US); Kondapavulur Venkateswara-Rao, San Jose, CA (US); Michelle Arney, San Francisco, CA (US)

(73) Assignee: Potrero Medical, Inc., Hayward, CA (US)

( * ) Notice: Subject to any disclaimer, the term of this patent is extended or adjusted under 35 U.S.C. 154(b) by 0 days.

(21) Appl. No.: 15/277,957

(22) Filed: Sep. 27, 2016

(65) Prior Publication Data
US 2017/0136209 A1    May 18, 2017

Related U.S. Application Data

(60) Provisional application No. 62/256,257, filed on Nov. 17, 2015, provisional application No. 62/270,022, (Continued)

(51) Int. Cl.
*A61M 25/00* (2006.01)
*A61M 27/00* (2006.01)
(Continued)

(52) U.S. Cl.
CPC ....... *A61M 25/0017* (2013.01); *A61B 5/0084* (2013.01); *A61B 5/205* (2013.01); (Continued)

(58) Field of Classification Search
CPC .............. A61M 1/0001; A61M 1/0025; A61M 1/0031; A61M 1/0033; A61M 1/0035; (Continued)

(56) References Cited

U.S. PATENT DOCUMENTS 1,444,565 A    2/1923    Smith
3,730,209 A *  5/1973    Binard ................... F16K 24/04
                                                  137/217
(Continued)

FOREIGN PATENT DOCUMENTS

WO    WO 2004/037334    5/2004
WO    WO 2006/046060    8/2006
(Continued)

*Primary Examiner* — Benjamin J Klein
(74) *Attorney, Agent, or Firm* — Levine Bagade Han LLP

(57) ABSTRACT

Systems, devices and methods for draining and analyzing bodily fluids are disclosed in which a drainage assembly is configured to prevent negative pressure build-up. The drainage assembly generally includes a catheter which may include a drainage lumen, a reservoir, a venting mechanism in fluid communication with the drainage lumen and a positive pressure lumen, and a controller. The venting mechanism may further include a valve which is configured to maintain a closed position, as well as a vent in fluid communication with the valve, where the venting mechanism is configured to inhibit wetting of the vent from fluid within the drainage lumen.

53 Claims, 88 Drawing Sheets

Related U.S. Application Data filed on Dec. 20, 2015, provisional application No. 62/270,623, filed on Dec. 22, 2015, provisional application No. 62/275,348, filed on Jan. 6, 2016, provisional application No. 62/290,878, filed on Feb. 3, 2016, provisional application No. 62/307,988, filed on Mar. 14, 2016, provisional application No. 62/317,746, filed on Apr. 4, 2016, provisional application No. 62/372,731, filed on Aug. 9, 2016.

(51) Int. Cl.

| | |
|---|---|
| A61M 1/00 | (2006.01) |
| A61B 5/00 | (2006.01) |
| A61B 5/20 | (2006.01) |
| A61B 5/0205 | (2006.01) |
| A61B 5/03 | (2006.01) |
| A61B 5/08 | (2006.01) |

(52) U.S. Cl.
CPC ............ *A61B 5/208* (2013.01); *A61B 5/6853* (2013.01); *A61M 1/0001* (2013.01); *A61M 1/008* (2013.01); *A61M 1/0025* (2014.02); *A61M 1/0031* (2013.01); *A61M 1/0033* (2014.02); *A61M 1/0035* (2014.02); *A61M 27/00* (2013.01); *A61M 27/002* (2013.01); *A61M 27/008* (2013.01); *A61B 5/02055* (2013.01); *A61B 5/036* (2013.01); *A61B 5/0816* (2013.01); *A61B 2562/0247* (2013.01); *A61M 1/006* (2014.02); *A61M 2202/0496* (2013.01); *A61M 2210/1021* (2013.01); *A61M 2210/1085* (2013.01); *A61M 2230/005* (2013.01)

(58) Field of Classification Search
CPC .. A61M 1/006; A61M 1/008; A61M 25/0017; A61M 27/00–008; A61M 2202/0496; A61M 2210/1021; A61M 2210/1085; A61M 2230/005; A61B 5/0084
See application file for complete search history.

(56) References Cited

U.S. PATENT DOCUMENTS

| | | | |
|---|---|---|---|
| 3,800,795 A * | 4/1974 | Walker | ................ A61F 5/441 604/138 |
| 3,851,650 A | 12/1974 | Darling | |
| 4,305,403 A | 12/1981 | Dunn | |
| 4,535,786 A | 8/1985 | Kater | |
| 4,638,805 A | 1/1987 | Powell | |
| 5,176,698 A | 1/1993 | Burns et al. | |
| 5,222,008 A | 6/1993 | Yamagishi et al. | |
| 5,573,007 A | 11/1996 | Bobo, Sr. | |
| 5,704,353 A | 1/1998 | Kalb et al. | |
| 5,738,656 A | 4/1998 | Wagner | |
| 6,434,418 B1 | 8/2002 | Neal et al. | |
| 6,447,462 B1 | 9/2002 | Wallace et al. | |
| 6,673,022 B1 | 1/2004 | Bobo et al. | |
| 6,935,999 B2 | 8/2005 | Schock et al. | |
| 7,004,899 B2 | 2/2006 | Tracey | |
| 7,112,170 B2 | 9/2006 | Schock et al. | |
| 7,229,403 B2 | 6/2007 | Schock et al. | |
| 7,524,315 B2 | 4/2009 | Blott et al. | |
| 7,739,907 B2 | 6/2010 | Boiarski | |
| 7,883,494 B2 | 2/2011 | Martin | |
| 7,892,217 B2 | 2/2011 | Boiarski | |
| 7,931,630 B2 | 4/2011 | Nishtala et al. | |
| 7,938,817 B2 | 5/2011 | Gelfand et al. | |
| 7,947,001 B1 | 5/2011 | Sarvazyan | |
| 7,976,533 B2 | 7/2011 | Larsson | |
| 8,157,775 B2 | 4/2012 | Bobroff et al. | |
| 8,192,368 B2 | 6/2012 | Woodruff et al. | |
| 8,403,884 B2 | 3/2013 | Nishtala | |
| 8,424,376 B2 | 4/2013 | Boiarski | |
| 8,486,051 B2 | 7/2013 | Larsson | |
| 8,491,550 B2 | 7/2013 | Ramella et al. | |
| 8,568,387 B2 | 10/2013 | Paz | |
| 8,715,254 B2 | 5/2014 | Nishtala | |
| 8,801,684 B2 | 8/2014 | Walti et al. | |
| 8,813,551 B2 | 8/2014 | Boiarski | |
| 8,827,924 B2 | 9/2014 | Paz et al. | |
| 8,953,159 B2 | 2/2015 | Cunningham et al. | |
| 9,216,242 B2 | 12/2015 | Nishtala et al. | |
| 2005/0090775 A1 * | 4/2005 | Harper | ................ A61M 27/006 604/9 |
| 2006/0100743 A1 | 5/2006 | Townsend et al. | |
| 2006/0155214 A1 * | 7/2006 | Wightman | ............... A61F 5/455 600/574 |
| 2006/0271019 A1 | 11/2006 | Stoller et al. | |
| 2007/0010798 A1 * | 1/2007 | Stoller | ................ A61M 1/0023 604/544 |
| 2008/0117416 A1 | 5/2008 | Hunter et al. | |
| 2008/0312550 A1 | 12/2008 | Nishtala et al. | |
| 2009/0149776 A1 | 6/2009 | Adams | |
| 2009/0163853 A1 | 6/2009 | Cull et al. | |
| 2009/0235935 A1 | 9/2009 | Pacey | |
| 2010/0130949 A1 | 5/2010 | Garcia | |
| 2010/0137743 A1 | 6/2010 | Nishtala et al. | |
| 2012/0035595 A1 | 2/2012 | Goedje et al. | |
| 2013/0172840 A1 | 7/2013 | Lampotang et al. | |
| 2013/0218106 A1 | 8/2013 | Coston et al. | |
| 2014/0074071 A1 | 3/2014 | Paz | |
| 2014/0182594 A1 | 7/2014 | Alam et al. | |
| 2014/0194835 A1 | 7/2014 | Ehlert | |
| 2014/0316219 A1 | 10/2014 | Paz et al. | |
| 2015/0362351 A1 | 12/2015 | Joshi et al. | |
| 2016/0183819 A1 | 6/2016 | Burnett et al. | |
| 2016/0310711 A1 * | 10/2016 | Luxon | ................... A61M 27/00 |
| 2017/0030758 A1 | 2/2017 | Joshi | |
| 2017/0100068 A1 | 4/2017 | Kostov | |
| 2017/0138027 A1 | 5/2017 | Chuang | |

FOREIGN PATENT DOCUMENTS

| | | |
|---|---|---|
| WO | WO 2009/142508 | 11/2009 |
| WO | WO 2015/105916 | 7/2015 |
| WO | WO 2015/192054 | 12/2015 |
| WO | WO 2015/192108 | 12/2015 |

* cited by examiner

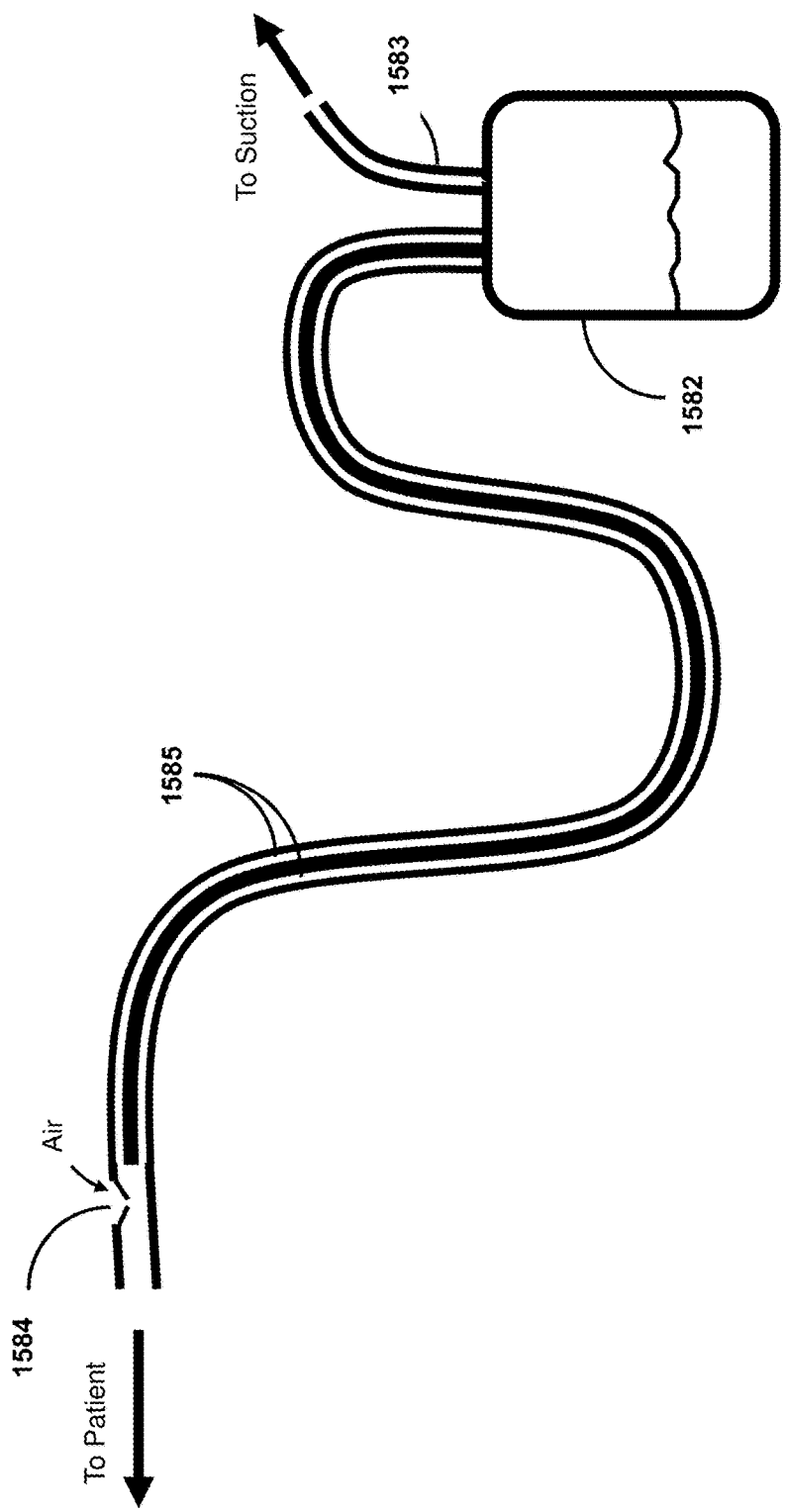

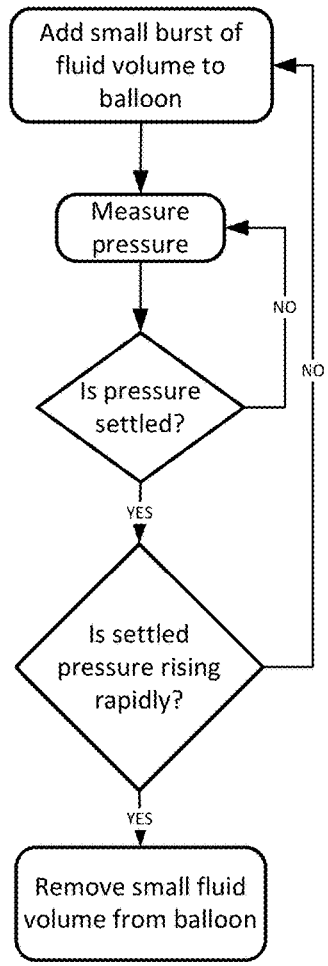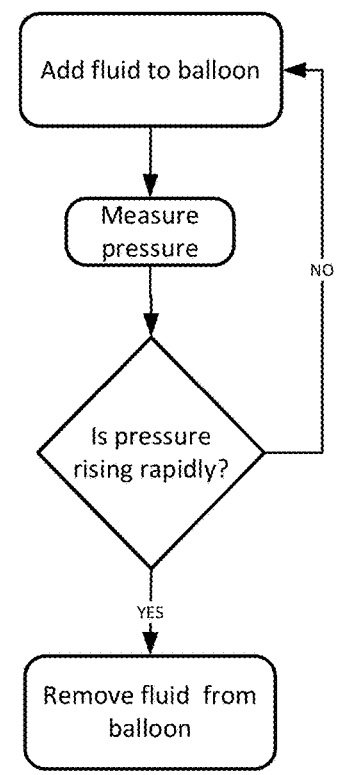
Fig. 27                    Fig. 28

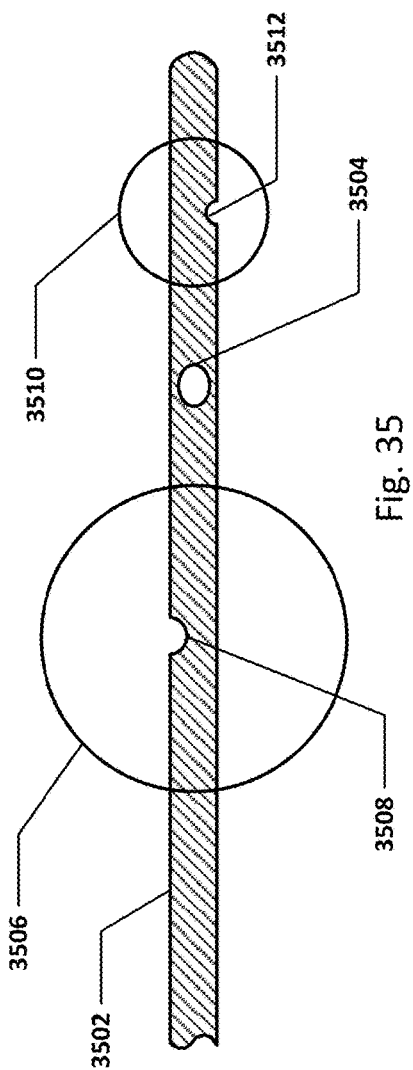
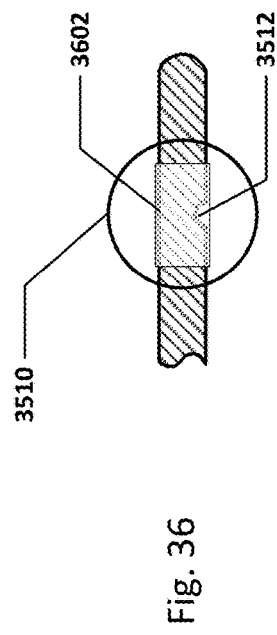

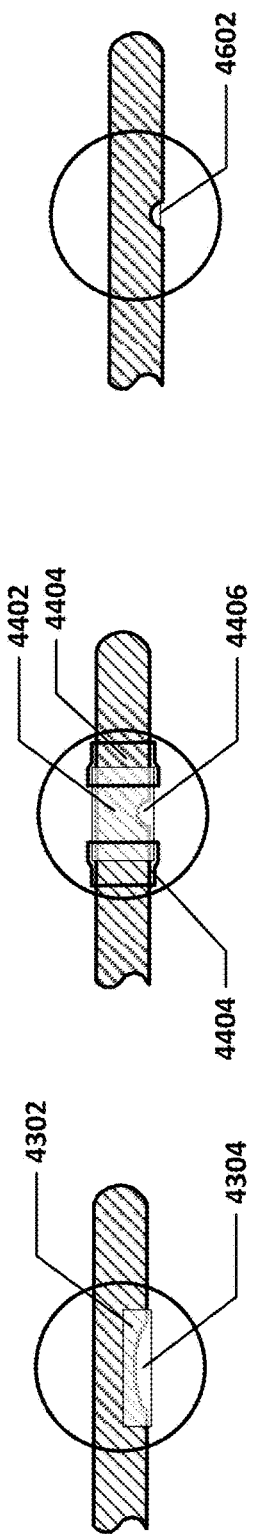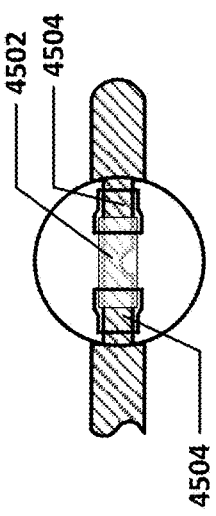
Fig. 46
Fig. 44
Fig. 45
Fig. 43

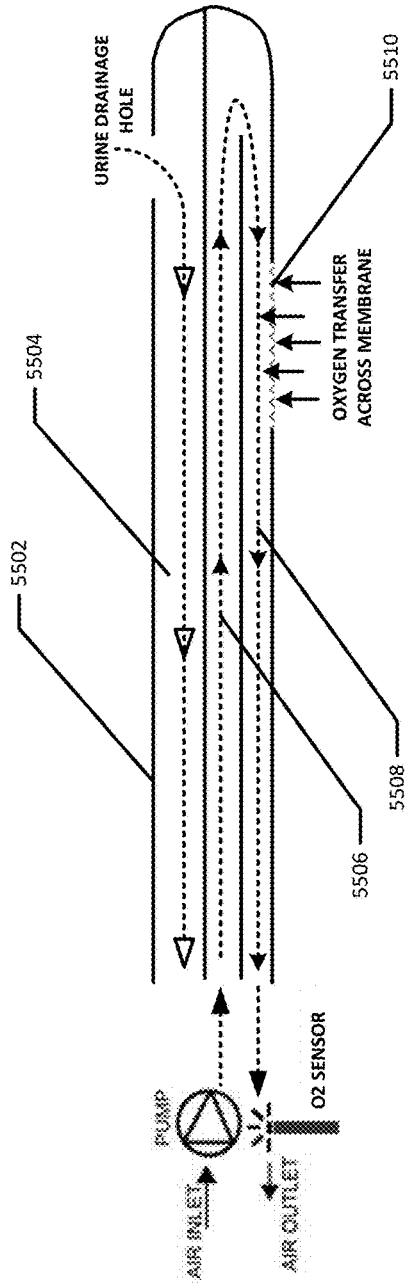
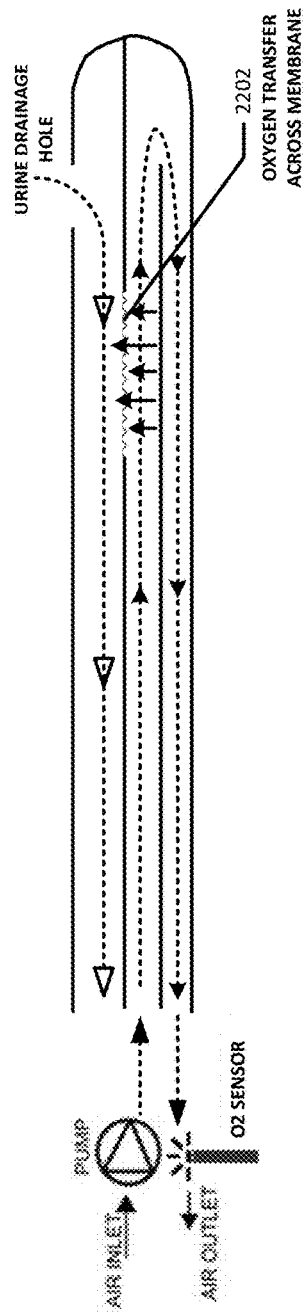
Fig. 55
Fig. 56

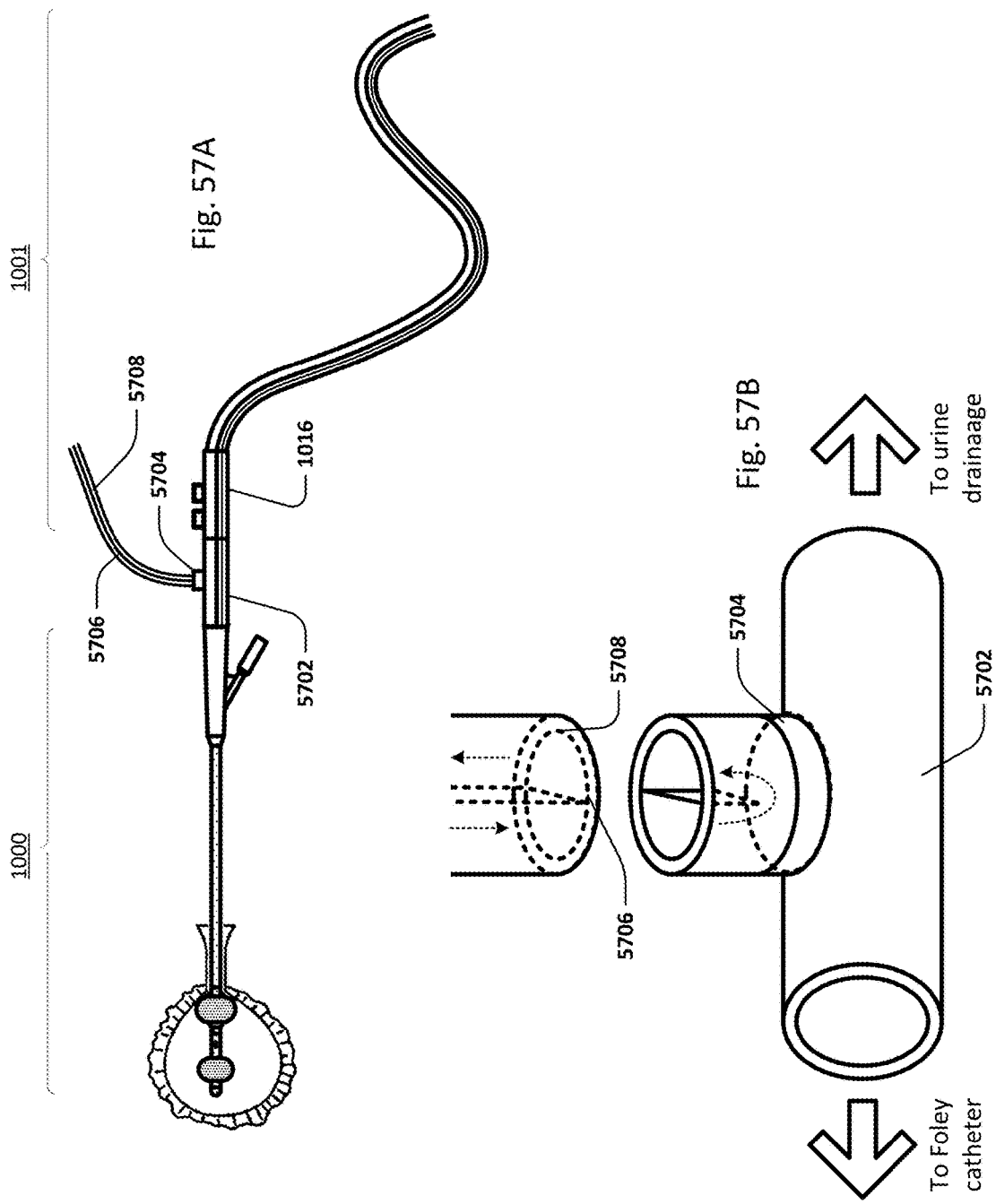

| Parameter | Condition | | | |
|---|---|---|---|---|
| | AKI | | | UTI |
| | Prerenal | Intrinsic | Postrenal | |
| Urine Oxygen Tension | ↓ then ↑ | ↓ then ↑ | - | ↓↓ |
| Urine Output | ↓↓ | ↓↓ | ↓↓↓ | - |
| Urine Conductance | ↓ | ↑ | ↑↑ | - |
| Specific Gravity | ↑ | ↓ | - | ↑ |

Fig. 58A

| Parameter | Condition | | |
|---|---|---|---|
| | Sepsis | AKI | ARDS |
| Urine Output | ↓ | ↓ | ↑ or ↓ |
| Heart Rate | ↑ then ↓ | ↓ | ↑ |
| Respiratory Rate | ↑ | ↑ or ↓ | ↑ |
| Temperature | ↑ then ↓ | - | - |
| Stroke Volume/Cardiac Output | ↑ then ↓ | ↑ or ↓ | ↑ |
| Abdominal Perfusion Pressure | ↑ then ↓ | ↓ | ↓ |

Fig. 58B

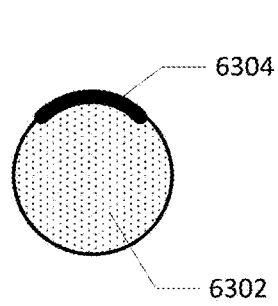
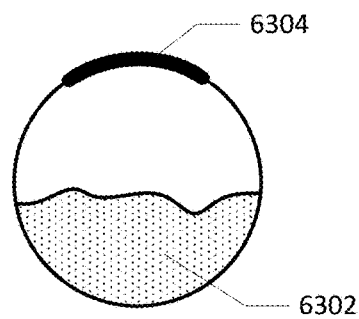
Fig. 63A                    Fig. 63B
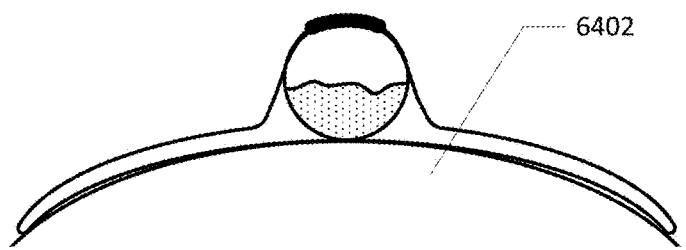
Fig. 64

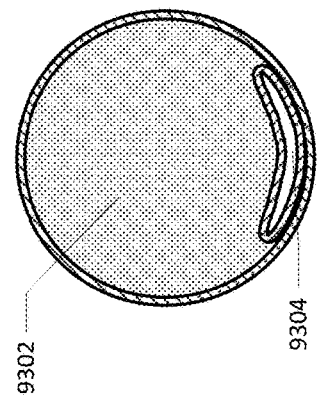
Fig. 93A
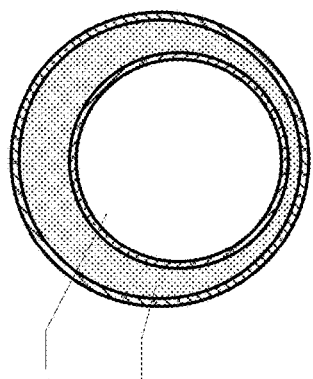
Fig. 93B
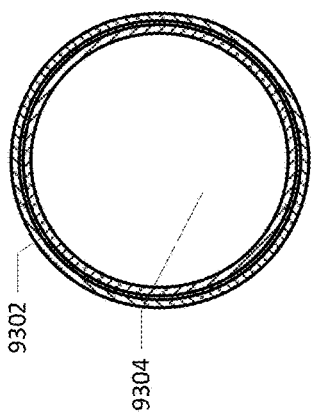
Fig. 93C
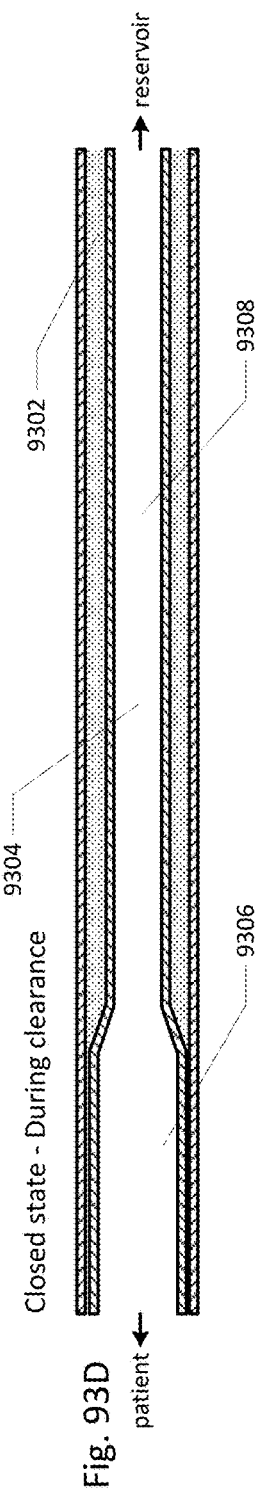
Fig. 93D Closed state - During clearance
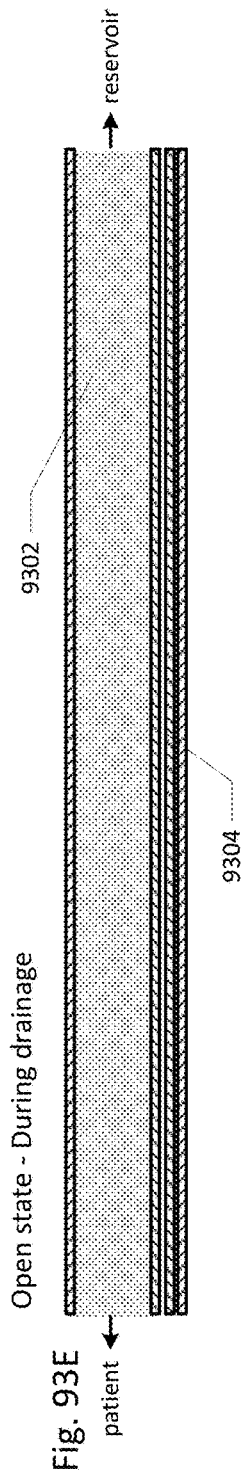
Fig. 93E Open state - During drainage

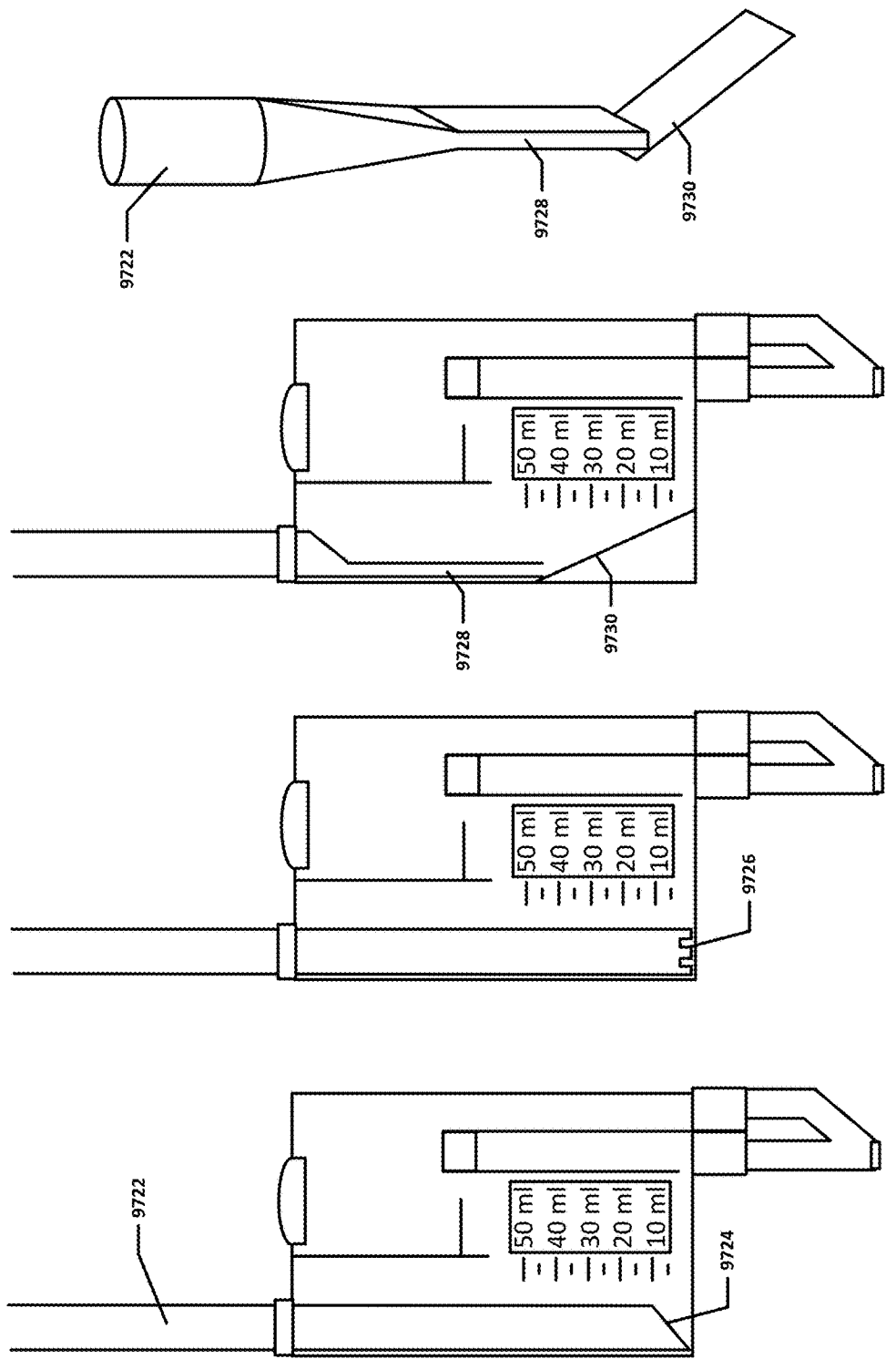

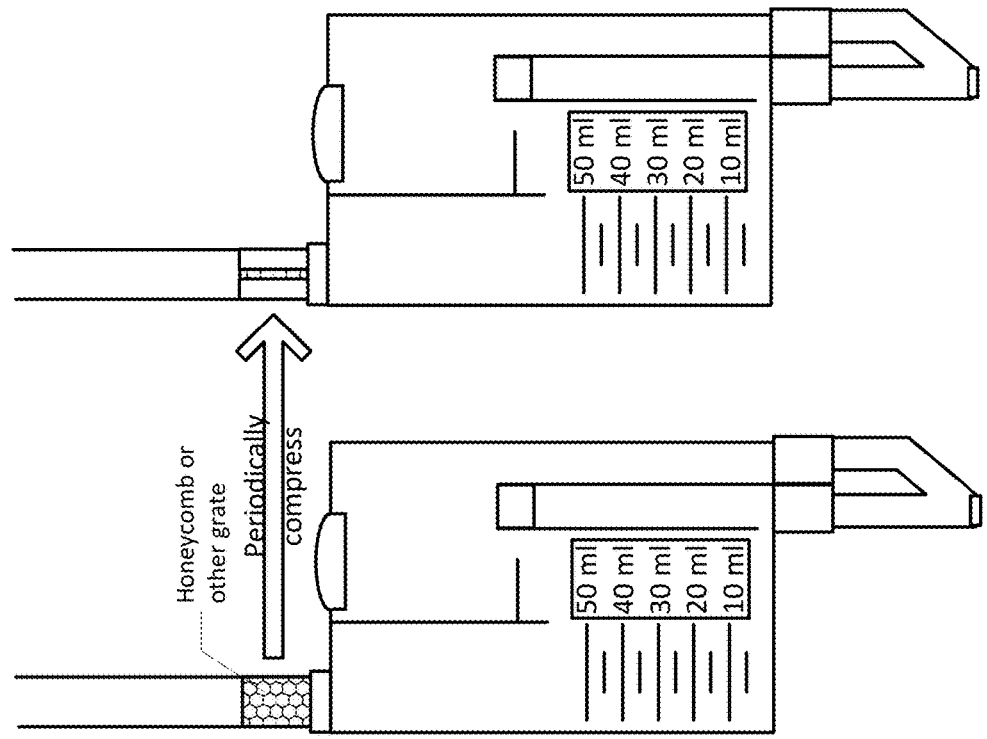
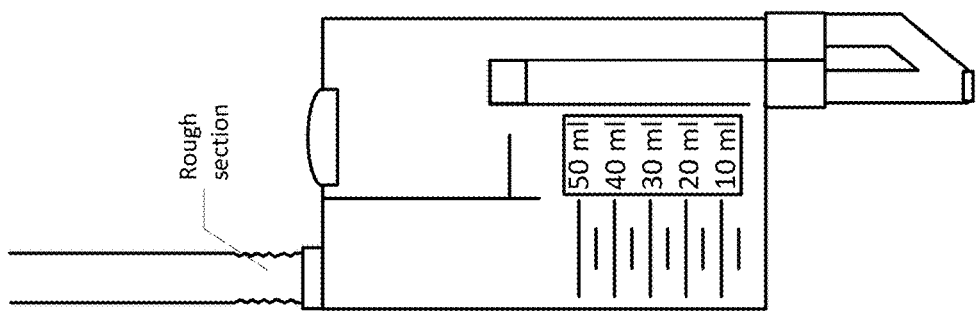
Fig. 99A  Fig. 99B  Fig. 99C

SYSTEMS, DEVICES AND METHODS FOR DRAINING AND ANALYZING BODILY FLUIDS

CROSS-REFERENCE TO RELATED APPLICATIONS

This application claims the benefit of priority to U.S. Provisional Application No. 62/256,257 filed Nov. 17, 2015 and U.S. Provisional Application No. 62/270,022 filed Dec. 20, 2015 and U.S. Provisional Application No. 62,270,623 filed Dec. 22, 2015 and U.S. Provisional Application No. 62/275,348 filed Jan. 6, 2016 and U.S. Provisional Application No. 62/290,878 filed Feb. 3, 2016 and U.S. Provisional Application No. 62/307,988 filed Mar. 14, 2016 and U.S. Provisional Application No. 62/317,746 filed Apr. 4, 2016 and U.S. Provisional Application No. 62/372,731 filed Aug. 9, 2016 and is related to PCT Application No. PCT/US2014/44565 filed Jun. 27, 2014, PCT Application No. PCT/US2015/010530 filed Jan. 7, 2015, and PCT Application No. PCT/US2015/52716 filed Sep. 28, 2015, each of which is incorporated herein by reference in its entirety.

TECHNICAL FIELD OF THE INVENTION

The present invention relates to the field of medical devices, in particular devices that aid emptying of the bladder, measure urine output and various urine parameters such as oxygen tension, urine conductance and urine specific gravity, monitor renal function, analyze urine parameters, including urine content, including the presence of infection, and track and/or control fluid administration. The present invention further relates to medical devices capable of sensing physiologic data based on sensors incorporated into a catheter adapted to reside in any of a urinary tract, gastrointestinal tract, rectal location, pre-peritoneal, pleural space or other body cavity.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

It is estimated that 10% of all hospitalized and long-term care patients receive an indwelling urethral catheter. Almost all critically ill patients receive one, and in the ICU it is routine procedure to monitor urine output every hour. The amount of urine produced is an indicator of fluid status and renal function. However, numerous sources of error can cause erroneous measurements of this important indicator.

The most common device used to drain the bladder is the Foley catheter. Since its introduction, the design of a flexible tube with an anchoring balloon and eyelets that allow urine to drain through a central lumen has remained largely unchanged. However, it has been found that the current design of Foley catheters can result in a large residual volume remaining in the bladder, for example greater than 50 mL in supine patients. See Fallis, Wendy M. Indwelling Foley Catheters Is the Current Design a Source of Erroneous Measurement of Urine Output? Critical Care Nurse 25.2 (2005): 44-51. In one study, mean residual volume was 96 mL in the ICU and 136 mL in the general ward. See, Garcia et al., Traditional Foley Drainage Systems-Do They Drain the Bladder?, J Urol. 2007 January; 177(1):203-7; discussion 207. A large residual volume of urine is also often found in the drain tube that connects the Foley catheter to the drainage bag, or elsewhere in the drainage system.

The residual urine in the bladder and drain tube is a result of large air bubbles (air locks) that are formed in the tube and prevent the flow of urine from the bladder to the drainage bag. As a result, it has become routine procedure for nurses to manipulate the drainage tube prior to measuring urinary output, which helps empty the tubing. In the ICU, where measurements are made as often as every hour, this is a very repetitive and imprecise process. A need exists for more accurate and automatic urine output measurement.

In addition, an opportunity exists, within the urine collection system, to measure and analyze urine parameters.

In addition to improving urine output measurement and urine parameter analysis, the urine drainage catheter itself offers an untapped opportunity to detect, collect and analyze additional patient parameters.

In addition, many types of medical devices are designed to control treatment and/or maintenance of a patient. For example, a respirator can control patient respiration rate, volume, and/or gas mixture, among other things. An IV (intravenous delivery) can deliver fluid and/or other substances, such as drugs, to a patient. Other devices include those that can deliver drugs or perform other actions. These types of medical devices can be tightly controlled via various settings etc. A nurse or other practitioner may check various patient parameters and adjust the medical treatment device settings accordingly. A controller which automatically or semi-automatically uses patient parameters to control the settings of medical treatment devices is needed.

SUMMARY OF THE INVENTION

A Foley type catheter, widespread in use, having a low cost, and easily put in place by health care professionals may be used as a vehicle for deriving critical diagnostic information, by modifying a Foley type catheter, and/or by adding functionality to a Foley type catheter. The technology disclosed herein provides for the delivery of highly resolved and previously unavailable diagnostic information, as may be derived from a Foley type catheter with intra-abdominal pressure (and other) sensing capability.

In addition, the development of air locks has been found to significantly skew intra-abdominal pressure readings. In addition, a bladder which is not empty can also adversely affect pressure readings within the bladder. The technology disclosed herein also provides for the detection and removal of air locks in the setting of intra-abdominal pressure measurements or otherwise, as well as more complete bladder drainage.

The technology disclosed herein seeks to more effectively drain the bladder, prevent airlocks from forming in the drainage tube and clearing them when they do, and increase the accuracy with which urine output is measured in an automated way. The disclosed technology also seeks to incorporate additional measurements of the urine, including oxygen tension, conductance, and specific gravity, gas pressures, turbidity, infection, sediment and others to improve the monitoring of fluid status, renal function, and other important patient parameters.

The disclosed technology also relates to a Foley type catheter for sensing physiologic data from the bladder and/or urinary tract of a patient, the physiologic data particularly including those gathered by high fidelity pressure sensing and transduction into signals suitable for processing. In some embodiments, the pressure-sensing Foley type catheter may further be enabled to sense temperature and analytes of clinical significance. Examples of physiological parameters that the sensing Foley catheter system may measure (time specific measurements and trends of values over time) include: urine output, respiration rate, heart rate, heart rate variability, stroke volume, stroke volume variability, intra-abdominal pressure (IAP), tissue oxygenation, tissue gas content, pulse transit time, pulmonary blood volume variability, temperature, blood content and other patient parameters One embodiment of a drainage assembly which is configured to prevent negative pressure build-up may generally comprise an elongate catheter having a first end configured for insertion within a body lumen. The catheter may have at least one opening near or at the first end in fluid communication with a catheter lumen defined therethrough, a drainage lumen in fluid communication with a second end of the catheter, a reservoir in fluid communication with the drainage lumen, and a venting mechanism in fluid communication with the drainage lumen and a positive pressure lumen. A valve may be positioned within the venting mechanism and configured to maintain a closed position until a first pressure level within the drainage lumen drops to a second pressure level such that the valve moves to an open position. Also, a vent may be positioned in fluid communication with the valve, wherein the venting mechanism is configured to inhibit wetting of the vent from fluid within the drainage lumen; and a controller in communication with the reservoir, wherein the controller is configured to determine a fluid volume collected within the reservoir.

In another embodiment, the drainage assembly may be configured to prevent negative pressure build-up, generally comprising an elongate catheter having a first end configured for insertion within a body lumen, the catheter having at least one opening near or at the first end in fluid communication with a catheter lumen defined therethrough. A drainage lumen may be in fluid communication with a second end of the catheter, a positive pressure lumen in fluid communication with the drainage lumen, a reservoir in fluid communication with the drainage lumen, and a venting mechanism coupled to the drainage lumen, wherein the venting mechanism is configured to inhibit wetting of a vent from a fluid within the drainage lumen. A controller may be in communication with the reservoir, wherein the controller is configured to determine a fluid volume collected within the reservoir, and a valve may also be included which is configurable between a closed position and an open position, wherein the valve moves from the closed position to the open position when a first pressure level imparted upon the valve drops to a second pressure level.

Certain patient parameters which may be measured and/or determined by the disclosed technology are impacted by, and/or impact, a patient's treatment by medical treatment devices. For example, a patient's urine output, respiration rate, heart rate, stroke volume, stroke volume variability, intra-abdominal pressure (IAP), tissue oxygenation, tissue gas content, temperature, blood content and other patient parameters may be impacted by, and/or impact, medical treatment. Some examples of medical treatments, which may be controlled by medical devices include respiration rate and content, controlled by respirators, IV rate and content controlled by an IV drip controller, drug delivery controlled by a drug delivery device or IV controller, urine output controlled by a urine output pump, abdominal fluid volume controlled by drain pumps, and other treatments controlled by other medical treatment devices.

One embodiment of a system for analyzing bodily fluids may generally comprise an elongated catheter having an expandable balloon positioned near or at a distal end of the catheter and further defining one or more openings in proximity to the balloon, a venting mechanism coupled to a proximal end of the catheter, the venting mechanism configured to pass air therethrough when negative pressure is applied to the venting mechanism, a first lumen coupled to the venting mechanism and in fluid communication with the one or more openings, a second lumen in fluid communication with the balloon, a reservoir coupled to a proximal end of the first lumen and in fluid communication with the one or more openings, and a controller which is configured to connect to the reservoir and is programmed to control a pressure within the first lumen, wherein the controller is further programmed to monitor a urine output received in the reservoir from a patient and determine an intra-abdominal pressure of the patient based in part upon changes in pressure within the balloon, and wherein the controller is further configured to store patient data.

In one exemplary method for analyzing one or more body parameters from a patient, the method may generally comprise positioning an elongated catheter having an expandable balloon positioned near or at a distal end of the catheter within a body lumen filled at least partially with a body fluid, receiving the urine through one or more openings defined along the catheter in proximity to the balloon, further receiving the body fluid within a reservoir located external to the body lumen and which is in fluid communication with the one or more openings via a fluid lumen, venting air through a venting mechanism which is in communication with the fluid lumen when negative pressure is applied to the fluid lumen, analyzing a volume of the urine received within the reservoir via a controller which is programmed to control the negative pressure to the venting mechanism, determining an intra-abdominal pressure of the patient based in part upon the changes in pressure within the balloon, and storing one or more parameters of patient data via the controller.

Some embodiments of the sensing Foley catheter system include a loop controller which receives one or more pieces of data relating to patient parameters, and uses this information to control one or more medical treatment device or devices. The loop controller may be integrated with either the device measuring the patient parameter, or the medical treatment device, or both.

A pressure measuring balloon on a catheter, such as that disclosed in international patent application number PCT/US14/44565, titled Sensing Foley Catheter (which is herein incorporated by reference in its entirety) is an example of a device which measures patient parameters. Additional embodiments are disclosed herein. A sensing Foley catheter system, may include a pressure measuring balloon and/or other sensors, as well as the ability to measure urine output and content to determine patient parameters such as urine output rate, IAP, respiratory rate, heart rate, stroke volume, tissue oxygenation, urine composition, temperature and other patient parameters.

Other parameters that may be measured and/or determined via a Sensing Foley type Catheter include urine specific gravity and pulse pressure variability. These parameters may be used to help control a medical treatment device such as a ventilator and/or infusion and/or hydrating device.

Urine specific gravity is a measure of the number and weight of solute particles in urine. Normal ranges are around 1.010 to 1.030. Measurements that are higher than this may indicate dehydration or other conditions. Measurements that are lower than this may indicate fluid overload or other conditions. Measurements may be done by sensors on a Sensing Foley Catheter. Measurement results may indicate increasing (in the case of dehydration) or decreasing (in the case of fluid overload) the infusion rate for a patient. Measurement results may also indicate a change in ventilation parameters or drug infusions etc.

Pulse pressure variability can be a predictor of fluid responsiveness to a medical treatment device such as a ventilator and/or fluid infusion device. A Sensing Foley Catheter can record a pressure waveform and the controller can identify the maximum and minimum pressure pulses, which coincide with the respiration cycle. The controller can calculate pulse pressure variability. Pulse pressure variability can help determine whether a given patient will or will not respond to fluid therapy. Pulse pressure variability can also be used by the controller to control therapy in a feedback loop. If pulse pressure variability is high, more fluid may be required by the patient. If pulse pressure variability is low, less fluid may be required.

A Sensing Foley catheter system can measure cardiac activity via pressure sensing in the bladder. Because a Sensing Foley Catheter is capable of measuring respiratory activity as well as cardiac activity, and the frequency of the respiratory rate and the cardiac rate of a patient can be similar to each other, a patient's respiratory measurements can distort the cardiac measurements. To overcome this issue, some embodiments of a controller may pause the respirator at the end of one or more inspiration points, and/or pause the respirator at the end of one or more expiration points (for just a few seconds each time, for example 1 to 3 seconds, or for example, 1 to 4 seconds) so that the cardiac waveform can be captured without respiratory distortion. Capturing detailed cardiac waveforms in this manner allows the controller to determine stroke volume variability (SVV) which is useful in the detection of sepsis and the prevention of fluid overload. As an alternative embodiment, the patient may be asked to hold his/her breath at an inspiration point and/or an expiration point.

BRIEF DESCRIPTION OF THE DRAWINGS

The novel features of the invention are set forth. A better understanding of the features and advantages of the present invention will be obtained by reference to the following detailed description that sets forth illustrative embodiments, in which the principles of the invention are utilized, and the accompanying drawings of which:

FIG. 15 shows an example of a clearing mechanism of the sensing Foley catheter system.

FIG. 26-28 show flow charts of possible logic in various embodiments of the invention.

FIG. 35 shows the distal end of an embodiment of the sensing Foley catheter.

FIG. 36 shows an embodiment of a filter within a balloon.

FIG. 43 shows an embodiment of a filter within a balloon.

FIG. 44 shows an embodiment of a filter within a balloon.

FIG. 45 shows an embodiment of a filter within a balloon.

FIG. 46 shows an embodiment of a filter within a balloon.

FIGS. 55 and 56 are schematic diagram of gas measuring catheter/controller systems.

FIGS. 57A and 57B show embodiments of a gas measuring add-on component.

FIG. 58A shows a table that lists combinations of parameters that allow for possible signatures for identifying Acute Kidney Injury and UTI based on patient parameters.

FIG. 58B shows a table that lists combinations of parameters that allow for possible signatures for identifying Acute Kidney Injury, sepsis, and acute respiratory distress syndrome, based on patient parameters.

FIGS. 63A-B show how a smaller diameter lumen can compare to a larger diameter lumen in the vent/filter area.

FIG. 64 shows a curved barb area.

FIGS. 93A through 93E show another embodiment of the drainage lumen

FIGS. 97A-D show embodiments of the sensing Foley catheter system with bubble reduction mechanisms.

FIGS. 99A-C show embodiments of the sensing Foley catheter system with bubble reduction mechanisms.

DETAILED DESCRIPTION OF THE INVENTION

The preferred embodiments of the present invention are described in detail herein. However, alternative embodiments of various features of the device are also possible. Examples of these embodiments are provided below, but the scope of the invention is not limited to these specific configurations.

Sensing Foley Catheter

Figure 1:
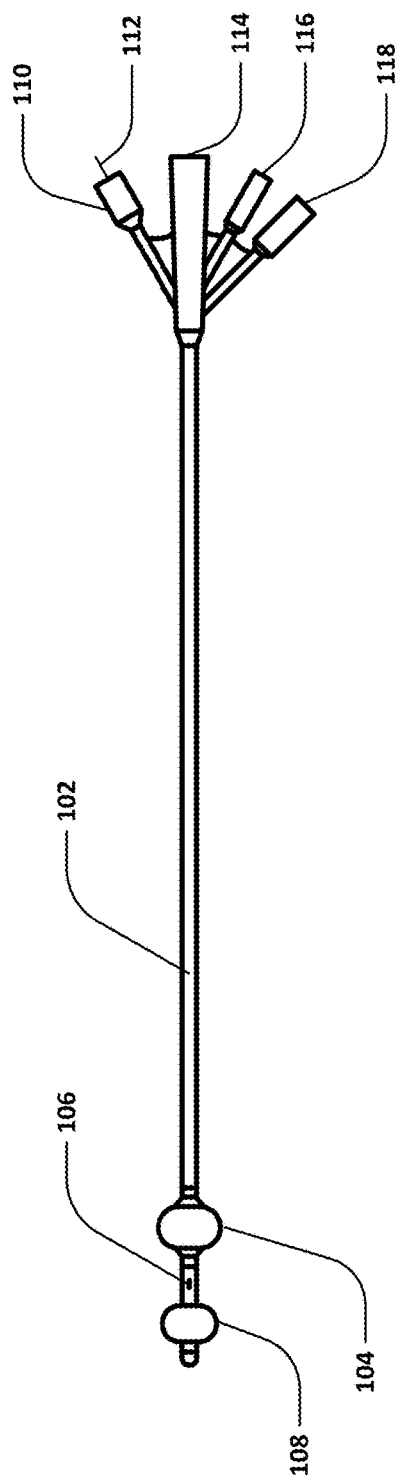
FIG. 1 shows an embodiment of a sensing Foley type catheter.

FIG. 1 shows an embodiment of a sensing Foley catheter and several of its features. A catheter may be understood to have various sections according to its disposition when the catheter has been inserted into a human subject, such as a proximal portion that remains external to the subject, a central or urethra-residing portion, and a distal or urinary bladder-residing portion.

Various internal lumens traverse the length of the catheter, such as an air or fluid lumen that communicates with a bladder retention balloon 104 and a retention balloon port 118. A urine drainage lumen has a distal opening or openings 106 that resides in the bladder portion of the catheter, and has an opening at the proximal end 114 of the catheter. The urine drainage lumen may be connected to a urine drainage tube that conveys the urine to a collecting receptacle. The urine drainage tube may be separate from, or integral with, the sensing Foley catheter. In some embodiments, the drainage lumen and distal opening in the bladder may also serve as an infusion conduit by which medicinal agents may be infused, or through which heating or cooling fluid may be infused. Analyte sensor(s) (not shown) or temperature sensor(s) (not shown) may be disposed on the catheter, either on the urethral portion or the bladder-residing portion of the catheter. Electrical or optical fiber leads may be disposed in a lumen that allows communication of sensing signals between distally disposed sensors and the proximal portion of the catheter, and then further communication to a data processing apparatus or controller.

An inflatable pressure-sensing balloon 108 (or a pressure sensing membrane arranged across an opening) may be positioned at or near the distal end of the catheter. Embodiments of a pressure-sensing balloon or pressure sensing membrane may be understood as comprising a pressure interface having a distal-facing surface exposed to pressure from within the bladder, and a proximal-facing surface exposed to a proximal fluid column. The pressure-sensing balloon or membrane is in fluid communication with a fluid column or lumen which is in fluid communication with a pressure port 116 at or near the proximal end of the catheter. Embodiments of the fluid column (filled with a fluid, either liquid or gas) may comprise a dedicated lumen, or a shared lumen.

In some embodiments, a temperature sensor may exist at or near the distal end of the catheter. Temperature port 110 may include temperature communication wire 112 which connects the temperature sensor to a display, connector and/or controller.

Note that although FIG. 1 shows the proximal end of the catheter comprising multiple separate ports, some or all of the ports may be integrated into a single port, or integrated into a urine drainage line which travels to a urine drainage system and/or controller. Other lumens and/or ports may also exist.

Pressure-based physiologic parameters that the sensing Foley catheter system may sense, and/or determine via a controller based on the sensed parameters, may include, by way of example, peritoneal pressure, respiratory rate, and cardiac rate, relative pulmonary tidal volume profile, cardiac output, relative cardiac output, and absolute cardiac stroke volume. Some embodiments of the Foley type catheter may be further equipped with any of a temperature sensor, one or more analyte sensors, electrodes, and paired light sources and sensors. Embodiments thus further equipped are capable of delivering other forms of physiologic data, as for example, blood pressure, oxygen saturation, pulse oximetry, EKG, and capillary fill pressure.

Embodiments of the sensing Foley catheter may be able to sense any one or more of a plurality of clinically relevant parameters, such as included in the following examples: urine pH, urine oxygen content, urine nitrate content, respiratory rate, heart rate, perfusion pressure of the bladder wall or the urethral wall, temperature inside the bladder or the urethra, electro-cardiography via sensors on the bladder wall or the urethra, respiratory volume, respiratory pressure, peritoneal pressure, urine glucose, blood glucose via urethral mucosa and/or bladder mucosa, urine proteins, urine hemoglobin, blood pressure. In some embodiments, the catheter can sense multiple parameters, but some embodiments may be limited to as few as a single parameter for focused applications (for example, respiratory rate in a patient in respiratory distress).

The disclosed technology captures a high-resolution chronological profile (pressure as a function of time) of peritoneal pressure from within the bladder that can be transduced and processed into distinct pressure profiles assignable to particular physiologic sources, including peritoneal pressure, respiratory rate, and cardiac rate. By tracking the pressure profile at a sufficiently rapid sampling rate, as provided by the technology, the pressure profile can be further resolved, and/or analyzed, into relative pulmonary tidal volume, cardiac output, relative cardiac output, and absolute cardiac stroke volume.

Accordingly, aspects of the disclosed technology relate to fidelity and resolution of a pressure signal generated in response to changes in pressure within the bladder, such changes being reflective of a pressure profile within the peritoneal cavity, such pressure profile including cumulative input from the aforementioned physiologic sources. Aspects of the technology further relate to fidelity and resolution of the transduction of the pressure signal into a highly resolvable electrical signal. Aspects of the technology relate still further to processing the totality of the electrical signal profile, a surrogate for the pressure profile within the peritoneal cavity, into component profiles that can be assigned to the physiologic sources.

The sensitivity of an inflated balloon as a pressure sensor is a function, in part, of the pressure differential across the balloon membrane as a baseline condition. The balloon has the greatest sensitivity to pressure when the baseline pressure differential is near zero. As the baseline pressure differential increases, the sensitivity of the pressure-sensing balloon degrades. Accordingly, the disclosed technology provides an automatic priming method that maintains the balloon in an inflated state, but with a minimal pressure differential.

To effectively capture physiologic pressure profiles, the profiles need to be sampled at a rate that is sufficient to resolve the inherent frequency of changes in the profile. This consideration is informed by the Nyquist-Shannon sampling theorem, which states that a sampling frequency of at least 2B samples/second is required to resolve an event that runs at a frequency of B cycles/second. As applied to a physiologic pressure cycle, for example, a cardiac rate of 70 beats/minute requires a sampling rate of at least 140 samples/minute to effectively capture the cycle. This relationship underlies aspects of the disclosed technology that specify the sampling rate particularly required to capture physiologic pressure cycles such as relative pulmonary tidal volume, cardiac output, relative cardiac output, and absolute cardiac stroke volume.

Embodiments of the technology include a pressure interface as may be represented by a balloon having either a compliant membrane or a non-compliant membrane.

Expandable pressure sensing balloons, per embodiments of the technology, may assume one or more of at least two basic forms, compliant or non-compliant. In compliant balloon types, which may be generally likened to a conventional party balloon, the pressure-sensing balloon is formed from or includes a compliant membrane. Accordingly, the surface area of the membrane expands or contracts as a function of the expansion of the balloon. The compliance of the membrane determines various features of the balloon, as a whole, at different levels of expansion. Upon expansion, the balloon, if unconstrained, maintains a substantially constant or preferred form or shape, as determined by the mandrel upon which the balloon is formed. Upon expansion of the balloon from a minimal volume to its maximal volume, the membrane of the balloon maintains a level of tautness. Within the limits of compliance of the compliant membrane, an increase in pressure during inflation results in a consequent expansion of volume. The balloon, on the whole may be considered partially compliant in that its shape responds to spatial constraints that it may encounter upon expansion or inflation, however the balloon does have a preferred or native shape, and such shape preference prevents a level of shape compliance or conformability such as that exhibited by a non-compliant balloon.

In a non-compliant balloon, the expandable pressure-sensing balloon is formed from or includes a non-compliant membrane, or a membrane that is substantially non-compliant. Accordingly, the surface area of the membrane does not expand or contract in accordance with the level of balloon expansion/pressurization. Non-compliant pressure-sensing balloons may be generally likened to a conventional Mylar® balloon. The lack of compliance of the membrane determines various features of the balloon, as a whole, at different levels of expansion. Upon expansion of the balloon from a minimal volume to a level near its maximal volume, the membrane of the balloon is supple, and has a level of slackness. Expansion of a non-compliant balloon occurs by way of outwardly directed smoothing of wrinkles and folds in the membrane. Deflation or compression of a non-compliant balloon occurs by way of generally inwardly directed wrinkling and infolding. When a non-compliant balloon is fully inflated (or substantially inflated) without being in a confining space, it assumes a preferred or native shape as determined by the geometry of the membrane or fabric of the balloon. However, in a state of partial inflation, the balloon, as a whole, is highly supple and conformable, broadly taking the shape as may be dictated by a confining space.

Expandable pressure sensing balloons, per embodiments of the technology, may also include features of both of the two basic forms, compliant and non-compliant. In these embodiments, the membrane may include regions that are compliant and regions that are non-compliant. A balloon of this hybrid type would, as a whole, behave in a manner drawing from behavioral aspects of both compliant and non-compliant balloons, as described above. Further, compliant balloons may be formed with a membrane that is not of a homogeneous composition or thickness. In such embodiments, regions of different thickness or composition could have varying degrees of compliance, thus affecting the behavior of these regions during expansion of the balloon. In still other embodiments, compliance of the membrane may have a bias or polarity that tends to permit compliance in one or more directions, and tends to disallow compliance in one or more other directions.

Embodiments of the sensing Foley catheter include a device utilizing a very small pressure lumen for air transmission. Pressure readings using inner lumen diameters of 3 mm, 1 mm, and 0.5 mm have been measured. Little degradation of the signal was seen when the air lumen diameter was decreased from 3 mm to 1 mm and 0.5 mm.

These data indicate the appropriateness of using the embodiment of the pressure transduction system in a small diameter pediatric catheter down to a size as small as 4F. In this embodiment, as well, the tip of the catheter can be lower profile than the rest of the catheter to allow for a consistently small diameter even with addition of the pressure sensing balloon. Thus, the catheter of the present invention is uniquely suited to the pediatric indication where there is a dire need for more appropriate, less invasive monitoring methods. In another embodiment, the retention balloon itself can be used as the pressure balloon, in order to minimize the number of required lumens. In one embodiment, the retention balloon is used in its fully inflated state, and is only used to track macro trends in IAP. In another embodiment, the retention balloon is only slightly inflated in order to increase balloon sensitivity to small changes in pressure. This embodiment allows for finer measurements of micro parameters, such as heart rate, relative stroke volume, relative cardiac output, respiratory rate, and relative tidal volume. A smaller pressure lumen also allows for more space in a larger catheter for other technologies, such as sensors etc.

In embodiments of the sensing Foley catheter where the retention balloon is used as the pressure balloon, the pressure measured within the retention balloon is offset by the pressure required to just inflate the balloon large enough for it to serve as a retention balloon. As a result, the inflation pressure, and possibly the pressure resulting from the retention balloon being in contact with the inner surface of the bladder, needs to be subtracted from the pressure reading. In this way, smaller pressure changes may be tracked similarly to those measured by the separate pressure balloon. The inflation pressure offset may be determined by measuring the pressure within the retention balloon when it is first inserted into the patient, or by measuring the retention balloon inflation pressure outside the patient, or by other means. The retention balloon may be filled with fluid, air or any other appropriate gas.

Embodiments of the disclosed technology may include embodiments in which the pressure sensor is a mechanical pressure sensor, such as those using fiberoptic, strain gage, magnetic, resonant, and/or other suitable technologies.

Figure 2:
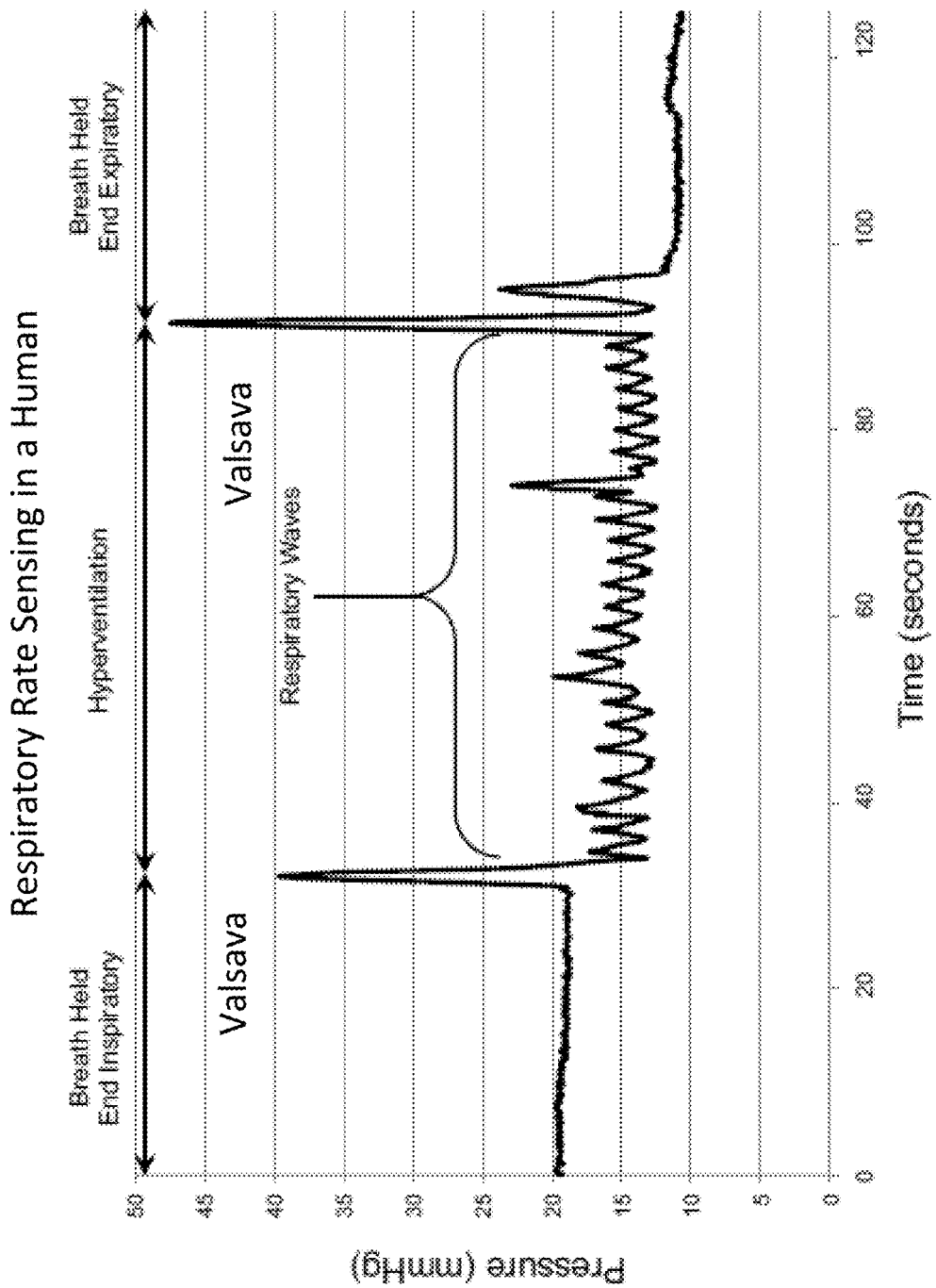
FIG. 2 shows an example of respiratory rate sensing data.

FIG. 2 shows an example of respiratory rate sensing data from a human subject, as provided by an embodiment of the sensing Foley catheter system. During this test period, the subject performs a respiratory sequence as follows: (1) breath being held at the end of an expiration, (2) valsalva, (3) hyperventilation, (4) valsalva, and (5) breath being held at the end of an expiration.

Figure 3:
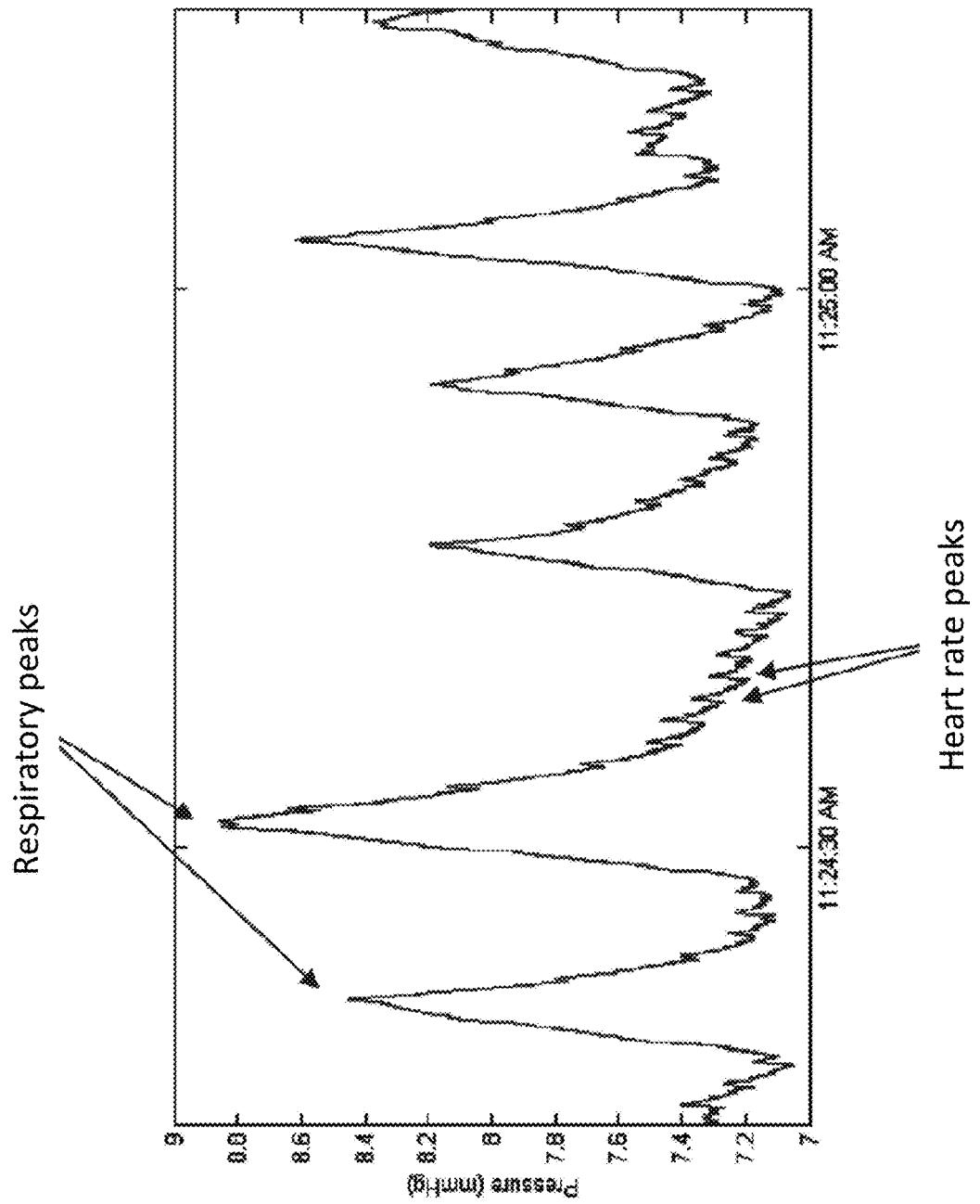
FIG. 3 shows a detailed portion of a respiratory profile.

FIG. 3 shows a detailed portion of the normal respiration period in a respiratory profile similar to that shown in FIG. 2. Note that the pressure curve clearly shows the respiratory peaks, and therefore respiratory rate can be determined, and heart rate peaks, and therefore heart rate can be determined.

Figure 4:
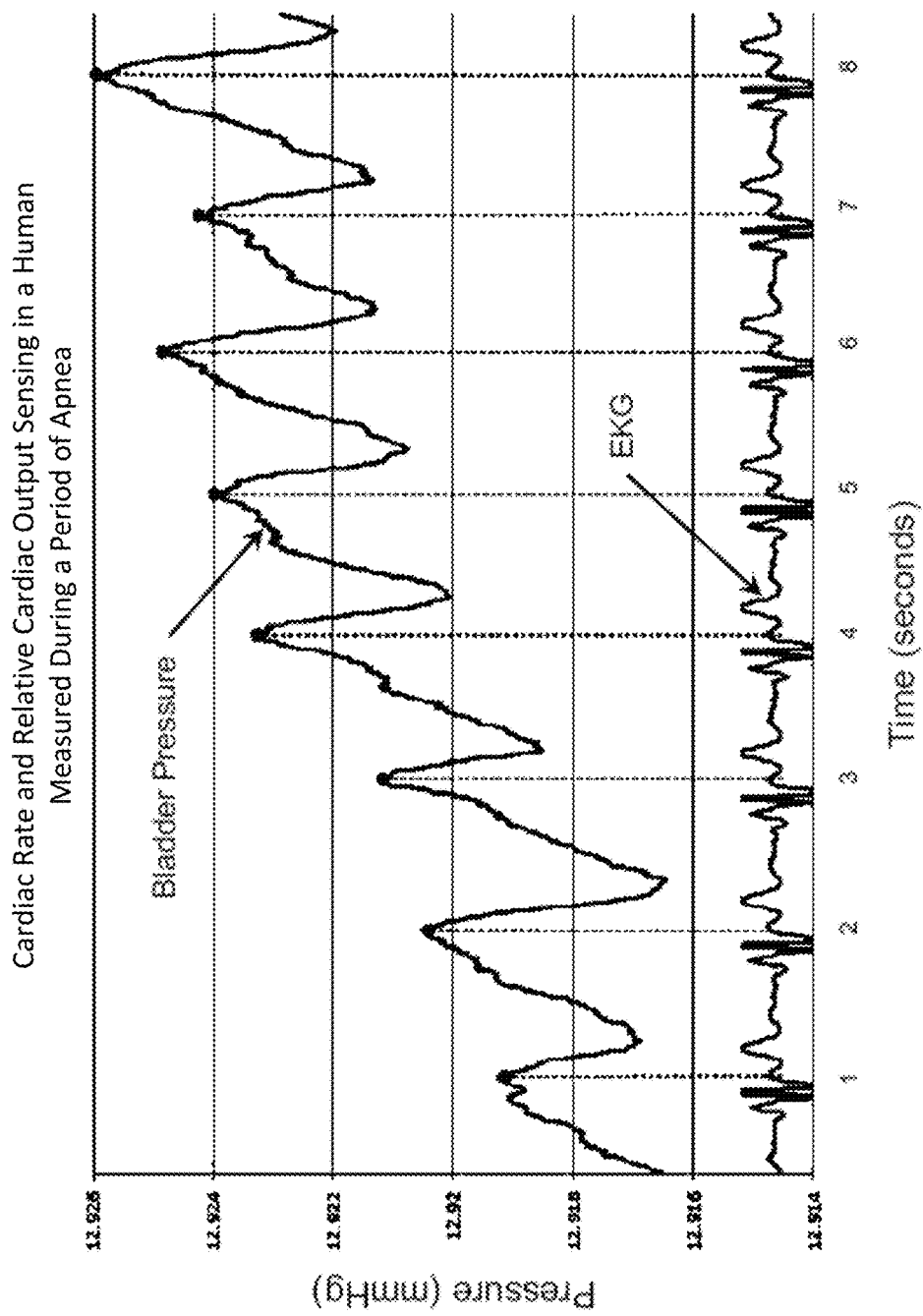
FIG. 4 shows an example of cardiac rate and relative cardiac output sensing data.

FIG. 4 shows an example of cardiac rate and relative cardiac output sensing data from a human subject, as provided by an embodiment of the sensing Foley catheter system, and an EKG trace as measured simultaneously and independently. This graph clearly shows that the heart rate peaks as measured by the sensing Foley catheter are aligned with the heart rate.

Figure 5:
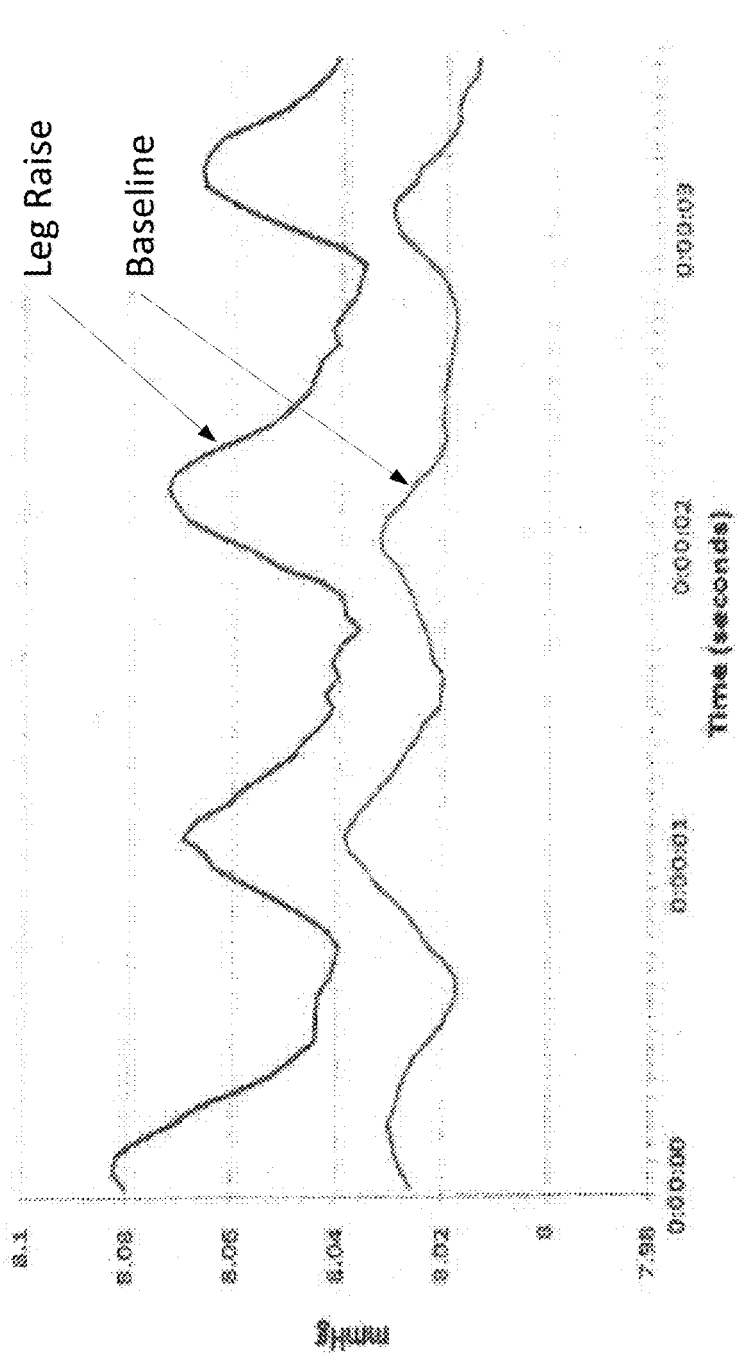
FIG. 5 shows data related to relative cardiac output sensing in a human leg raising exercise.

FIG. 5 shows data related to relative cardiac output sensing in a human leg raising exercise in which cardiac output increases, as demonstrated by an increased amplitude of the cardiac pulse.

Figure 6:
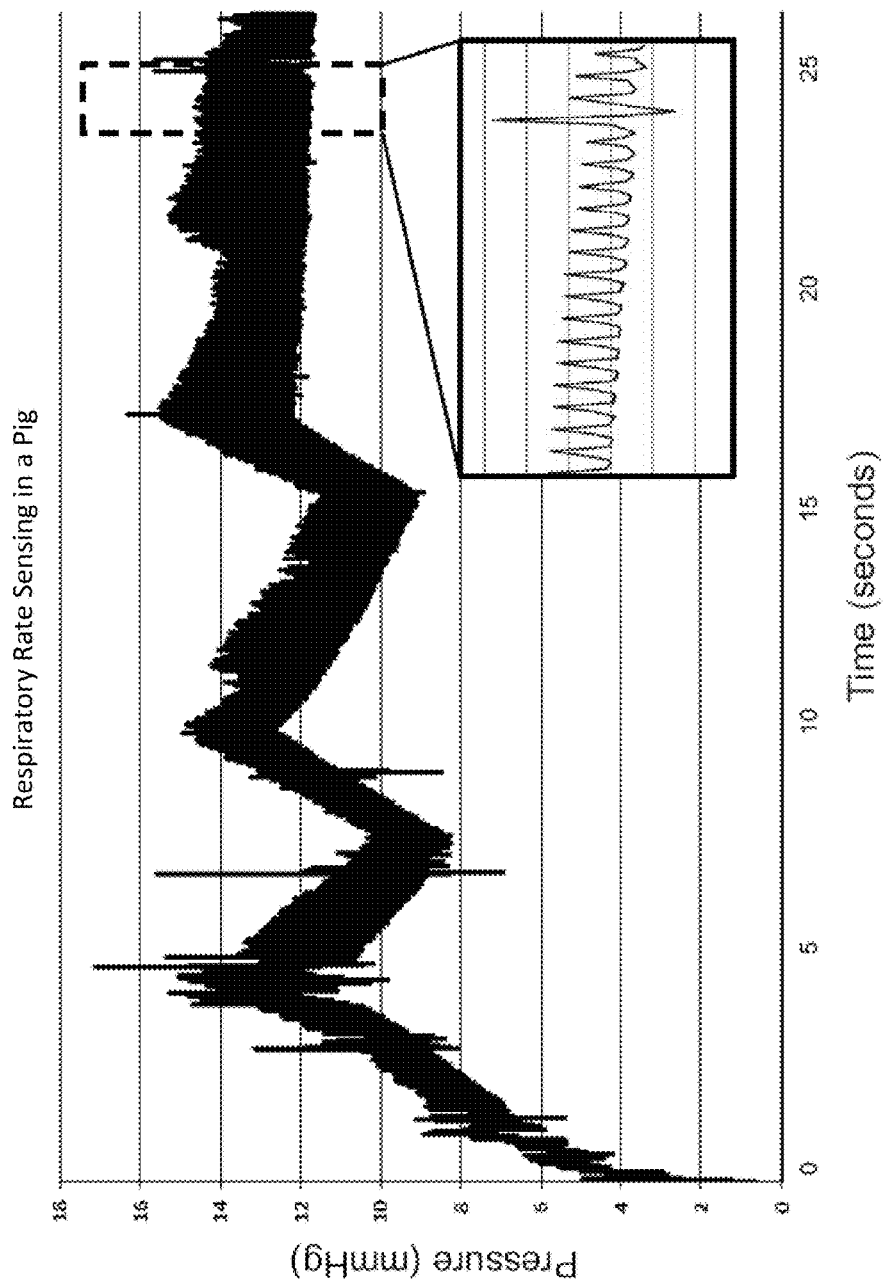
FIG. 6 shows an example of peritoneal sensing data.
Figure 7:
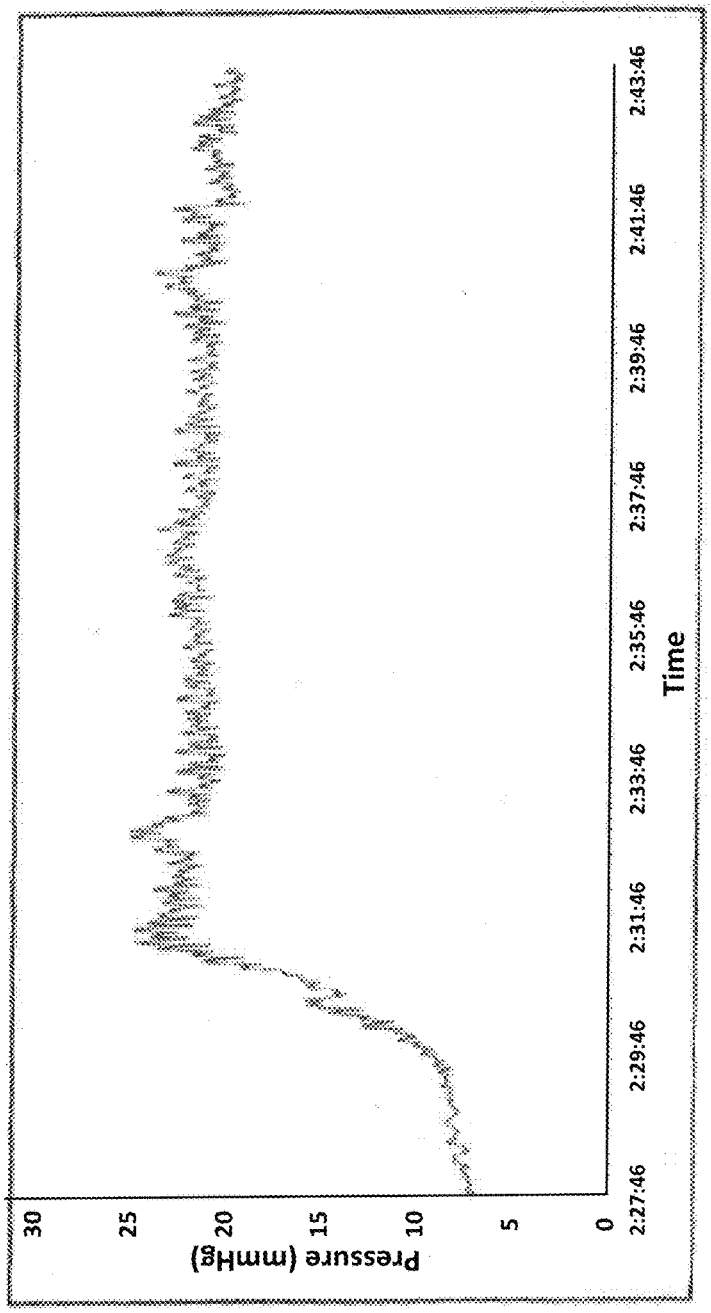
FIG. 7 shows an example of peritoneal sensing data.

The data shown in FIGS. 6 and 7 were derived from studies done with Yorkshire pigs under IACUC-approved protocols. FIG. 6 shows an example of peritoneal sensing data, with a focus on respiratory rate from a pig, as provided by an embodiment of the sensing Foley catheter system. FIG. 7 shows an example of pig study that demonstrates the capability of an embodiment of the sensing Foley catheter system to detect intra-abdominal hypertension. In this study, the peritoneal cavity was accessed with a 5 mm Tenamian trocar. The trocar was then attached to a 5 L bag of Lactated Ringers solution via a peristaltic pump, and the solution was infused at a rate of about 1 L per minute. Fluid flow was discontinued once a pressure of about 20 mmHg was obtained after which there was no net fluid flow in or out of the cavity.

Figure 8:
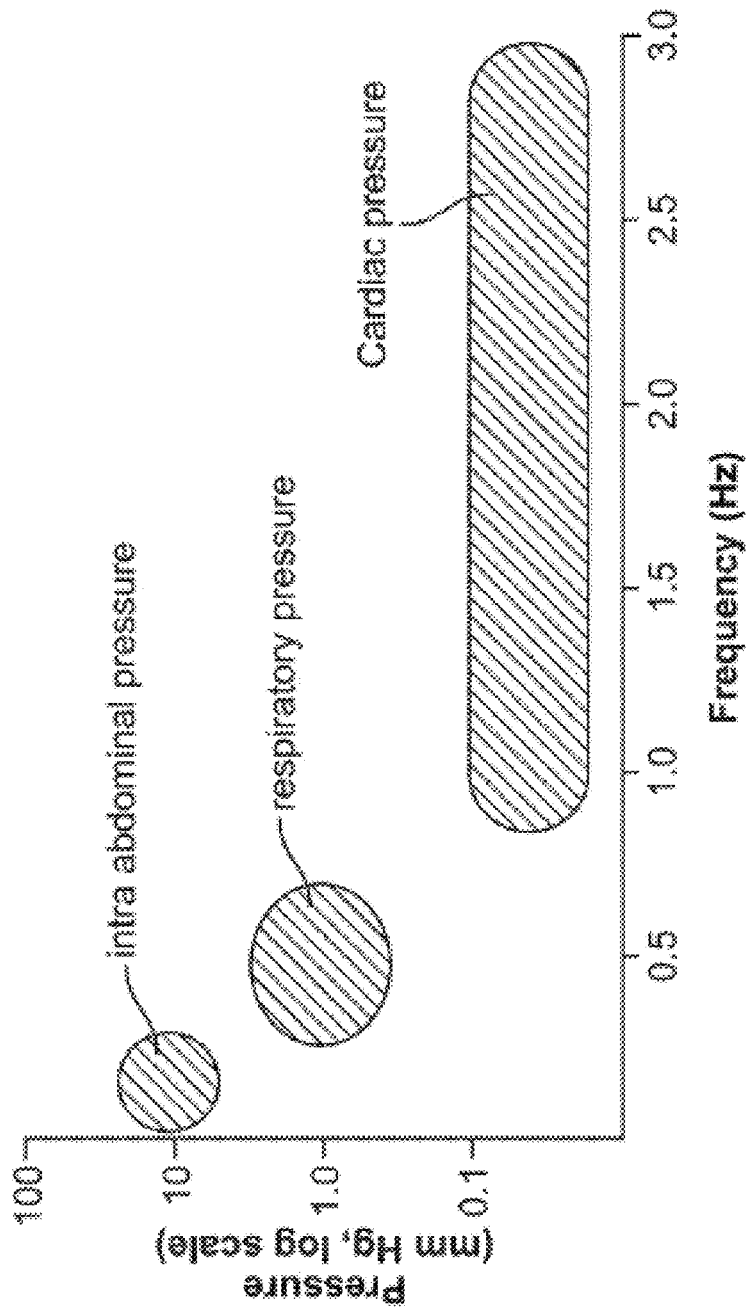
FIG. 8 shows the relationship among intraabdominal pressure, respiratory wave pressure, and cardiac pressure.

FIG. 8 shows intraabdominal pressure, respiratory wave pressure, and cardiac pressure schematically arrayed as a two dimensional plot of pressure (mm Hg on a logarithmic scale) vs. frequency (Hz). It can be seen that there is an inverse relationship between pressure and frequency, and the various physiologic pressure-related parameters occupy distinct sectors when arrayed in this manner. It is by the distinctness of both these pressure and/or frequency profiles that embodiments of the method, as disclosed herein, can resolve a single overall chronological pressure profile into the distinct subprofiles, in accordance with their physiologic origin. Intra-abdominal pressure measurements may be resolved in the frequency range of about 0 Hz to about 0.5 Hz. Respiratory pressure measurements may be resolved in the frequency range of about 0.25 Hz to about 0.75 Hz. Cardiac pressure measurements may be resolved in the frequency range of about 0.75 Hz to about 3.0 Hz. Intra-abdominal pressure measurements may be resolved in the amplitude range of about 5 mm Hg to about 30 mm Hg. Respiratory pressure measurements may be resolved in the amplitude range of about 0.5 mm Hg to about 5 mm Hg. Cardiac pressure measurements may be resolved in the amplitude range of about 0 mm Hg to about 0.5 mm Hg. Sampling frequencies—the frequency with which pressure measurements are taken—are preferably about twice that of the resolution frequency. For example, sampling frequency may be about 0 Hz-1 Hz for intra-abdominal pressure measurements, 0.5 Hz-1.5 Hz for respiratory pressure measurements, and 1.5 Hz-6 Hz for cardiac pressure measurements.

Figure 9:
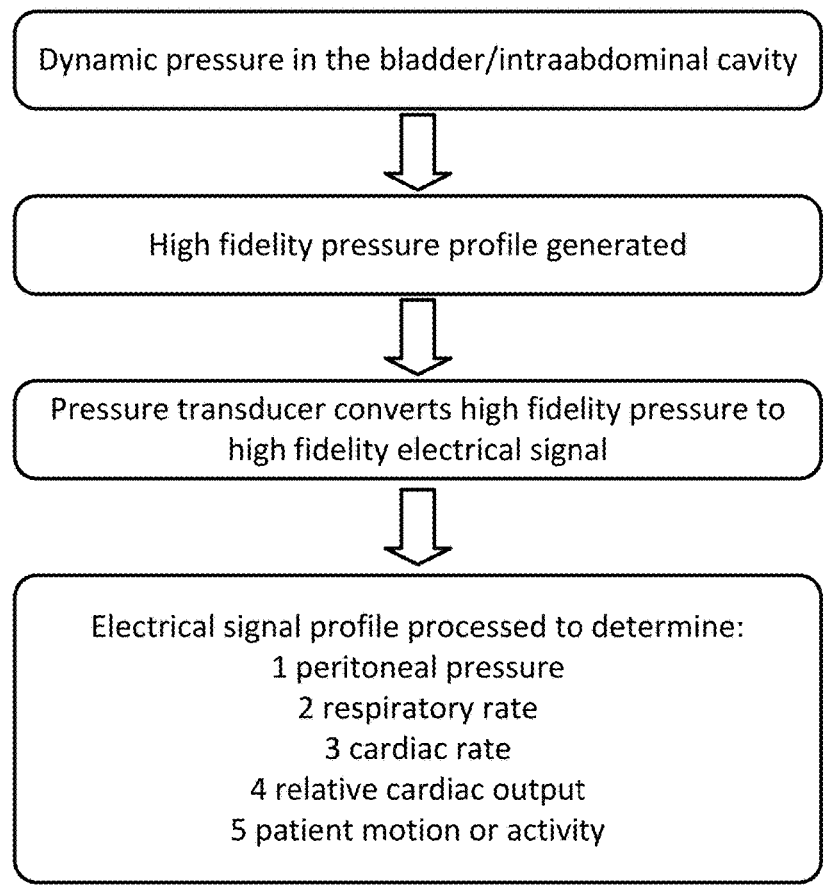
FIG. 9 provides a flow diagram of an embodiment of the method.

FIG. 9 provides a flow diagram of an embodiment of the method of monitoring pressure as it occurs dynamically as waves of varied frequency and amplitude in the intraabdominal cavity, as detected from within the urinary bladder. Through the agency of a pressure interface, a high fidelity pressure profile is generated and transmitted proximally through a fluid column. More proximally, a pressure transducer converts the high fidelity pressure wave into a high fidelity electrical signal that is informative of pressure frequency and amplitude. The generated high fidelity electrical signal is then processed by a controller to yield data subsets that are reflective of components within the overall pressure profile, such subsets being attributable to particular physiologic sources, such as peritoneal pressure, respiratory rate, cardiac rate, relative cardiac output, and patient motion or activity.

Sensing Foley Catheter System

Figure 10A:
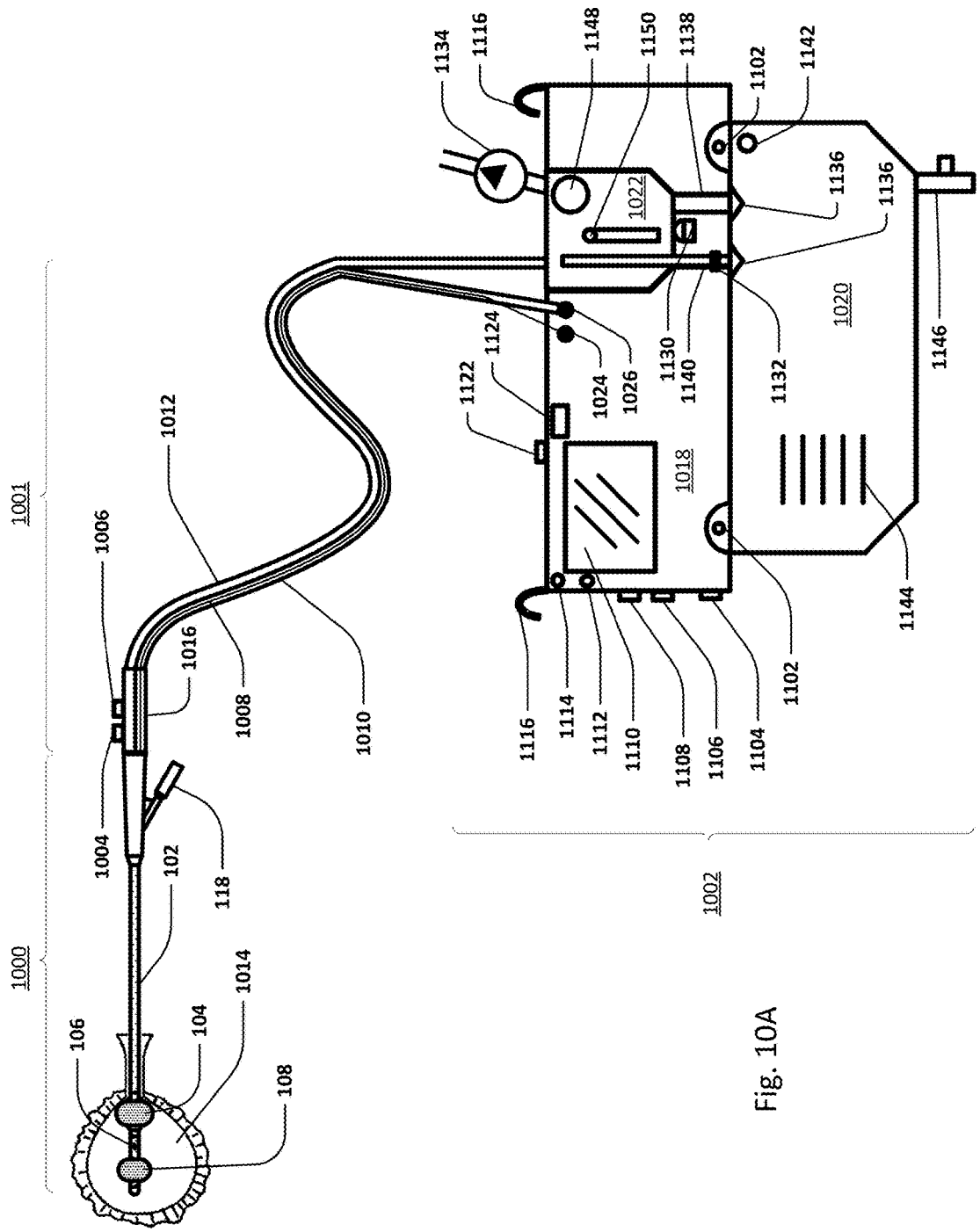
FIG. 10A shows an embodiment of the sensing Foley catheter system.

FIG. 10A shows an embodiment of the sensing Foley catheter used in conjunction with an embodiment of an airlock clearing mechanism and fluid collection & analysis system. Both urine drainage and pressure readings benefit from the elimination or reduction of airlocks in the urine drainage line.

Sensing Foley catheter 1000 is similar to the sensing Foley catheter shown in FIG. 1. The sensing Foley catheter is shown in use in bladder 1014. Note that several of the ports at the proximal end of the catheter shown in FIG. 1 are combined in the embodiment shown in FIG. 10A. Urine drainage tube 1001 is also shown here. The urine drainage tube may be combined with the sensing Foley catheter or may be a separate component. Urine drainage tube 1001 and/or sensing Foley catheter may also include vent barb 1016, or the vent barb may be a separate component. Airlock clearing mechanism and fluid collection & analysis system 1002 is also shown here, and is in fluid communication with urine drainage tube 1001 which is in fluid communication with sensing Foley catheter 1000. Airlock clearing mechanism and fluid collection & analysis system includes base/controller 1018, fluid collection bag 1020 and reservoir or cassette 1022. The combination of the sensing Foley catheter 1000, the urine drainage tube 1001, and the airlock clearing mechanism and fluid collection & analysis system 1002 are also referred to herein as the sensing Foley catheter system. The sensing Foley catheter, urine drainage line, and reservoir/cassette may be disposable and may be sold as a unit. This disposable assembly is shown in FIG. 10C, which includes sensing Foley catheter 1000, urine drainage tube 1001 (including vent barb) and reservoir/cassette 1022.

Vent barb 1016 may include vent, or vents, 1006 as well as urine sampling port 1004. In this embodiment, vent 1006 is preferably made from a membrane that permits the transmission of gases, but not liquids, such as hydrophobic membranes. An example of one such exemplary vent is a PTFE (Polytetrafluoroethylene), cPTFE (Expanded PTFE), or Versapor® (from Pall Corporation of Port Washington, N.Y.), membrane, although other materials may be used. The vent allows air to enter the system when negative pressure is applied to the drainage tube, and may allow air to exit the system when positive pressure is created due to airlocks in the drainage line. Such a mechanism prevents suction trauma, for example at the bladder wall. Vents 1006 may incorporate a one-way valve which prevents air from exiting the drainage line, or entering the drainage line. In a preferred embodiment, a one-way valve is used to prevent air from exiting the drainage line, but allows air to enter the drainage line, via vents 1006. In this manner, the valves also prevent urine from coming into contact with vents 1006.

Urine drainage tube 1001 may include several lumens, including pressure lumen 1010, temperature lumen 1008, and urine lumen 1012. Pressure lumen 1010 is in fluid communication with pressure sensing balloon 108 as well as pressure transducer interface 1026 in controller 1018. Temperature lumen 1008 communicates with the temperature sensor (not shown) in the sensing Foley catheter and also temperature connecter 1024 in the controller. Urine lumen 1012 is in fluid communication with opening or openings 106 and urine reservoir or cassette 1022.

Figure 59:
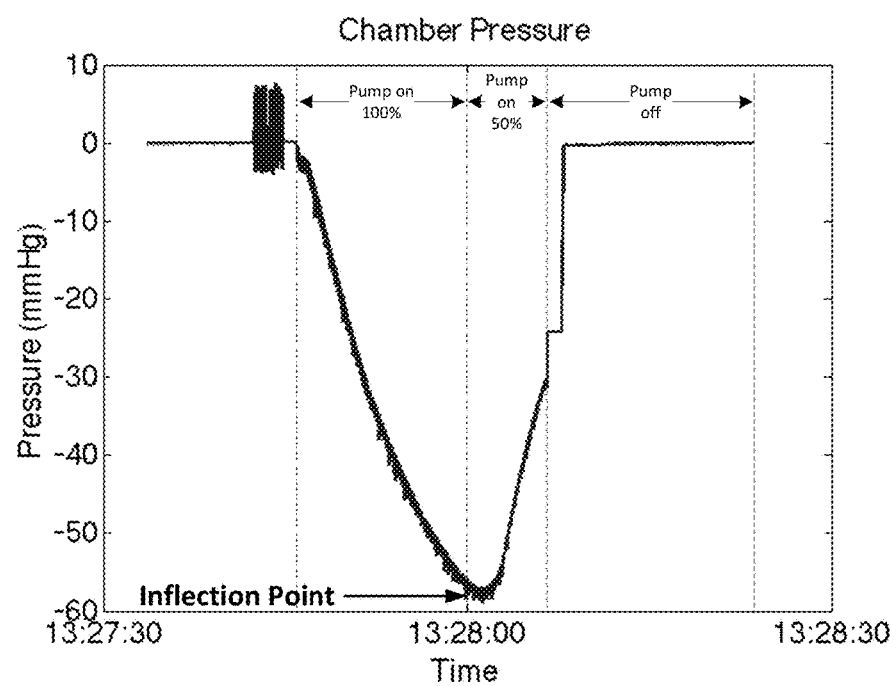
FIG. 59 shows a pressure signature curve within the collection chamber during clearance of an airlock.

Disposable measurement vessel, collection vessel, chamber or cassette component 1022 is designed to fit into cassette mount, base or controller 1018 and to interface with the components of the controller. Controller pump interface (behind cassette pump interface 1148) connects to pump 1134 and to cassette pump interface 1148 on the disposable cassette component. The pump is designed to create a vacuum inside the cassette component, which is then transferred to the urine drainage lumen in the drainage line. Preferably, the collection vessel/cassette is rigid in order to maintain a constant volume when the pump applies negative pressure. The level of negative pressure applied may be monitored by a pressure sensor. During clearance of an airlock, the pressure follows a signature curve as shown in FIG. 59. The pressure decreases as suction is applied, eventually reaching an inflection point when the meniscus of the urine passes the lowest point in the drainage tubing. At this point, less suction is required to continue clearing the airlock, so the pump power can be reduced in order to minimize the amount of suction transmitted to the bladder once the airlock is completely cleared. A larger vessel without this pressure-sensing feature for example, would transmit substantial negative pressure to the bladder once the airlock is cleared and the before the vessel has time to equilibrate with atmosphere. Controller pressure interface (behind cassette pressure interface 1150) connects to a pressure measurement device, such as a pressure transducer, and to cassette pressure interface 1150. The pressure measurement device is designed to measure volume of the urine, or other fluid, based on the pressure exerted on the pressure measurement device, which may be a pressure transducer. Ultrasound transducer interface 1130 is also to provide urine volume measurements. The ultrasonic measurements can be used in conjunction with the pressure measurements, or either can be used to determine urine, or other fluid, volume output. Active pinch valve 1132 is designed to connect to the outflow tubing of the cassette. The pinch valve is to control the emptying of the cassette vessel and the pinch valve is controlled by the controller so that it releases urine/fluid when the urine output reaches a certain volume in the cassette, as determined by the pressure and/or ultrasonic measurements. The volume of urine in the cassette is measured, and when the urine gets to a certain volume, the urine is emptied via the pinch valve into urine drainage bag 1020. For example, the cassette may be emptied when the volume of urine in the cassette reaches about 50 ml. Alternatively, the cassette may be emptied when the volume of urine in the cassette reaches about 40 ml. Alternatively, the cassette may be emptied when the volume of urine in the cassette reaches about 30 ml. Alternatively, the cassette may be emptied when the volume of urine in the cassette reaches about 20 ml. Alternatively, the cassette may be emptied when the volume of urine in the cassette reaches about 10 ml. In this way the urine output volume can be accurately measured over time.

Alternatively, the controller may utilize a set time between cassette emptyings and measure the volume of urine in the cassette just prior to emptying. Alternatively, the controller may empty the cassette upon an event, such as air-lock removal triggered by pump activation. For example, the controller may set up a periodic air-lock clearance cycle, followed by measuring of the volume of urine in the cassette, followed by emptying of the cassette.

For example, the controller may control the pinch valve to empty the reservoir/cassette when the urine volume reaches about 50 ml. Alternatively the controller may control the pinch valve to empty the reservoir/cassette every hour after measuring the urine volume within the cassette. Alternatively the controller may control the pinch valve to empty the reservoir/cassette during, or after, a urine drainage event, such as a running of the pump. Or the controller may control the pinch valve to empty the reservoir/cassette using a combination of these triggers.

Other technologies may be used to measure urine volume in addition to, or instead of, pressure and/or ultrasound, including pressure-based, resistance-based, capacitance-based, ultrasonically-based, or optically-based technologies. More than one technology may be used so that the measurements can be compared to each other to improve the accuracy of the volume measurements. More than one volume measurement made by one or more technologies may be used for redundancy, or backup, or in conjunction with each other to obtain more accurate urine volume measurements.

Bed hooks 1116 are for hooking the controller to the bed, or other device, as needed. They can also be used to hook the controller to a portable device for patient transport. Collection bag hooks/holes 1102 are to mount a drainage bag where the urine/fluid is ultimately collected, after the urine/fluid passes through the pinch valve. Collection bag hooks 1102 may be designed to provide strain measurements such that the weight of fluid in the bag can be determined and therefore provide another method for determining the volume of fluid in the bag. For example, piezo-electric transducers may be used. Specific gravity determinations may also be used by the controller to determine useful volume measurements based on weight and specific gravity.

Screen 1110 is for displaying information including current urine/fluid volume status, system status, etc. Screen 1110 may also be a touch screen and receive inputs, including settings, screen display changes, menu changes, etc. Pressure port 1026 connects to the bladder pressure line 1010, which measures bladder pressures using a sensing Foley catheter, if used. Alternatively, pressure port may be located within the cassette mount underneath cassette 1022 or elsewhere in the controller/base. Temperature in port 1024 connects to a thermistor/temperature sensor which measures body temperature, either via a sensing Foley catheter via lumen 1008, or by other means. Temperature out port 1122 is for transmitting any temperature measurements to an external device and/or monitor. Adapter port 1124 is for adapting the controller to other devices, such as in the case of a RFID adapter. This could be used to activate any additional/advanced features, such as measurements of LAP, respiratory rate, heart rate, cardiac output, or any other parameters that may be measured by the sensing Foley catheter. This allows the additional parameters to be activated and paid for by the hospital only when that information is desired. The activation of advanced features may also be controlled by use of different disposable components for example. Alternatively, advanced features may be activated by software upgrades which are purchased, either as part of the disposable, or separately. Software upgrades may be delivered wirelessly, by USB dongle, by micro-SD card, by EPROM card, or by other suitable technology. Data for each patient and/or aggregated patients may also be saved by the controller. The patient data may be saved to memory, USB, micro-SD card, EPROM card, hard drive, or otherwise. The patient data may be transferred wirelessly or by wired connection to another storage device, such as a server on the internet or an intranet. Patient data may be anonymized. Patient data, such as the patient ID, may be stored in an RFID adapter so that data specific to a particular patient is recognized by the controller and associated with the disposable component used by that patient.

Power LED/indicator 1114 is an indication that the power is on or off. Error LED/indicator 1112 is an indicator if any error has occurred within the system. Error details can be displayed on screen 1110, but indicator 1112 alerts users that an error exists. Indicators may also incorporate sounds or other alerts.

Port 1108 is for downloads, uploads, software upgrades, connecting to other devices etc., such as integration with an EMR (Electronic Medical Record) system. Port 1108 may be a USB port or other appropriate port. SD port 1106 is for data downloads. Power port 1104 is for connecting the controller to the wall or other power source to power the controller.

Urine/fluid drainage bag 1020 includes one way valves 1136 connected to overflow tubing 1138 and outflow tubing 1140 to prevent urine/fluid from exiting the drainage bag once collected. These valves also prevent air from entering the collection vessel 1022 when pump 1134 is pulling vacuum so that the vacuum acts on the drainage tubing and not the bag. In a preferred embodiment, a single valve is used for both the overflow and outflow tubings. Mounting hooks/holes 1102 allow drainage bag 1020 to be removably attached to controller 1018. Vent 1142, which may be a hydrophobic or other vent, allows air or gas to exit the drainage bag, but does not allow fluid to exit the bag. This prevents excessive air, and potentially pressure, buildup in the bag, and thus allows for efficient filling of the drainage bag. Graduated markings 1144 show a somewhat crude measurement of the fluid volume in the bag as it is collected. Outflow valve 1146 may be used to empty the bag of fluid/urine. Preferably, the valve is operable easily by one person. Collection bag hooks 1102 when designed as strain measurement elements may also force an alarm to sound if the bag is reaching full capacity and needs to be emptied. An alarm may also sound if there is unnecessarily excessive force on the bag, for example if the bag is being pulled or is caught on an obstacle as a patient is being moved.

The drainage bag may be made out of clear vinyl or other suitable material. The one-way valves may be made out of vinyl or other suitable material. The hydrophobic vent may be made out of ePTFE, Versapor, or other suitable material. The outflow valve may be made out of PVC, PC, or other suitable material.

Pressure readings from the sensing Foley catheter may be used to trigger the pump and therefore the emptying of the drainage tubing. For example, when pressure sensed in the bladder exceeds a preset number, the pump may engage to move urine more quickly through the drainage tubing.

The controller/base and/or the reservoir/cassette may include an accelerometer, or other sensor, to determine when the controller/cassette is level and when it is not. An alarm may sound when the controller/cassette is not level. Alternatively, urine volume measurements may be adjusted to account for the different angle in the system.

The bottom of the urine reservoir in the cassette may have rounded edges, or be configured in such a way that urine is completely emptied from the cassette when the pinch valve is opened.

Figure 10B:
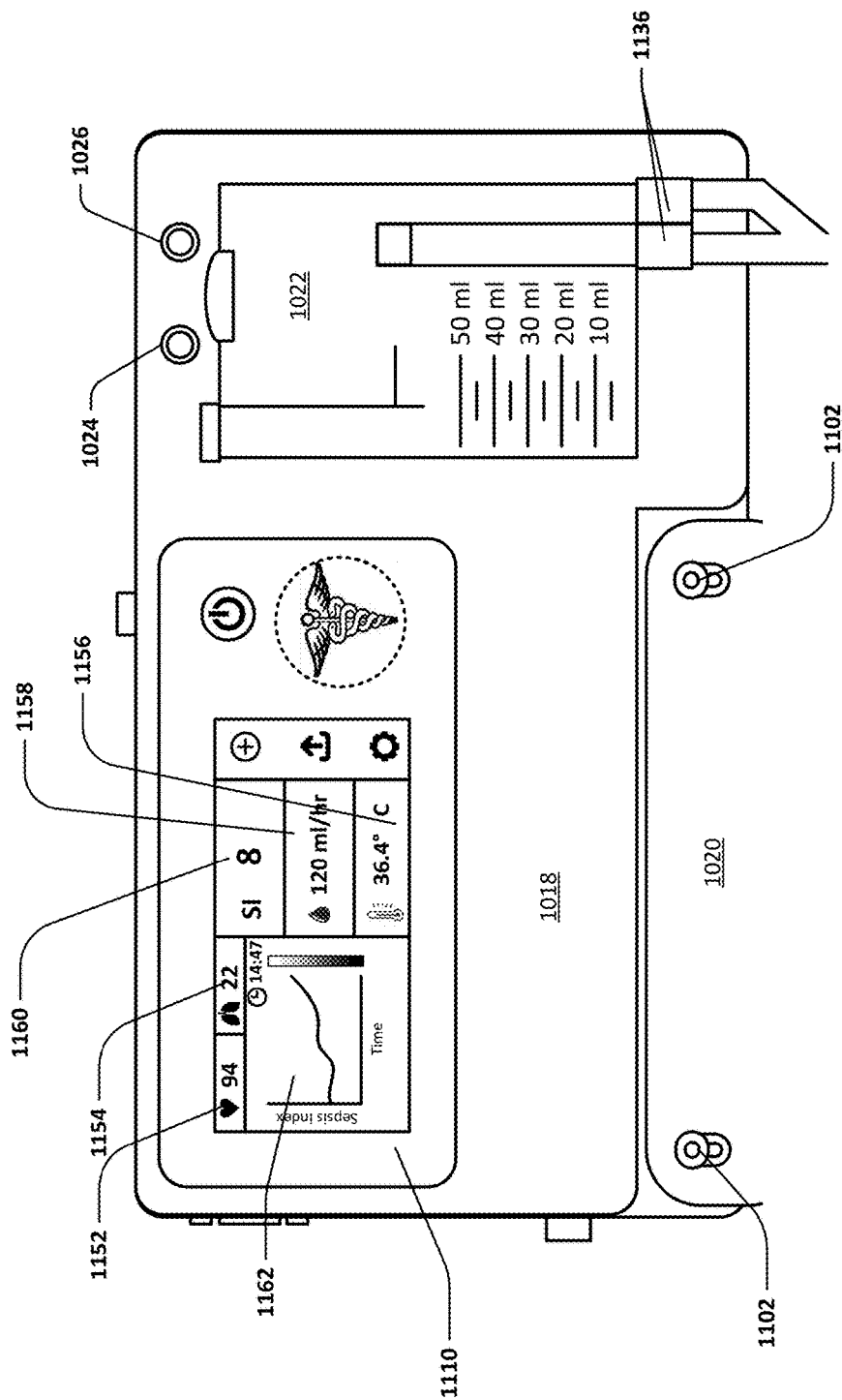
FIG. 10B shows a detail view of airlock clearing mechanism and fluid collection & analysis system of FIG. 10A.
Figure 10C:
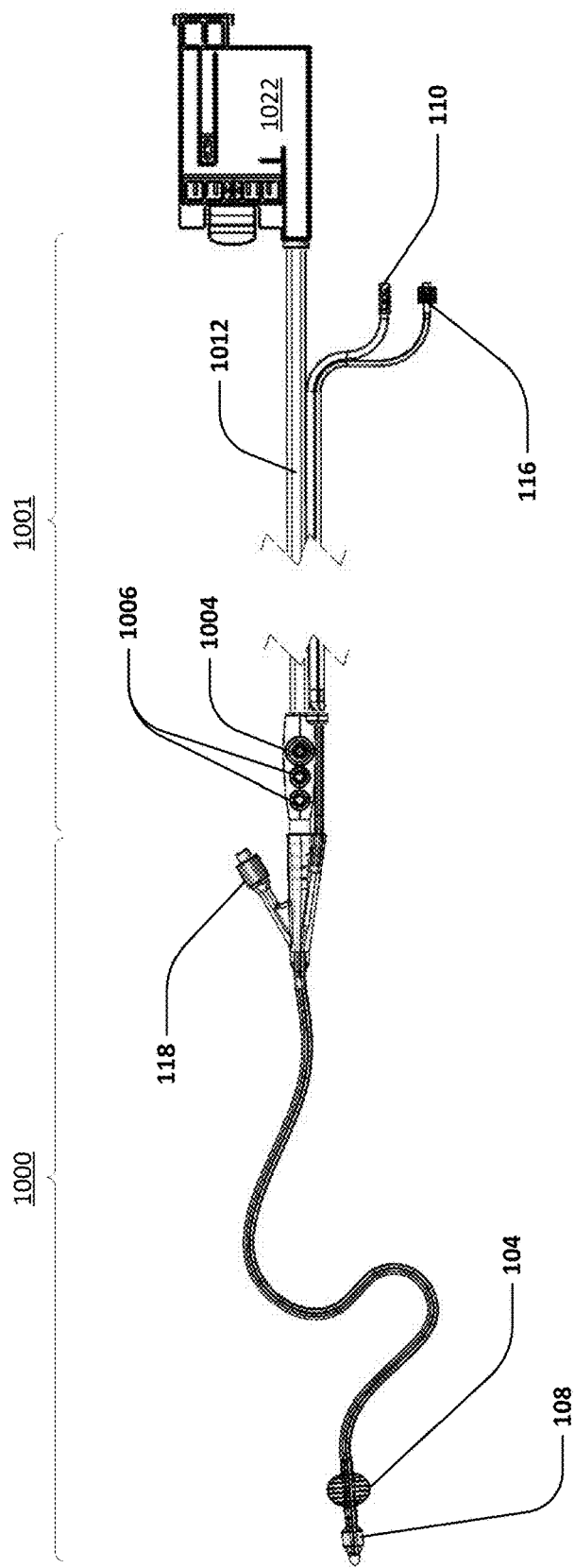
FIG. 10C shows the disposable components of an embodiment of the sensing Foley catheter system.

FIG. 10B is a detail view of airlock clearing mechanism and fluid collection & analysis system 1002. Screen 1110 displays the user interface including patient parameters as well as touch screen, or other, control functions. Heart rate area 1152 shows the patient's heart rate which is determined by the controller based on intra-bladder pressure measurements sensed by the sensing Foley catheter. Respiratory rate area 1154 shows the patient's respiratory rate which is determined by the controller based on intra-bladder pressure measurements sensed by the sensing Foley catheter. Core body temperature area 1156 shows the patient's core body temperature as sensed by the temperature sensor in the sensing Foley catheter or otherwise. Urine output area 1158 shows the patient's current and/or average urine output which is determined by the controller based on urine volume measurements as measured by pressure measurement device connected to pressure interface 1150 and/or ultrasound transducer interface 1130. Sepsis Index area 1160 shows the patient's likelihood of sepsis which is determined by the controller based on one or more patient parameters collected and/or calculated. For example, temperature, heart rate abnormalities, respiratory rate abnormalities and/or urine output or other factors may be considered in determining sepsis risk. Trending in these parameters may also be used in assessing risk. For example, reduced urine output, increased heart rate, increased or decreased core temperature may be indicators of sepsis.

Other risk assessments may be determined by the controller and displayed in addition to, or as an alternative to, the Sepsis Index. These include risk assessments of acute kidney injury, urinary tract infection, intra-abdominal hypertension, abdominal compartment syndrome, infection risk, sepsis, ARDS (Acute respiratory distress syndrome) and others. For example, a sample risk algorithm of acute kidney injury and urinary tract infection is shown in FIG. 58A. A sample risk algorithm for acute kidney injury, sepsis and acute respiratory distress syndrome is shown in FIG. 58B. Measured urine parameters may include conductance, specific gravity, urine output, presence of infection, bacteria, white blood cells, oxygen tension and others.

Graphical indicator 1162 shows historical data of any of these areas. For example, a user may be able to toggle the graphical display by touching the screen and show the patient's history of urine output, temperature, heart rate, respiratory rate. Sepsis Index, risk of acute kidney injury, urinary tract infection, intra-abdominal hypertension, abdominal compartment syndrome, infection risk and others, or any other pertinent parameter. The time frame for the history may be all time, daily, hourly, or any period set by the user. Any risk factor that is out of range, so at an elevated risk, may be shown automatically here or elsewhere on the display. Alerts and/or ranges may be set by the user, and may include absolute values, as well as trends over time. For example, an increase in core body temperature of more than 2 degrees over a specific time frame may display a visual or sound an audible alert.

Figure 11:
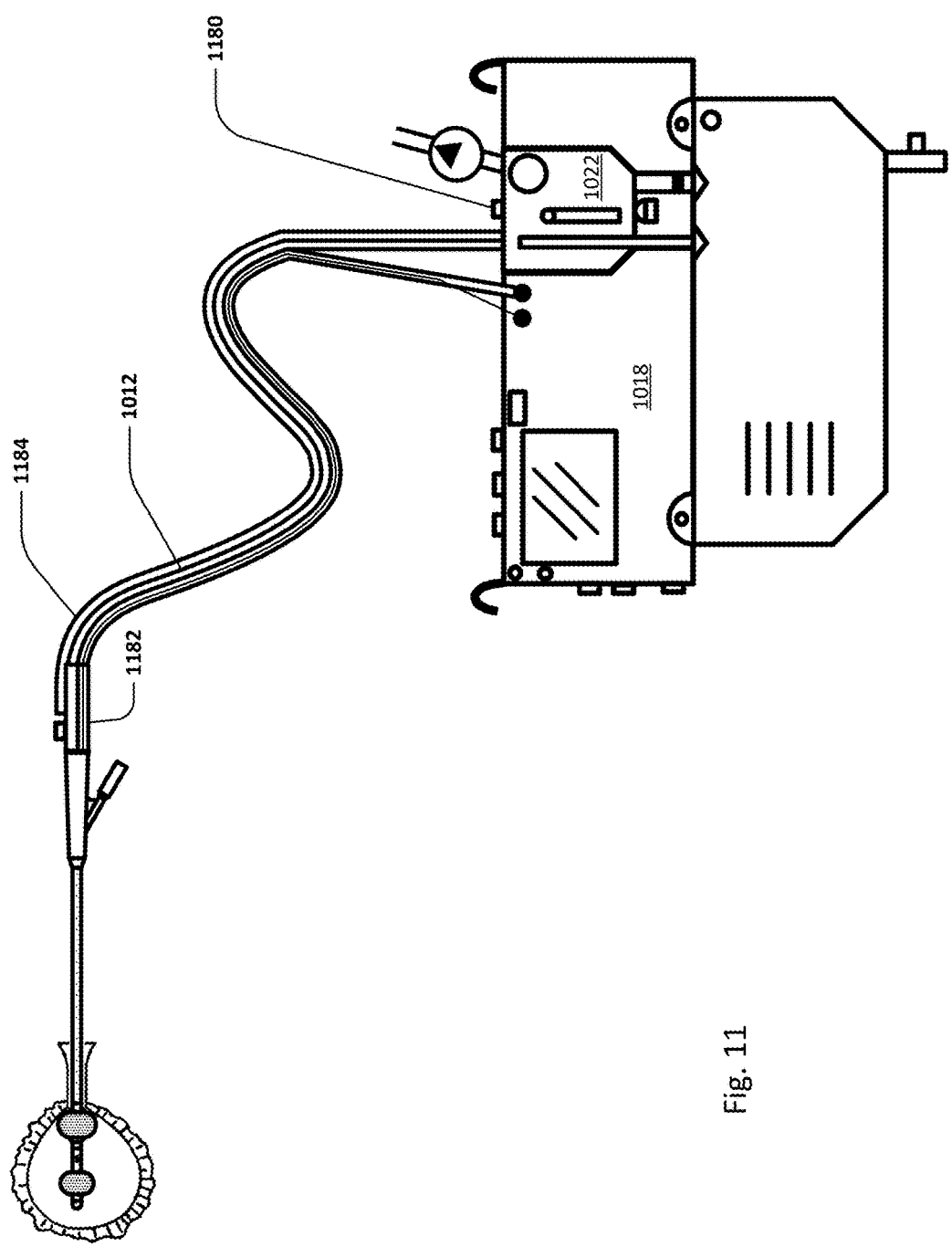
FIG. 11 shows another embodiment of the sensing Foley catheter system.

FIG. 11 shows an embodiment of the sensing Foley catheter system (including airlock clearing mechanism, fluid drainage, collection & analysis system/controller) similar to that shown in FIG. 10A where vent 1180 is located on controller 1018 or reservoir/cassette 1022, instead of on vent barb 1182. In this embodiment, vent 1180 is in fluid communication with urine drainage lumen 1012 via vent lumen 1184 which fluidly connects to urine lumen 1012 at barb 1182. In this embodiment the barb design is simplified and the drainage tubing simply has an additional lumen compared to the embodiment shown in FIG. 10A. The vent may be located anywhere in the system and the fluid interface with the urine lumen may be anywhere in the system as well.

Figure 12:
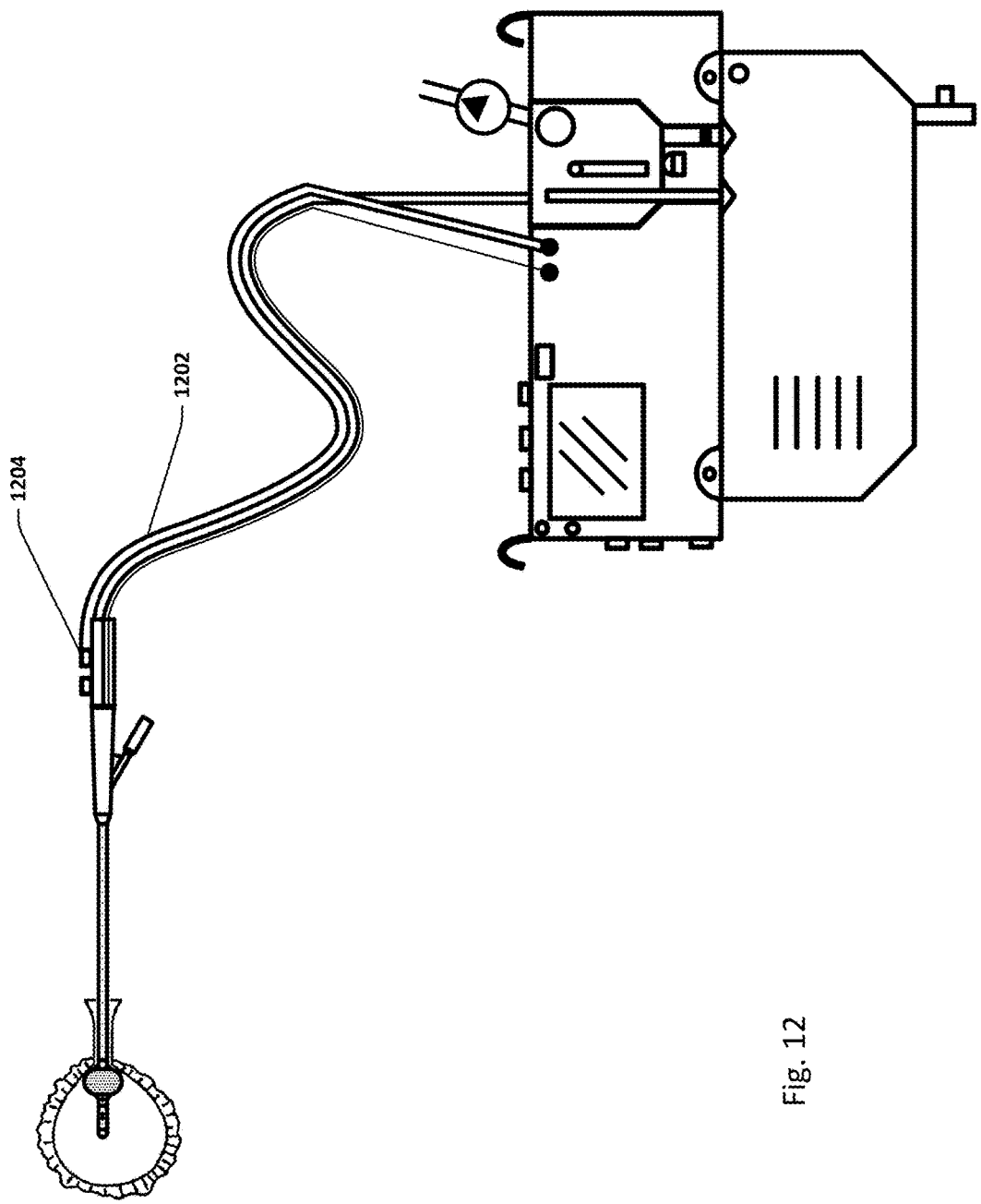
FIG. 12 shows another embodiment of the sensing Foley catheter system.

FIG. 12 shows an embodiment of the sensing Foley catheter system similar to that shown in FIG. 10A where, as opposed to the system shown in FIG. 10A, no pressure balloon is utilized. Instead, pressure is measured inside the bladder via the urine lumen (or other lumen) in the sensing Foley catheter. In this embodiment, the pressure lumen 1202 is connected to the vent 1204, or elsewhere in the system outside the patient, and is, at lease periodically, in fluid communication with the drainage/urine lumen of the catheter. In this embodiment, the sensing Foley catheter system may be used with any standard Foley catheter. Note that any embodiments of the sensing Foley catheter system may be used with a standard Foley catheter. The system shown in FIG. 12 may also be used without pressure lumen 1202, and with a standard Foley catheter, if pressure measurements in the bladder are not desired.

Figure 13:
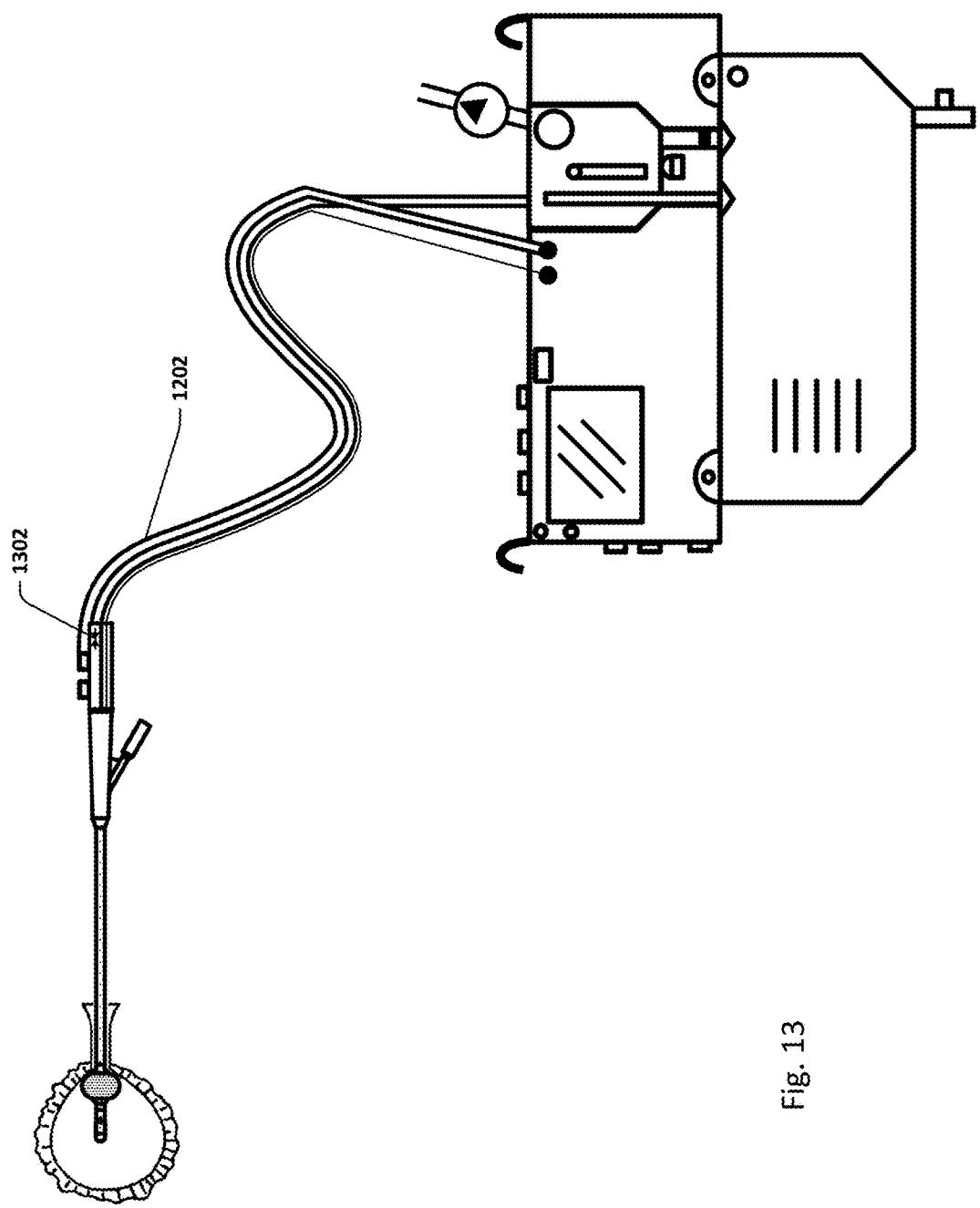
FIG. 13 shows another embodiment of the sensing Foley catheter system.

FIG. 13 shows an embodiment of the sensing Foley catheter system similar to that shown in FIG. 12. In this embodiment, valve 1302 may be utilized to periodically close pressure lumen 1202 to the urine drainage lumen. The valve can be opened, by the controller or manually, when a pressure measurement is taken, and closed, again by the controller or manually, when a bladder pressure reading is not needed.

FIGS. 10A, 10B, 11 and 12 show embodiments of the sensing Foley catheter system which include a vent near the patient end of the drainage tube that allows air to enter the drainage tube if negative pressure is created either due to a siphon in the drainage tube or due to the pumping mechanism or both. Without a vent/filter, such negative pressure can lead to suction trauma, such as trauma caused to the mucosal lining of the bladder. Note that these embodiments are different than devices where the vent(s) allow air to escape, but not enter, the drainage tube.

Urine drainage lumens preferably have an inner diameter less than about 0.25 inches such that liquid in the lumen maintains circumferential contact with the lumen, which forms a seal and allows the liquid to advance when a pumping mechanism is activated. There may be multiple drainage lumens to prevent blockage of flow if the pumping mechanism fails. In these embodiments, the drainage lumens are preferentially generally empty, which may require continuous activation of the pumping mechanism. Alternatively, the pumping mechanism may be activated prior to making a measurement of volume to ensure that all the liquid has been drained, which reduces the power requirements of the device.

Some embodiments of the sensing Foley catheter system include detecting a pressure spike in the drainage line while a pressure within the bodily organ remains constant; and using a pump to create negative pressure through the drainage line until the pressure in the drainage line equals the pressure in the bodily organ.

In one embodiment, the vent has a resistance to airflow that is greater than the resistance to liquid flow from the patient, such that any buildup of liquid in the patient is purged into the drainage line before air enters through the vent. For example, in the case of urine drainage, a full bladder will be emptied into the drainage line before air enters through the vent as long as the resistance of airflow through the vent is greater than the resistance of urine flowing through the patient's catheter. However, the vent preferably has the smallest possible resistance to airflow while meeting this requirement in order to minimize suction trauma.

In another embodiment, the vent has very little resistance to airflow so that the bladder is further protected from suction, and the controller pump is activated to clear airlocks at more frequent intervals, for example every 1 minute, every 5 minutes, or every 10 minutes, to keep the drainage line clear of urine. When the pump is activated, it may continue to run until it detects that no more urine is draining, indicating that the bladder has completely emptied. Alternatively, the pump may run for a set period of time, for example about 30 seconds, about 1 minute, about 3 minutes, about 5 minutes or about 10 minutes.

The pumping mechanism used can be any suitable mechanism, including, but not limited to peristaltic pumps, diaphragm pumps, vane pumps, impeller pumps, centrifugal pumps or any other suitable pump. The pump may be powered by a wall outlet, battery, human power, or any other suitable source. In some embodiments, the vacuum is in the range of about 0 to −50 mmHg. The negative pressure may alternatively be supplied by wall vacuum, often present in hospital rooms. Pumping mechanisms may include a peristaltic-like pump or suction applied directly to the collection vessel. The pump may be located on the patient side of the drainage reservoir, or the pump preferably may be located on the non-patient side of the drainage reservoir/cassette, so that the reservoir is between the patient and the pump. In order to function properly, the pump should preferably be capable of generating negative pressures equal to the maximum liquid column height in the drainage tube. This may be half the length of the drainage tube. With urine drainage tubes having a maximum length of 60 in, the maximum negative pressure required would be around 30 inH$_2$O, or 56 mmHg.

Other technologies may be used to urge urine through the tubing and/or system including pulsatile mechanical, vibratory acoustic, thermal, vibratory, pinching, rolling or electromagnetic stimulus to cause at least one of a movement of the drainage line and the bodily fluids within. In some embodiments, the rolling stimulus comprises compressing multiple lumens sequentially such that the lumens are never all compressed at the same time.

Figure 14B:
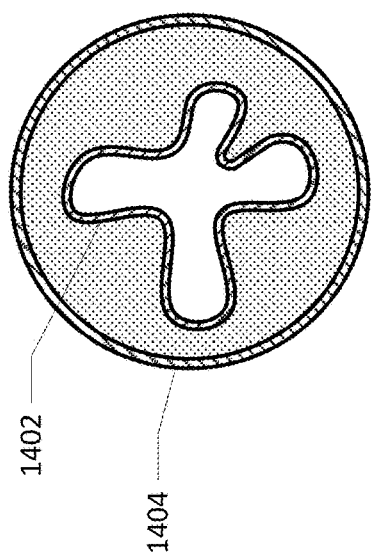
FIGS. 14A and B show an embodiment of a collapsible drainage tube that resides in a kink-resistant tube.
Figure 14A:
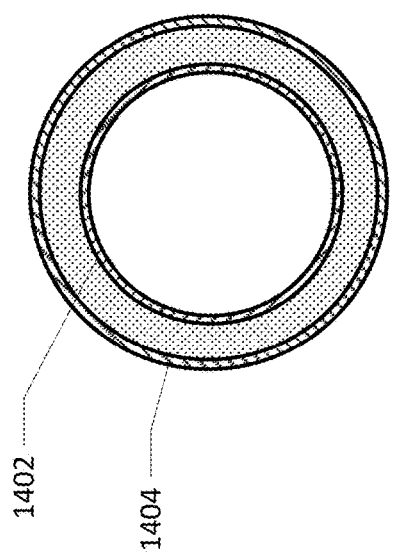

In another embodiment, air locks are removed by means of a collapsible drainage tube that resides in a more stiff kink-resistant tube. FIG. 14A shows such an embodiment in its un-collapsed form. Inner collapsible drainage tube 1402 is inside outer kink-resistant tube 1404. FIG. 14B shows the embodiment with the inner collapsible tube collapsed. Periodically, the drainage tube is collapsed, such as by applying a positive pressure to the space between the collapsible tube and the kink-proof tube or by applying negative pressure to the inside of the collapsible tube. Collapsing of the drainage tube then urges urine away from the patient and toward the collection vessel.

In another embodiment, the drainage lumen clearing mechanism comprises a tube with an inner diameter less than about 0.25 inches, such that no air pockets are able to move up the length of the tube. This is possible due to the surface tension within the smaller tubes, which prevent movement of fluid when one end of the tube is closed to atmosphere (as in the case of the bladder). Thus, the drainage tube always remains full of urine, and for each volume of urine produced the same volume of urine must exit the drainage tube, as urine is incompressible. In another embodiment, the inner diameter is less than 0.125 inches. In another aspect, said drainage tube acts as a siphon and provides a small, safe amount of vacuum to the bladder. Alternatively, with a small lumen drainage tube, air is allowed to periodically enter the tube lumen via the vent/valve. The negative pressure caused by the pump may encourage this. Urine is encouraged to continue flowing into the collection reservoir due to the negative pressure caused by the pump, thus preventing airlocks.

The use of small-diameter tubing also results in a smaller volume of residual urine in the drainage tube compared with the prior art. Having a smaller residual volume is preferential, as it allows urine to move more quickly from the patient's bladder to the collection vessel. The speed of this transport is important in order to take measurements of the urine that has been produced more recently. This is particularly important for patients with low rates of urine production, as it takes their urine even longer to be transported from the bladder to the collection vessel. For example, for a patient producing only 10 mL/hr of urine with a standard drainage tube (around 40 mL residual volume), measurements of their urine in the collection vessel will lag true urine production by 4 hours. By contrast, with smaller tubing (such as tubing having around 5 mL residual volume), measurements will only lag true production by 30 minutes. In some embodiments utilizing a small diameter lumen, with or without a vent/valve, a pump, to supply negative pressure to the drainage line, is not required.

FIG. 15 shows an embodiment of the device that is well-suited for draining chest tubes or other drainage tubes that apply constant negative pressure to the patient. Although these embodiments may also be suitable for draining urine from the bladder or fluid from other cavities. Any of the features disclosed in relation to chest tube drainage may also be applied to bladder drainage or other body cavity drainage. Liquid is drained from the patient through drainage lumens 1585, which connect to collection vessel 1582. Drainage is assisted by pulling negative pressure on the collection vessel 1582, for example by attaching a suction tube 1583 to the hospital wall suction. Suction may also be applied with other methods, such as with a pump as disclosed elsewhere herein. Air enters the drainage lumens 1585 through a valve 1584, which has a crack pressure equal to the desired negative pressure. By choosing the correct crack pressure (for example, −15 to 0 mmHg, or −10 mmHg), the pressure applied to the patient will remain at this pressure as long as the hospital wall suction/pump can generate sufficient suction at the collection vessel 1582. Preferably, the drainage lumen(s) used for draining chest tubes are as large as possible while maintaining a siphon. Suitable inner diameters include, but are not limited to, about ¼", about 5/16", or about ⅜".

Figure 16:
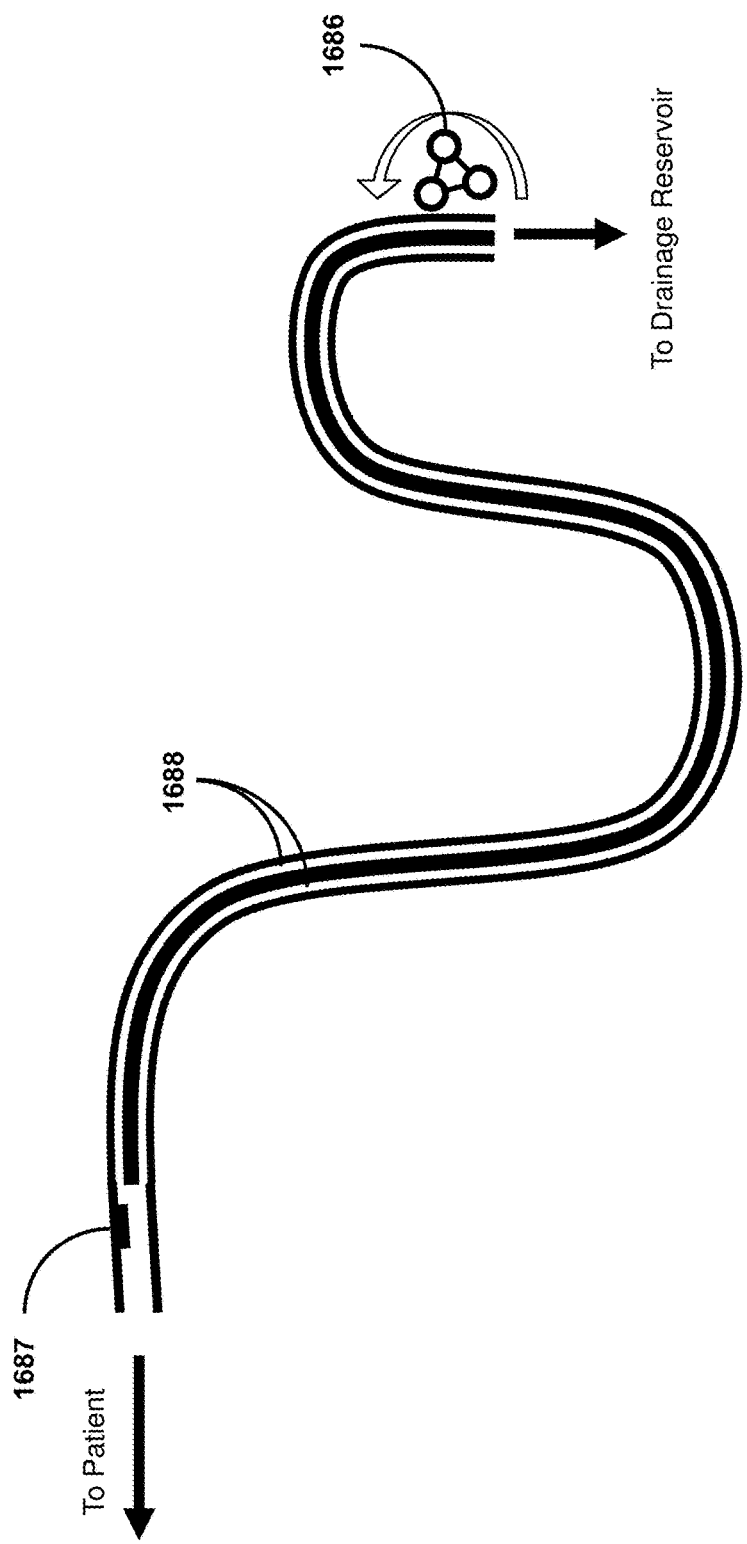
FIG. 16 shows an example of a clearing mechanism of the sensing Foley catheter system.

FIG. 16 shows another embodiment of the device that is well-suited for draining chest tubes or other drainage tubes that apply constant negative pressure to the patient. Liquid is drained from the patient through drainage lumens 1688, and negative pressure is applied using a pumping mechanism 1686. A pressure sensor 1687 resides within drainage tube at the patient end, and thereby measures the pressure applied to the patient. The measurement value obtained by the sensor 1687 is sent back to the controller controlling the pumping mechanism 1686, and the pressure generated by the pumping mechanism 1686 is adjusted in order to keep the pressure at the sensor 1687 (and patient) at the desired level. Pressure sensor 1687 may also be located elsewhere in the system. The sensor may also be used for passive monitoring of pressure at the patient end of the tube to provide clinicians with information about the level of suction being applied. Although FIG. 16 shows the pump on the patient side of the drainage reservoir, the pump may alternatively be on the other side of the drainage reservoir, so that the reservoir is between the patient and the pump.

In another embodiment of the invention used for draining chest tubes, the volume of the fluid drained is measured in order to provide information to clinicians about the drainage status of the chest tube. This measurement can be accomplished by any suitable means, particularly those described within for measuring urine volume.

In addition to eliminating air locks, several of the air lock clearance designs detailed above have been found to effectively clear deposits and blood clots from urine drainage lines. These problems plague current urine drainage tubes, particularly those with smaller lumen drain tubes and monitoring technologies at the drainage bag, and this invention provides an advance in the state of the art by automating the clearing of these drainage blocking debris and clots. This feature is particularly useful when used in conjunction with pressure sensing either in a balloon at the tip of the Foley or in fluid communication with the bladder. This allows for the monitoring of pressure and vacuum in the bladder and allows for more aggressive pumping based on actual bladder pressure until the clot/obstruction is cleared. Without this pressure/vacuum sensing, the pumping of fluid in the drain tube may generate clinical sequelae in the bladder, such as suction trauma, due to the exposure of the bladder mucosa to excessive vacuum.

Figure 17:
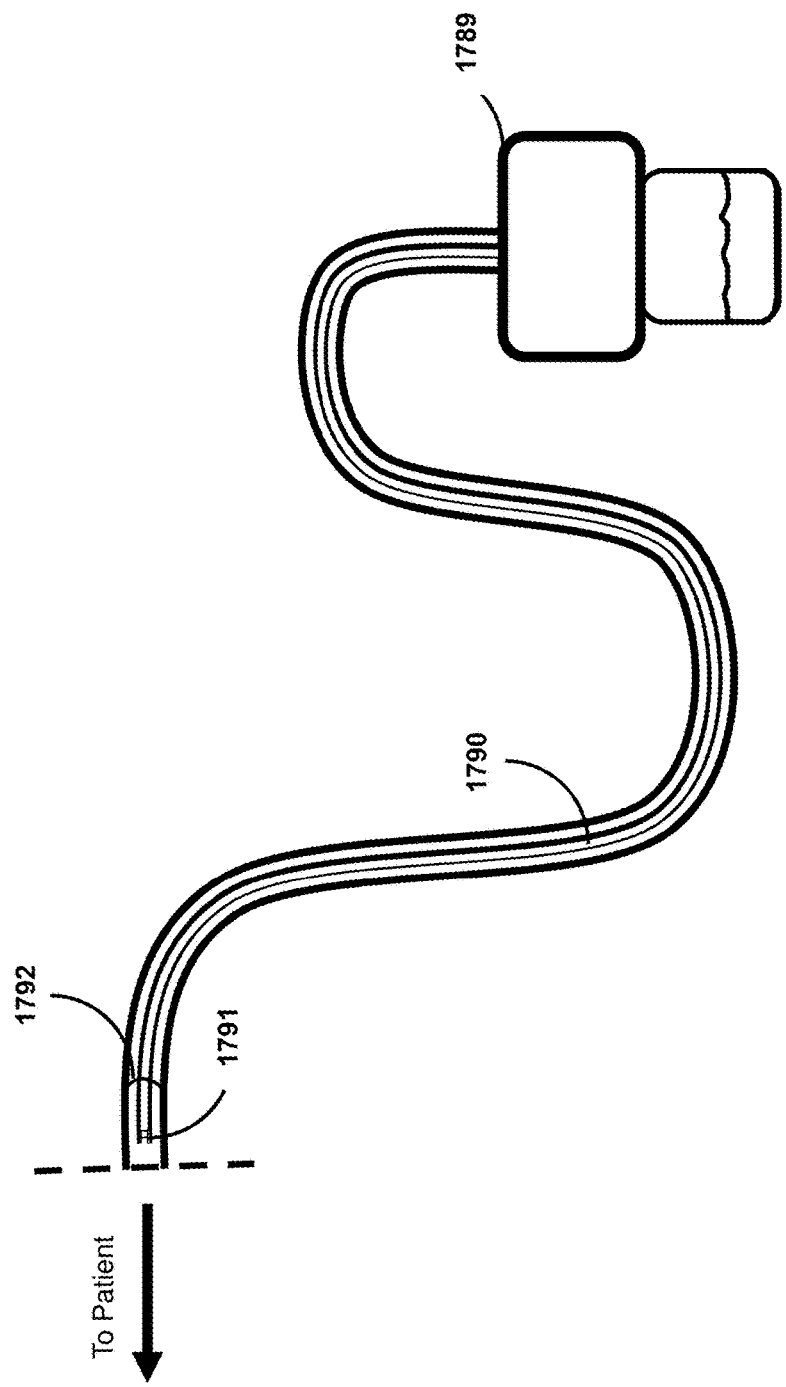
FIG. 17 shows an embodiment of the sensing Foley catheter system with a drainage tube with a gas-sampling lumen.

In another embodiment, shown in FIG. 17, a gas-sampling lumen 1790 runs the length of the drainage tube and terminates with a gas-permeable but liquid-impermeable filter 1791 that remains in contact with urine, the meniscus 1792 of which is further from the patient than the filter. When a measurement of oxygen, carbon dioxide, or any other gas is needed, the air within gas-sampling lumen 1790 is pulled into base 1789 of the drainage device for analysis. This configuration allows for accurate gas analysis even with embodiments of the device that allow air into the drainage line such as those illustrated in FIGS. 10 through 16.

Figure 18:
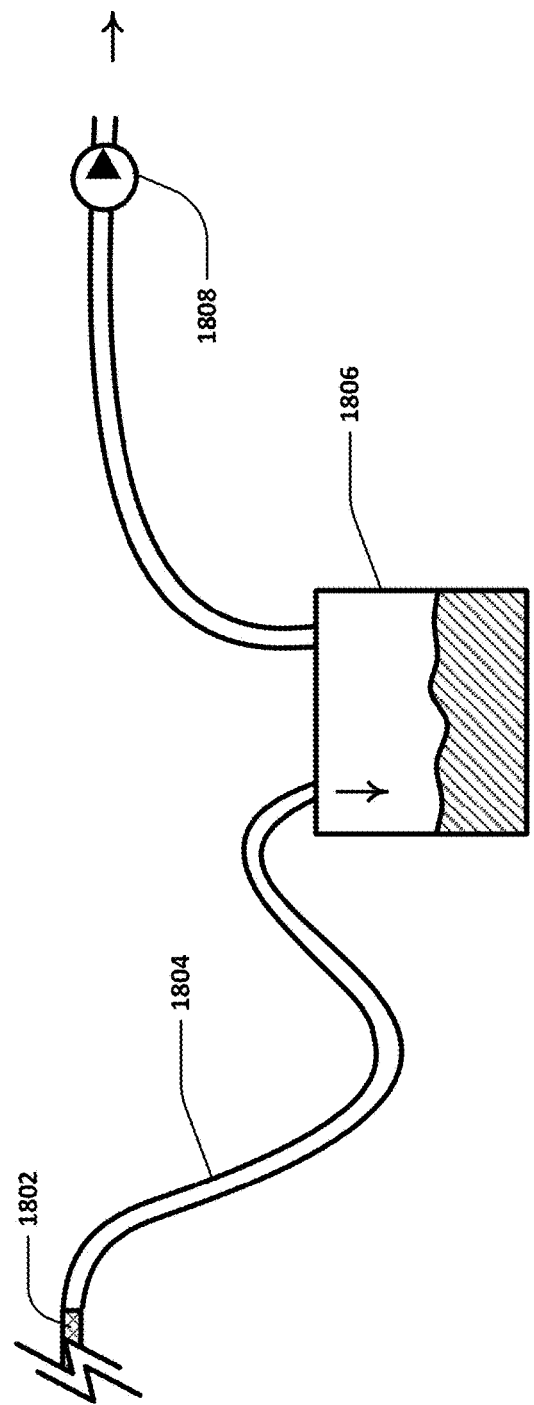
FIG. 18 shows an active vented system with a vent and pump.

As shown in FIG. 18, an active vented system comprises air vent 1802, drainage line 1804, collection vessel 1806, and pump 1808. The vented side of the drainage line is connected to the patient. In one embodiment, the fluid drained is urine, and the connection is made to a urinary catheter. Fluid flows from the patient through the drainage line and collects in the collection vessel. The pump in this embodiment is not acting directly on the drainage line, but is pulling a vacuum on the collection vessel. The pump facilitates drainage by pulling negative pressure on the collection vessel, which urges fluid through the drainage line. Preferably, the collection vessel is rigid in order to maintain a constant volume when the pump applies negative pressure. The vent on the patient side of the drainage tube is preferably a vent that allows the transmission of gas (preferably air), but prevents the transmission of liquid. The vent thereby prevents substantial negative pressure from being applied to the patient by allowing atmospheric air to enter the system. Such a mechanism prevents suction trauma, for example at the bladder wall.

The pump in this system can be any suitable pump for pumping gases, including, but not limited to peristaltic pumps, diaphragm pumps, or centrifugal pumps. In order to function properly, the pump should preferably be capable of generating negative pressures equal to the maximum liquid column height in the drainage tube. This may be half the length of the drainage tube. With urine drainage tubes having a maximum length of 60 in, the maximum negative pressure required would be around 30 inH2O, or 56 mmHg.

Figure 19:
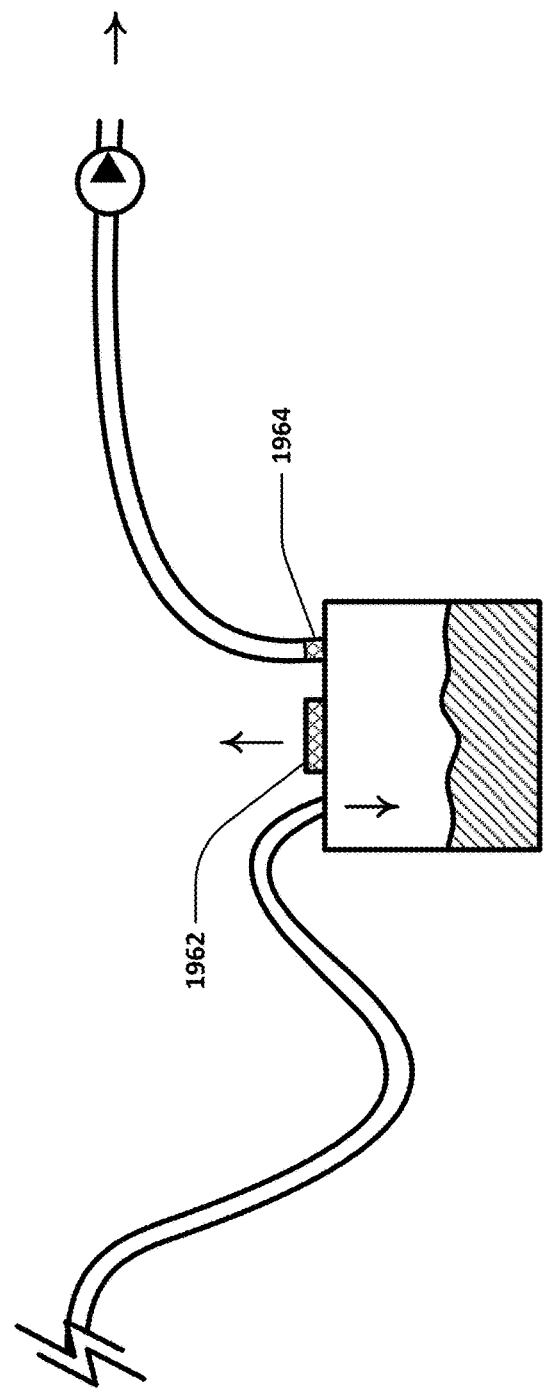
FIG. 19 illustrates an embodiment of the sensing Foley catheter system with additional vents for pressure relief and sterility.

As shown in FIG. 19, an active vented system for draining bodily fluids may have additional vents. One such vent, vent 1962, may be located on the collection vessel and allows air to escape the collection vessel. This prevents the buildup of pressure as new fluid enters the vessel, by allowing each volume of fluid entering the system to be offset by the same volume of air exiting the system. Another such vent, vent 1964, may be located between the collection vessel and the pump. This vent allows the transmission of gas (preferably air), but prevents the transmission of liquid, in order to prevent bacteria or viruses from entering or exiting the collection vessel and drainage tube. Preferably, this vent is sterility-grade, meaning air that passes through is considered to be sterile. A vent (not shown here) may or may not be present at the patient end of the drainage line.

Figure 20:
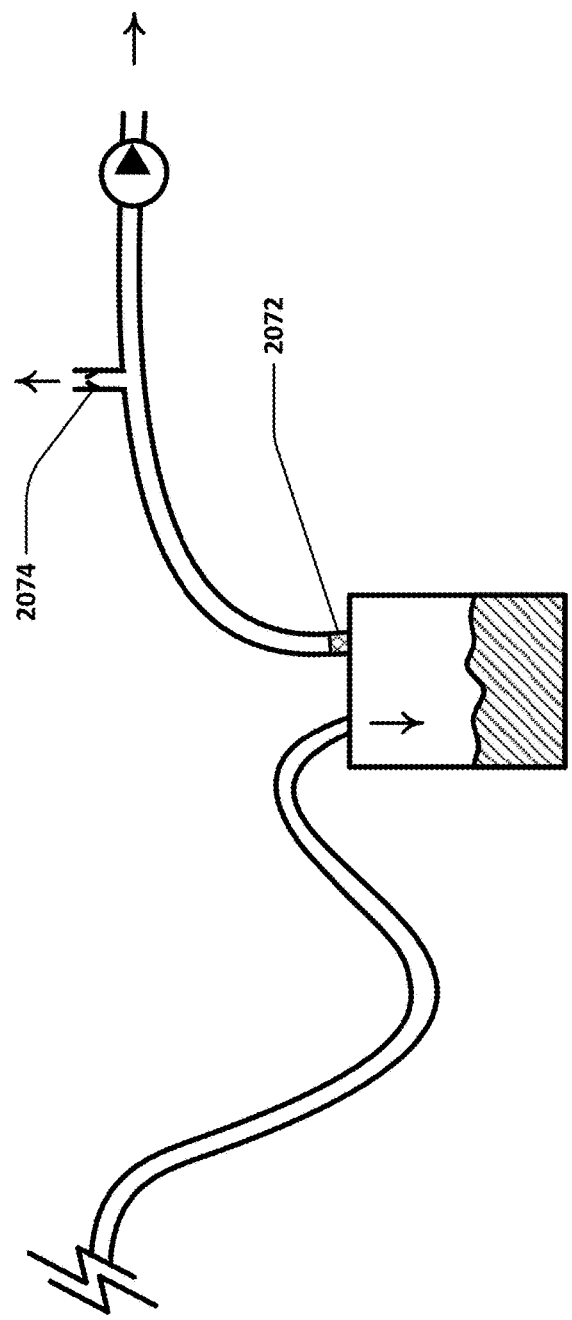
FIG. 20 illustrates an embodiment of the sensing Foley catheter system with a pressure relief vent and relief valve.

As shown in FIG. 20, pressure offsetting may be accomplished with a single vent on the collection vessel. In this case, the vent, vent 2072, may be between the collection vessel and pump as before, but an additional valve 2074 allows air to escape the collection vessel in the presence of positive pressure. This valve is preferably a one-way valve that allows air to exit, but not enter, the system. When the pump activates, the one-way valve closes, and air must be pulled from the collection vessel, thereby generating negative pressure in the collection and facilitating flow of fluid through the drainage line. A vent may or may not be present at the patient end of the drainage line (not shown here).

Detecting Infection

Figure 21:
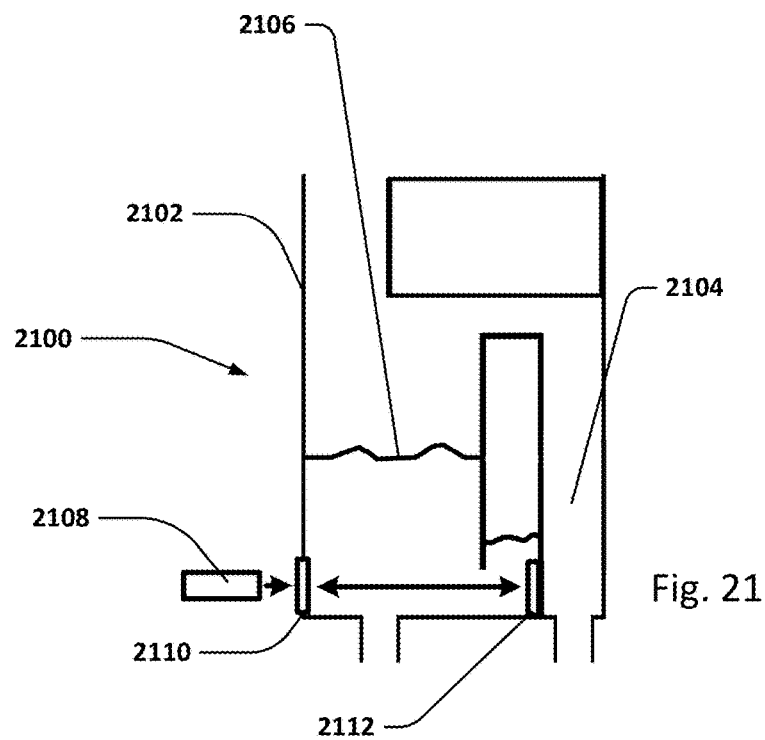
FIG. 21 shows an embodiment of a collection vessel, chamber or cassette which may be included in the sensing Foley catheter system to detect bacteria, blood and/other substances in the urine using UV/light spectroscopy.

FIG. 21 shows an embodiment of a collection vessel, chamber or cassette which may be included in the sensing Foley catheter system to detect bacteria, blood and/other substances in the urine using UV/light/Raman spectroscopy. Cassette 2100 includes container wall 2102, which is preferably rigid. Urine 2106 is collected in the cassette. If urine is collected too quickly, or there is some impediment to the cassette's emptying, overflow area 2104 will allow any excess urine to drain from the cassette. Cassette 2100 may include an optically clear section 2110 which is preferably incorporated into an outside wall of the cassette, and reflector section 2112, which is preferably on, or incorporated into, an inner wall of the cassette. "Optically clear" here means able to transmit light at the needed analysis wavelength(s) through the optically clear section. Preferably the optically clear section made of a material which is able to transmit UV light, such as polymethylmethacrylate, polystyrene, acrylic, quartz, etc. The wall thickness may need to be thin enough to allow the appropriate UV wavelength(s) to be transmitted through the optically clear section. For example, the thickness of the optically clear section may be from around 0.5 mm to around 0.7 mm thick. Alternatively the thickness of the optically clear section may be from around 0.5 mm to around 0.6 mm thick. Alternatively the thickness of the optically clear section may be from around 0.6 mm to around 0.7 mm thick. Alternatively the thickness of the optically clear section may be less than around 0.7 mm thick.

UV/light transmitter/receiver 2108 transmits UV or other wavelength light in the appropriate wavelength through optically clear section 2110, through the urine in the cassette, to reflector 2112 in the cassette. The UV/light transmitter/receiver may be incorporated into, or connected to, the controller component of the sensing Foley catheter system. The light is reflected back to the UV/light receiver which then transmits the collected data to the controller for signal analysis. More than one UV/light wavelength may be analyzed either simultaneously or serially. Light outside of the UV range may be used in addition to light within the UV range. The volume of urine physically between the transmission and receiving of the light is preferably maximized for a stronger signal reflecting the concentration of one or more substances in the urine. The transmitter/receiver may be located as shown in FIG. 21, or in other areas of the cassette. The receiver may be in a different location than the transmitter and the reflector may or may not be necessary nor present. Because the urine in the cassette is frequently emptied, the UV/light absorption measurements can be collected over time and increases and/or decreases in the level of one or more substances in the urine can be tracked over time, in essentially, or nearly, real time. This is particularly important in identifying infection quickly, including urinary tract infection and Catheter-associated Urinary Tract Infection (CAUTI). The UV/light detection may also be performed elsewhere in the sensing Foley catheter system, including in the drainage tubing, a separate sampling area etc.

Figure 22:
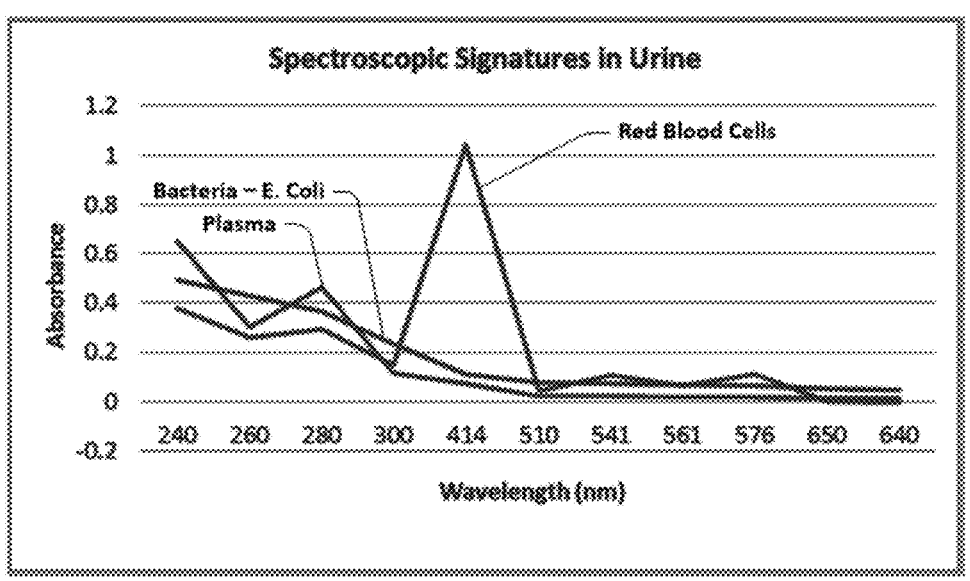
FIG. 22 shows the various absorption wavelengths of *E. coli*, red blood cells, and plasma in urine to light.

Infection may be identified by analyzing the urine for bacteria, red blood cells, and plasma and/or white blood cells using UV/light spectroscopy. FIG. 22 shows the various absorption wavelengths of *E. coli*, red blood cells, and plasma in urine to light. The presence of plasma/white blood cells and/or bacteria in urine are both indicators of infection. The presence of red blood cells may not be indicative of infection. Therefore it is desirable to distinguish between red blood cells and bacteria/plasma/white blood cells in the urine. Since the spectroscopic signature for red blood cells differs significantly from those of either bacteria or plasma/white blood cells, at a wavelength of about 414 nm, the signal for red blood cells can be separated from those of bacteria and/or plasma/white blood cells, and an infection can be identified by analyzing the absorption of light at this wavelength. Because the signature for plasma and bacteria differ from each other at the wavelengths of 260 nm and 280 nm, these wavelengths can be used to distinguish between plasma and bacteria. However, it is likely that both plasma and bacteria may be present during an infection.

Other wavelengths and other technologies may also be used to detect various substances in urine or any collected/drained bodily fluid. UV/light absorption may also be used to detect turbidity. A dye or drug or reactive substance may also be introduced into the system, or be coated on the inside of the system, cassette, etc, to react with a substance in the urine to aid in analysis. Any type of sensor may be used to sense any substance or quality of the collected urine in either an intermittent or continuous basis, real-time basis. For example, sensor(s) to detect Magnesium in the urine may be used to diagnose preeclampsia or eclampsia. Lactate sensors may be used to test for lactate (or lactate dehydrogenase) in the urine. The identification of lactate in urine may be an early indicator of sepsis. Lactate sensors may include enzymatic lactate sensors. For example, lactate sensors as disclosed in Weber (Weber J., Kumar A., Kumar A., Bhansali S. Novel lactate and pH biosensor for skin and sweat analysis based on single walled carbon nanotubes. Sens. Actuators, B. Chem. 2006; 117:308-313), and/or Mo (Mo, J W, Smart, W. Lactate biosensors for continuous monitoring. Front Biosci. 2004 Sep. 1; 9:3384-91), both of which are incorporated herein by reference in their entirety, may be used.

Drug or drug residue may be detected in the collected urine using appropriate sensors. Other substances or characteristics of the collected urine which may be sensed include color, clarity, odor, specific gravity, osmolality, pH protein, glucose, creatinine, nitrites, leukocyte esterase (WBC esterase), ketones, red or white blood cells, casts, crystals, bacteria, yeast cells, parasites, Squamous cells, etc.

CAUTI or infection may be identified and/or reduced by several methods including: analyzing the urine using spectroscopy, light wavelength analysis etc. to identify contaminates early, reducing trauma caused to the bladder by suction, reducing urinary retention in the bladder, reducing bacterial or microbial presence by the use of an antimicrobial coating or embedded material such as silver or other material, increasing the accuracy of pressure measurements within the bladder by reducing suction within the bladder, increasing accuracy of urine output measurement by reducing airlocks in the system and suction within the bladder. Pressure spikes caused by suction in the bladder may be defined as pressure readings below about −20 mmHg. Alternatively, pressure spikes caused by suction in the bladder may be defined as pressure readings below about −10 mmHg to about −20 mmHg. Alternatively, pressure spikes caused by suction in the bladder may be defined as pressure readings below about −10 mmHg.

Figure 23:
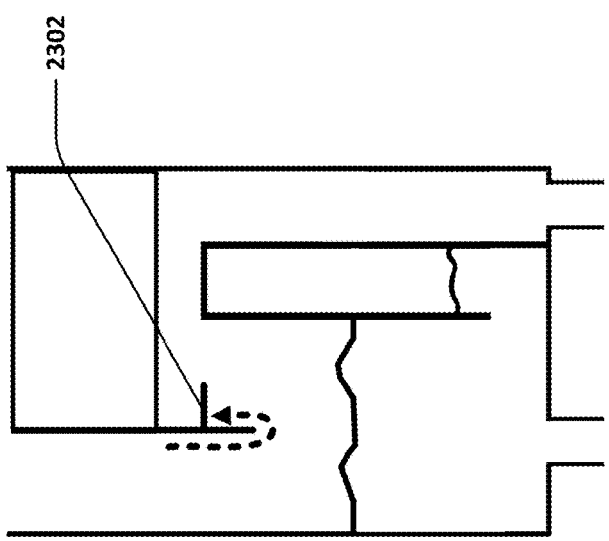
FIG. 23 shows an embodiment of the cassette which includes baffle or flap.

FIG. 23 shows an embodiment of the cassette which includes baffle or flap 2302. This baffle/flap is meant to prevent urine from wicking along the inside walls of the cassette as shown by the dotted arrow. The baffle will prevent the urine from wicking beyond the point of the baffle so the urine will fall back into the measurement reservoir below.

Priming

An aspect of the disclosed technology that is particularly advantageous in achieving a high resolution signal from which pressure profiles from particular physiologic sources (such as peritoneal pressure, respiratory rate, and cardiac rate, relative pulmonary tidal volume, cardiac output, relative cardiac output, and absolute cardiac stroke volume) may be monitored relates to adjusting and maintaining a balance of pressure on either side of the pressure interface represented by the membrane of the pressure sensing balloon. This balance of pressure may be referred to as a pressure differential. In some embodiments the preferred pressure differential is at or around zero. In some embodiments the preferred pressure differential may be a different value. Pressure impinging on the external face of balloon (facing the internal aspect of the bladder) is subject to change according to the physiology of the patient. Pressure on the internal face of the balloon (which is in fluid communication with the fluid column) is subject to degradation because of fluid leakage and imperfect seals.

Upon first insertion of the sensing Foley catheter, external pressure is typically applied to the fluid column and against the pressure interface to a first approximation of pressure being exerted on the pressure interface from within the bladder. Pressure signals, as measured across a pressure interface, have a maximal amplitude when the pressure differential is about zero. Accordingly, the amplitude of a pressure signal can be used to tune the pressure being applied from the fluid column against the pressure interface. This process of applying an appropriate amount of pressure against the interface may be referred to as priming the fluid column or priming the balloon. Inasmuch as pressures on either side of the pressure interface may change, as described above, the fluid column may need to be re-primed or re-tuned, from time to time. The necessity of re-priming can be monitored by testing small changes in pressure so as to achieve maximal amplitude of a pressure signal profile.

Alternatively, the priming can automatically occur via the controller on a periodic basis.

Embodiments of the disclosed system and method include automatic pressure tuning by a controller. Accordingly, the tuning system can detect the optimum target pressure and volume to inflate the balloon by monitoring sensed pressure signals and adding or removing air or fluid volume as needed. For example, upon insertion of the catheter, a pressure tuning circuit that regulates the balloon volume and pressure may inflate the balloon until it detects a physiologic-sourced pressure rate. Upon sensing that rate, the pressure tuning controller may add or subtract minute amounts of air in a routinized or programmed sequence of steps until the amplitude of the sensed wave is greatest. The control feedback loop between the optimally tuned pressure (manifesting as balloon pressure and volume) and the sensed physiologic pressure profile iterates continuously and or as needed to ensure high fidelity measurement of the physiologic data. In some embodiments, automatic pressure tuning may be performed in the apparent background while the physiologic data is being transmitted and displayed; in other embodiments the system may suspend transmission of physiologic data during a pressure tuning sequence.

Embodiments of the disclosed technology include a gas delivery system that can deliver gas in a priming operation, whereby pressure can be applied to a fluid column proximal to the proximal-facing aspect of the pressure interface. A source of gas, such as compressed air or liquid is held in a storage tank. Using $CO_2$ as an example, $CO_2$ is controllably released from the storage tank through a pressure regulator that can step pressure in the tank (for example, pressure of about 850 psi) down to the range of about 1 psi to about 2 psi. Released gas passes through a filter and a pressure relief valve set at about 2.5 psi. The pressure relief valve is a safety feature that prevents flow through of gas at a level greater than 2.5 psi in the event of failure of the upstream regulator. $CO_2$ exiting the pressure relief valve next passes through a first solenoid-controlled fill valve to enter the catheter line, ultimately filling the balloon that comprises the pressure-sensing interface. Pressure within the balloon is allowed to rise to a level as high as 30 mm Hg, whereupon the first solenoid-controlled valve closes. A second solenoid-controlled valve, distal to the first valve operates as a drain valve, which can release pressure from the catheter to a target pressure. Alternatively, the drain valve may be activated until a respiratory waveform is detected after which the balloon will be optimally primed and the valve will be closed. The drain valve may be subject to proportional control, operably based on voltage or pulse-width modulation (PWM), which allows a drain rate sufficiently slow that the target pressure is reached and the valve can be closed prior to overshoot. Alternatively, a peristaltic or other air pump may be utilized to fill the balloon with room air.

Figure 24:
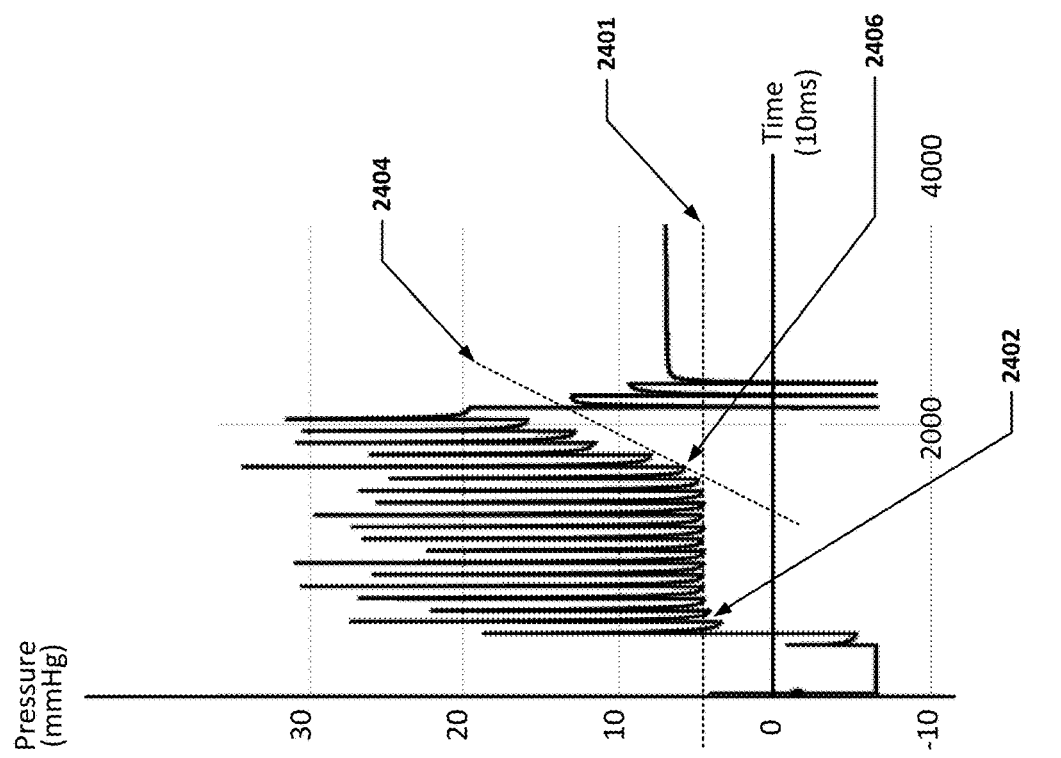
FIGS. 24 and 25 show graphs representing pressure balloon priming methods in some embodiments.

FIG. 24 shows a graph representing a pressure balloon priming method in some embodiments. Here, small volume bursts (roughly about 0.3 cc) of fluid volume are added to the pressure sensing balloon and the pressure within the balloon is measured. Small volume bursts of fluid are introduced until the measured pressure within the balloon settles to a stable pressure 2401. This transition is shown at inflection point 2402. Volume bursts are introduced past this point until the measured pressure starts to rapidly increase (for example if slope 2404 of the curve is greater than about 2 mmHg/10 ms). This inflection point is shown at 2406. At this point the pressure within the balloon is reduced to a pressure around or slightly above stable pressure 2401. This pressure represents the prime pressure measuring pressure in some embodiments. This process is also represented in the flowchart in FIG. 27.

Alternatively, priming of the pressure balloon may involve pressurizing the pressure balloon well above zero mm Hg, then removing small volumes of air/gas/fluid and monitoring the pressure balloon pressure. The pressure balloon pressure will stabilize, or plateau, as it approaches optimal primed pressure. To determine this optimal pressure, pressure measurements are taken as small volumes of air are removed from the pressure balloon, when subsequent pressure measurements are essentially the same (within about 2 mm Hg of each other), the balloon is at optimal primed pressure. If 2 subsequent measurements are not essentially equivalent, the pressure balloon is re-pressurized well above zero mm Hg and the process is repeated. The pressure measurements taken as small volumes of air are removed from the pressure balloon may be taken over about 5 to about 15 seconds to compensate for the effect of respiration on the pressure measurements. In some embodiments, the pressure signal may require a short stabilization period after the small volume of air/gas/fluid is removed from the pressure balloon before the pressure measurement is taken.

The small volume bursts of fluid may be from around 0.2 cc to around 0.4 cc. The small volume bursts of fluid may be from around 0.1 cc to around 0.5 cc. The small volume bursts of fluid may be up to around 0.5 cc. The small volume bursts of fluid may be up to around 1.0 cc.

Figure 25:
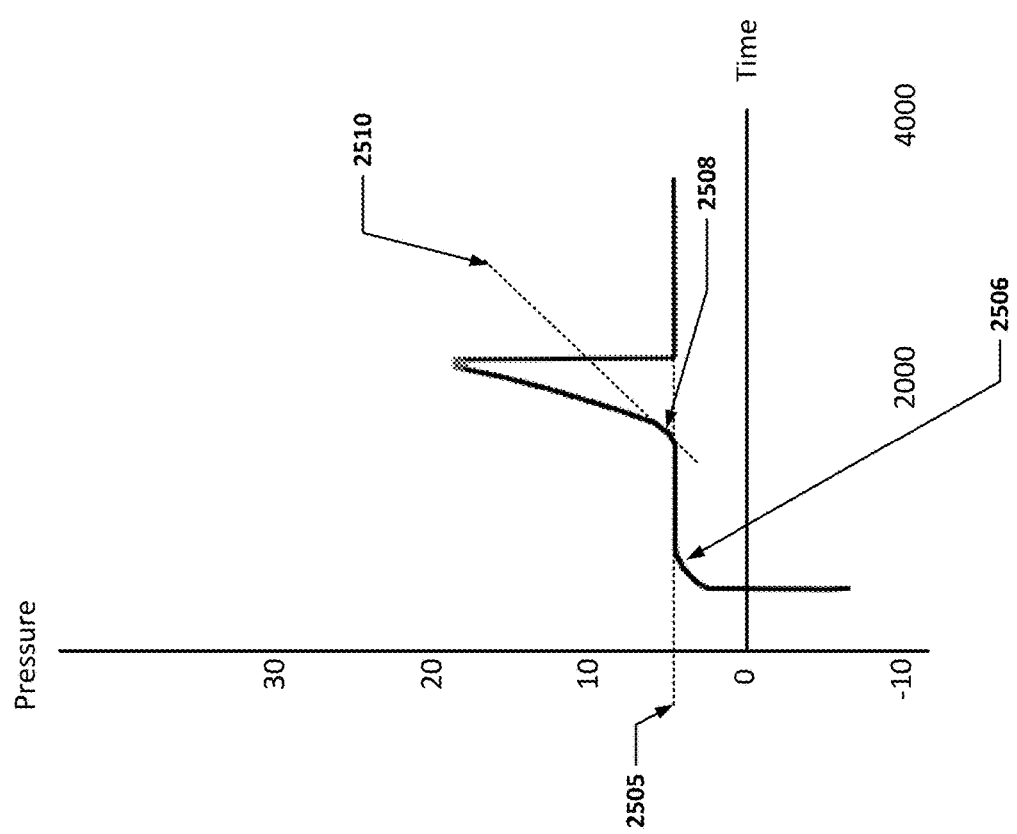

FIG. 25 shows a graph representing a pressure balloon priming method in some embodiments. This method is similar to that shown in FIG. 24, except that the pressure is increased within the pressure sensing balloon more smoothly, without the bursts shown in FIG. 24. Fluid volume is added to the pressure sensing balloon and the pressure within the balloon is measured. Balloon pressure is increased until the measured pressure within the balloon settles to stable pressure 2505. This transition is shown at inflection point 2506. Balloon pressure is increased past this point until the measured pressure starts to rapidly increase (for example if slope 2510 of the curve is greater than about 2 mmHg/10 ms). This inflection point is shown at 2508. At this point the pressure within the balloon is reduced to a pressure around or slightly above stable pressure 2505. This pressure represents the optimal, or prime, pressure in some embodiments. This process is also represented in the flowchart in FIG. 28.

Figure 26:
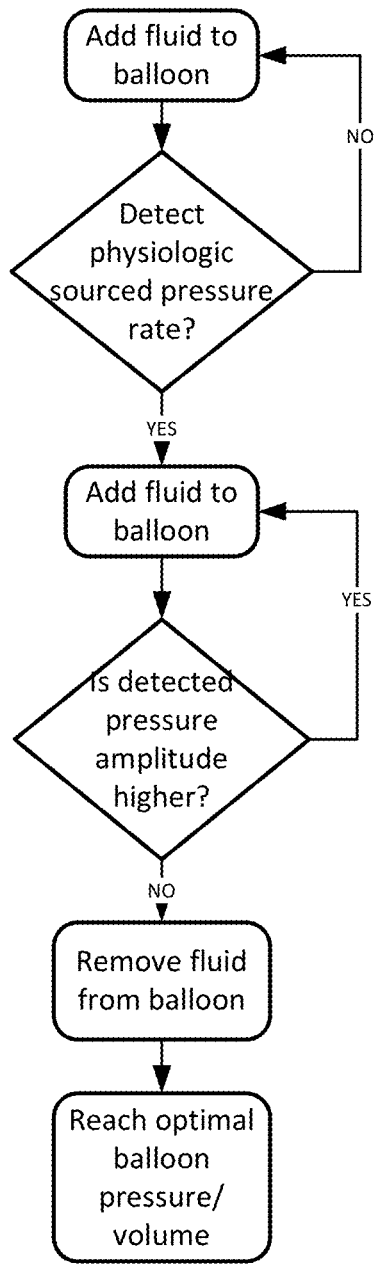

FIG. 26 shows a flowchart of the balloon priming process of certain embodiments of the invention. Embodiments of the disclosed system and method include automatic pressure tuning by a controller. Accordingly, the tuning system can detect the optimum target pressure and volume to inflate the balloon by monitoring sensed pressure signals and adding or removing air volume as needed. For example, upon insertion of the catheter, a pressure tuning circuit that regulates the balloon volume and pressure will inflate the balloon until it detects a physiologic-sourced pressure rate. Upon sensing that rate, the pressure tuning controller will add or subtract minute amounts of air or fluid (roughly about 0.3 cc) in a routinized sequence until the amplitude of the sensed wave is greatest. The control feedback loop between the optimally tuned pressure (manifesting as balloon pressure and volume) and the sensed physiologic pressure profile iterates continuously and or as needed to ensure high fidelity measurement of the physiologic data. In some embodiments, automatic pressure tuning may be performed in the apparent background while the physiologic data is being transmitted and displayed: in other embodiments the system may suspend transmission of physiologic data during a pressure tuning sequence.

The minute amounts of air or fluid may be from around 0.2 cc to around 0.4 cc. The minute amounts of air or fluid may be from around 0.1 cc to around 0.5 cc. The minute amounts of air or fluid may be up to around 0.5 cc. The minute amounts of air or fluid may be up to around 1.0 cc.

Loop Controller

Certain patient parameters measured by the sensing Foley catheter system, and by other means, are impacted by, and/or impact, a patient's treatment through medical treatment devices.

The loop controller can be integrated with the controller of the sensing Foley catheter system (either in the same device or in separate devices) to interpret the patient parameters to control medical treatment of the patient.

For example, IAP may be used to control IV infusion rate. If IAP becomes too high, infusion rate may be reduced or stopped until the IAP returns to an acceptable range. IAP in combination with relative stroke volume and/or stroke volume variability (variability in the size of the cardiac pulses seen in the bladder, etc. during the respiratory cycle) may allow for superior control of IV fluid or blood product infusion using IAP as indicator of excess fluid and relative stroke volume increase and reduction in stroke volume variability as indicators that additional fluid is required. Urine output may be further added to the control loop providing an indicator that fluid status has been restored with return of urine output. Heart rate in combination with respiratory rate may be used to control drug infusion (drug type, infusion rate, frequency, dosage etc.). In this way, drugs may be used to bring the patient to a more stable condition which is determined by the heart and respiratory rate. IAP and respiratory rate may also be used to control a mechanical ventilator or respirator. As IAP rises, the positive end-expiratory pressure (PEEP) delivered by the mechanical ventilator should also rise to overcome this pressure. An indicator that the ventilation is not adequate can be seen in the tissue oxygenation and/or the natural respiratory rate which may be seen as a signal underlying the mechanical ventilation. This signal may either be extracted during mechanical ventilation or, preferably, the loop controller may pause the mechanical ventilator to allow more precise and accurate detection of the underlying respiratory rate/respiratory drive. This IAP, tissue oxygenation and/or respiratory rate may be used to alert the provider to a worsening of the patient's condition and/or may be used to provide automated adjustment of ventilator settings including respiratory rate, PEEP, % O2 inspired and other settings. In the ideal scenario these parameters may be used by the loop controller to monitor and control therapies in a manner that is informed by machine learning and algorithmic tuning. These are just a few examples, but many combinations exist. One or more parameters can be used to control one or more treatment devices.

Figure 29:
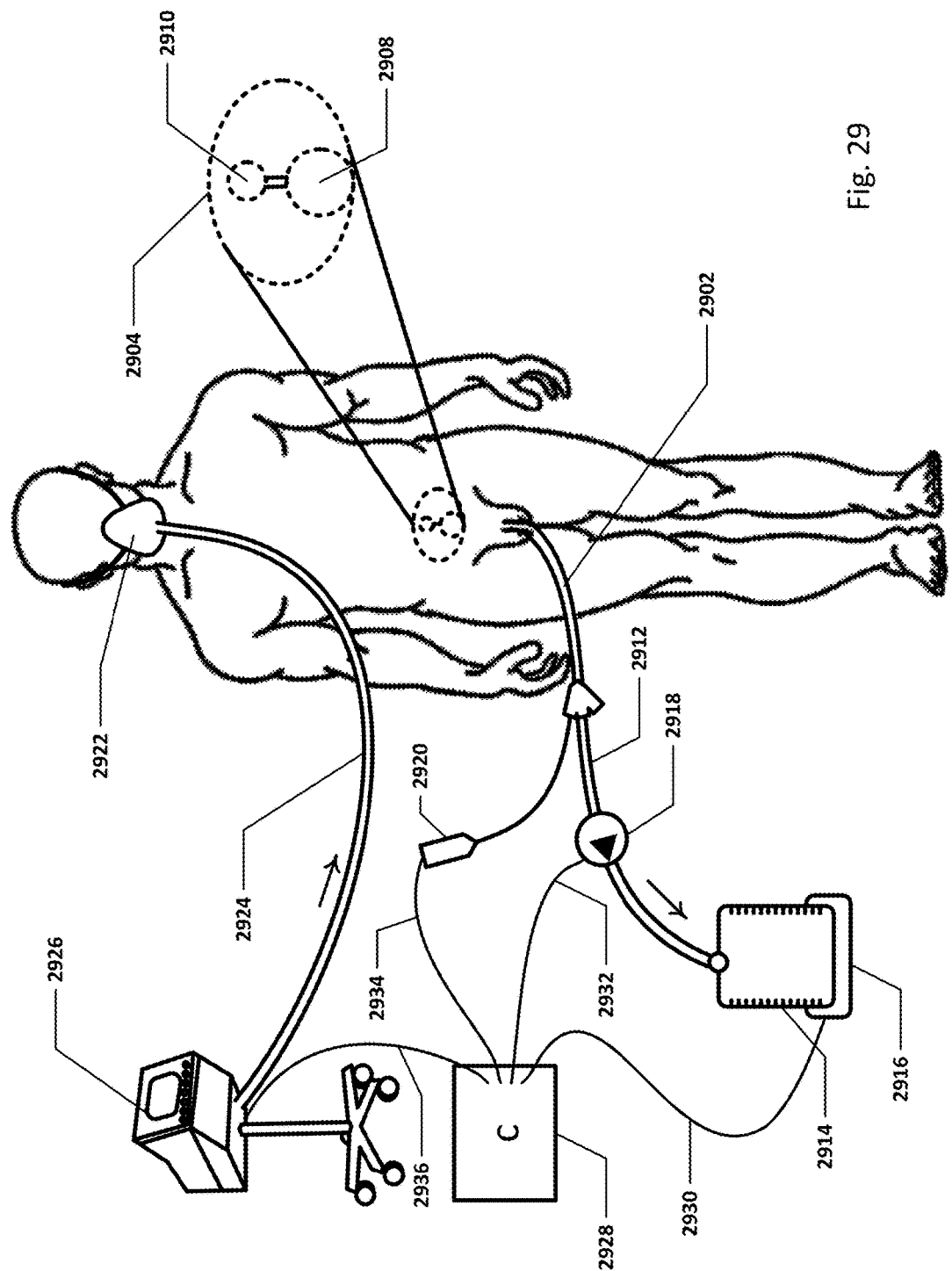
FIG. 29 shows an embodiment of the sensing Foley catheter system with a loop controller in a patient environment.

FIG. 29 shows an embodiment of a loop controller in a patient environment. In this example, the loop controller is receiving patient parameter input from sensing Foley catheter 2902. The sensing Foley catheter resides in patient bladder 2904 and includes retention balloon 2908 and pressure sensing balloon 2910. The sensing Foley catheter may include other sensors as disclosed herein.

Sensing Foley catheter 2902 includes a retention balloon inflation lumen, a pressure balloon sensing lumen, and a urine lumen. Pressure sensing balloon 2910 is connected to the pressure sensing lumen which is connected to pressure transducer 2920 which may be incorporated into controller 2928. The urine lumen is connected to urine output tube 2912. The urine output tube empties into urine reservoir 2914 which may be connected to urine volume measurement device 2916 or may be incorporated into the controller as disclosed herein. In addition, urine output may be controlled by urine pump 2918, which may be located on the urine drainage tubing, or may be incorporated into the controller, or may be located on the non-patient side of the controller as disclosed elsewhere herein.

This patient is shown with respirator mask 2922, which is fed by respirator tube 2924. The flow and makeup of the respiration gas is controlled by respirator 2926.

Loop controller 2928 is connected to urine volume measurement device 2916, urine pump 2918, pressure transducer 2920, and respirator 2926 via connectors 2930, 2932, 2934, and 2936 respectively. The connectors may be wired or wireless. Alternatively, in this and other embodiments, some or all of urine volume measurement device 2916, urine pump 2918, and/or pressure transducer 2920 may be incorporated into controller 2928.

In this example, loop controller 2928 receives patient parameter inputs from urine volume measurement device 2916 and pressure transducer 2920 and using the information provided by these parameters, can control urine pump 2918 and respirator 2926. Some parameters which the loop controller may receive from the sensing Foley catheter include IAP, respiratory rate, heart rate, stroke volume, tissue oxygenation, tissue perfusion pressure, temperature, urine analytes, urine output rate, and other parameters, including those disclosed herein.

For example, if the loop controller receives parameter information indicating that the patient's IAP is elevated, the loop controller may control the respirator perfusion rate, pressure or other parameters. The loop controller may incorporate data from one or more input parameters and control one or more treating medical devices. For example, based on elevated IAP and abnormal tissue oxygenation parameters received, the loop controller may control the output of respirator 2926 and also the urine output rate by controlling urine pump 2918.

The loop controller continues to monitor the patient parameter(s) and adjust the treating medical device(s) accordingly. As the patient parameters normalize, the control of the treating medical devices is adjusted accordingly so that the feedback loop controlled by the loop controller may be a closed loop. The loop may also be adjusted manually when necessary in which case the loop may be an open loop or semi-closed loop.

Figure 30:
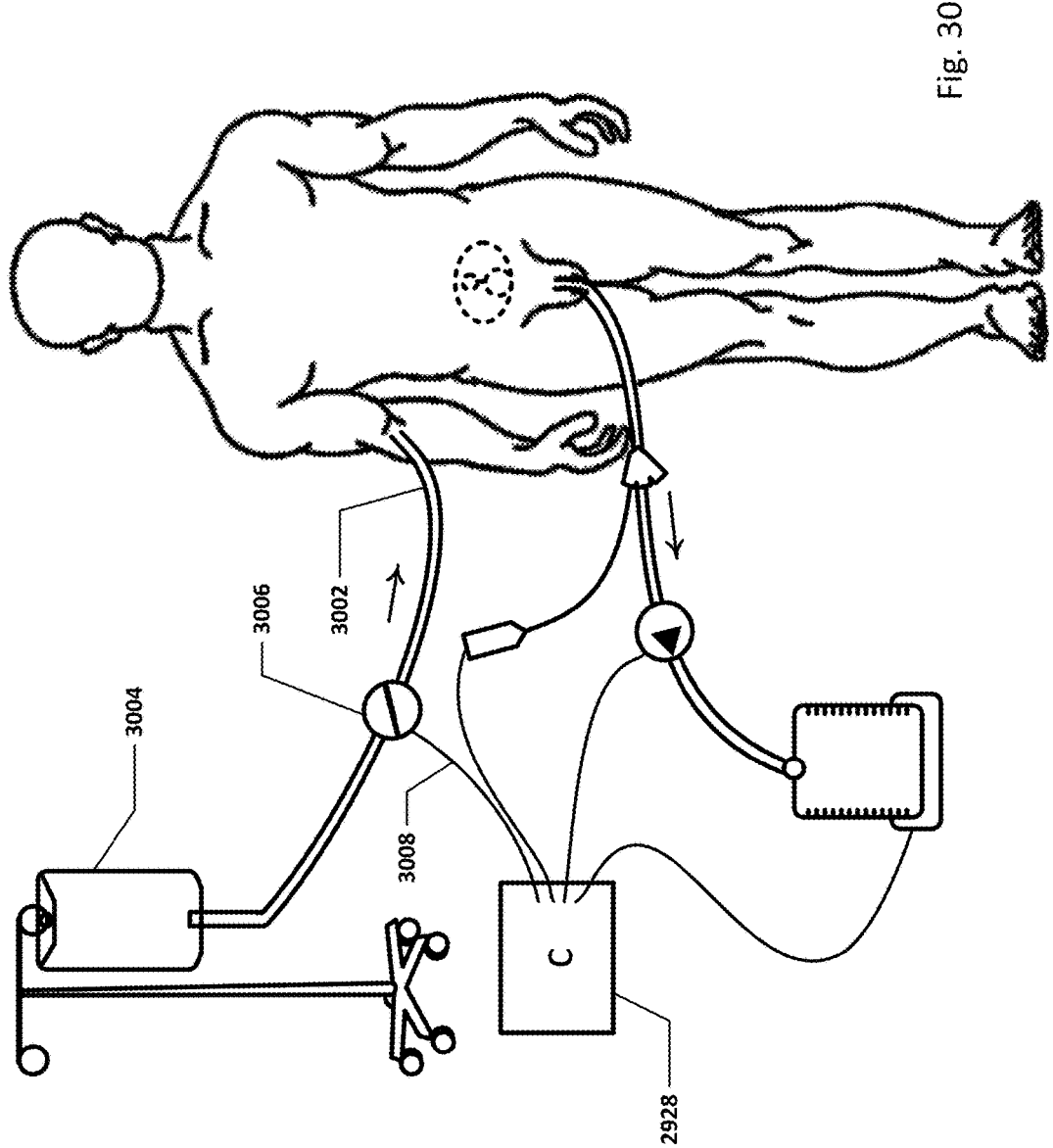
FIG. 30 shows an embodiment of the sensing Foley catheter system with a loop controller in a patient environment.

FIG. 30 shows another example of the loop controller in a patient environment. In this example, the patient has intravenous (IV) line 3002 in a blood vessel in an arm. IV fluid bag 3004 is elevated to allow the IV fluid to drip and/or flow into the patient via IV line 3002. Valve 3006 controls the flow rate of the IV fluid into the patient by allowing the fluid to flow freely, restricting the flow, or stopping the flow. Here valve 3006 is controlled by loop controller 2928 via connection 3008. IV fluid bag 3004 may contain hydrating fluid and/or medications. One or more than one IV bag may be involved and one or more than one valve may control the IV bag(s). The loop controller may control the flow and content of IV fluid(s) to the patient based on patient parameters received by the loop controller.

Figure 31:
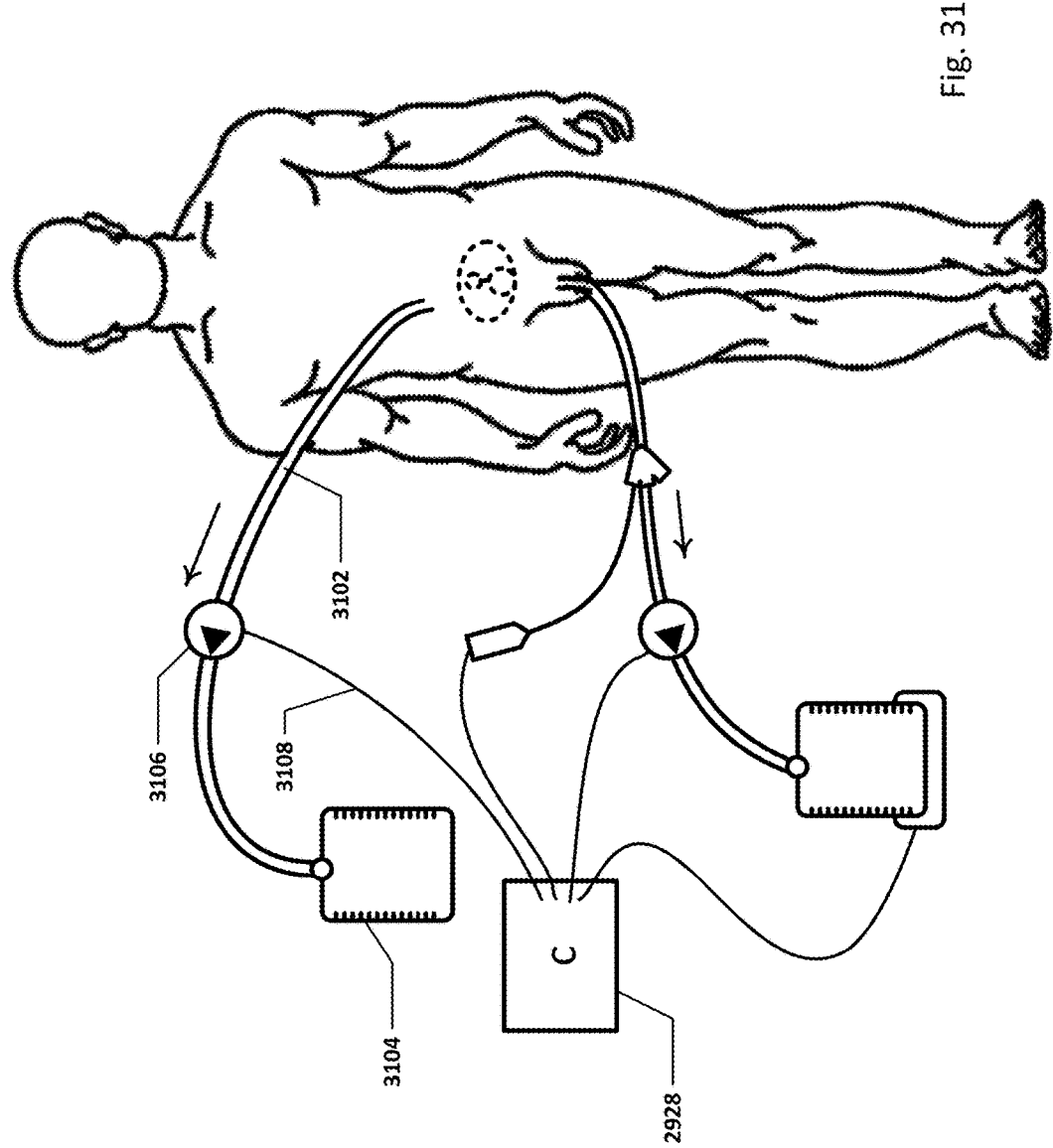
FIG. 31 shows an embodiment of the sensing Foley catheter system with a loop controller in a patient environment.

FIG. 31 shows another example of the loop controller in a patient environment. In this example, the patient has fluid drainage line 3102 inserted into the abdomen. Fluid from the abdomen may flow from the patient to receptacle 3104. The flow of fluid may be controlled by pump 3106 which is controlled by loop controller 2928 via connection 3108. The loop controller may control the flow of fluid from the patient to receptacle 3104 via pump 3106 based on patient parameters received. For example, if IAP is abnormally high, loop controller may increase the rate of, or initiate, fluid removal from the patient by controlling pump 3106.

Figure 32:
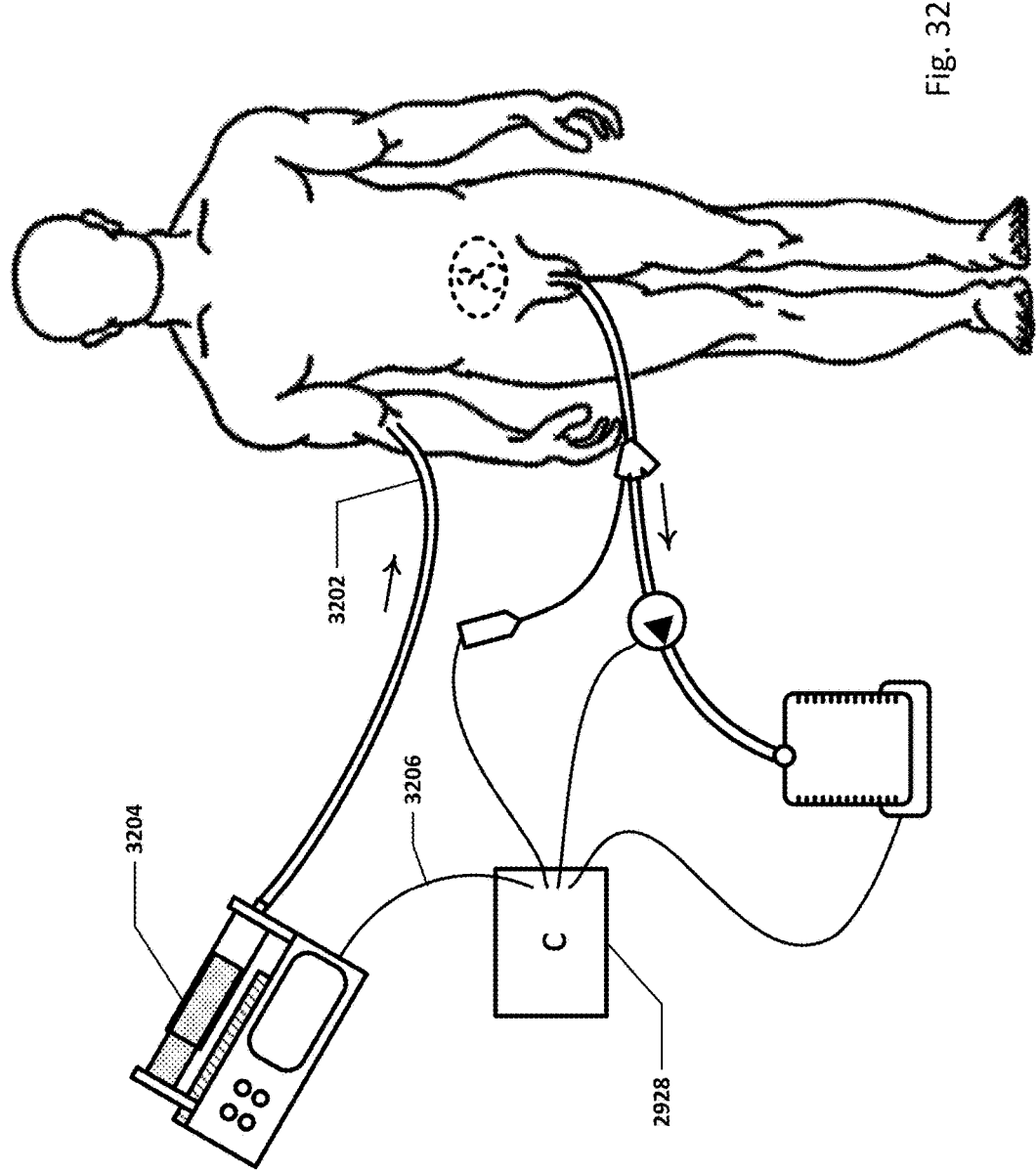
FIG. 32 shows an embodiment of the sensing Foley catheter system with a loop controller in a patient environment.

FIG. 32 shows another example of the loop controller in a patient environment. In this example, the patient has intravenous (IV) line 3202 in a blood vessel in an arm. Drug infusion device 3204 controls the flow rate of a drug into the patient via IV line 3202. More than one drug infusion device may be used. Here drug infusion device 3204 is controlled by loop controller 2928 via connection 3206. Drug infusion device 3204 may contain any appropriate fluid and/or medications. The loop controller may control the flow and content of a drug or drugs to the patient based on patient parameters received by the loop controller.

These examples show some of the medical treatment devices which can be controlled by the loop controller, but any medical treatment device can be used.

Figure 33:
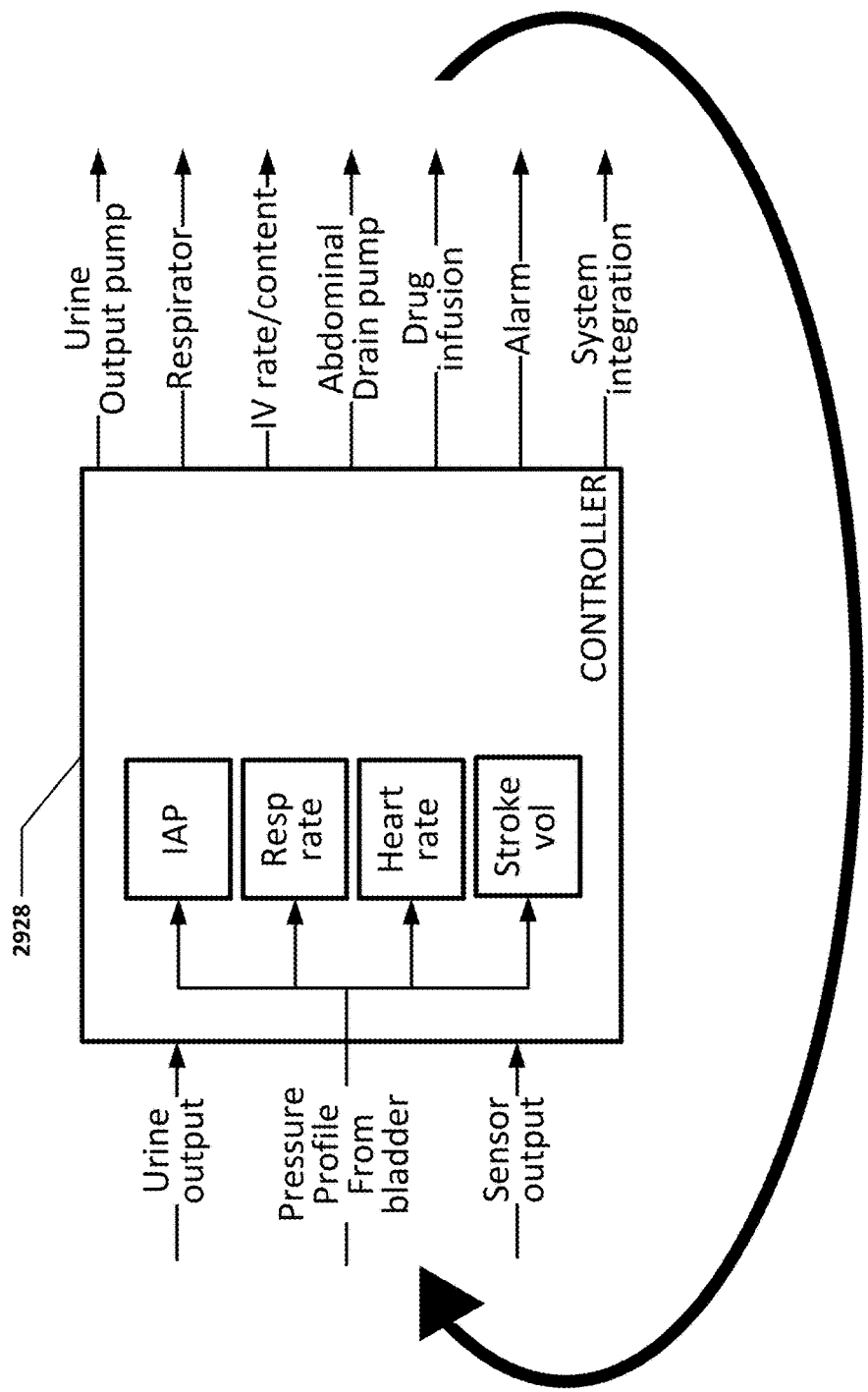
FIG. 33 shows details of a loop controller with possible input parameters and output actions.

FIG. 33 is a detailed diagram of the loop controller. Loop controller 2928 can receive one or more patient parameter inputs from a sensing Foley catheter or other device. These inputs include, but are not limited to, urine output volume and rate, pressure profile from the bladder, and sensor info from a sensing Foley catheter or other device. Pressure profile info from the bladder can be further analyzed to determine IAP, respiratory rate, heart rate, stroke volume, sepsis index, AKI index and other patient parameters. This analysis may be performed in loop controller 2928 or in a separate controller which is connected to loop controller either by a wired or wireless connection. The connection may be via an internet, intranet, WAN, LAN or other network, or it may be local via Bluetooth, Wi-Fi, etc.

The loop controller receives the input or inputs and analyzes the data to determine whether a medical treatment device controls needs to be changed. One or more medical treatment devices may be controlled to bring patient parameters into target ranges. Once patient target ranges are achieved, the loop controller may place the controlled medical treatment device(s) back into a standard state. A standard state will be different for each medical treatment device and likely also different for each patient. Patient parameter target ranges will likewise also be different for each patient, and also for patient status. For example, the respirator rate target range may be different depending on whether the patient is sedated.

Embodiments of the technology may also automatically adjust intravenous fluid or drug infusion rates based on feedback from the cardiac output or respiratory rate sensed. In one such embodiment, a patient-controlled analgesia pump may be deactivated if a respiratory rate drops too low. Respiratory depression can be fatal in this group and this safeguard would prevent overdose. An automated feedback system may also be advantageous in a large volume resuscitation procedure, wherein fluid infusion can be tailored based on intraabdominal pressure to prevent abdominal compartment syndrome by sounding an alert and slowing infusion rates as the intraabdominal pressure rises. Yet another automated feedback feature may provide direct feedback to a ventilator system to provide the optimal pressure of ventilated gas. In the setting of increased abdominal pressure, typical ventilator settings do not provide sufficient respiration for the patient. An automated adjustment of the ventilator settings based on intraabdominal pressure feedback from this embodiment may advantageously provide for optimal patient ventilation. Embodiments of the technology may also be applied as a correction in the application or understanding of other diagnostic measurements. For example, central venous pressure may be dramatically distorted in the setting of elevated intraabdominal pressure. Providing direct access to these data by the central venous pressure reporting system allows for the automatic correction and accurate reporting of this critical physiologic parameter. Embodiments of the technology may also be used in a variety of other ways to automate therapy including infusion of fluids that may further include active agents, such as pressors or diuretics in response to increased or decreased cardiac output or other parameters.

In addition to directly controlling medical treatment device(s), loop controller 2928 may also sound alarms, including audible alarms, emailed alarms, texted alarms, pager alarms, etc. Loop controller 2928 may also provide output to other systems for system integration, such as outputting information to an Electronic Health Record or other data archiving system, or other systems. Loop controller 2928 may also receive inputs from various EHR, EMR, or other systems.

Medical treatment may be administered to the patient as a result of data collected by and/or analyzed by, the sensing Foley catheter system. This treatment may be a medication administered automatically, via a loop controller, or it may be administered manually, via traditional drug methods, i.e. orally, injection etc.

Further medical diagnoses may also be performed based on the results of the sensing Foley catheter system.

Specific Gravity

Figure 34:
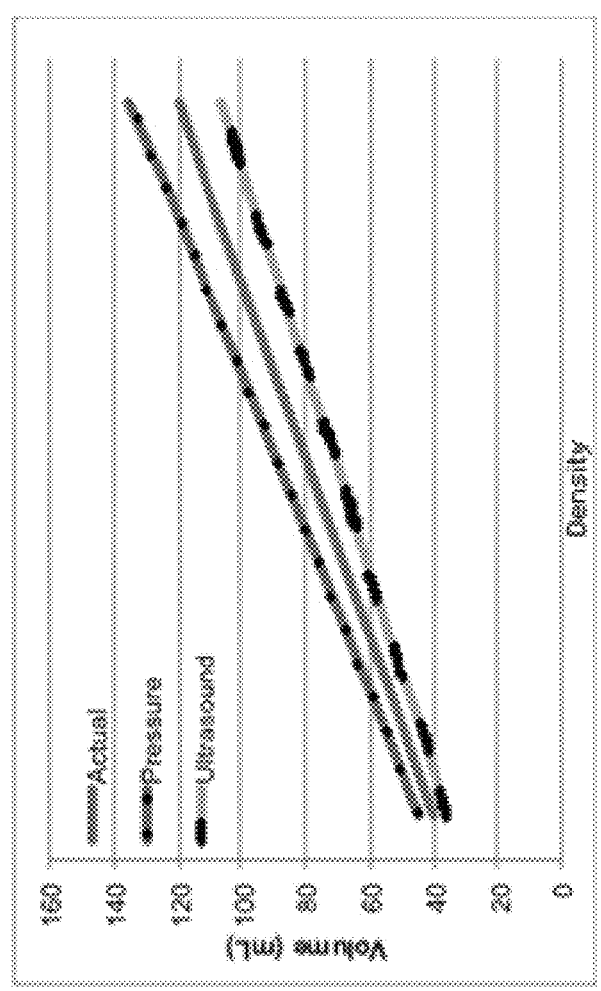
FIG. 34 is a plot of ultrasonic and pressure measurements of volume divergence.

Urine specific gravity may be measured using pressure and ultrasound measurements using a Sensing Foley Catheter. FIG. 34 shows a plot illustrating how ultrasonic and pressure measurements of volume diverge with liquid density. The liquid being measured is synthetic urine concentrate, with a specific gravity of around 1.100.

For a liquid with specific gravity of 1.000, the two measurement techniques are calibrated to provide the same volume measurements. However, as density increases, they begin to diverge. With pressure, an increase in density results in an increased volume reading, since $V=A*h$ and $P=\rho*g*h$, or $V=A*\rho*g/P$. With ultrasound, an increase in density results in a decreased volume reading, since $V=A*h$, $v=h*2/t$, and $v=(E/\rho)^{(1/2)}$, so $V=A*(E/\rho)^{(1/2)}*t/2$.

V: volume
A: cross-sectional area
h: height of liquid
P: pressure
$\rho$: liquid density
g: gravity
v: speed of sound
t: time for sound to reflect
E: bulk modulus elasticity of liquid In simpler terms, as the liquid increases in density, the pressure increases and skews that measurement high. At the same time, the sound travels faster and skews the ultrasound measurement low. By measuring how much they have diverged, the density of the liquid can be determined. This assumes the temperature is not changing, however, temperature can also be monitored to correct for temperature variability. Volume measurements via ultrasound and pressure can be performed with a Sensing Foley Catheter, as can temperature measurements. In this way, a Sensing Foley Catheter in combination with a controller can determine urine specific gravity.

Reducing Condensation

Balloon catheters, especially balloon catheters that are designed to reside in a human or animal body for relatively long periods of time, may leak over time. For example, a balloon inflated with air or another gas, may leak air out of the balloon over time. Alternatively, a balloon filled with a liquid may leak liquid out over time. The opposite is also true. A balloon filled with gas or air which resides in fluid, such as urine, blood etc., may experience leakage of the fluid into the balloon over time. This is particularly true if the balloon is inflated at a relatively low pressure.

A sensing Foley catheter is an example of a balloon which is designed to be inflated for relatively long periods of time and at relatively low pressures. In this example, where a balloon is designed to measure pressure, the balloon may be inflated at a relatively low pressure and as a result, may be manufactured out of a relatively soft and thin material. Because of the low inflation pressure and soft thin balloon material, it is possible that liquid may leak into the balloon over time. Liquid in a pressure measuring balloon can adversely affect very sensitive pressure measurements, particularly if the liquid migrates into the catheter lumen through which the pressure measurements are taken.

One embodiment to solve this problem is to place a very small pore filter, or hydrophobic filter, between the pressure measuring balloon, and the pressure measuring lumen of a catheter. This allows the balloon to be inflated, and continually primed to maintain its pressure, as well as pressure measurements to be taken via the catheter lumen. Air or gas can pass through the filter, but fluid cannot.

Another embodiment comprises making a balloon out of a low moisture permeability material.

Another embodiment comprises refreshing the gas within the balloon by alternatively applying vacuum and pressure to the balloon, either through one lumen, or more than one lumen.

Another embodiment comprises circulating the gas within the balloon by having more than one lumen access the balloon. One lumen may be used to introduce gas into the balloon and another lumen may be used to pull gas from the balloon.

Another embodiment includes using a desiccant within the balloon, the balloon lumen, the gas supply to the balloon, or any combination of these.

FIG. 35 shows the distal end of a Foley type balloon catheter which may benefit from condensation reduction. In this example, the balloon catheter is designed to be placed in the bladder of a patient to aid in draining urine from the bladder. The catheter has a retention balloon 3506 which anchors the catheter within the bladder. Catheter shaft 3502 contains the lumens of the catheter. Opening 3504 allows urine from within the bladder to drain through the catheter and exit the proximal end of the catheter (not shown). Opening 3508 is for inflating and deflating the retention balloon. Pressure sensing balloon 3510 is inflated and deflated via opening 3512. Pressure sensing balloon 3510 transmits pressure signals from within the bladder through a pressure lumen within the catheter shaft and to a pressure transducer proximal to the proximal end of the catheter.

Under certain circumstances, over time, fluid may leak into pressure balloon 3510. In addition, fluid may migrate from within pressure balloon 3510, through opening 3512 and into catheter shaft 3502. Fluid inside the pressure lumen may adversely impact pressure readings from the pressure balloon. As a result, it is desirable to prevent fluid from migrating from within the pressure balloon through opening 3512, or, if possible, to reduce the amount of fluid from entering into the pressure balloon.

FIG. 36 shows an embodiment of a filter within a balloon. Filter 3602 resides between the interior of balloon 3510 and the pressure lumen inside of the catheter at opening 3512. Filter 3602 is preferably made of a material which allows gas to pass through it, but not fluid. For example, a filter may be made from a hydrophobic membrane such as Versapor, PTFE, ePTFE. The filter may be made out of a polymer, such as Nylon, or any other suitable material. The pore size may be around 3 microns, or may be around 5 microns or may range from around 0.2 microns to around 5 microns, or may range from around 5 microns to around 10 microns. The thickness of the filter may range from around 6 mils to around 12 mils. Alternatively the thickness of the filter may range from around 1 mil to around 6 mils. The pore size is related to the balloon sensitivity. For example, a 5 micron pore size filter may be appropriate for a balloon inflated to around 5 mm Hg to around 20 mm Hg, with the ability to sense pressure differences down to the 0.01 mm Hg resolution range. A smaller pore filter may be used if pressures measured via a pressure balloon may be less sensitive. A larger pore filter may be used if pressures measured via a pressure balloon need to be more sensitive.

FIG. 36 shows a filter in the form of a tubing which encircles the catheter shaft at opening 3512, completely covering the opening. The filter may be adhered at its ends to the catheter shaft using any suitable adhesive or other means, such as heat shrinking. The seal between the filter and the catheter is ideally gas impermeable so that gas entering and exiting balloon 3510 via opening 3512 must pass through filter 3602.

Figure 37:
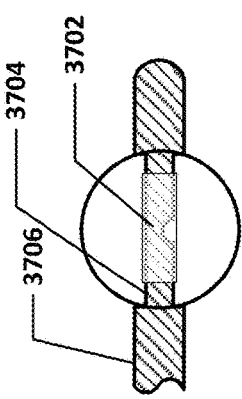
FIG. 37 shows an embodiment of a filter within a balloon with the balloon inflated.

FIG. 37 is another embodiment of the present invention which comprises a smaller catheter shaft where the filter is attached within the balloon. Catheter shaft 3704 within the balloon is a smaller diameter than catheter shaft 3706 which is not under the balloon. This prevents the added bulk of filter 3702 from increasing the diameter of the deflated balloon.

Figure 38:
FIG. 38 shows an embodiment of a filter within a balloon with the balloon deflated.

FIG. 38 shows the embodiment shown in FIG. 37 with the balloon deflated and it can be seen that the reduced diameter of the catheter shaft under the balloon area prevents a significant bulge in the balloon catheter.

Figure 39:
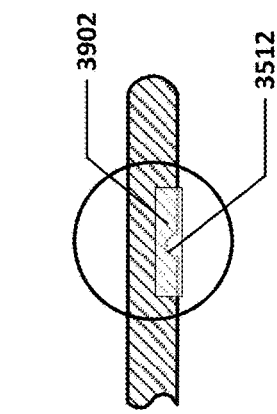
FIG. 39 shows an embodiment of a filter within a balloon.

FIG. 39 shows another embodiment of a filter under a balloon. Filter 3902 in this embodiment does not go all the way around the shaft of the catheter, but is instead a flat or curved piece of filter which is adhered to the catheter shaft via adhesive or other suitable means. The adhesive preferably seals the filter all the way around its edges without infringing on the balloon inflation/deflation/pressure measuring opening 3512.

Figure 40:
FIG. 40 shows an embodiment of a filter within a balloon.

FIG. 40 shows another embodiment of a filter 4002 where the filter is shorter in length.

Figure 41:
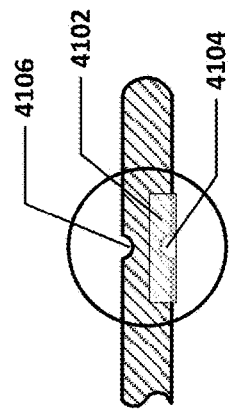
FIG. 41 shows an embodiment of a filter within a balloon.

FIG. 41 shows another embodiment of a balloon catheter with filter. In this embodiment, the balloon catheter has 2 lumens in fluid communication with the balloon. Filter 4102 is covering opening 4104 while opening 4106 is uncovered. In this embodiment, openings 4104 and 4106 may each access separate lumens of the catheter, or the same lumen. In the embodiment where they access separate lumens, balloon inflation, deflation, and pressure measurements may be performed via either lumen. For example, pressure measurements may be taken via the lumen in fluid communication with opening 4106 until liquid buildup in the lumen adversely affects the pressure measurements. At this point, the pressure transducer may be switched to the lumen in fluid communication with opening 4104 so that pressure measurements may be taken through a lumen clear of liquid.

Alternatively, pressure measurements may be taken via the lumen in fluid communication with opening 4106 until liquid buildup in the lumen adversely affects the pressure measurements. At this point, gas may be introduced into the lumen in fluid communication with opening 4106 to clear the lumen of fluid. Simultaneously, the gas may be pulled from the balloon via the lumen in communication with opening 4104. In this way, liquid can be cleared from the lumen in communication with opening 4106 and pressure measurements may be resumed through that lumen. This line clearing procedure can be programmed to take place on a periodic basis.

Figure 42:
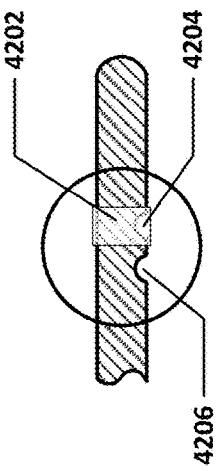
FIG. 42 shows an embodiment of a filter within a balloon.

FIG. 41 shows the two balloon openings 4102 and 4106 on different sides of the catheter with filter 4104 only covering one of the openings. Alternatively, FIG. 42 shows an embodiment similar to that of FIG. 41, except that the 2 openings, 4204 and 4206, may be side by side, where filter 4202 only covers one of the openings.

FIG. 43 shows an embodiment of the present invention where filter 4302 covers larger opening 4304. A larger opening may be desirable to obtain more accurate pressure measurements from the balloon. In addition, a larger opening may be possible with the addition of filter 4304 because of the extra integrity that the filter, and possibly its adhesive means, provides to the area of the catheter around opening 4304.

FIG. 44 shows an embodiment of the present invention where filter 4402 is attached to the catheter shaft via heat shrink tubing segments 4404. This allows a gas-tight seal between the filter and the catheter while ensuring that the catheter opening 4406 remains clear.

FIG. 45 shows an embodiment similar to that of FIG. 44 where the catheter shaft is reduced under the balloon area. This allows the balloon to deflate without causing a bulge on the catheter where the filter is attached. Filter 4502 is attached to the catheter shaft via heat shrink tubing segments 4504. This allows a gas-tight seal between the filter and the catheter while ensuring that the catheter opening remains clear.

FIG. 46 shows an embodiment of the present invention where filter 4602 is attached to the inside of the catheter at the opening.

Figure 47:
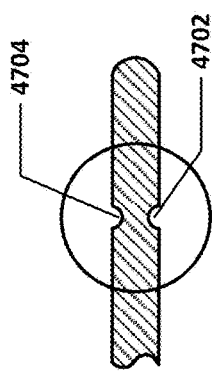
FIG. 47 shows an embodiment of a balloon with multiple access lumens.

FIG. 47 shows an embodiment of the present invention where the balloon has two access lumens, 4702 and 4704. In this embodiment, the balloon catheter has two lumens in fluid communication with the balloon. In this embodiment, openings 4702 and 4704 may each access separate lumens of the catheter, or the same lumen. In the embodiment where they access separate lumens, balloon inflation, deflation, and pressure measurements may be performed via either lumen. For example, pressure measurements may be taken via the lumen in fluid communication with opening 4702 until liquid buildup in the lumen adversely affects the pressure measurements, or up until a set period of time. At this point, gas may be introduced into the lumen in fluid communication with opening 4702 to clear the lumen of fluid. Simultaneously, the gas may be pulled from the balloon via the lumen in communication with opening 4704. The inverse can also be done—fluid may be introduced into the lumen in fluid communication with opening 4704 and removed from the lumen in fluid communication with opening 4702. In this way, liquid can be cleared from the lumen in communication with opening 4702 and pressure measurements may be resumed through that lumen. This line clearing procedure can be programmed to take place on a periodic basis. Openings 4702 and 4704 are shown here opposed to each other, but the openings may be staggered.

Figure 48:
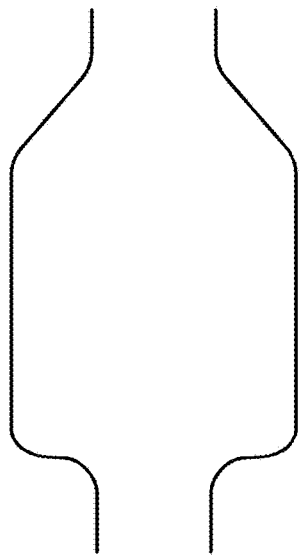
FIGS. 48 and 49 show embodiments of a balloon.
Figure 49:
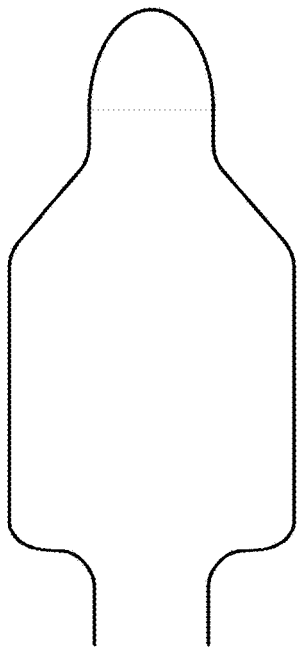

FIGS. 48 and 49 show two different pressure balloon designs, although any suitable design and/or shape may be used. Depending on the balloon material, a balloon may be manufactured in different ways. Some materials are better suited to blow molding while some are better suited to dip molding. Other manufacturing techniques, for example, resistive heat sealing, may be used as well. FIG. 48 shows an example of a blow molded balloon. FIG. 49 shows an example of a dip molded balloon.

Some examples of materials from which a balloon may be manufactured include urethane, polyurethane, polyethylene, Nylon, polyvinylidene fluoride, or any other suitable polymer or other material or any combination of materials.

Balloon coatings may also be utilized to reduce fluid permeability of the balloon. An example of such a coating is poly(p-xylylene) polymer, or Parylene.

In some embodiments, it is desirable to prevent any moisture vapor from entering the pressure balloon. In these embodiments a water, or fluid, impermeable material may be used for the balloon. Some of the materials mentioned herewithin are suitable. In addition, Biaxially-oriented polyethylene terephthalate (BoPET), often going by the brand name, Mylar, may be used. Also a metalized polymer or any other suitable material may be used.

In some embodiments, the sensing Foley type catheter is configured to report the presence of a water droplet or other obstruction in an air-filled lumen (such as the pressure lumen), and then handle or resolve the droplet. In a hypothermic setting, in particular, moisture in an air lumen can condense and form obstructive water droplets. Water droplets in an air-filled lumen (or air bubbles in a water-filled lumen) can disturb or complicate pressure signals due to the surface tension of the water. Accordingly, a pressure-transmission lumen in some embodiments of the disclosed technology may include a hydrophilic feature (such as a coating on the wall of the lumen itself, or a hydrophilic fiber running the length of the lumen) to wick moisture away from the lumen in order to maintain a continuous, uninterrupted air channel. In some embodiments, a hygroscopic composition (silica gel, for example) may be used in line with the air infusion line or within the air infusion lumen itself to capture water or humidity. In some embodiments, a hygroscopic composition may be included within the catheter so that the air infusion circuit need not be serviced to replace this material.

In some embodiments, desiccated air or gas may be used in the pressure lumen and pressure balloon to prevent moisture accumulation.

In some embodiments a hydrophobic or hydrophilic coating may be used in the pressure lumen and/or pressure balloon.

Gas Content

Another embodiment includes using a hydrophobic filter or membrane as an interface with the urine in the bladder, or the mucosal lining of the urethra, to measure relative oxygen, or other gas, content of the urine or tissue.

In some embodiments of the sensing Foley catheter, it is desirable to measure the gas content tissue and/or urine or changes in gas content over time. Potential gasses of interest include oxygen, carbon dioxide, nitrogen, gases associated with anesthesia or other gasses. In some embodiments the membrane is permeable to gas, but not to liquid, for example, a hydrophobic membrane, or other suitable membrane, may be used. The pore size of the hydrophobic membrane may be around 5 microns. Alternatively, the pore size of the hydrophobic membrane may be about 3 microns to about 7 microns.

Figure 50:
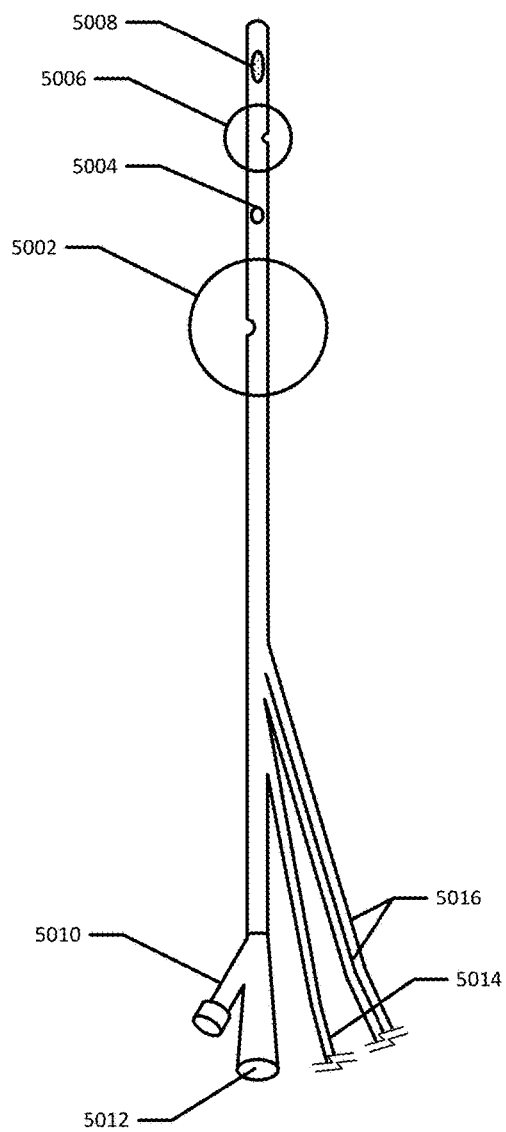
FIGS. 50-53 show various embodiments of a balloon catheter with an gas permeable membrane.

FIG. 50 shows a sensing Foley catheter with an oxygen permeable membrane. Retention balloon 5002 is in fluid communication with inflation/deflation port 5010. Urine flows through opening 5004 through the catheter and out of port 5012 which is in fluid communication with opening 5004. Pressure sensing balloon 5006 is in fluid communication with lumen 5014. Gas permeable membrane 5008 is covering an opening at the distal end of the catheter which is in fluid communication with lumens 5016.

Figure 51:
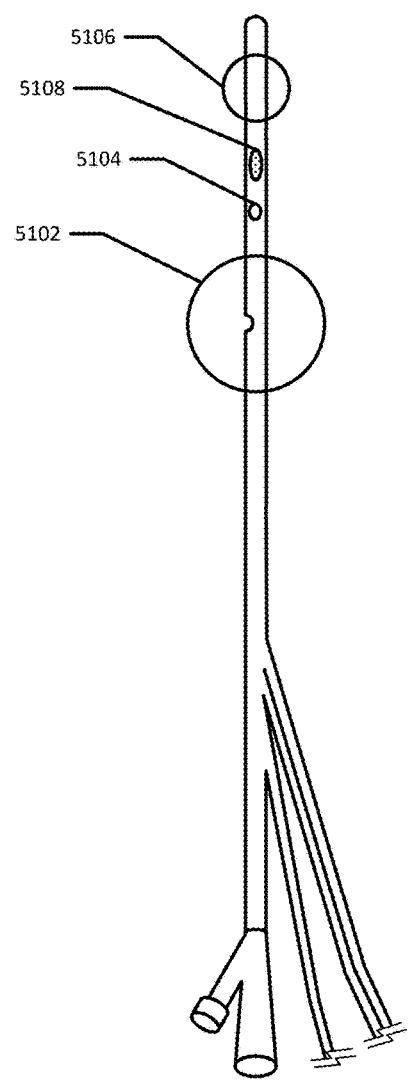

FIG. 51 shows a sensing Foley catheter with an oxygen permeable membrane which is similar to that shown in FIG. 50 except that membrane 5108 is between pressure sensing balloon 5106 and retention balloon 5102. Opening 5104 for urine may be placed anywhere distal to retention balloon 5102.

Figure 52:
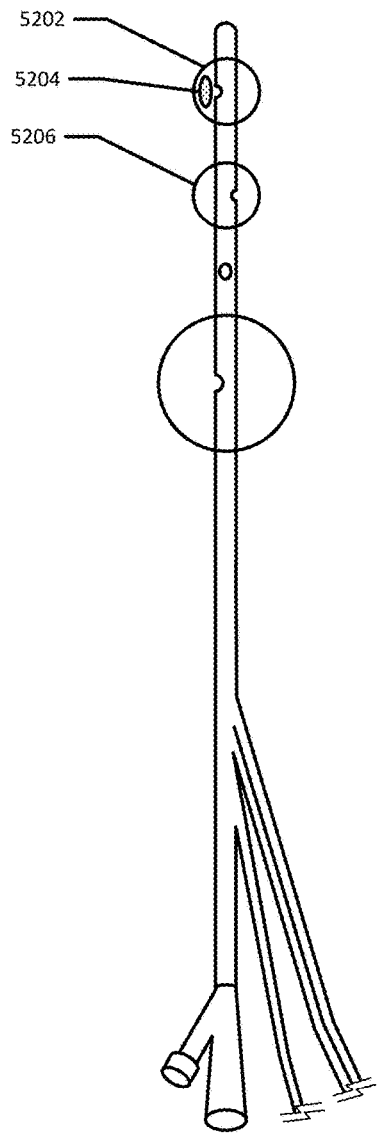
Figure 53:
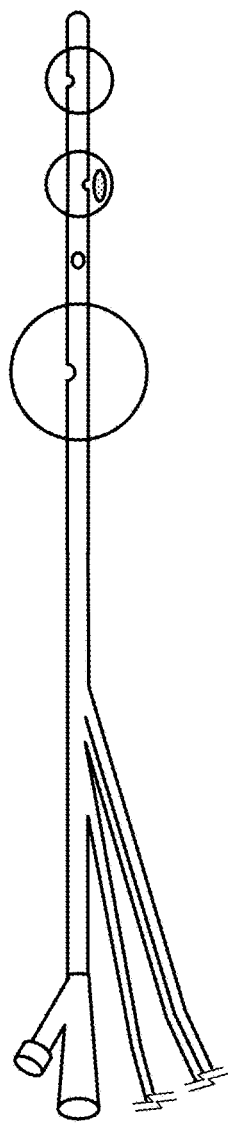

FIG. 52 shows an embodiment of a sensing Foley catheter where membrane 5204 is incorporated into gas sensing balloon 5202. In this figure, gas sensing balloon 5202 is distal to pressure sensing balloon 5206, however another embodiment is shown in FIG. 53 where this is not the case. Gas sensing balloon 5202 may be made out of silicone, polymer, or any other suitable material.

The membrane material may be similar to hydrophobic membrane materials described in other embodiments herein. The membrane is permeable to gasses, or to particular gas or gasses, but not to liquids, such as urine. In this way, gasses can pass through the membrane and into the catheter for measurement of gas content of the tissue and/or urine, and/or changes in gas content over time. Gasses measured include oxygen, nitrogen, carbon dioxide, or other gasses.

The catheter may be placed in the patient such that the membrane is in either the bladder or in the urethra. The membrane is shown here on a sensing Foley catheter with a pressure sensing balloon, but the gas permeable membrane may be placed on any body dwelling catheter, including catheters that reside in blood vessels or other body cavities. The membrane may be in direct or indirect contact with fluid, gas, or body tissue.

Figure 54:
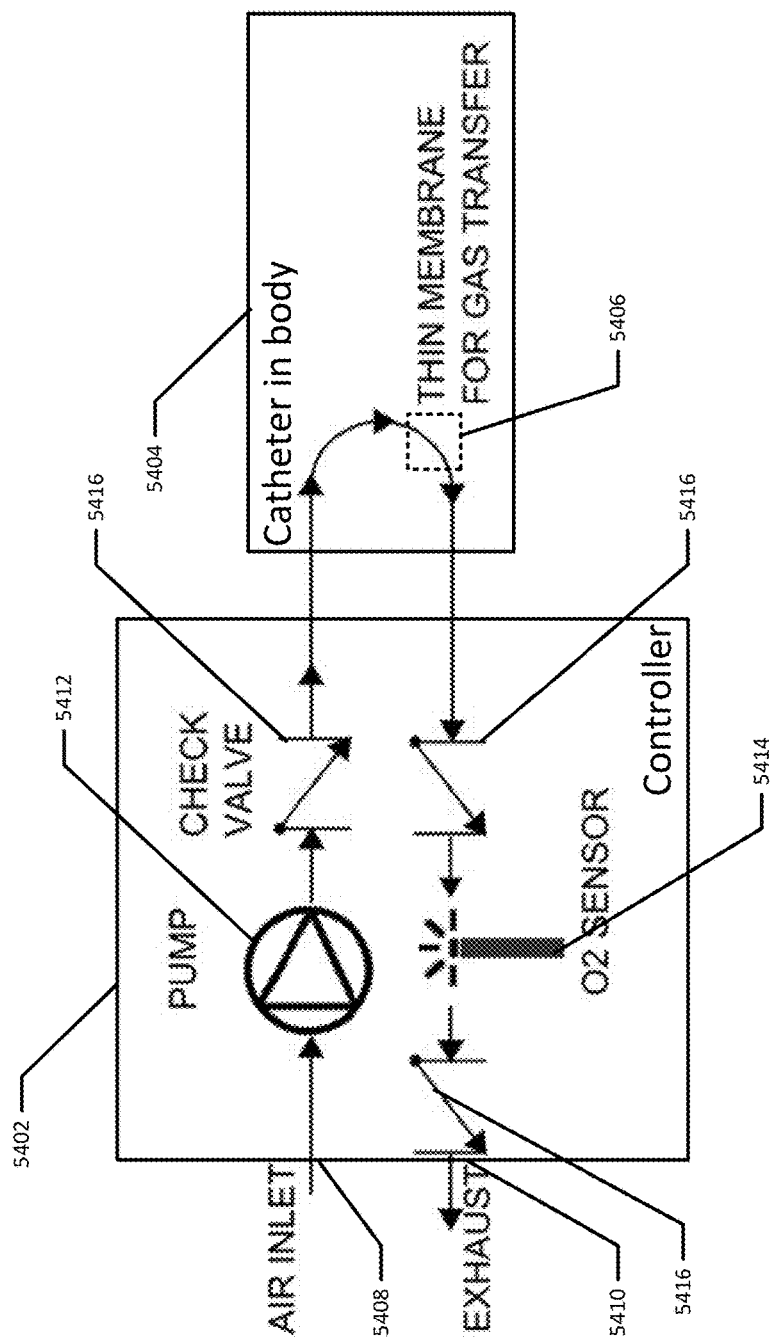
FIG. 54 shows a controller for measuring gas content via a balloon catheter.

FIG. 54 shows a controller which controls the measurements of oxygen or other gas(es). The controller will generally be external to the patient and connect to the catheter via ports, for example, ports 5016. The controller may also control the pressure sensing function or other functions of a sensing Foley catheter, or it may be a separate controller.

Gas measuring controller 5402 is shown here along with a representation of a catheter 5404 and gas transfer membrane 5406. Gas measuring controller 5402 includes air, or gas, inlet 5408, air, or gas, exhaust 5410, pump 5412, oxygen, or other type of sensor 5414 and check valves 5416.

In this embodiment, pump 5412 periodically pushes small amounts of air, or other gas, through tubing into the catheter. Air passes membrane "window" 5406 and the oxygen content of the air changes based on the oxygen content of mucosal lining (if gas transfer membrane is in the urethra) or urine (if gas transfer membrane is in the bladder). Further downstream (back in gas measuring controller box 5402) the oxygen percentage of the air is measured using a fiber optic, or other type of, oxygen sensor. The pump may only operate for short periods of time to allow air in the system time to equilibrate with the tissue/fluid.

Check valves 5416 help limit mixing of air that has passed through the system with outside air or air from an earlier measurement interval.

Measured oxygen, or other gas, content may be very small. Measurements may indicate either absolute gas levels or relative gas levels. For example, gas measuring controller measurements may show relative oxygen content in the patient over time to indicate a change in the status of the patient.

FIG. 55 shows a schematic of how the gas measuring controller interacts with the catheter to measure gas content of the urine or patient tissue. Catheter 5502 includes urine draining lumen 5504 as well as gas measurement lumens 5506 and 5508, which are in fluid communication with gas transfer membrane 5510. Lumen 5506 contains air, or other gas, entering the catheter and lumen 5508 contains air, or other gas, exiting the catheter after the carrier gas has passed the gas transfer membrane. The oxygen, or other gas, level in the exiting gas is measured to determine oxygen levels or oxygen level changes in the urine and/or tissue of the patient. The incoming gas measurement lumen 5506 may be open to atmospheric air, or other source, or it may be a closed system, so that the gas within lumens 5506 and 5508 is continuously circulated so that the gas content changes can be readily determined over time. In other words, air, or gas, inlet 5408, and air, or gas, exhaust 5410 in FIG. 54 may be fluidly connected to each other.

Where the incoming gas measurement lumen 5506 is open to atmosphere, the pump may be run intermittently so that the gas within the gas measuring lumens has more time to equilibrate across the membrane surface. This results in a higher intermittent concentration of the measured gas and therefore a more sensitive measurement.

The pump may be run continuously or intermittently regardless of whether the system is closed or open, but may result in more sensitive measurements if it is run intermittently in the open system mode. In the closed system mode, trends may be more apparent as the measured gas within the system equilibrates with the gas level of the urine, fluid, or tissue being measured.

In this embodiment the urine lumen and the gas measurement lumens are separate. However, the gas transfer membrane may also be situated between the urine lumen and a gas measurement lumen as shown in FIG. 56, where gas transfer membrane 5602 is in fluid communication with the urine lumen.

FIGS. 57A and 57B show embodiments of a gas measuring add-on component. Gas measuring component 5702 may be inserted between the sensing Foley catheter 1000, or any Foley catheter, and the urine drainage tube 1001, or any urine drainage tube. Gas measuring component 5702 includes hydrophobic filter 5704, which may be made of materials disclosed elsewhere herein. Gas inlet lumen 5706 and gas outlet lumen 5708 allow gas to pass over filter 5704 which is in gas communication with the urine within the drainage system. The air, or gas, near filter 5704 very quickly becomes equilibrated with the gases within the urine within the drainage system. FIG. 57B shows the path of air flow across filter 5704. Gas outlet lumen 5708 is in fluid communication with a controller (not shown here) which analyzes the gas within the lumen for the relevant gas or gasses. Gas inlet lumen 5706 may be open to atmosphere, another gas, or may be in a closed loop with gas outlet lumen 5708 within the controller. The controller may be the same controller which measures urine output, mentioned elsewhere herein, or may be a separate controller. Lumens 5706 and 5708 may be incorporated into drainage tube 1001 or may be separate. Gas measuring component 5702 may be a separate component, as shown here, or may be incorporated into vent barb 1016. Gas measuring component 5702 may alternatively be located anywhere in the system.

Detecting/Determining Certain Conditions

FIG. 58A shows a table that lists combinations of parameters that allow for a fingerprint or signature (combination of parameters) for the different indicators of AKI (pre-renal, intrinsic and obstructive). In addition, there may be a fingerprint or signature with respect to the timing of changes of the parameters, which may also determine the causes of AKI (e.g. it is plausible that some parameters change faster for intrinsic AKI caused by glomerulonephritis versus intrinsic AK caused by acute tubular necrosis). This multiparametric approach may also facilitate the choice of effective therapies to treat AKI since different causes of AKI have different effective therapies (e.g. recombinant alkaline phosphatase is effective at treating intrinsic (septic) AKI but ineffective at treating non-septic AKI).

FIG. 58B shows a table that lists combinations of parameters that allow for a fingerprint or signature (combination of parameters) for the different indicators of sepsis, AKI, and acute respiratory distress syndrome (ARDS). These signatures involve the increase, decrease, or both of various patient parameters including urine output, heart rate, respiratory rate, temperature, stroke volume, cardiac output, and abdominal perfusion pressure. Abdominal perfusion pressure is the mean arterial pressure (MAP) minus intra-abdominal pressure (IAP). Mean arterial pressure is equal to the diastolic pressure (DP) plus ⅓ of the pulse pressure (PP). (The pulse pressure equals systolic pressure minus diastolic pressure.) In short, MAP=DP+⅓PP Other patient parameters may also be used. One, some, or all relevant parameters may be used by the controller to communicate a diagnosis and/or risk to the user or to another device. Patient parameters captured by the sensing Foley catheter system may be used on their own, or in conjunction with parameters obtained elsewhere, such as an EKG, a blood pressure measuring device, or info from an EMR.

The sensing Foley catheter system provides real-time, automatic, precise physiological parameter monitoring for the early detection of various medical conditions. By utilizing real time multivariate (point value) and times series (trending) analyses of these high frequency data streams to inform our machine learning-powered model, a highly sensitive physiologic signature for early sepsis onset (or other medical condition determination) may be developed. This will improve clinical outcomes by enabling earlier diagnosis and intervention. The signatures relating to the data relating to the physiologic changes that occur prior to and/or during the onset of certain medical conditions can be continuously improved using machine learning via artificial neural networks to strengthen the relevant parameters, weaken the less relevant parameters and build or destroy connections. This will enable the controller to utilize algorithm to distinguish medical conditions from one another and from normal and other pathologies.

Some embodiments of the present invention may measure urine output immediately after the patient has been given a diuretic. This type of test can be a strong indicator of whether a patient with AKI will progress to a more severe stage and/or die. If a patient's urine output increases after administration of the diuretic, this indicates that the patient is less likely to progress to a more severe stage of AKI. If a patient's urine output does not significantly increase after administration of the diuretic, this indicates that the patient is more likely to progress to a more severe stage of AKI. The present invention is able to quickly and accurately measure urine output in real time. Therefore the response to the diuretic can be detected more quickly (minutes rather than hours) than with traditional urine measurement techniques.

This test can be automated with the controller which provides a controlled dose of a diuretic, and then monitors the urine output over minutes, or hours, preferably only minutes. The diuretic given may be furosemide, or any other suitable loop diuretic or other diuretic. The diuretic may be given, and data collected, as disclosed in Chawla L S, Davison D L, Brasha-Mitchell E, Koyner J L, Arthur J M, Tumlin J A, Shaw A D, Trevino S, Kimmel P L, Senff M G. *Development and standardisation of a furosemide stress test to predict the severity of acute kidney injury. Crit Care.* 2013 Sep. 20; 17(5):R207, herein incorporated by reference.

In addition to detecting AKI, the present invention is capable of detecting urinary tract infections (UTIs), as indicated by decreasing oxygen tension, carbon dioxide levels, increasing specific gravity, and relatively stable urine output and conductance. The detection of UTI can be achieved in the absence of AKI, and possibly in the presence of AKI, by combining urinary markers for a unique fingerprint of UTI. The unique UTI fingerprint can alert clinicians to the presence of UTI.

In addition to detecting AKI and UTI using the described parameters, these parameters may be used in combination with intra-abdominal pressure (IAP), respiratory rate (RR), heart rate (HR), cardiac output (CO), relative stroke volume (RSV), temperature (Temp), pulse pressure (PP), urine conductance (UC), urine output (UO) and/or stroke volume (SV) readings, which are already used for detecting conditions such as intra-abdominal hypertension (IAH), abdominal compartment syndrome (ACS) and sepsis. Adding IAP, RR, HR, CO, RSV, Temp, PP, UC, UO and/or SV measurements to the algorithm described herein may increase the sensitivity and specificity of detecting AKI or UTI. On the other hand, adding the measurements obtained by the present invention to an IAP, RR, HR, CO, RSV, Temp, PP, UC, UO and/or SV measurement algorithm may increase the sensitivity and specificity of detecting IAH, ACS or sepsis. Other clinical applications include the treatment of trauma and burns.

In addition to absolute measurements of IAP, RR, HR, CO, RSV, Temp, PP, UC, UO, gas concentrations and/or SV, trending data of these parameters may also be used to detect IAH, ACS, sepsis or other conditions. For example, the slope of values of these parameters over time, and/or the variability of values of these parameters over time may also be used. Another example of using data trends is the use of pulse pressure waveform analysis and pulse wave velocity (or pulse transit time). Pulse transit time can be determined by capturing a cardiac signal, such as the EKG, from leads on the sensing Foley catheter, and/or elsewhere, and determining the time that a pulse wave pressure signal to travel to the bladder. Multiple parameters and/or parameter trends may be used to determine the presence of IAH. ACS, sepsis or other conditions.

Some examples of using trending data include:
  A decreasing UO in the setting of stable vitals (otherwise) may indicate acute kidney injury. If stroke volume is decreasing, then the kidney may be ischemic. If urine volume surges in the setting of stable vitals, it may indicate toxic acute kidney injury.
  An increasing respiratory rate along with decreasing stroke volume may indicate a pulmonary embolism, hemorrhage or other volume depletion.
  An increasing respiratory rate in the setting of stable vitals may indicate an impending airway obstruction.

A decreasing respiratory rate in the setting of stability in other parameters may indicate narcotic overdose. This is a big problem with patient controlled analgesia.

Increasing intraabdominal pressure (IAP) in the setting of stable stroke volume and increasing urine output may be an indicator of impending fluid overload.

Increasing IAP with decreasing UO and decreasing cardiac output may be an indicator of cardiorespiratory insufficiency. This may be due to fluid overload, sepsis, etc.

The present invention can be used in a variety of hospital settings (e.g. emergency room, operating room, intensive care unit, ward). At any time, the device may be used to monitor the progression of AKI, and whether it is improving or declining. Its algorithms work to alert clinicians to a newly developed case of AKI or to a change in the status of AKI. The device may be placed before insult to the kidney occurs (e.g. patients undergoing cardiac surgery to detect if insult to the kidneys begins intra-operatively) in order to detect initiation of AKI. It may be placed when insult to the kidney injury is already present in order to detect the degree of insult at that time. The device may also be used to monitor the response the therapy/therapeutic intervention (e.g. renal replacement therapy, fluid resuscitation).

Alternative Embodiments

Embodiments of the technology may also report patient movement in the detection or diagnosis of seizure disorder. In this embodiment, the pressure variations may trigger an EEG or recording equipment to allow for intense period of monitoring during an episode suspected of being a seizure. In addition, or alternatively, a pressure sensor, acoustic sensor or other sensors may be used to detect bowel activity, including peristalsis, patient movement, seizure activity, patient shivering, frequency of coughing, severity of coughing, sleep duration, sleep quality, speech detection, patient compliance (movement or lack thereof), and may alert the healthcare provider that the patient has not moved and must be turned or rolled. This movement-related information may also be relayed to a hypothermia device, a drug delivery device or other device to control or mitigate seizure activity, shivering and/or coughing.

In some embodiments, the sensing Foley type catheter is configured to report the presence of a water droplet or other obstruction in an air-filled lumen (such as the pressure lumen), and then handle or resolve the droplet. In a hypothermic setting, in particular, moisture in an air lumen can condense and form obstructive water droplets. Water droplets in an air-filled lumen (or air bubbles in a water-filled lumen) can disturb or complicate pressure signals due to the surface tension of the water. Accordingly, a pressure-transmission lumen in some embodiments of the disclosed technology may include a hydrophilic feature (such as a coating on the wall of the lumen itself, or a hydrophilic fiber running the length of the lumen) to wick moisture away from the lumen in order to maintain a continuous, uninterrupted air channel. In some embodiments, a hygroscopic composition (silica gel, for example) may be used in line with the air infusion line or within the air infusion lumen itself to capture water or humidity. In some embodiments, a hygroscopic composition may be included within the catheter so that the air infusion circuit need not be serviced to replace this material.

In some embodiments of the disclosed technology, air may also be intermittently (and automatically) infused and extracted into the pressure-sensing balloon so that the balloon is in a constant state of being optimally primed, as described in further detail above. In the case of the wicking fiber or hydrophilic coating in the lumen, the air extraction may also contribute to removing and trapping any water from the air line. In the instance of a liquid-filled lumen, a hydrophilic fiber or a hydrophilic coating on the inside of the pressure lumen will provide similar benefit in allowing this lumen to handle an air bubble. In this instance, an air bubble may distort the signal, but the air water interface surface tension is defused by a hydrophilic coating in the lumen of the catheter.

Additionally, a custom extrusion and lumen shape may also be used to prevent obstruction in the case of liquid and/or air-filled lumens. In some embodiments of the technology, for example, a Foley type catheter may have a lumen that is stellate in cross sectional profile. Such a lumen is generally immune from obstruction by a water droplet, as the droplet tends to cohere to itself and push away from the hydrophobic walls. This behavior tends to disallow filling of a cross-sectional space, and allows for an air channel to remain patent around the water droplet and communicate to the sensor. The same logic applies to an air bubble in water in a hydrophilic, stellate water lumen. In this instance the hydrophilic liquid will cling to the walls and allow for a continuous water column that excludes the air bubble to the center of the lumen. The same applies for a hydrophobic liquid in a hydrophobic lumen. In some embodiments, the catheter may include an air channel, and a sensor incorporated within the catheter itself or a fluid lumen that is capable of transmitting the pressure back to a sensor.

The drainage tube may be a multi-lumen tube to contain the urine drainage line, the pressure lumen, and the wires of the thermocouple and is connected to the barb on one end and the controller on the other end.

The Foley catheter may be extruded with BaSO4 or have attached radiopaque markers to provide fluoroscopic observation.

The thermistor located at the tip of the catheter may be fixed in place using a number of extrusion profiles and assembly techniques.

In some embodiments, the sensing Foley catheter may include a blood pressure sensing element that may take any of several forms. In one embodiment, a blood pressure sensing element includes a pressure delivery balloon (either a separate, dedicated balloon or a balloon in fluid communication with a device retention balloon or a pressure sensing balloon) that can be optically analyzed as it is inflated to determine at which pressure the vessels within the bladder or urethra are blanched and blood flow is stopped. This approach provides a reading of the perfusion pressure of the tissue abutting the pressure delivery balloon, such reading reflective of both the systemic blood pressure and vascular resistance. This embodiment of a perfusion pressure device may be used to provide early detection or monitoring of a variety of acute or emergent medical conditions such as sepsis, shock, hemorrhage, and can be particularly advantageous in detecting these conditions at an early stage. In predicting sepsis, embodiments of the invention may be capable of receiving white blood cell count information to better predict sepsis.

Other modalities may be used to detect that the tissue has been blanched or ischemic, as well, with the common methodological aspect being that of the intermittent inflation within the lumen, body cavity or bodily tissues to provide the compression of the vasculature. Embodiments of this device and associated methods may also be used to detect perfusion pressure in other areas of the body with an intermittently inflatable member and optical detection of blood flow or the presence of blood.

Tissue perfusion information may also be provided by way of sensors disposed on the shaft of the catheter such that they contact the urethral wall when the catheter is in place. These sensing technologies may include microdialysis, pyruvate, lactate, $pO_2$, $pCO_2$, pH, perfusion index, near-infrared spectroscopy, laser Doppler flowmetry, urethral capnography, and orthogonal polarization spectroscopy. Any of these tests may also be performed on the urine or the bladder wall itself to generate measurements of tissue perfusion.

Another embodiment of the sensing Foley catheter system includes an embodiment of the clearing mechanism including a device and/or port for positive airflow near the start of the drainage line. The positive airflow facilitates drainage by forcing urine to flow through the drainage line. The positive airflow device may include a one-way valve at the end of the urine catheter that allows urine to only flow toward the urine collection device, and prevents air from entering the catheter.

In some embodiments, a urine clearing mechanism comprises a coating on the inside of the urine drainage tube to reduce surface tension and facilitate drainage. In one aspect, said coating is a hydrophobic polymer, including but not limited to PTFE or FEP.

In yet another embodiment, the clearing mechanism comprises a tubular hydrophobic vent filter that can be inserted into the drainage lumen of the device such that air will be evacuated throughout its length. A segmental hydrophobic vent can also be incorporated at set intervals to ensure that air is evacuated from the tube as it passes these regions. In this embodiment, the hydrophobic vent will be interspaced at minimum of 1-2 foot intervals to prevent submersion of the vents in urine. By providing redundancy the multiple vent/filters prevent the failure of any one filter/vent due to its submersion. In the ideal configuration the vent will be a PTFE or ePTFE material and will be affixed with a barb and or grommetted into the tube at intervals to allow for easy manufacturability. In an alternative embodiment, the vent takes the form of a slit or spiral that runs the length of the drainage tube, thereby allowing air to escape the tube at any point. This prevents the drainage tube from being positionally dependent when preventing and/or eliminating airlocks.

In an alternative embodiment, air locks are prevented by means of an extendable drainage tube, which prevents pockets of air from forming in the high portions of the tube and urine from gathering in the low portions. An extendable tube prevents this from occurring by keeping the tube as straight as possible between the urinary catheter and the collection bag. In one aspect, the extendable drainage tube is composed of multiple telescopic sections that can be extended or collapsed to match the distance from the patient to the collection bag. In another aspect, the drainage tube is pleated to form an accordion, which can be extended or collapsed or deformed as necessary. In yet another aspect, the tube is coiled. In yet another aspect, the drainage tube is retractable by means of a spring coil that wraps the tubing around a wheel to achieve the appropriate length.

Relative cardiac output and relative tidal volume may also be calculated, based on the deflection of the pressure sensor and/or other force gauge. If sampled with sufficient frequency (e.g., 1 Hz or greater), respiratory excursions can be quantified in a relative manner to the amplitude of the excursions at the time of catheter placement. Larger excursions generally relate to heavier breathing, or in the setting of an upward drift in the baseline, a higher peritoneal pressure. The small peaks on the oscillating respiratory wave, caused by the pumping heart, may be tracked as well by using faster sampling rates (e.g., 5 Hz or greater), and the amplitude of this wave may be used, in the setting of a relatively constant peritoneal pressure, to determine the relative cardiac output, in the setting of a known, stable peritoneal pressure, absolute stroke volume and/or cardiac output.

Intrabdominal pressure or bladder pressure, as sensed by an embodiment of the disclosed technology, may also be used to detect the level of patient movement (as may vary, for example, between substantially no movement to a high level of movement) and to report the movement level to a healthcare provider. A short burst of peaks and valleys in bladder pressure activity can serve as a proxy for body movement in that such a bladder pressure profile is a strong indicator that the patient is using their abdominal muscles, as, for example, to sit up or get out of bed. This embodiment may be of particular benefit for patients that are at risk of falling. In a patient that is a fall-risk, a healthcare provider may be notified that the patient is sitting up and respond accordingly. Alternatively, the device may be used to report inactivity of a patient and/or lack of patient movement.

Pulse oximetry elements allow for a determination of blood oxygen concentration or saturation, and may be disposed anywhere along the urethral length of the catheter. In some embodiments, the sensor or sensors are disposed within the tubing of the device to ensure approximation to the urethral mucosa. With this technology, a healthcare provider can decompress the bladder with a urinary catheter and obtain pulse oximetry data in a repeatable and accurate manner. The power source for pulse oximetry may be incorporated within the urinary collecting receptacle or within the catheter itself. In some embodiments, the pulse oximeter is reusable and the catheter interface is disposable; in this arrangement the pulse oximeter is reversibly attached to the disposable catheter and removed when oxygen measurements are no longer desired. Embodiments of the sensing Foley catheter may include an optically transparent, or sufficiently transparent, channel for the oximetry signal, such as a fiber-optic cable, transparent window, and an interface for the reusable oximeter. This method and device for urethral pulse oximetry may be used in conjunction with any of the other embodiments detailed herein or may be a stand-alone device.

An antibacterial coating, or a material impregnated with an anti-bacterial compound, may be used on the sensing Foley catheter to prevent infection. Examples of antibacterial coatings/materials include silver, silver citrate, Parylene, or any other suitable material.

Pulmonary Blood Volume Variability may also be determined by the sensing Foley catheter system to aid in assessing existence or risk of heart failure. Reduced left ventricular function can lead to an increase in the pulmonary blood volume (PBV) or a decrease in the pulmonary blood volume variation. PBV variation is defined as the change in PBV over time during the cardiac cycle. PBV can be determined as a product of the cardiac output and the pulmonary transit time (PTT). Cardiac output can be determined as the product of stroke volume and heart rate where stroke volume is the area under the flow-time curve for one cardiac cycle. Pulse transit time may be obtained by looking at the delay between the QRS complex in an EKG vs. the appearance of the signal in the bladder. The EKG signal may be obtained from a separate EKG lead, a lead incorporated into the sensing Foley catheter, a lead incorporated into the catheter insertion kit, or elsewhere. An EKG lead may also be able to read the EKG signal from within the urine, anywhere in the system. 2 leads may be used to more accurately determine the pulse transit time.

It has been found that stroke volume, ejection fraction, and PBV variation decrease after myocardial infarction, and that the greatest change is seen in PBV variation. Therefor determining PBV variation and identifying a decrease in PBV variation may be a strong indication of heart failure, or heart failure risk.

Data collected by the sensing Foley catheter system may be stored in a database and analyzed for trending or other uses. For example, data may be collected from several patients and aggregated anonymously to be used to better treat, monitor, or predict the behavior of future patients. For example, data collected over time relating to heart rate, respiratory rate, temperature infection etc., may be aggregated and analyzed by the controller to find trends, such as the relationship between or among the various parameters and results. For example, certain trends in temperature alone, or in combination with other parameters, may be a predictor of infection, the onset of sepsis, ARDS and/or AKI. FIG. 58 shows some known examples, but other and currently unknown trends may emerge from the aggregated patient data.

Data collected by the sensing Foley catheter system may be integrated with Electronic Health Records (EHRs) or Electronic Medical Records (EMRs) and/or other systems. Data collected by the sensing Foley catheter system controller may directly or indirectly interface with an EMR/EHR system. Data, such as patient demographic, or medical history data, from an EMR/EHR may also integrate with the sensing Foley catheter system.

Example of Data Processing System

Figure 60:
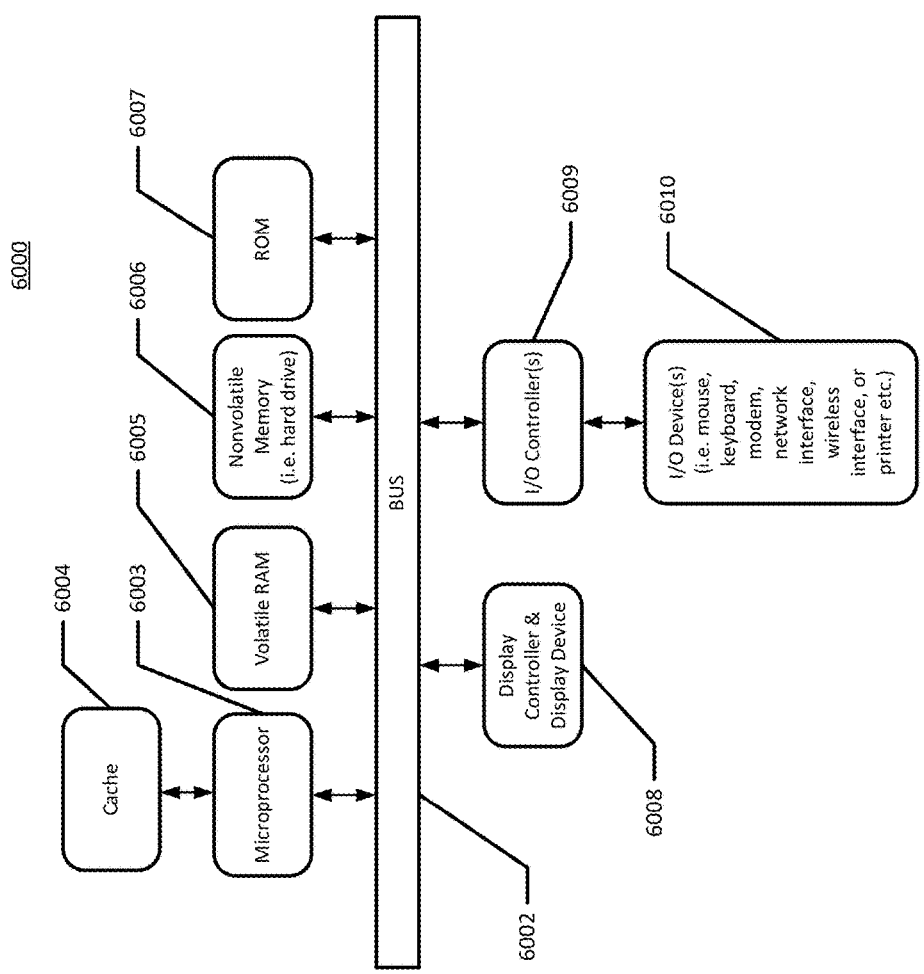
FIG. 60 is a block diagram of a data processing system, which may be used with any embodiments of the invention.

FIG. 60 is a block diagram of a data processing system, which may be used with any embodiment of the invention. For example, the system 6000 may be used as part of a controller as shown in several embodiments herein. Note that while FIG. 60 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 60, the computer system 6000, which is a form of a data processing system, includes a bus or interconnect 6002 which is coupled to one or more microprocessors 6003 and a ROM 6007, a volatile RAM 6005, and a non-volatile memory 6006. The microprocessor 6003 is coupled to cache memory 6004. The bus 6002 interconnects these various components together and also interconnects these components 6003, 6007, 6005, and 6006 to a display controller and display device 6008, as well as to input/output (I/O) devices 6410, which may be mice, keyboards, modems, network interfaces, printers, and other devices which are well-known in the art.

Typically, the input/output devices 6010 are coupled to the system through input/output controllers 6009. The volatile RAM 6005 is typically implemented as dynamic RAM (DRAM) which requires power continuously in order to refresh or maintain the data in the memory. The non-volatile memory 6006 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 60 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 6002 may include one or more buses connected to each other through various bridges, controllers, and/or adapters, as is well-known in the art. In one embodiment, the I/O controller 6009 includes a USB (Universal Serial Bus) adapter for controlling USB peripherals. Alternatively, I/O controller 6009 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory: flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Unless defined otherwise, all technical terms used herein have the same meanings as commonly understood by one of ordinary skill in the medical arts. Specific methods, devices, and materials are described in this application, but any methods and materials similar or equivalent to those described herein can be used in the practice of the present invention. While embodiments of the invention have been described in some detail and by way of illustrations, such illustrations are for purposes of clarity of understanding only, and are not intended to be limiting. Various terms have been used in the description to convey an understanding of the invention: it will be understood that the meaning of these various terms extends to common linguistic or grammatical variations thereof. Further, while some theoretical considerations may have been advanced in furtherance of providing an understanding of the technology, the appended claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims appended to the patent application, including the full range of equivalency to which each element thereof is entitled.

Some embodiments of the sensing Foley catheter system include using UV light, or light of an appropriate wavelength, to sterilize the collection chamber itself or other components of the system. A UV light source may direct UV light through the walls of the collection chamber, or, alternatively, the UV light source may be located inside the collection chamber. The UV light source may be used to sterilize the collection chamber when the chamber is empty, full, or partially full. The UV sterilization process may happen continually, or intermittently. A UV light source may be located anywhere in the sensing Foley catheter system.

Spectroscopy—Spectrophotometry

Figure 61:
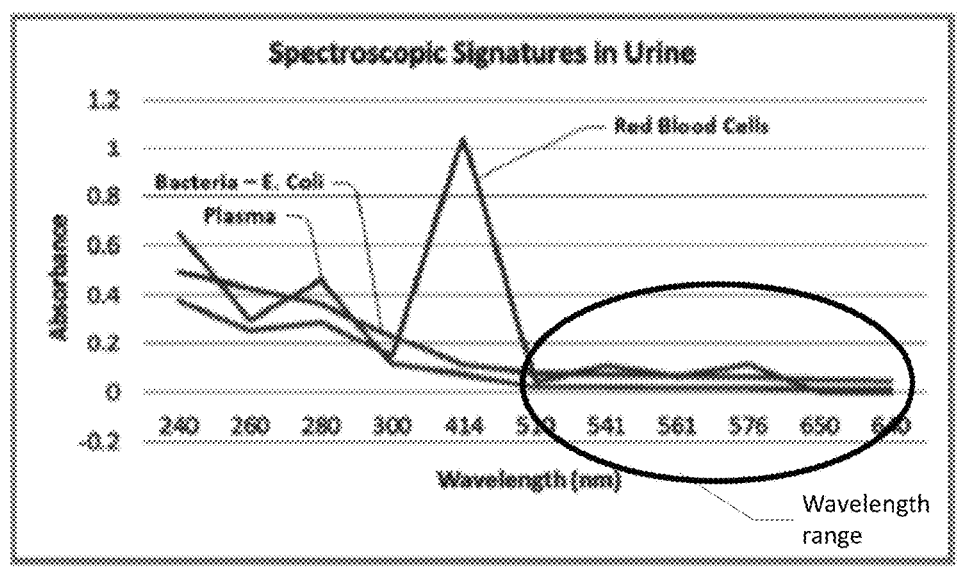
FIG. 61 shows alternative wavelengths that can be used to identify red blood cells, and/or plasma/white blood cells.

Some embodiments of the sensing Foley catheter system include using light wavelengths in the range of around 520 nm to around 650 nm to identify bacteria, red blood cells, and/or plasma/white blood cells. See area inside oval of FIG. 61.

Some embodiments of the sensing Foley catheter system include combining spectrophotometry to identify white blood cells and bacteria in combination with identifying a decrease in $PO_2$ and/or an increase in $CO_2$ to identify infection.

Figure 62:
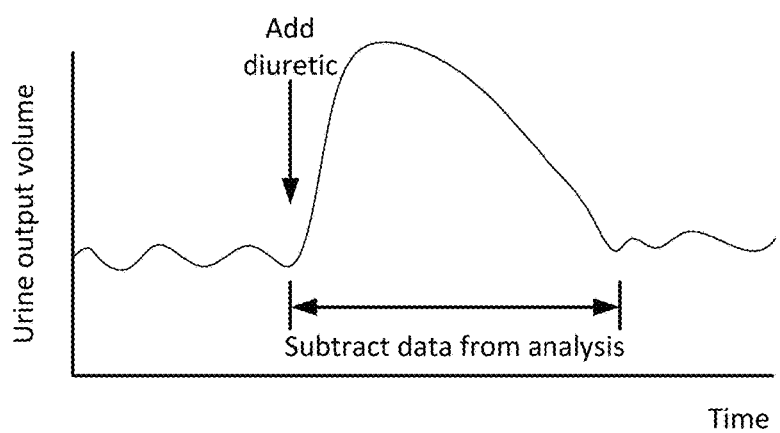
FIG. 62 shows urine output data immediately following the administering of a diuretic.

Some embodiments of the sensing Foley catheter system include the controller filtering the urine output data to compensate for increased urine output immediately following the administering of a diuretic. Urine output generally increases immediately following the administration of a diuretic. However in certain situations it is beneficial to essentially ignore the increased urine output data associated with administration of a diuretic. The controller of the sensing Foley catheter system can automatically ignore the urine output data associated with the administration of a diuretic by identifying the shape of the urine output curve associated with the administration of a diuretic, and subtracting and/or ignoring the data associated with this increase. The identification of the curve shape may be done by slope, length of increase, amplitude of increase, shape, etc. Subtraction of diuretic induced urine output data may be beneficial in determining, or predicting, the onset of AKI. See FIG. 62. For example, where urine output rises above about 2,000 ml/hour (peak), the controller may identify this as a situation where a diuretic has been administered.

Increased urine output caused by the administration of a diuretic can be differentiated from increased urine output caused by clamping, or otherwise blocking, of the urine drainage tube and/or Foley catheter. In the situation where the drainage lumen is clamped, urine output prior to the increase will be essentially zero, or very low, for example less than 5 ml/hour. Contrastingly, in the situation of an administered diuretic, urine output immediately prior to the administration of the diuretic may be very low, but will likely be above zero, for example, above about 5 ml/hour. In addition, in the situation where the drainage lumen is clamped, increased urine output following the unclamping of the drainage lumen will be for a relatively short period of time, for example, about 30 seconds to about 5 minutes. Contrastingly, in the situation of an administered diuretic, increased urine output will be for a longer period of time, for example, about 30 minutes to about 2 hours. In addition, in the situation where the drainage lumen is clamped, urine output following the unclamping of the drainage lumen will likely be less than around 1000 ml. Contrastingly, in the situation of an administered diuretic, the urine output after the administration of the diuretic will likely be more than about 1000 ml. Any or all of these factors may be used by the controller to analyze the urine output volume over time curve to determine when a diuretic has been administered and to subtract the increased urine output volume attributable to the diuretic from the urine output presented to the user.

In this way, the controller may automatically determine when a diuretic is administered. Alternatively, the user interface of the controller may include a button or other user input device (touch screen, voice control etc.) which indicates that a diuretic has been administered. The controller will then look for an increased urine output and subtract the increased urine output attributable to the diuretic from the urine output data presented to the user.

Some embodiments of the sensing Foley catheter system include the controller determining abdominal perfusion pressure (APP). APP is defined as the difference between the mean arterial pressure and the intra-abdominal pressure (IAP). Mean arterial pressure can be determined in conventional ways and combined with the controller's determination of LAP to determine APP. The controller may further automatically alter the infusion of fluids and/or pressors/vasopressors to increase or decrease blood pressure.

Prevent Wetting of Filter/Vent

Some embodiments of the sensing Foley catheter system include one or more vents and/or filters to prevent negative pressure from building within the Foley catheter and causing suction trauma to the bladder. A filter/vent may be located at the junction of the Foley catheter and the drainage tube or elsewhere, such as within the collection vessel or even within the lumen of the drainage tube or Foley catheter themselves, as will be described below.

The filter/vent in some embodiments is designed to repel fluids, i.e. from hydrophobic materials. However, despite using hydrophobic materials, the filter/vent can still be susceptible to wetting by fluid, especially urine. Some embodiments include a larger lumen, or lumen area, where the filter/vent is located to reduce the likelihood that the surface tension of the fluid causes the fluid to fill the lumen. FIG. 63A shows a smaller diameter lumen where FIG. 63B shows a larger diameter lumen in the vent/filter area. Note that when vent/filter 6304 is facing upward or outward, the smaller lumen may still allow wetting of the filter/vent with fluid 6202, where a larger lumen may reduce the likelihood of wetting of the filter/vent.

In embodiments in which the filter/vent is located at or near the junction of the Foley catheter and the drainage tube, the area under or near the filter/vent may be taped to the patient's leg to stabilize the Foley catheter once it is in place. The larger lumen tube helps prevent wetting of the filter/vent in this situation, especially if the vent/filter is oriented away from the leg, so away from the patient. In some embodiments the vent barb may be designed so that the vent/filter is facing outward when the barb or barb area is taped to the patient's leg. For example, the barb may be curved, or attached to a curved base, as shown in FIG. 64, to better attach, and orient, to patient leg 6402.

In some embodiments the barb area may be elongated, for example between 6 and 12 inches, with the vent/filter placed further from the patient, to allow the vent/filter to be placed easily in a location and manner to prevent wetting.

In some embodiments, vent/filters may be placed in multiple locations around the diameter of the draining lumen within the barb or elsewhere. Alternatively a vent may encircle all, or most, of the circumference of the lumen. In these embodiments, a reinforcing cuff or other structure may surround the vent to provide structural integrity to the lumen. Filter/vents may also be placed along the length of the drainage tube.

Figure 65:
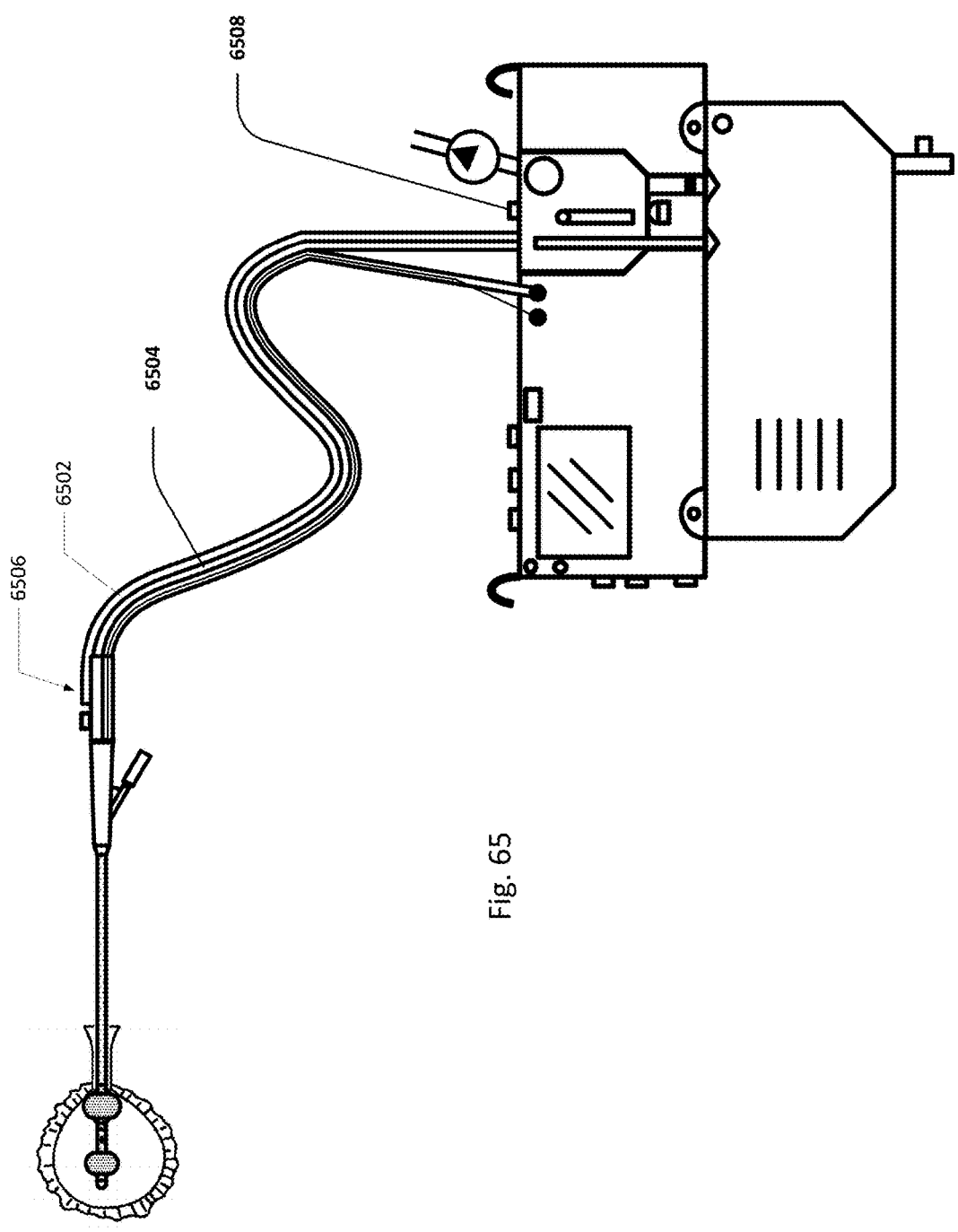
FIG. 65 shows an embodiment of the sensing Foley catheter system with a vent tube.

The embodiment shown in FIG. 65 will also prevent wetting of the vent/filter. This embodiment includes vent tube 6502 with an inner lumen which connects to drainage lumen 6504 near barb area 6506, and is vented to atmosphere, or other air/gas/fluid via one or more filter/vents 6508 along the vent tube and/or near the other end. The filter/vent may be in the collection vessel as is shown in FIG. 65, or may be elsewhere, such as separate from the collection vessel.

A vent lumen may be incorporated into the drainage lumen, either alongside the urine drainage lumen, or within the urine drainage lumen. A vent lumen may alternatively be separate from the drainage lumen and connected to the drainage lumen at a vent tube/drainage tube junction, for example, near barb area 6506.

Figure 66:
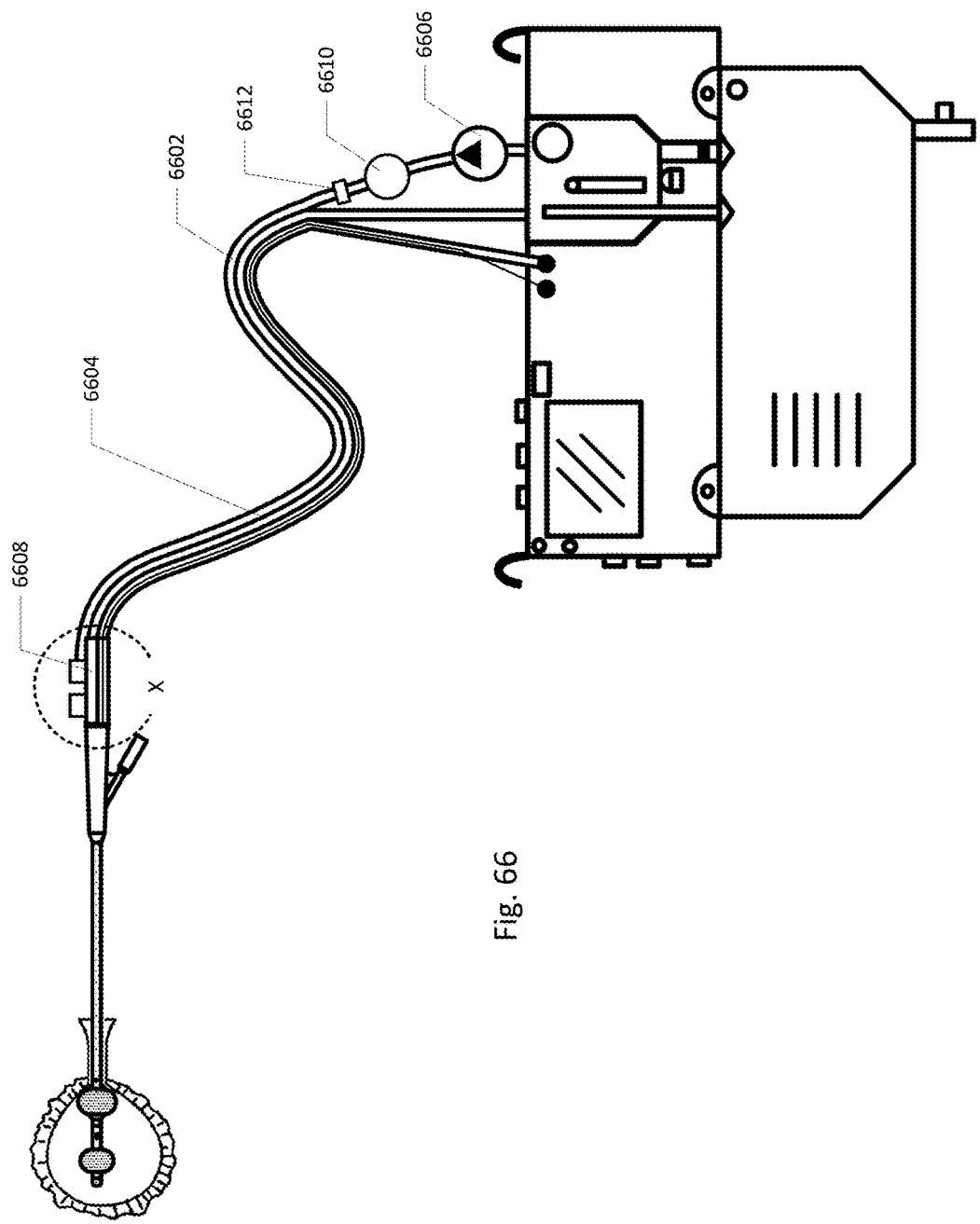
FIG. 66 shows the sensing Foley catheter system with a separate positive pressure vent tube.

The embodiment shown in FIG. 66 shows the sensing Foley catheter system with a positive pressure vent tube 6602 which has an inner lumen which is in fluid communication with urine drainage lumen 6604 and pump 6606. The positive pressure vent tube may include filter 6612 anywhere along its length, in-line or otherwise. The positive pressure vent tube may include a vent at either end of the tube, anywhere along the tube, or may include multiple vents.

The pump pulls a negative pressure on the urine drainage lumen and instead of pumping the positive pressure into the atmosphere, the positive pressure is pumped back into the urine drainage lumen via the positive pressure tube. Alternatively, different pumps may be used for the negative and positive pressures. In this way, an exact negative or positive pressure can be controlled at the junction 6608 of the urine drainage lumen and the positive pressure vent tube. Preferably, the pressure in junction 6608 is either slightly negative or neutral to prevent fluid flow from going back into the Foley catheter. For example the pressure in the junction may be maintained at about 0 mm Hg. Alternatively, the pressure in the junction may be maintained at about −2 mm Hg. Optional regulator 6610 may control the negative pressure with respect to the positive pressure, by magnitude, timing, etc. For example, the regulator (which is controlled by the controller) may implement a slight delay so that negative pressure is pulled on the urine drainage line first, then at a set time later, or when a particular negative pressure is achieved, positive pressure is applied to the positive pressure tube and ultimate the positive pressure tube/drainage tube junction. This will prevent the net pressure at the positive pressure tube/drainage tube junction from being positive and causing urine to flow into the bladder rather than out of the bladder. The optional regulator may be in the form of a vent, of particular dimension (lower surface area or denser filter material for more resistance, larger surface area or looser filter material for less resistance). The positive pressure vent tube may connect to the urine drainage lumen via a valve, such as an umbrella valve with a set crack pressure.

Alternatively, the positive pressure tube may be pressurized by compressed sterile fluid/gas/air.

In addition, precise control of the negative pressure exerted on the bladder may allow for duplication of the normal filling and draining of the bladder. For example, a neutral, or zero, pressure may be maintained, or even a slightly positive pressure may be maintained at the base of the Foley for a period of time so that the bladder fills normally. Then, either after a set period of time, or after a certain pressure is reached (i.e., the pressure required to maintain a neutral pressure at the base of the Foley catheter), the pressure is reduced allowing for the bladder to empty, or drain. This process can be controlled by the controller which controls the pressure regulator to repeat this process to emulate normal filling and emptying of the bladder.

In some embodiments, a valve may be used at the base of the Foley catheter to better control the pressure in that area, including pressure (negative or positive) exerted on the bladder.

Note that the positive pressure tube embodiments may be used with any of the sensing Foley catheter system embodiments, including those with different filter/vent configurations than those shown herein. In addition, any of the anti-airlock embodiments may be used with a regular, i.e. non-sensing, Foley catheter, or other catheters or drainage tubes.

FIGS. 67-86 show magnifications of the barb area, X, of FIG. 66 to show examples of different embodiments of this area.

Figure 67:
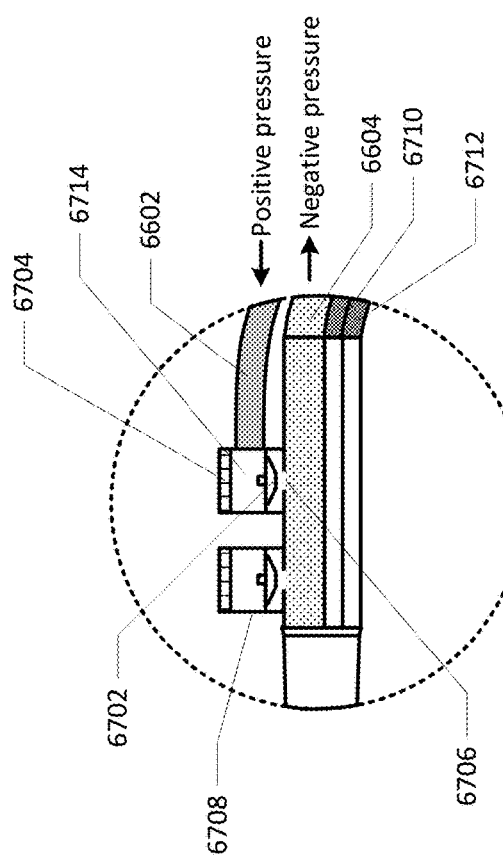
FIG. 67 shows a magnification of the barb area of FIG. 66.

In the embodiment shown in FIG. 67, valve 6702, such as an umbrella valve with a set crack pressure is shown between the lumen of positive pressure vent tube 6602 and the urine drainage lumen 6604. The valve may be a one-way valve. Vent 6704 is shown between the positive pressure vent tube and the atmosphere. Configurations may also exist where only the vent, or only the valve are present. Opening 6706 is in fluid communication with urine drainage lumen 6604 and chamber 6714 (with valve 6702 periodically cutting off fluid communication to the chamber). Chamber 6714 is in fluid communication with the lumen of positive pressure vent tube 6602. Periodically, or continuously, positive pressure is applied through positive pressure lumen 6702 and/or negative pressure is applied to urine drainage lumen 6604. When the crack pressure of valve 6702 is exceeded, fluid, preferably gas, flows through valve 6702 and through opening 6706 and through the lumen of urine drainage lumen 6604. This serves both to clear the line of airlocks or any blockages, and to clear chamber 6714 of any fluid, which reduces the likelihood of vent 6704 becoming wetted. It also serves to clear vent 6704 if it has been wetted. The crack pressure of valve 6702 refers to the pressure differential between positive pressure lumen 6702 and urine drainage lumen 6604. If the pressure in the urine drainage lumen is below the pressure in the positive pressure lumen by the crack pressure, the valve opens allowing fluid to flow from the positive pressure lumen, through the chamber, through opening 6706 and through the drainage lumen. For example, the crack pressure may be less than about 1 mm Hg. Alternatively the crack pressure may be less than about 2 mm Hg. Alternatively the crack pressure may be less than about 3 mm Hg. Alternatively the crack pressure may be less than about 4 mm Hg. Alternatively the crack pressure may be less than about 5 mm Hg. Alternatively the crack pressure may be less than about 10 mm Hg.

The pressure in the urine drainage lumen may periodically or continually be about −5 mm Hg. Alternatively, the pressure in the urine drainage lumen may periodically or continually be about −7 mm Hg. Alternatively, the pressure in the urine drainage lumen may periodically or continually be about −10 mm Hg. Alternatively, the pressure in the urine drainage lumen may periodically or continually be about −15 mm Hg. Alternatively, the pressure in the urine drainage lumen may periodically or continually be about −20 mm Hg. Alternatively, the pressure in the urine drainage lumen may periodically or continually be about −25 mm Hg. Alternatively, the pressure in the urine drainage lumen may periodically or continually be about −30 mm Hg.

The positive pressure in the positive pressure lumen may periodically or continually be about 5 mm Hg. Alternatively, the positive pressure in the positive pressure lumen may periodically or continually be about 7 mm Hg. Alternatively, the positive pressure in the positive pressure lumen may periodically or continually be about 10 mm Hg. Alternatively, the positive pressure in the positive pressure lumen may periodically or continually be about 15 mm Hg. Alternatively, the positive pressure in the positive pressure lumen may periodically or continually be about 20 mm Hg. Alternatively, the positive pressure in the positive pressure lumen may periodically or continually be about 25 mm Hg. Alternatively, the positive pressure in the positive pressure lumen may periodically or continually be about 30 mm Hg.

A vent may also, or alternatively, be present elsewhere along the positive pressure vent tube, for example, close to the pump, or as part of a pressure regulator. A second vent/valve assembly 6708 is shown on the barb in FIG. 67, however this second vent/valve assembly may or may not be present. Optional thermistor 6710 and optional pressure lumen 6712 are also shown. The positive pressure vent tube may alternatively be exposed to atmospheric pressure.

Figure 68:
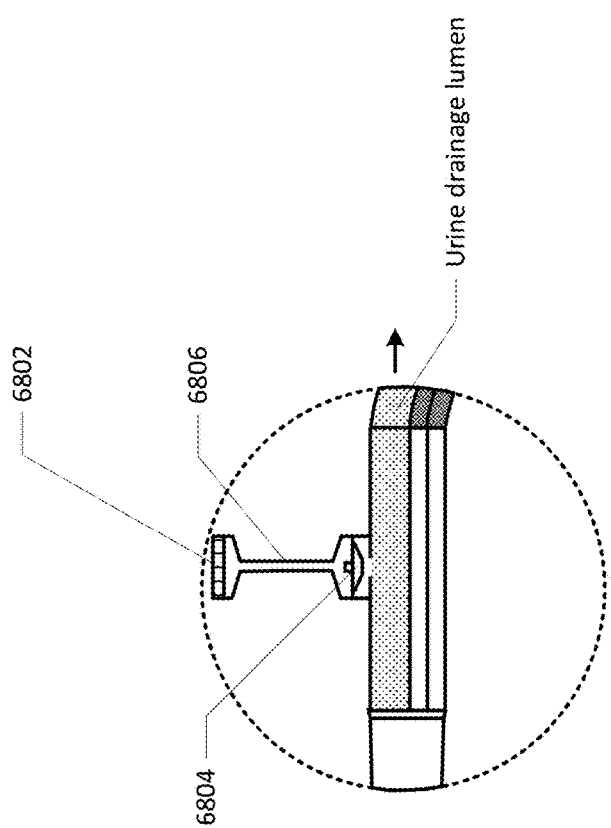
FIGS. 68-86 show the barb area of various embodiments of the sensing Foley catheter system.

FIG. 68 shows an embodiment of the barb area which includes vent 6802, valve 6804 and a small cross sectional area 6806 which is large enough to allow air/gas to flow freely from the vent to the urine drainage lumen, but small enough to prevent liquid flow to the vent. For example narrowed portion 6806 may be less than about 1 mm in diameter. Alternatively, the narrowed portion may be less than about 2 mm in diameter. Alternatively, the narrowed portion may be less than about 3 mm in diameter. Alternatively, the narrowed portion may be less than about 4 mm in diameter. The narrowed portion may be about 1-5 mm in length. Alternatively, the narrowed portion may be about 5 mm-30 mm in length. The embodiment shown in FIG. 68 may or may not include a positive pressure tube—it is shown without a positive pressure tube (i.e. exposed to atmosphere). This embodiment may or may not include the valve.

Figure 69:
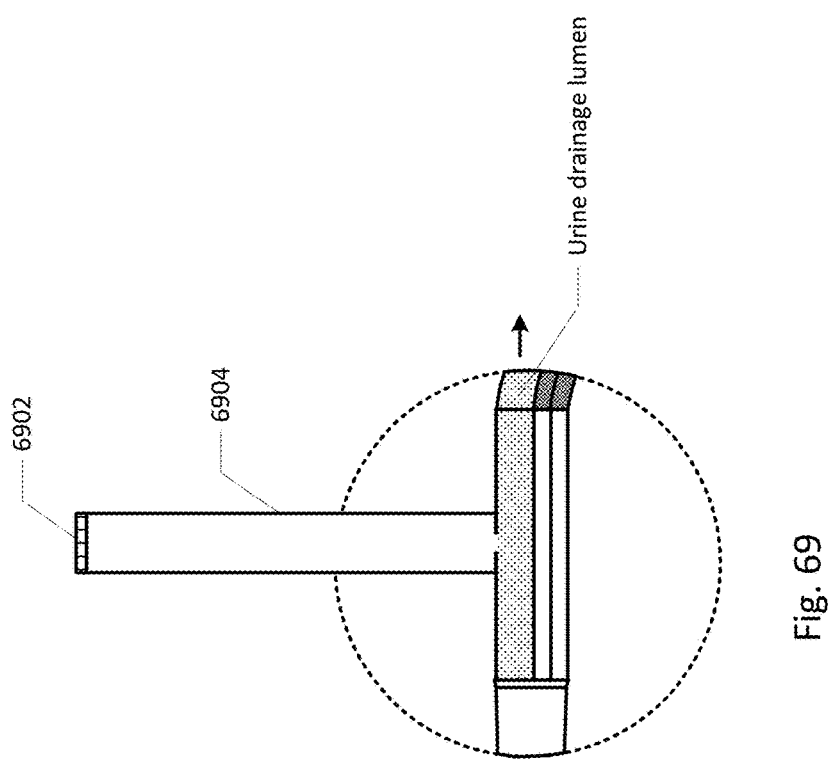

FIG. 69 shows an embodiment of the barb area which includes vent 6902 and a long vent tube 6904 which allows air/gas to flow freely from the vent to the urine drainage lumen, but is long enough to prevent liquid flow to the vent. For example, vent tube portion 6904 may be about 1-10 mm in diameter and may be about 1-10 cm in length. For example, the vent tube portion 6904 may be over about 2 cm in length. Alternatively, the vent tube portion 6904 may be over about 4 cm in length. Alternatively, the vent tube portion 6904 may be over about 10 cm in length. The embodiment shown in FIG. 69 may or may not include a positive pressure tube—it is shown without a positive pressure tube. This embodiment may or may not include a valve.

Figure 70:
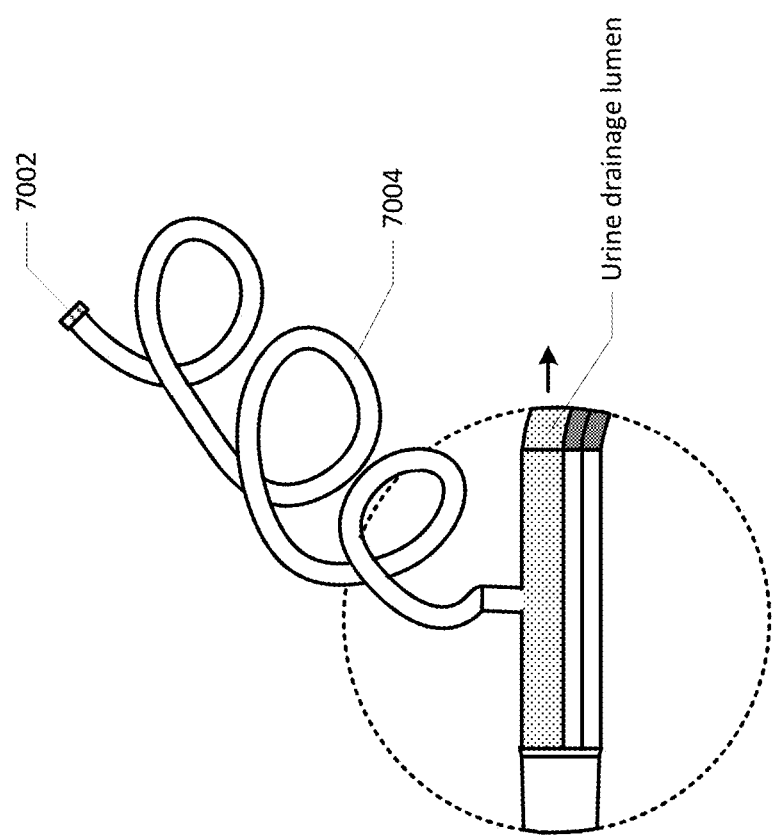

FIG. 70 shows an embodiment of the barb area which includes vent 7002 and a long tortuous vent tube 7004 which allows air/gas to flow freely from the vent to the urine drainage lumen, but is tortuous enough to prevent liquid flow to the vent. For example, vent tube portion 7004 may be a coil. The embodiment shown in FIG. 70 may or may not include a positive pressure tube—it is shown without a positive pressure tube. This embodiment may or may not include a valve.

Figure 71:
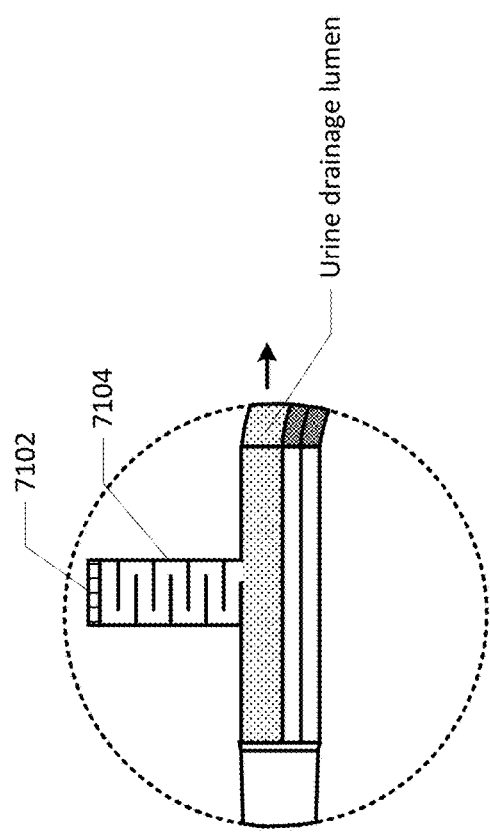

FIG. 71 shows an embodiment of the barb area which includes vent 7102 and a compact tortuous vent tube 7104 which allows air/gas to flow freely from the vent to the urine drainage lumen, but is tortuous enough to prevent liquid flow to the vent. For example, vent tube portion 7104 may be a tube with baffling, or mesh, in the inner lumen. The embodiment shown in FIG. 71 may or may not include a positive pressure tube—it is shown without a positive pressure tube. This embodiment may or may not include a valve.

Figure 72:
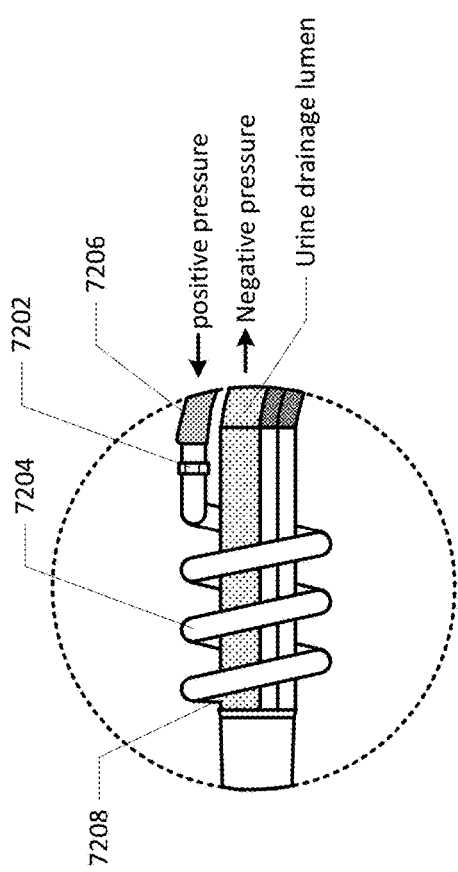

FIG. 72 shows an embodiment of the barb area which includes vent 7202 and vent tube 7204. In this embodiment, the vent tube is in fluid communication with positive pressure tube 7206, and vent 7202 is in line with positive pressure lumen, so that fluid under positive pressure passes through/across the vent and into the drainage lumen via opening 7208. Vent tube 7204 is shown coiled here, to help prevent any back flow of urine into the vent tube, however, vent tube 7204 may be of any configuration, including straight tubing, or a lumen built into the barb area. Vent 7202 is shown here near the junction of vent tube 7204 and positive pressure tube 7206, however, the vent may be anywhere along the positive pressure lumen, including near the pump/cassette, or near opening to the drainage lumen 7208. This embodiment may or may not include a valve.

Figure 73B:
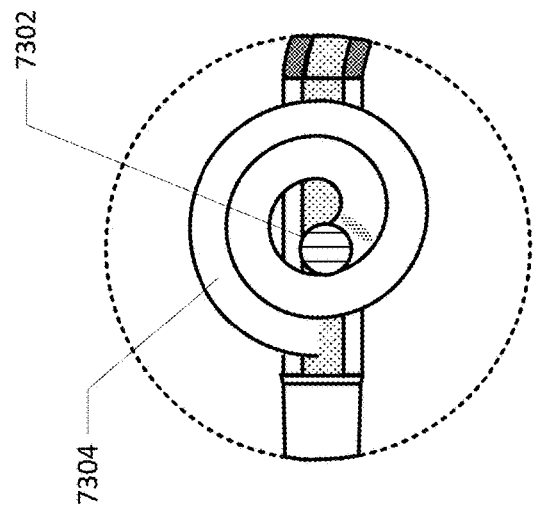
Figure 73A:
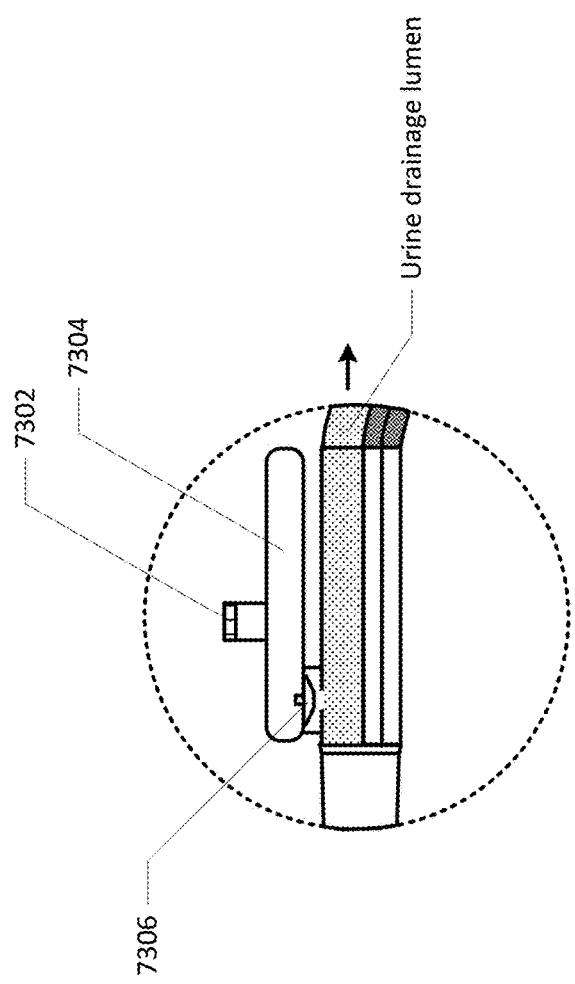

FIGS. 73A and B show an embodiment of the barb area which includes vent 7302 and a compact tortuous vent tube 7304 which allows air/gas to flow freely from the vent to the urine drainage lumen, but is tortuous enough to prevent liquid flow to the vent. In addition, the vent end of vent tube 7304 may be configurable or bendable or deformable so that it can be oriented upward after the barb area has been affixed to the patient's leg. By orienting the vent end of the vent tube upward, the chance of the vent's exposure to liquid is reduced. For example, vent tube portion 7304 may be essentially a flattened coil. The embodiment shown in FIG. 73 may or may not include a positive pressure tube—it is shown without a positive pressure tube. This embodiment may or may not include valve 7306.

Figure 74:
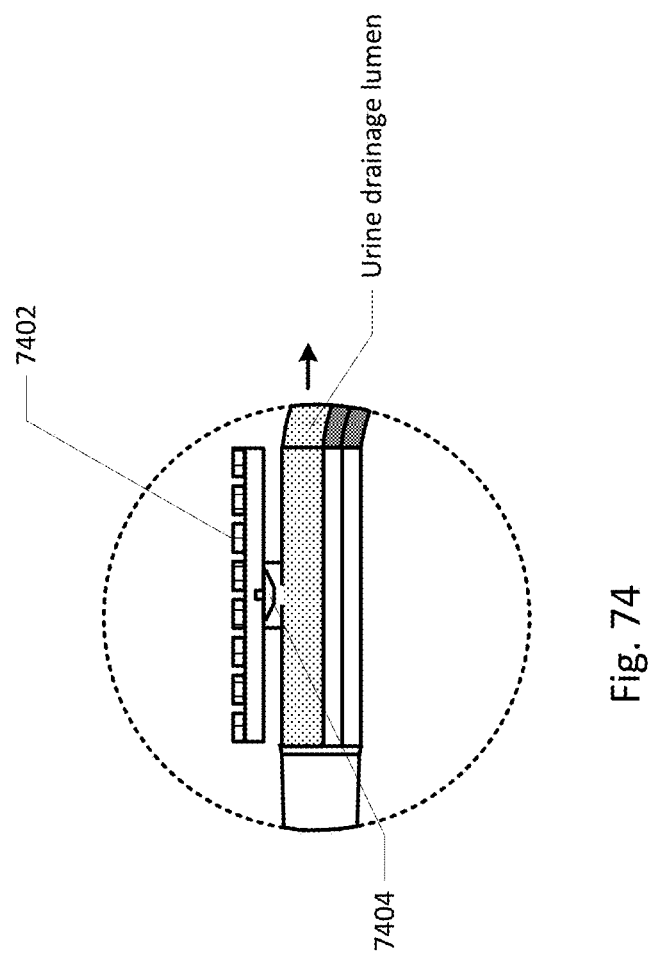

FIG. 74 shows an embodiment of the barb area which includes multiple vents 7402 and optional valve 7404. The multiple vents reduce the chances of all the vents becoming wetted from urine. The multiple vents may be in any suitable configuration including a line, a circle, etc. The multiple vents may be on one side of the barb or may encircle the barb partially or fully. For example, 2 vents may be includes, or for example, 3 vents may be included, or for example, 4 vents may be included or for example, 5 vents may be included or for example, 6 vents may be included or for example, 7 vents may be included or for example, 8 vents may be included or for example, 9 vents may be included or for example, 10 vents may be included. The embodiment shown in FIG. 74 may or may not include a positive pressure tube—it is shown without a positive pressure tube. This embodiment may or may not include a valve.

Figures 75A, 75B:
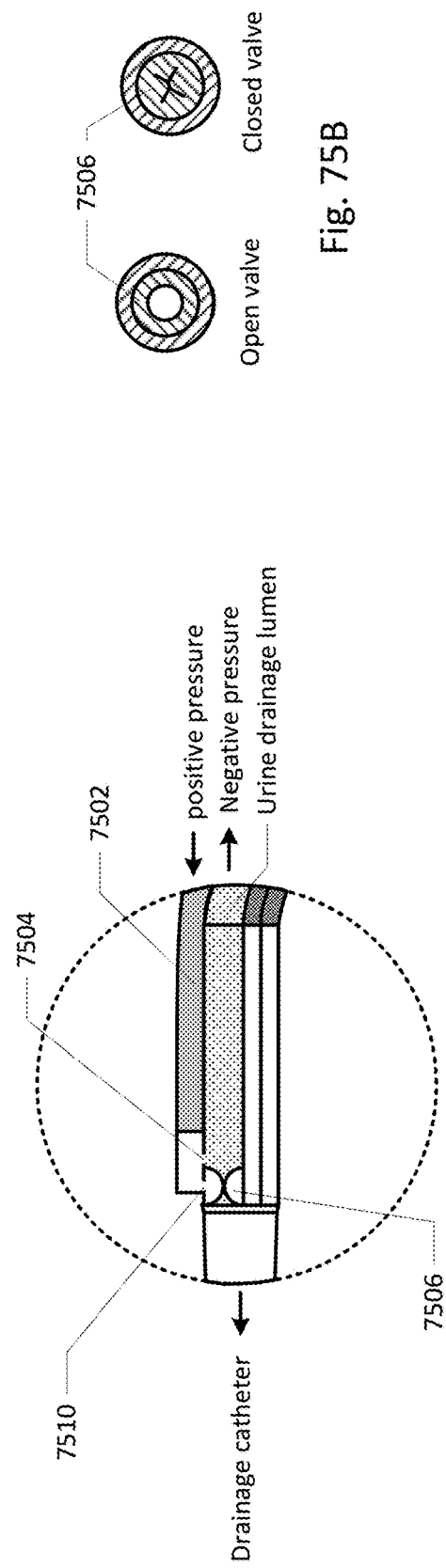

FIG. 75A shows an embodiment of the barb area which does not rely on a vent, although it may still include one or more vents. In this embodiment positive pressure tube 7502 is in fluid communication with the urine drainage lumen via opening 7504. In addition, valve, preferably a pressure sensitive valve, 7506 is between opening 7504 and the drainage catheter and in fluid communication with a positive pressure source via opening 7510. Valve 7506 is depicted in FIG. 75A as an inflatable valve, such as an annular balloon (also shown in FIG. 75B). Valve 7506 may be inflated via the same pressure source which is connected to positive pressure tube 7502 or a separate source. Valve 7506 may be in fluid communication with the lumen of positive pressure tube 7502 as is shown here or may be inflated via a separate positive pressure lumen.

In this embodiment, valve 7506 closes when positive pressure is periodically applied to the drainage lumen via positive pressure tube 7502. The closing of the valve prevents air or positive pressure from reaching the bladder and allows the positively pressurized fluid (gas or liquid) to purge the drainage lumen. When positive pressure in the positive pressure tube is reduced, the valve is opened and urine is again permitted to drain from the bladder. A slight positive pressure may be maintained in the positive pressure tube to offset the negative pressure in the urine drainage line. If higher pressure is required to clear the line of airlocks, valve 7506 is closed for the duration of the higher pressure flushing.

Figure 76:
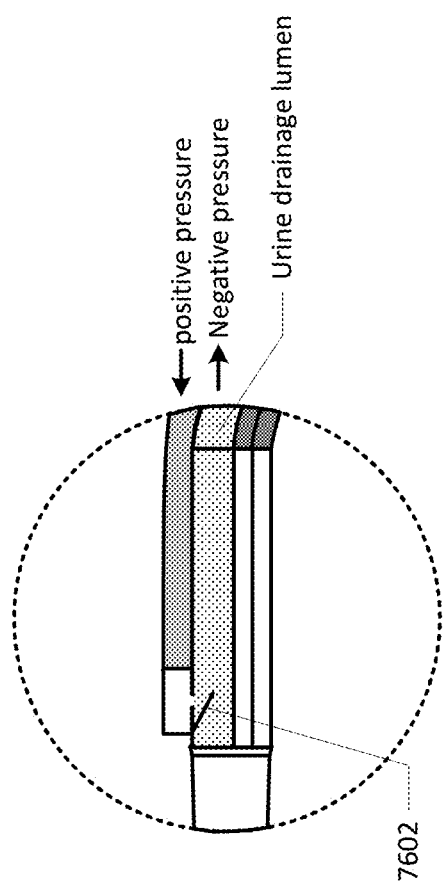

FIG. 76 shows an embodiment similar to that shown in FIG. 75, however in this embodiment, valve 7602 is a passive mechanical valve. Valve 7602 is normally in the flat, or open, position. When the positive pressure in the positive pressure tube is higher than any negative pressure in the drainage lumen, the valve automatically closes so that fluid/positive pressure is not transferred to the Foley catheter/bladder of the patient.

Alternatively, a venturi may be used to control the negative and positive pressures exuded on the barb area, similar to an automobile carburetor.

Figure 77B:
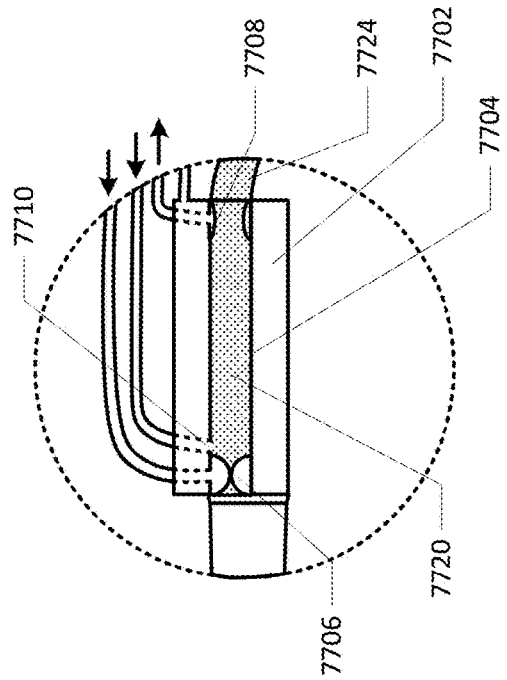
Figure 77A:
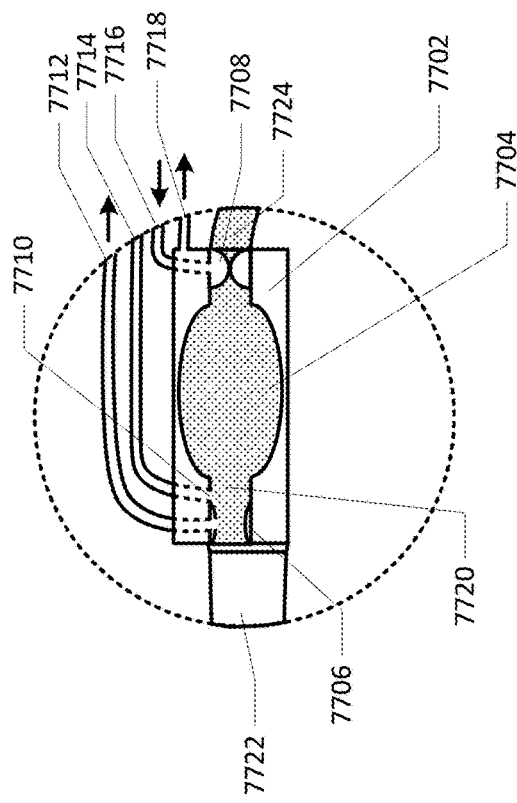

FIGS. 77A and B show another embodiment which uses a more active valve system. This embodiment includes suction chamber 7702, compliant portion 7704, patient-side valve 7706, drainage-side valve 7708, drainage lumen inlet 7710 and pressure lines 7712, 7714, 7716, 7718.

In the passive, or open, position, both patient-side valve 7706 and drainage-side valve 7708 are open. i.e., the balloon/bladders are not inflated, so that urine may pass freely from the drainage catheter 7722, through the drainage lumen 7720 of the barb, and through the drainage tubing 7724. In the open position, compliant portion 7704 is in a neutral position. When a blockage event occurs, such as an airlock, or periodically to prevent blockages, the drainage-side valve 7708 is closed by applying pressure, such as pressurized fluid (gas or liquid) through pressure line 7716. Compliant portion 7704 is expanded by applying negative pressure through pressure line 7718. Pressure line 7714 remains neutral, or closed. Pressure line 7712 remains neutral, or closed, or negative to completely deflate valve 7706. This configuration effectively applies a negative pressure to the drainage catheter by expanding compliant portion 7704 while closing off fluid flow to drainage line 7724. This configuration is shown in FIG. 77A.

The configuration of FIG. 77A lasts only a short time, for example for about 0.5 to 1 seconds, or about 1-3 seconds, or about 3-5 seconds. Then patient-side valve 7706 is closed by applying positive pressure to pressure line 7712 and drainage-side valve is opened by reducing the pressure in pressure line 7716 to neutral, or applying negative pressure to pressure line 7716. The volume of compliant portion 7704 is reduced by increasing the pressure in pressure line 7718 to neutral or applying positive pressure to pressure line 7718. Positive pressure may also be applied to pressure line 7714. This configuration is shown in FIG. 77B. In this configuration, fluid in drain lumen 7720 and drainage line 7724 is flushed with fluid (gas/liquid) through pressure line 7714 and/or by the positive pressure applied by the reduction of volume of compliant portion 7704, effectively flushing the urine through the drainage line. After flushing, the system is brought back to a neutral position where patient-side valve 7706 and drainage-side valve 7708 are both open and compliant portion 7704 is in a neutral position.

Figure 78:
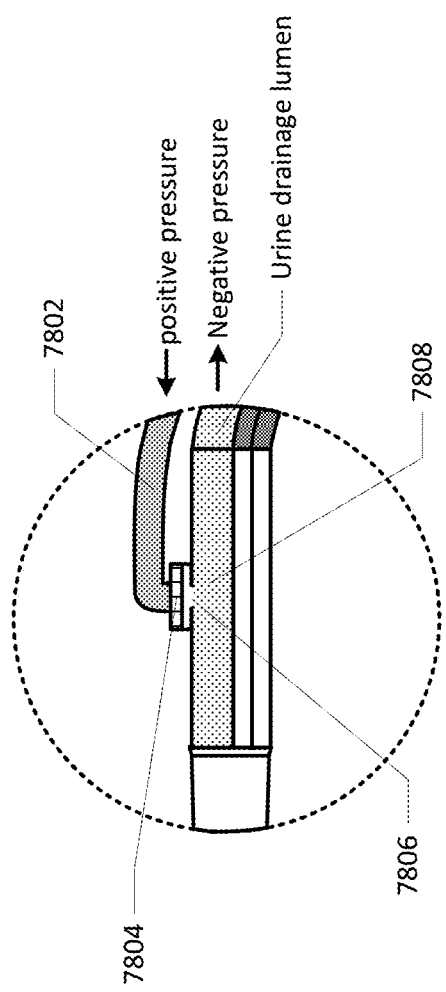

FIG. 78 shows an embodiment similar to that shown in FIG. 72, but with a positive pressure vent tube 7802, and not a separate vent tube. Vent 7804 is in fluid communication with, and in line with, the lumen of positive pressure vent tube 7802. Vent 7804 is also in fluid communication with barb area of the urine drainage lumen 7808, and is connected to area 7808 by opening 7806. Fluid/air/gas under positive pressure is passed across vent 7804, through opening 7806, and into area 7808 which is in fluid communication with the drainage lumen. In other words, positively pressured fluid/air/gas passes across the filter to the inside of the barb. The wetting of vent 7804 is prevented by controlling the positive pressure within the positive pressure tube, and across vent 7804, as well as the negative pressure of the drainage lumen. In some embodiments, the pressure within the barb area of urine drainage lumen 7808 is close to about zero. Vent 7804 may be anywhere along the length of positive pressure vent tube 7802. The embodiment shown in FIG. 78 may or may not include a one-way valve between the filter and the opening. The positively pressurized fluid/air/gas may be passed through the vent continuously, intermittently, sporadically, etc. The positively pressurized fluid/air/gas may be passed through the vent as a stream, or a puff or pulse.

Figure 79:
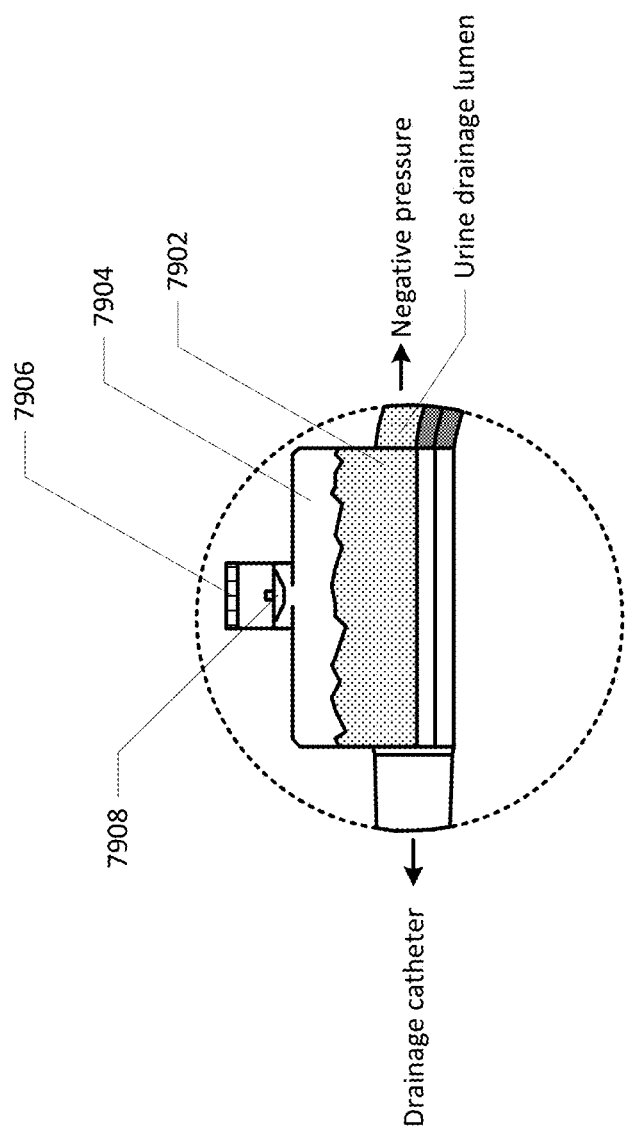

FIG. 79 shows an embodiment where the area within the barb which is in fluid communication with the urine drainage lumen has a larger volume. Fluid 2902, such as urine, flows from the drainage catheter, into large reservoir 7904, and then into the urine drainage lumen. Reservoir 7904 is large enough that it is unlikely to ever be filled completely with liquid. The volume of the reservoir which is not filled with liquid will be filled with air or gas. One way valve 7908 may also be present. Since reservoir 7904 always has some air/gas in it, vent 7906 may be situated so that it is seldom in contact with the urine/fluid in the reservoir. In other words, the vent may be on the side of the bubble within the reservoir. More than one vent may be present to make sure that at least one vent is always in fluid communication with the gas bubble within the reservoir. In some embodiments, the volume of reservoir 7904 may be larger than the volume of the inner lumen of the drainage tube.

Figure 80B:
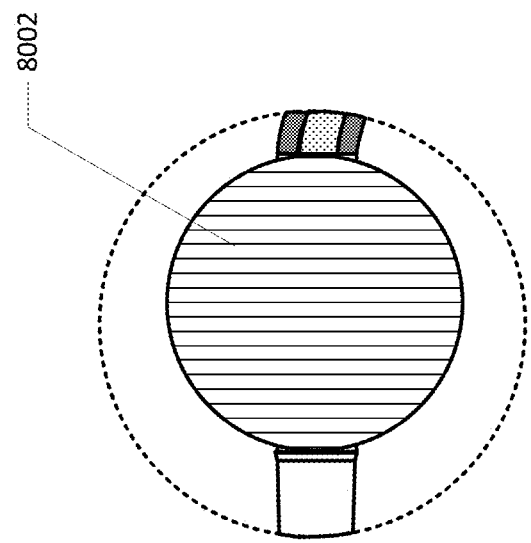
Figure 80A:
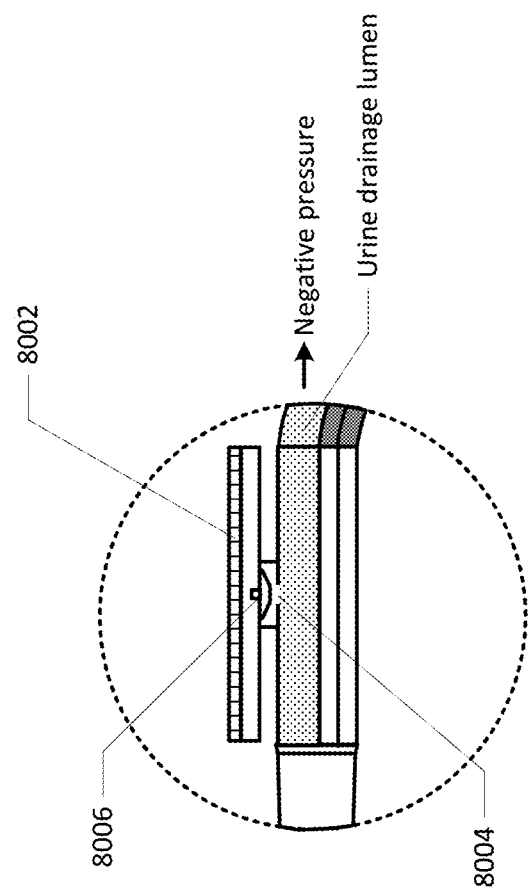

FIGS. 80A and 80B show an embodiment in which the area of the vent is very large. Vent 8002 is shown here to be a large flat circle or disc, however the vent may be any shape and size. The vent may be flat or curved, such as to wrap around the barb area. The embodiment here is shown with one opening 8004 and a one-way valve 8006, however other embodiments may have more than one opening and may or may not have a valve. Some embodiments may have a filter surface of greater than about 1 cm2. Some embodiments may have a filter surface of greater than about 2 cm2. Some embodiments may have a filter surface are of about 3 to about 4 cm2. Alternatively, some embodiments may have a filter surface are of about 2 to about 4 cm2. Alternatively, some embodiments may have a filter surface are of about 4 to about 6 cm2. Alternatively, some embodiments may have a filter surface are of about 6 to about 10 cm2.

Figure 81:
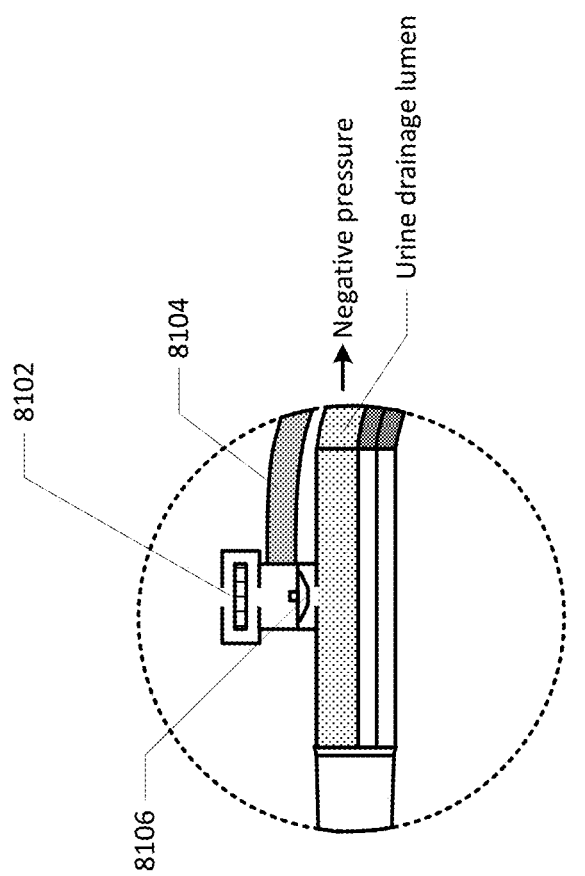

FIG. 81 shows an embodiment with a replaceable vent. Replaceable vent 8102 is shown here in an embodiment with positive pressure tube 8104 and one-way valve 8106, however embodiments may also exist without the positive pressure tube and/or valve. Replaceable vent 8102 may be removed and replaced via an attachment mechanism such as a luer-lock, a snap lock, a slide-in lock, a press-fit, or any other suitable mechanism. Vent replacement may be performed periodically, such as once per day, or as needed, for example when the controller alerts the user that the vent is no longer working properly, or when the user notices that the vent is no long functioning. The vent may have a chemical sensitive to urine or a component of urine which changes color to indicate that it has been wetted. For example, a pH sensitive, or other chemical or attribute sensitive paper may be used in the replaceable vent which changes color and is visible to the user. The replaceable vents may be disposable.

Figure 82B:
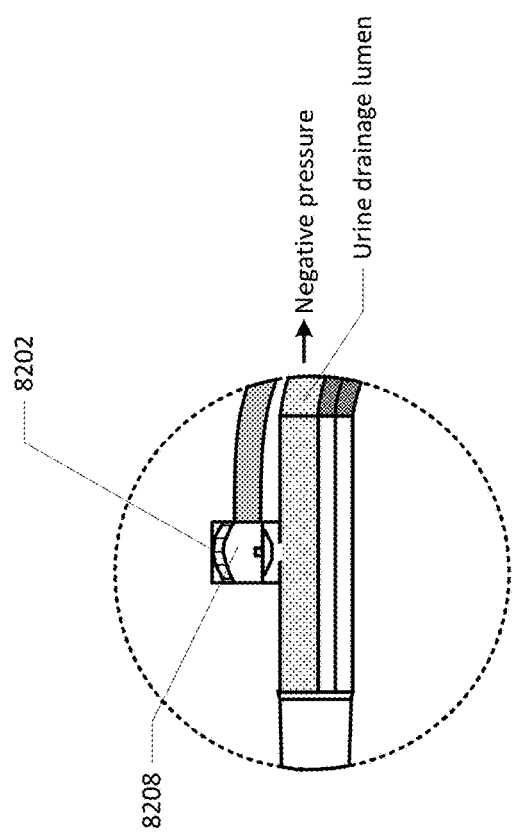
Figure 82A:
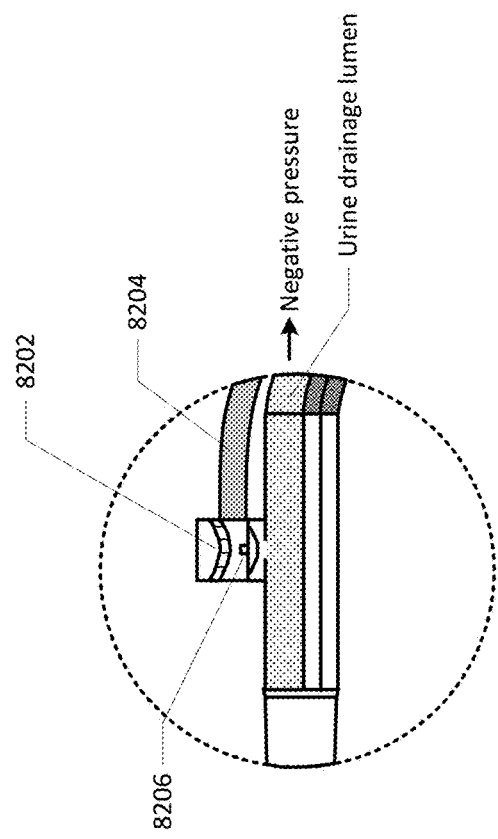

FIGS. 82A and 82B show an embodiment where the filter is flexible. In this embodiment, filter 8202 may be flexible or deformable, i.e. it may be convex/concave, or loose in its housing, the movement of flexible filter 8202 may help unclog the filter if it has been wetted or contaminated. The movement of the filter may be controlled by positive pressure via positive pressure tube 8204, negative pressure via the urine drainage lumen, valve 8206, or any single or combination of the above. Some embodiments may also include a mechanical mechanism to agitate, shake, vibrate, bend and/or move filter 8202. FIG. 82A, for example, shows an example of an embodiment where negative pressure in the urine drainage lumen causes the filter to be concave. FIG. 82B shows the same example after positive pressure has been applied to the vent via positive pressure tube 8204. The pressure within vent housing 8208 may be controlled by the crack pressure of the one-way valve, or by the relative negative and positive pressures within the urine drainage lumen and the positive pressure tube. Similar embodiments may also exist where the filter is not flexible, but pressure is controlled within vent housing 8208 in a similar way which keeps the filter dry.

Alternatively, the filter (flexible or otherwise) may be wiped or scraped mechanically, either manually or automatically. Alternatively, the filter may include a chemical which inhibits protein adhesion and/or build-up, such as an enzymatic detergent. Alternatively, the filter may include a chemical which inhibits biofilm, such as an antibacterial agent.

Figure 83:
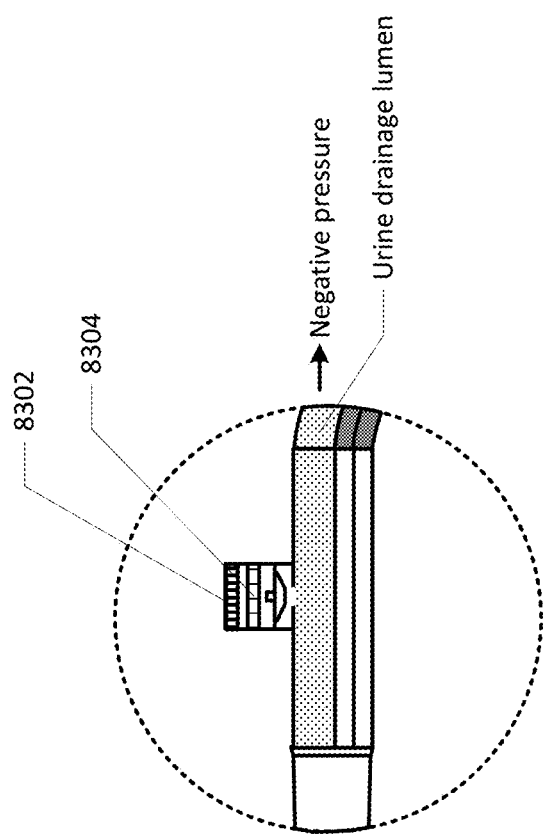

FIG. 83 shows an embodiment with multiple stacked filters. Filters of different pore sizes may be used in a stacked fashion. For example, courser pore filter 8304 may protect fine pore filter 8302 from wetting. Course pore filter 8304 may be placed between the fluid/urine and fine pore filter 8302. In this configuration, liquid/urine would need to pass courser filter 8304 to contact fine filter 8302. More than 2 filters can be stacked in this manner, either with graduated pore sizes, or similar pore sizes, or any pore sizes. For example, increasingly fine pore filters may be stacked so that the finer pore filters are further from the urine/liquid. Alternatively, one or more course pored filters, of the same or different pore size, may be placed between the urine/liquid and a fine pored filter. A one-way valve may or may not be present. The pore size of courser pore filters 8304 may be around 10 microns. Alternatively, the pore size of courser pore filters 8304 may be around 10 to around 20 microns. Alternatively, the pore size of courser pore filters 8304 may be around 10 to around 30 microns.

Figure 84:
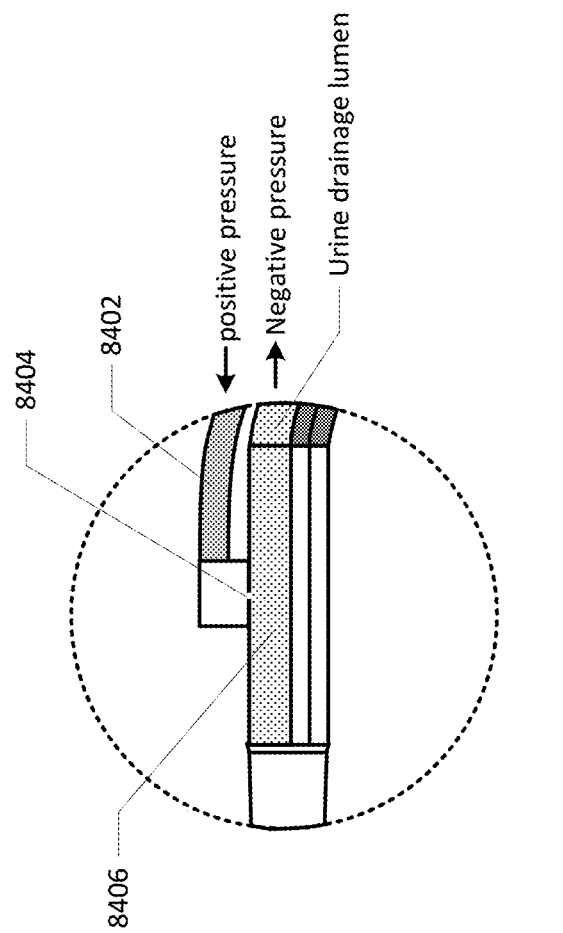

FIG. 84 shows an embodiment with continual positive pressure exerted on the barb area by the fluid within the positive pressure tube. Positive pressure tube is under substantially constant positive pressure so that fluid (preferably air/gas) is continually passing through opening 8404. The positive pressure exerted on the fluid in interior 8406 of the barb is controlled so that fluid does not backflow into the urine drainage catheter. In other words, the negative pressure exerted on the fluid in interior 8406 is always greater or about the same as the positive pressure exerted on the fluid in interior 8406. The positive pressure may be controlled at the controller, and/or it may be controlled by the size of opening 8404, for example, by sizing opening 8404 very small. For example, the diameter of opening 8404 may be less than about 1 mm. Alternatively, the diameter of opening 8404 may be less than about 2 mm. Alternatively, the diameter of opening 8404 may be less than about 3 mm. Alternatively, the diameter of opening 8404 may be less than about 4 mm.

Figure 85:
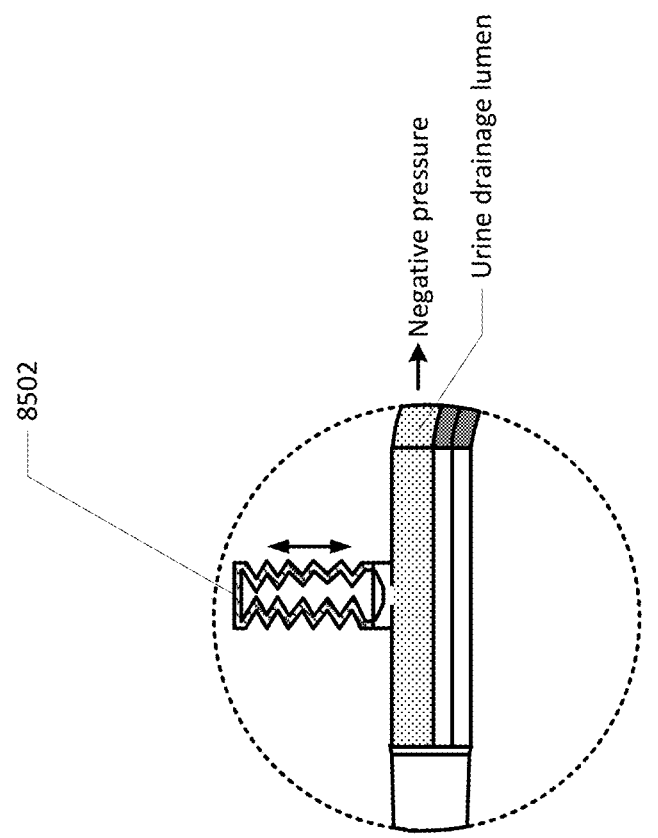

FIG. 85 shows an embodiment with an accordion shaped vent. Vent 8502 in this embodiment is shaped like an accordion. The vent may be compressed in the direction of the double headed arrow. This compression may clear the vent of clogs/wetting etc. The compression may be done manually, automatically/mechanically, and/or using pressure (negative and/or positive) within the vent area.

Figure 86:
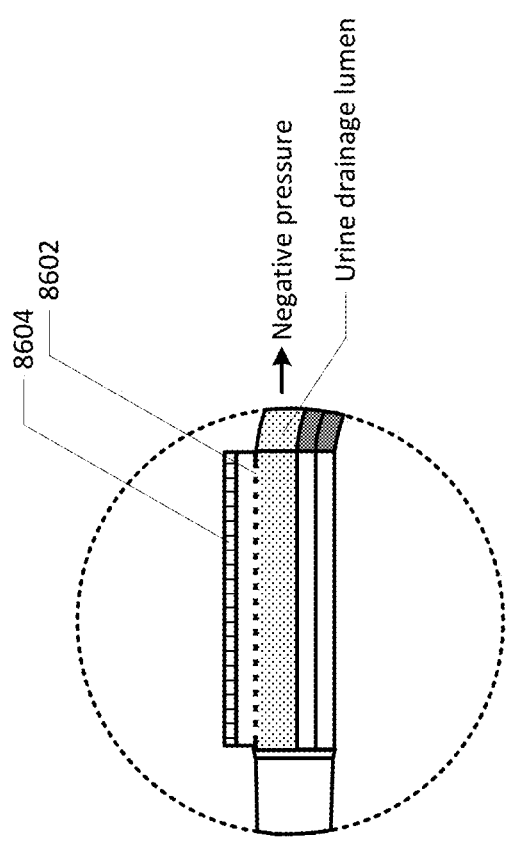

FIG. 86 shows an embodiment with a single vent and multiple openings. In this embodiment, more than one small openings 8602 separate the urine drainage lumen from vent 8604. The small openings prevent fluid from coming in contact with vent 8604. The multiple openings may serve as redundancy, so that if one or more openings become clogged, other openings remain open. The openings may also be used to control the passage of air/gas/fluid through vent 8604—more holes result in less resistance to air flow, fewer holes results in higher resistance to air flow.

Any of the embodiments herein may include physiological pressure measurements or they may be used without physiological pressure measurements. For example, the system shown in FIG. 67 through FIG. 86 and other embodiments may not include the thermistor nor the pressure lumen and may be used with a standard Foley catheter.

In some embodiments, pressure may be measured at the positive pressure tube/drainage tube junction. Alternatively, the pressure may be measured at the sensing Foley catheter/drainage tube junction, or in the area of the barb. Pressure may be measured at any of these locations by incorporating an additional tube or lumen, which is in fluid communication with the pressure tube/drainage tube junction, or with the area of the barb at one end, and in fluid communication with a pressure sensor or transducer at the other end. For example, this pressure measuring lumen may be in fluid communication with the controller which houses a pressure sensor at one end (the sensor end), and in fluid communication with the positive pressure tube/drainage tube junction on the other end (the sensing end). A pressure sensitive membrane may be present at the sensing end to prevent urine contamination of the lumen.

Airlocks may also be detected so that they can be optimally cleared and/or avoided. Using any of the embodiments herein, the controller may apply a slight positive or negative pressure to the urine drainage lumen and sense the response. A dampened response may indicate the presence of airlocks, a less dampened response may indicate fewer airlocks since air is more compressible than urine. If excessive airlocks are detected, the controller may initiate airlock clearing, for example by applying negative pressure to the drainage lumen.

Figure 87:
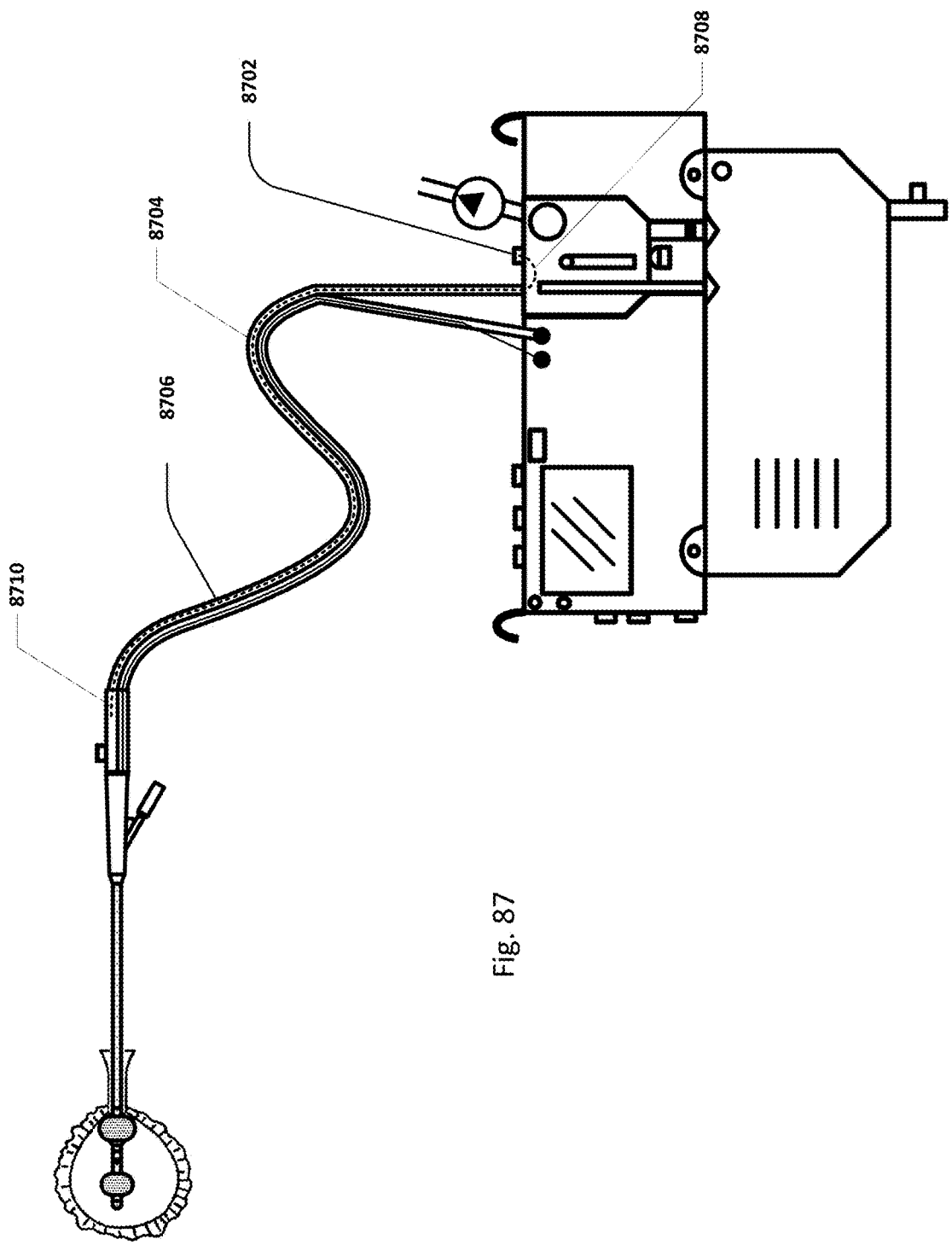
FIG. 87 shows an embodiment of the sensing Foley catheter system with an internal vent tube.

The vent tube may be a separate tube from the drainage tube and may be inserted within the drainage lumen or even within the Foley catheter. FIG. 87 shows an embodiment of the sensing Foley catheter system where the vent tube is inside the urine drainage tube. This type of embodiment has the advantage that it can be used with any standard drainage tube. The vent tube essentially places a vent anywhere within the drainage lumen, either within the drainage tube, or within the Foley catheter. The vent tube may be slidably inserted within the drainage tube and/or the Foley catheter, and may be moved at any time.

In the embodiment shown in FIG. 87, vent tube 8704 may be open to vent/filter 8702 (which is open to atmospheric pressure) within the collection reservoir at one end (the "air end" 8708), and open at the other end (the "urine end" 8710) which is within urine drainage lumen 8706. Although the vent tube is shown here to terminate within the barb at the base of the Foley catheter, the vent tube may terminate anywhere within the urine drainage lumen including anywhere within the drainage tube or within the Foley catheter. The vent tube may remain in one location, or may be moved within the system to maximize urine drainage and minimize airlocks and damage to the bladder caused by negative pressure within the bladder.

Figure 88:
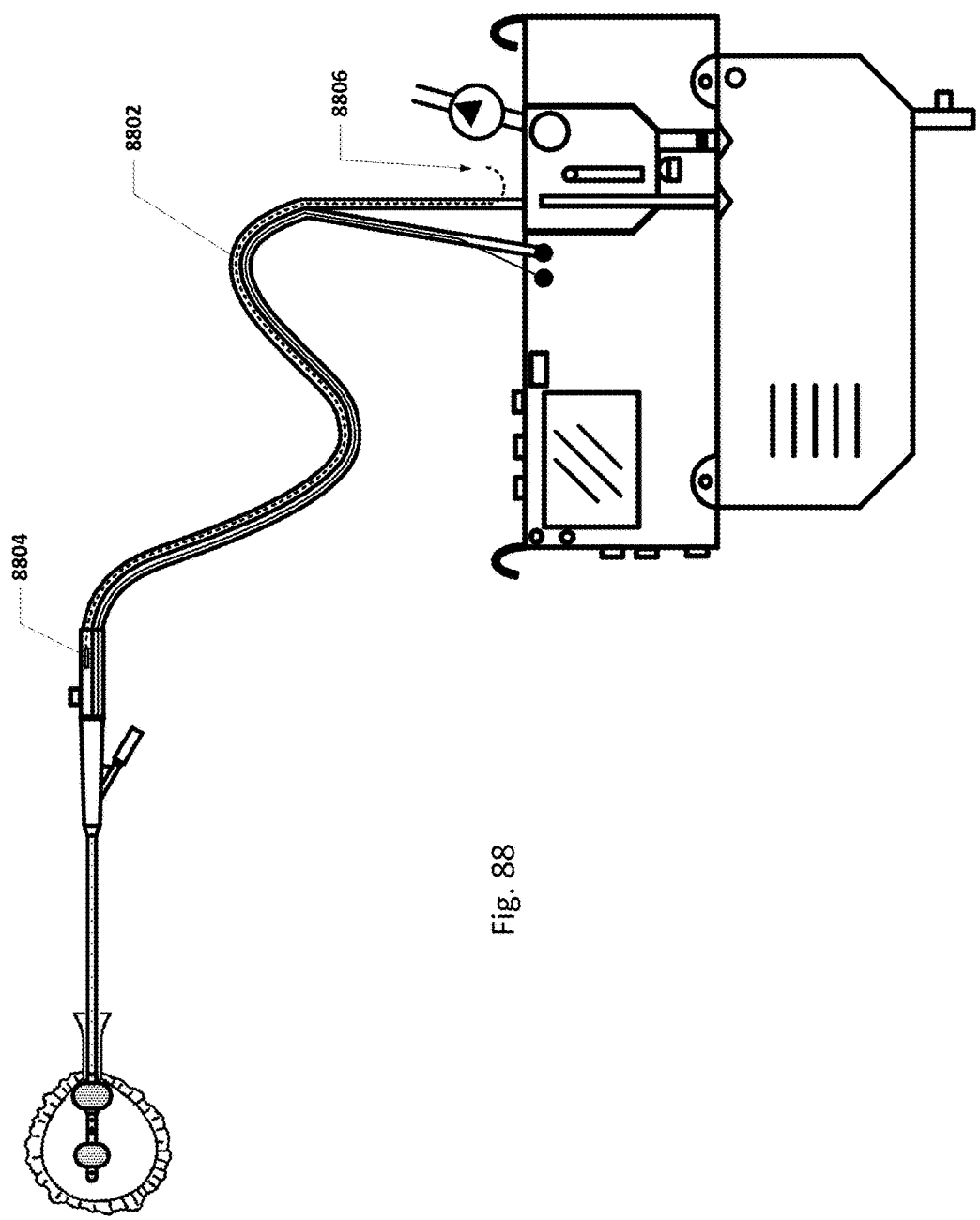
FIG. 88 shows an embodiment of the sensing Foley catheter system with an internal vent tube.

FIG. 88 shows another embodiment of the sensing Foley catheter system where vent tube 8802 has vent/filter 8804 at the "urine end" of the tube, and is open to atmosphere on the "air end" 8806 of the tube. There may also be a filter/vent at both ends. The "air end" of the vent tube may exit the drainage lumen via a y-arm adapter, a stopcock or other standard ways. The "air end" of the vent tube may exit the system from within the collection vessel, via a channel or port incorporated into the collection vessel. Again, the vent tube may be used with any urine drainage tube including a standard urine drainage tube.

Figure 89:
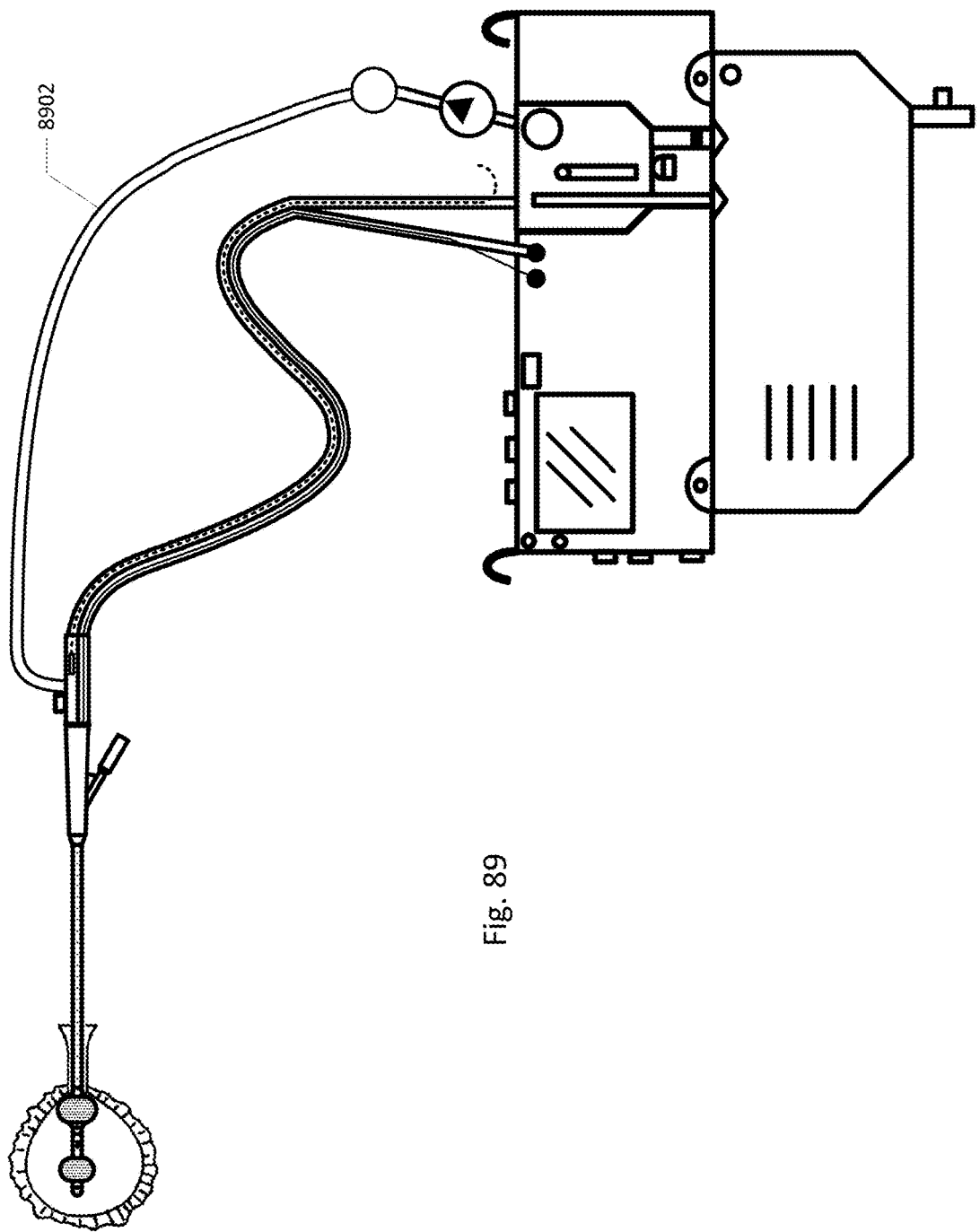
FIG. 89 shows an embodiment of the sensing Foley catheter system with an internal vent tube and a positive pressure tube.

FIG. 89 shows an embodiment similar to that shown in FIG. 88 with the addition of positive pressure tube 8902.

Figure 90:
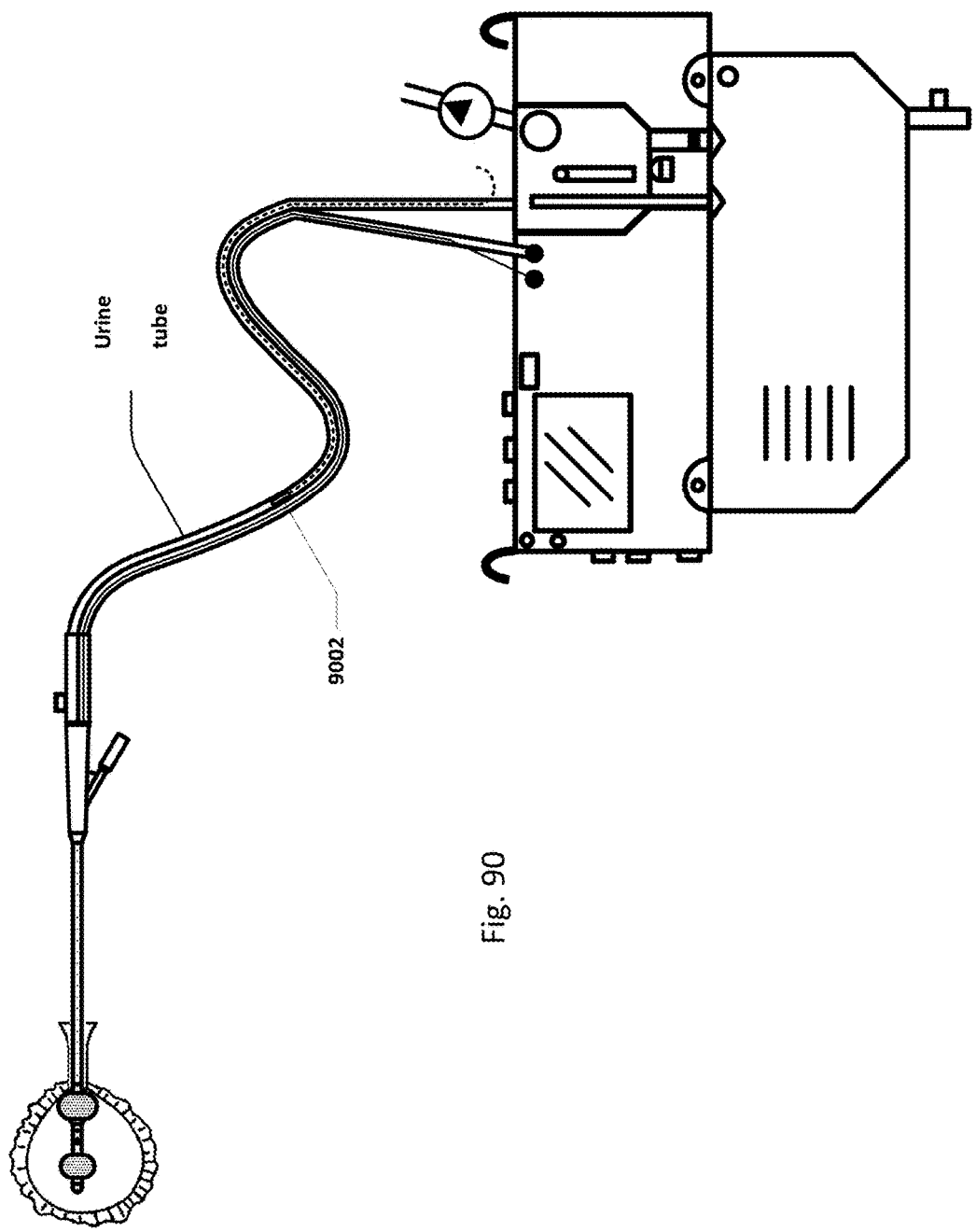
FIG. 90 shows an embodiment of the sensing Foley catheter system with an internal vent tube.
Figure 91:
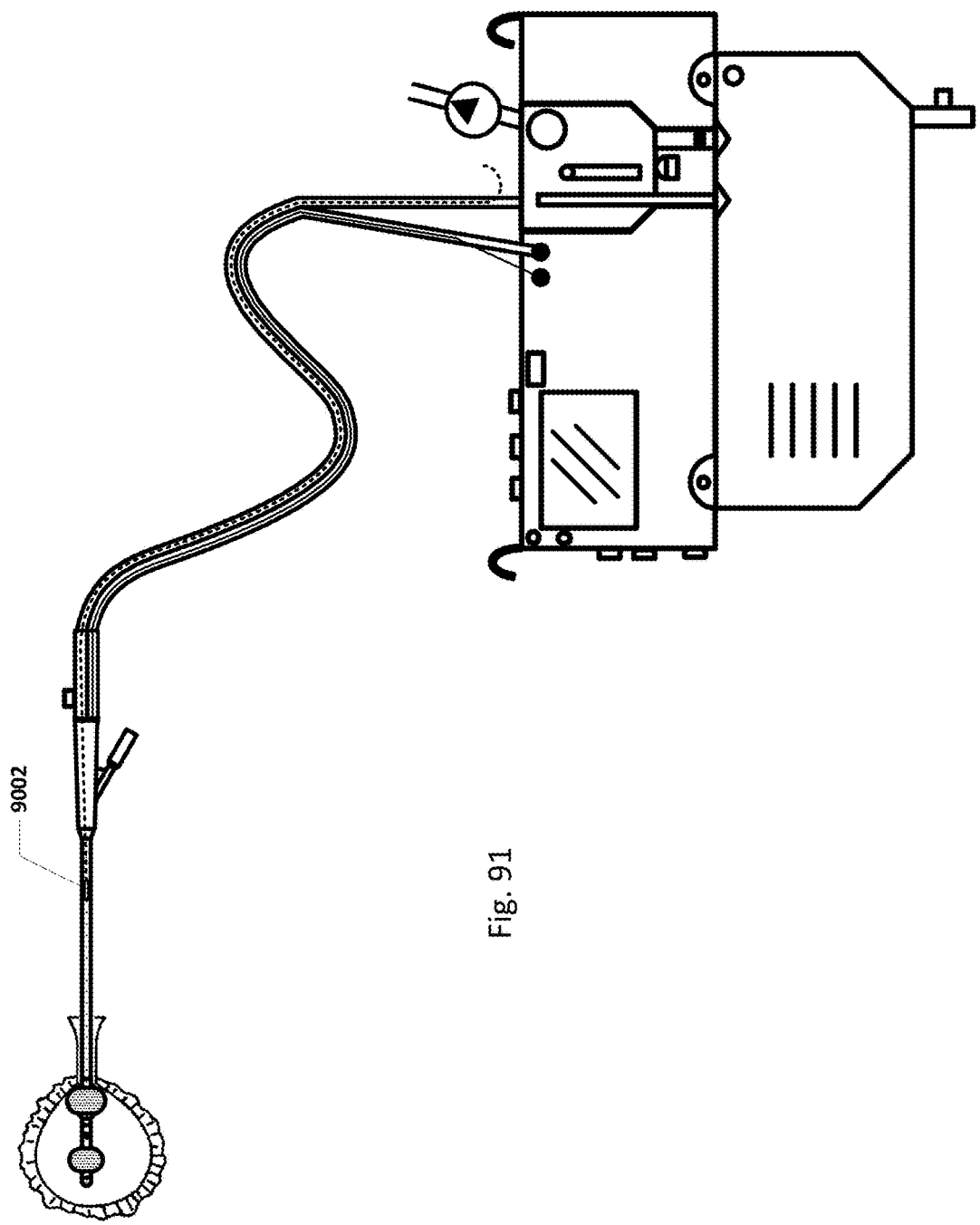
FIG. 91 shows an embodiment of the sensing Foley catheter system with an internal vent tube.

FIGS. 90 and 91 show the vent tube at different locations within the sensing Foley catheter system. In FIG. 90, the "urine end" 9002 of the vent tube is only part way within the drainage tube. For example the vent tube may be inserted through approximately half of the drainage tube. Or for example the vent tube may be inserted through approximately one third of the drainage tube. Or for example the vent tube may be inserted through approximately two thirds of the drainage tube. In FIG. 91, the "urine end" 9002 of the vent tube is within the Foley catheter. The location of the "urine end" of the vent tube is determined based on maximizing urine drainage and minimizing the effect of airlocks on the drainage and minimizing negative pressure within the bladder.

The vent tube may incorporate one or more than one filter/vents. The vent tube may incorporate one or more than one cutouts that are in fluid communication with the inner lumen of the vent tube, and which are ultimately in fluid communication with a vent/filter, either in the collection reservoir or elsewhere. The multiple filter/vents or multiple cutouts may be around, or along the vent tube or both. The vent tube may include a UV light directed at the filter, at the "urine end", or elsewhere, to maintain sterility.

Figure 92B:
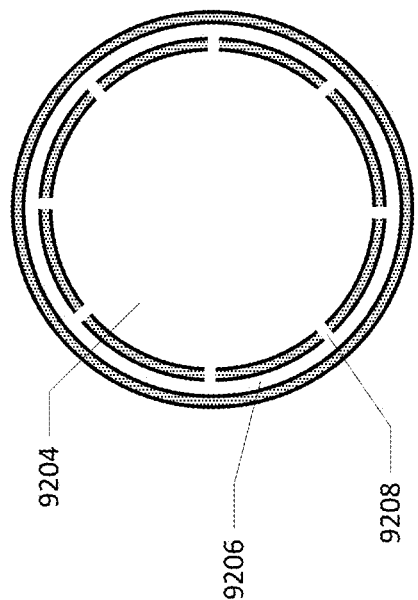
FIGS. 92A and 92B show some embodiments of the drainage lumen.
Figure 92A:
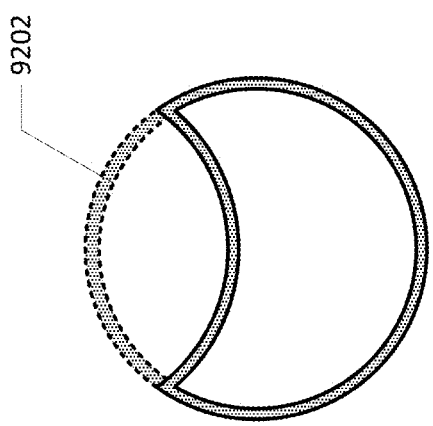

FIGS. 92A and 92B show some possible embodiments of the drainage lumen, for example drainage lumen 1012 shown in FIG. 10A. FIG. 92A shows a drainage lumen with collapsible/expandable portion 9202. Portion 9202 may be manufactured from a lower durometer material than the rest of the drainage lumen, allowing it to collapse or expand depending on the pressure within. The lumen will collapse down to a lower internal area/volume in lower or negative pressures and will expand with higher or positive pressures. Airlocks may be reduced by this change of lumen volume at different pressures. This type of lumen may be incorporated into any of the embodiments herein.

FIG. 92B shows an embodiment of a drainage lumen which includes 2 lumens. The inner lumen shown here is a negative pressure/urine drainage lumen 9204. The outer lumen is a positive pressure lumen 9206. Between the two lumens are openings 9208. The openings may or may not include a filter membrane. The two lumens may be concentric, as shown here, or adjacent. Positive pressure lumen serves essentially the same role as the positive pressure vent tube shown elsewhere herein. Either constantly, or periodically, positive pressure is exerted on positive pressure lumen 9206 as negative pressure is exerted on drainage lumen 9204, resulting in clearance of drainage lumen 9204.

FIGS. 93A through 93E show another embodiment of the drainage lumen. This embodiment also includes drainage lumen 9302 and positive pressure lumen 9304. In this embodiment, positive pressure lumen 9304 is expandable and collapsible. In the positive pressure lumen's expanded state, it partially or fully blocks the drainage lumen. In the positive pressure lumen's collapsed state, the drainage lumen is substantially open allowing fluid to flow freely through the drainage lumen. FIG. 93A shows the drainage lumen in the closed state near the patient side of the drainage tube. FIG. 93B shows the drainage lumen in the closed state further from the patient. FIG. 93C shows the drainage lumen in the open state.

FIG. 93D shows a longitudinal view of the drainage tubing in the closed state. FIG. 93E shows a longitudinal view of the drainage tubing in the open state. In the open state, as shown in FIGS. 93C and 93E, positive pressure lumen 9304 as collapsed and does not substantially obstruct drainage lumen 9302, allowing urine to flow freely from the body to the reservoir. When airlock or other blockage clearance of the drainage tube is performed, the positive pressure lumen is inflated to urge the urine/liquid down the drainage tube toward the collection reservoir. The patient end 9306 of the positive pressure lumen may be of a larger diameter and/or a lower durometer than the reservoir end 9308 of the positive pressure lumen. This allows the patient end of the positive pressure lumen to inflate before the reservoir end inflates. In this way, the drainage lumen is blocked first nearest the patient, and then the either substantially all of the drainage lumen is filled or part of the drainage lumen is filled with the inflation of the remainder of the positive pressure lumen. The positive pressure lumen may be inflated at either the patient end or the reservoir end of the drainage tube. One or more filters may be present along the length of the drainage lumen.

Embodiments of the sensing Foley catheter system may include the ability to measure pressure within the bladder via a pressure balloon connected to the Foley catheter, or via a pressure balloon or other pressure sensor inserted within the drainage lumen of the drain tube and/or the Foley catheter. For example, see FIGS. 94A-94C.

Figure 94A:
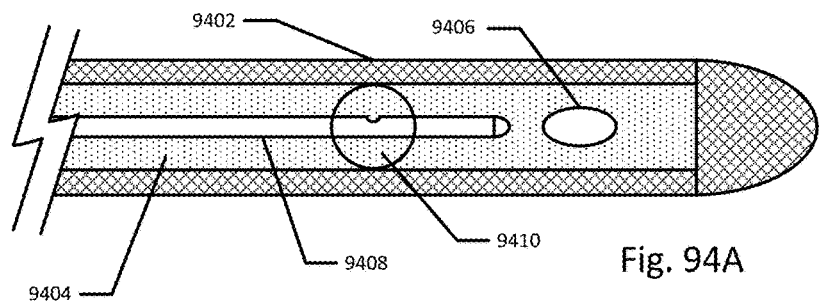
FIGS. 94A-94C show embodiments of the sensing Foley catheter system where the pressure sensor is on a separate catheter.
Figure 94B:
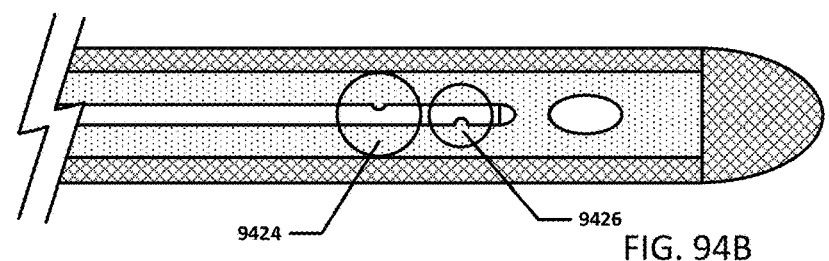
Figure 94C:
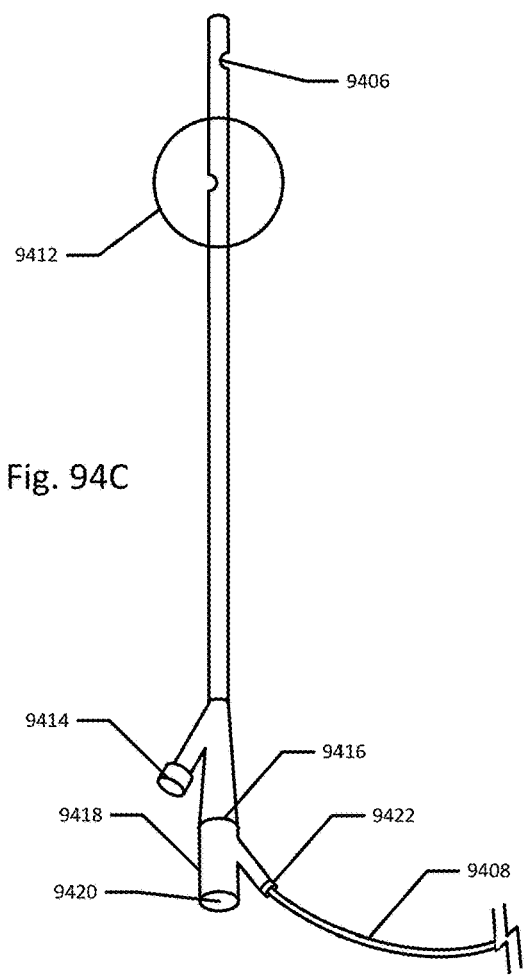

FIGS. 94A-94C show embodiments of the sensing Foley catheter system where the pressure sensor is in fluid communication with the urine lumen of a Foley catheter, but may reside on a separate catheter. Foley type catheter 9402 is shown with urine lumen 9404 and urine drainage opening 9406. Small pressure sensing catheter 9408 with pressure sensing balloon 9410 is shown inside the urine drainage lumen of the Foley type catheter. The outer diameter of the pressure sensing catheter is small enough so that it fits within the urine drainage lumen of a Foley type catheter. For example the outer diameter of the pressure sensing catheter may be less than about 4 mm, alternatively the outer diameter of the pressure sensing catheter may be less than about 3 mm, alternatively the outer diameter of the pressure sensing catheter may be less than about 2 mm, alternatively the outer diameter of the pressure sensing catheter may be less than about 1 mm.

The pressure sensor on the pressure sensing catheter may be near the distal end of the pressure sensing catheter, or it may be anywhere along the length of the catheter. The pressure sensor may be a pressure sensing balloon, or it may be any type of pressure sensor, such as a piezoelectric sensor, a mechanical sensor, etc. In the case of a pressure sensing balloon, the inflated balloon may be smaller than the inner diameter of the urine drainage lumen of the Foley type catheter, or the inflated balloon may be large enough to fill the urine drainage lumen of the Foley type catheter.

The inflated pressure sensing balloon may fill the urine drainage lumen of the Foley type catheter allowing for better pressure measurements. The pressure sensing balloon may be periodically deflated or partially deflated to allow urine to flow from the bladder through the Foley type catheter. The controlling of the pressure sensing balloon inflation cycle may be controlled by the controller of the present invention.

FIG. 94B shows an embodiment of the pressure sensing catheter which has both occluding balloon 9424, and pressure sensing balloon 9426. The occluding balloon occludes the urine drainage lumen so that the pressure sensing catheter is only sensing pressures between the occluding balloon and the bladder, which may more accurately and precisely measure the pressures within the bladder.

The outer diameter of the inflated pressure sensing balloon may less be than about 5 mm, alternatively the outer diameter of the pressure sensing catheter may be less than about 4 mm, alternatively the outer diameter of the pressure sensing catheter may be less than about 3 mm, alternatively the outer diameter of the pressure sensing catheter may be less than about 2 mm, alternatively the outer diameter of the pressure sensing catheter may be less than about 1 mm.

FIG. 94C shows a standard Foley type catheter with retention balloon 9412, urine drainage opening 9406, retention balloon port 9414, and urine drainage port 9416. Adapter 9418 is shown connected to urine drainage port 9416. Adapter 9418 has two ports, urine drainage port 9420 and secondary urine lumen port 9422. Pressure sensing catheter 9408 is shown in urine lumen port 9422. In this way the pressure sensing catheter is in fluid communication with the urine drainage lumen of the Foley type catheter. Proximal end of pressure sensing catheter 9408 is connected to a pressure sensor such as a pressure transducer, similar to other embodiments herein. Pressure sensing catheter 9408 may have only a single lumen, the sensing balloon lumen, or it may contain other lumens. In the case where the pressure sensor of the pressure sensing catheter is a mechanical pressure sensor, the pressure sensing catheter may have no lumens, or the pressure sensing catheter may have a balloon for sealing the urine drainage lumen of the Foley type catheter.

The pressure sensing catheter may also be inserted through the urine drainage lumen of the drainage tube.

Pressure measurements can be taken over time using the pressure sensing catheter and analyzed in any of the ways disclosed herein. To improve pressure measurements, drainage port 9420 may be periodically closed or blocked. Blocking of drainage port 9420 may be done mechanically, with a stopcock or valve, or automatically, for example with a solenoid valve connected to the controller. An advantage of this embodiment is that pressure sensing catheter 9408 can be used with any Foley type catheter to measure pressure. In addition, pressure sensing catheter 9408 can be inserted and removed from a Foley type catheter after the Foley type catheter is already in place in the patient's bladder.

The pressure sensing catheter may be combined with the vent tube shown in other figures. In this way, the pressure sensing, urine drainage, anti-airlock, venting components of the sensing Foley catheter system can be used with any standard Foley catheter and drainage tube. Alternatively, a pressure sensing catheter/vent tube combination may be used with a more specialized Foley catheter and/or drainage tube.

In any of the embodiments that include any type of airlock clearing mechanism, the airlock clearing may be performed continuously, periodically, on demand, or when an airlock condition is sensed. The airlock clearing mechanism prevents or reduces airlocks. For example, the airlock clearing mechanism may reduce airlocks such that airlocks are cleared at least every 60 minutes. Alternatively, airlocks may be cleared at least every 45 minutes. Alternatively, airlocks may be cleared at least every 30 minutes. Alternatively, airlocks may be cleared at least every 20 minutes. Alternatively, airlocks may be cleared at least every 10 minutes. Alternatively, airlocks may be cleared at least every 5 minutes. Alternatively, airlocks may be cleared at least every 1 minute.

In any of the embodiments that include a vent or filter or vent tube as part of the barb area or drainage tube, fluid (i.e. urine) drainage may be discontinuous, i.e. interrupted, because of gas/air introduced into the drainage lumen via the vent/filter/vent tube. In other words, the drainage lumen may alternate liquid (i.e. urine) and gas.

In any of the embodiments that include measuring urine output volume in real time, real time may mean urine output volume measurements reported are accurate to within about 1 minute. Alternatively, real time may mean urine output volume measurements reported are accurate to within about 5 minutes. Alternatively, real time may mean urine output volume measurements reported are accurate to within about 10 minutes. Alternatively, real time may mean urine output volume measurements reported are accurate to within about 20 minutes. Alternatively, real time may mean urine output volume measurements reported are accurate to within about 30 minutes. Alternatively, real time may mean urine output volume measurements reported are accurate to within about 60 minutes.

Bubbles in urine—prevent bubbles and/or prevent impact on measurements

On occasion protein, or other components, in the urine may cause excessive bubbling in the urine within the drainage lumen and/or the collection vessel which may cause problems such as wetting of the vent/filter(s), urine entering the overflow area of the collection vessel, inaccurate measurements etc. Some embodiments of the sensing Foley catheter system incorporate anti-bubble mechanisms.

In some embodiments, such as those that incorporate a positive pressure tube, precise control of the pressure within the urine drainage can be obtained. It is possible to occasionally exert a slight positive pressure within the drainage system (i.e. the drainage lumen and/or the collection chamber) to collapse any bubbles which are present or to prevent bubble from forming.

A surfactant, such as silicone, may be added to the system. For example, a slow dissolving silicone capsule may be added to the collection reservoir. Alternatively a surfactant coating may be used on the inside of the drainage lumen and/or the inside of the collection vessel.

Figure 95C:
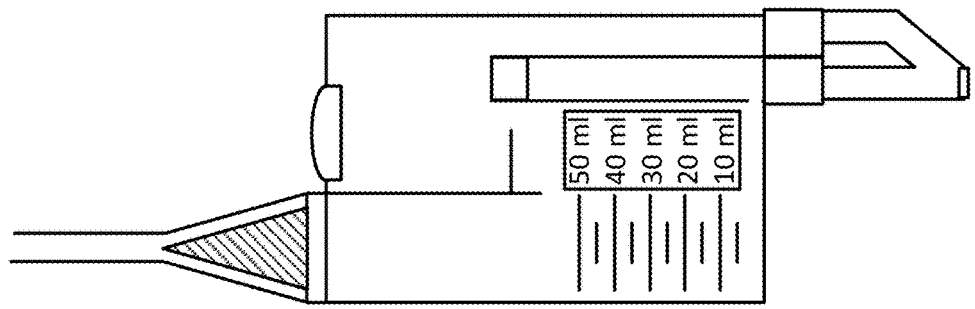
FIGS. 95A-C show embodiments of the sensing Foley catheter system with bubble reduction mechanisms.
Figure 95B:
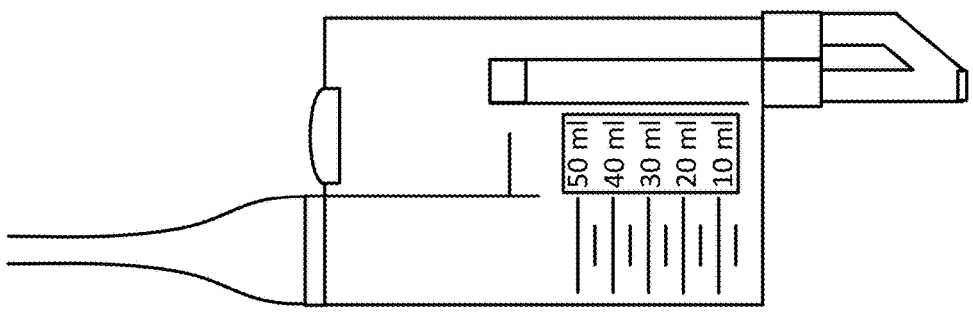
Figure 95A:
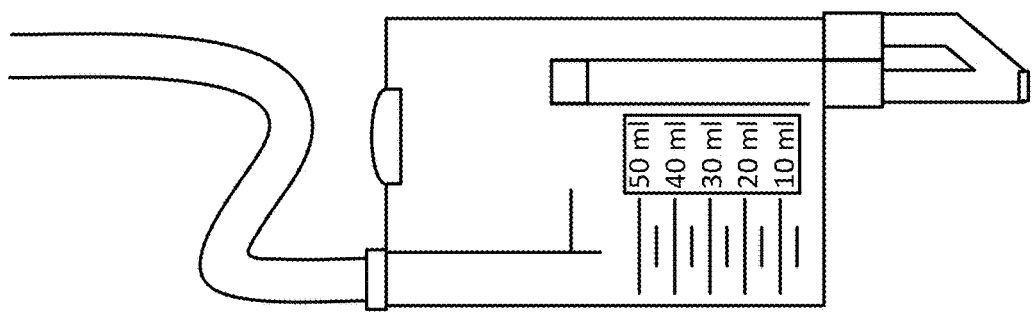

Bubble may be eliminated or reduced at the junction of the drain tubing and the collection vessel. Some embodiments are shown in FIGS. 95A-C. For example, the base of the drainage tubing may be S-drain shaped (as in the drain under a sink), the inner diameter of the drainage tubing may expand near the junction with the collection vessel, or elsewhere. The drainage tubing may be bulb shaped or cone shaped. The drain lumen may become annularly shaped, as is shown in FIG. 95C. In this embodiment, the fluid is forced to flow down the side of a slanted cone surface to reduce bubbles, similar to how beer is poured down the side of a glass instead of into the center of a glass to reduce beer foam. The bubble reducing feature is shown here at the base of the drainage tube, but may be in any part of the drainage tube or the system. In some embodiments, the drainage lumen may be flattened, again to force the urine in contact with surfaces. For example, the urine drainage lumen may flatten down to less than about 1 mm. The urine drainage lumen may flatten down to less than about 2 mm. The urine drainage lumen may flatten down to less than about 3 mm.

Figure 96D:
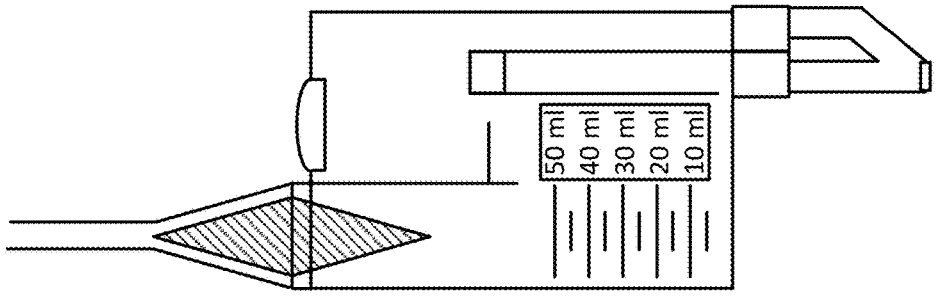
FIGS. 96A-D show embodiments of the sensing Foley catheter system with bubble reduction mechanisms.
Figure 96C:
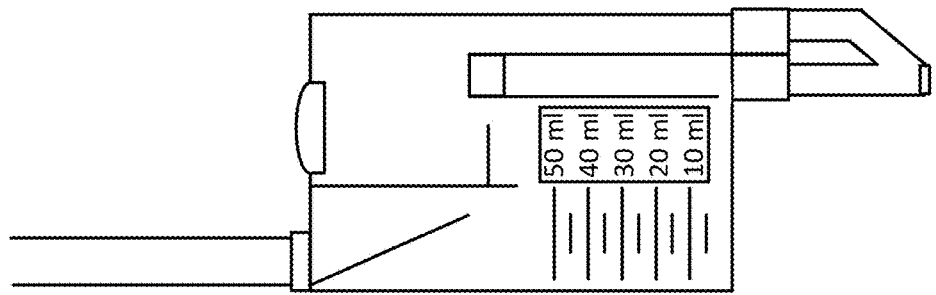
Figure 96B:
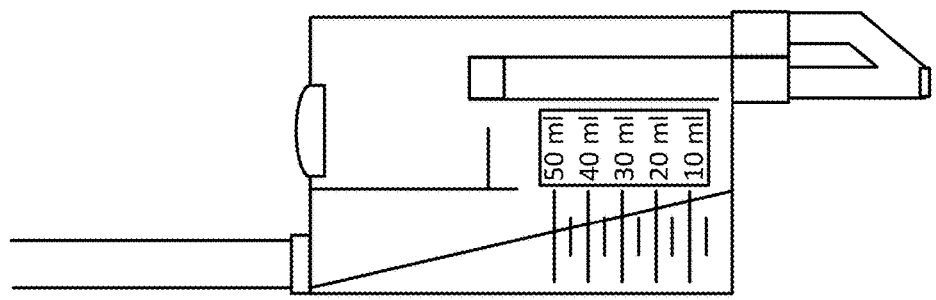
Figure 96A:
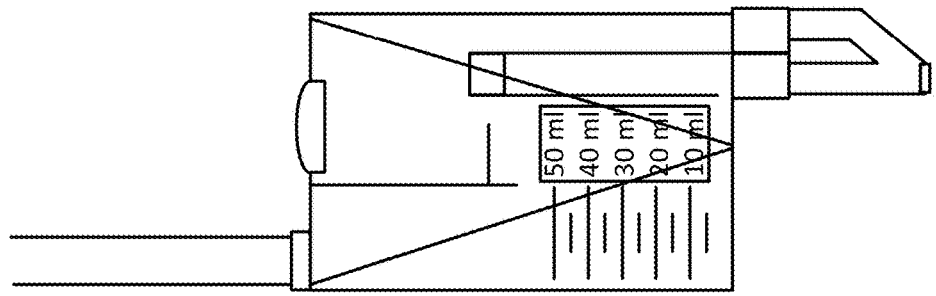

Urine may also be forced to flow to a point, as is shown with the inverse cone embodiment in FIG. 96A. The cone may have angles as shown here, or may be more curved. The cone shape generally transitions from a small to large area, and/or from a large to a small area. This and other bubble reducing mechanisms may also be within the collection vessel. For example as is shown in FIGS. 96B-D, an angled baffle may be incorporated into the collection reservoir to force the fluid down an angled surface. The angled surface may extend all the way to the bottom of the collection vessel or only partially into the collection vessel. Different angles may be used, for example, angles from about 10 degrees to angles of about 80 degrees.

Angled baffles, as shown by embodiments in FIG. 96C and FIG. 96D may also be preferred to improve the accuracy of urine volume measurement, especially under critical care conditions where the patient has low urine output and continuous measurement of urine output (ml/min or ml/sec) is desired to diagnose patient's vulnerability for the onset of AKI, sepsis, or other conditions. Accurate measurement of small urine volumes is better measured in a conical or angled baffle, due the greater height of the urine column, for a given urine volume, compared to a flat-bottomed baffle or cassette. The ultrasonic transducer or similar transducers on the controller can more reliably measure height and provide an accurate measure of urine volume and rate of urine output, especially when the patient's kidney is injured and makes little urine. In addition, an angled/baffle or cassette (urine collection chamber) may be less sensitive to changes in the tilt angle of the controller and reduce measurement error, compared to a flat surfaced cassette, for small urine volumes.

FIG. 97A shows an embodiment of the sensing Foley catheter system where the drainage lumen extends into the collection vessel/cassette so that the fluid generally drains into the collected fluid below the fluid level. The drainage end of the drainage lumen may be cut at an angle to prevent the tubing from abutting the bottom of the cassette which may block fluid flow. The angle cut 9724 may be about 45 degrees, about 10-80 degrees or any suitable angle. Other shapes may be used at the drainage end of the drainage lumen to achieve the same result. For example, FIG. 97B shows a drainage lumen, the tubing of which is castellated at the drainage end. Castellations 9726 may be of any shape include rounded, rectangular, triangular, scalloped, etc.

FIG. 97C shows an embodiment of the sensing Foley catheter system where the drainage lumen extends into the cassette, and includes a flattened area 9728. In this embodiment the cross sectional area of the drainage lumen may stay the same, increase or decrease in the flattened area, however preferably at least one dimension increases to force increased surface area contact with the fluid flow. The flattened area may direct flow downward, as is shown in FIG. 97C, or the flattened portion may be angled to force fluid to flow in contact with at least one side of the lumen's interior surface. Alternatively, or in addition, an angled baffle, such as baffle 9730 shown in FIG. 97D may be used. The angle of baffle 9730 may be about 45 degrees, about 10-80 degrees or any suitable angle. The angled baffle, or flattened area, may be used with any of the drainage tubing/lumen designs shown herein.

Figure 98D:
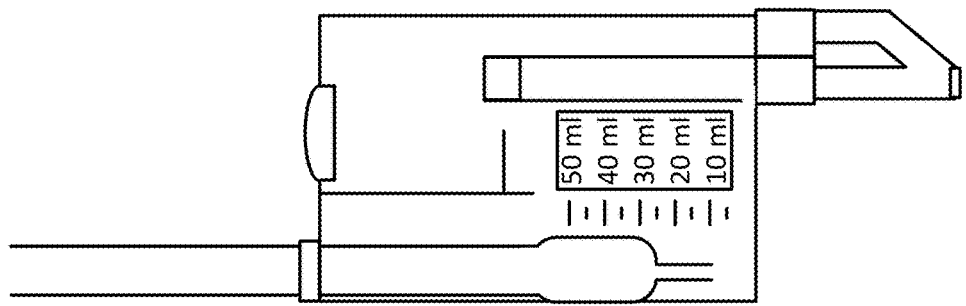
FIGS. 98A-D show embodiments of the sensing Foley catheter system with bubble reduction mechanisms.
Figure 98C:
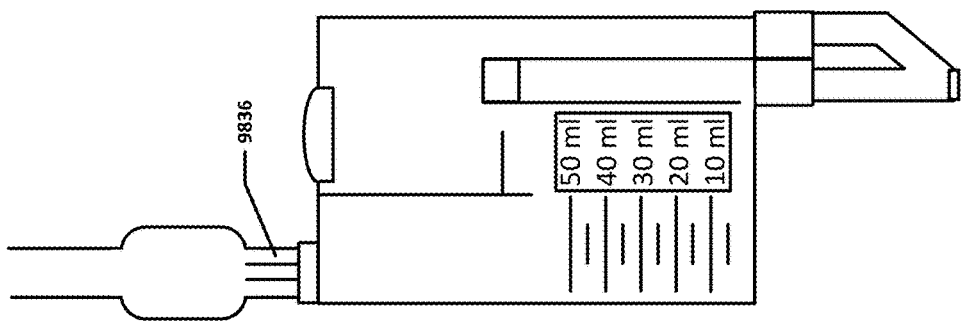
Figure 98B:
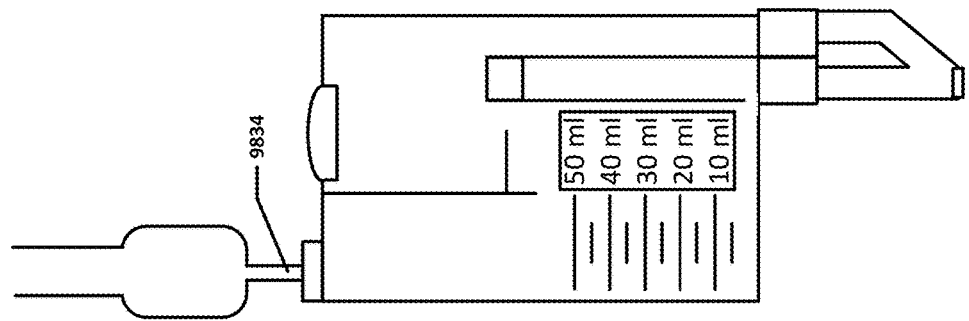
Figure 98A:
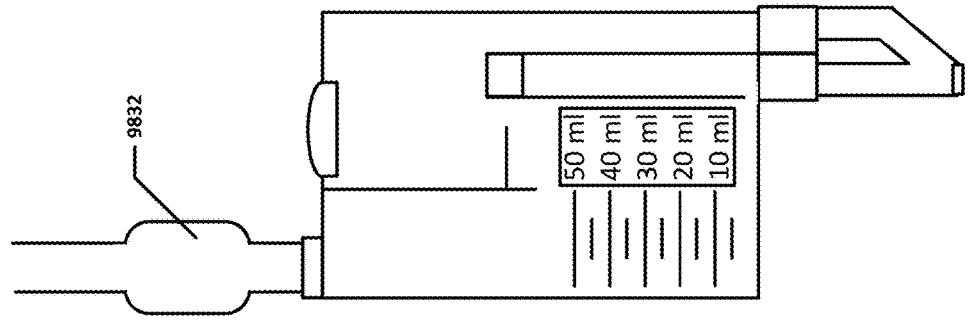

FIG. 98A shows an embodiment of the sensing Foley catheter system where the drainage lumen area increases and decreases. Bulb 9832 may be incorporated into the drainage tubing above the cassette, within the cassette, as is shown in FIG. 98D, or anywhere along the drainage lumen. The area above and below the bulb may be essentially identical, or the area below the bulb may be less than the area above the bulb as shown in FIG. 98B. Reduced drainage lumen area portion 9834 may be relatively short, for example portion 9834 may be about 1 mm-10 mm long. Alternatively portion 9834 may be about 1 mm-2 mm long. Alternatively portion 9834 may be about 10 mm long. FIG. 98C shows an embodiment where narrowed section 9836 includes more than one reduced area fluid drainage lumens. This allows increased surface contact of the drainage lumen without significantly reducing the area of the drainage lumen. Narrowed section 9836 may be used in conjunction with bulb 9832 or without the bulb.

Note that any of the bubble reduction embodiments enclosed herein may be used anywhere in the drainage lumen, including the drainage tubing outside the cassette, and drainage tubing/lumen within the cassette. For example, FIG. 98D shows an embodiment similar to that shown in FIG. 98B where the bulb is within the cassette.

FIG. 99A shows an embodiment of the sensing Foley catheter system where at least part of the drainage lumen is rough to cause bubbles to disperse and/or pop.

FIGS. 99B and 99C show another bubble reducing embodiment. In this embodiment a grate, or honeycomb, or mesh is inside the base of the drainage tube. The mesh helps to break up bubbles and may be periodically compressed to clear the area of fluid and also to help break down the bubbles.

Alternatively, or in addition, a flat mesh may be inserted anywhere within the system, for example at the drainage tube/collection vessel junction.

In some embodiments the cassette and/or drainage lumen may be vibrated either continuously or intermittently to break up bubbles.

Figure 100C:
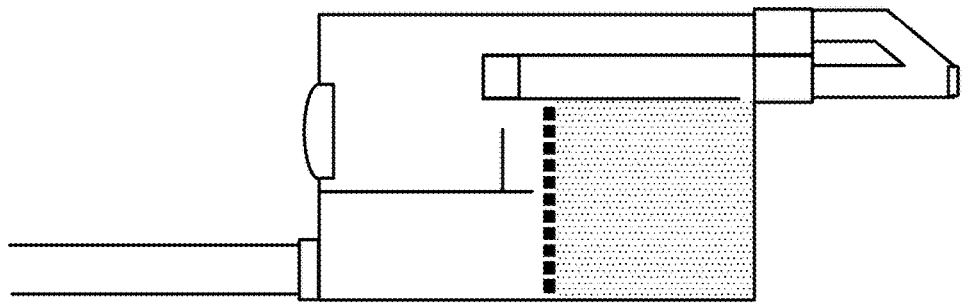
FIGS. 100A-C show embodiments of the sensing Foley catheter system with bubble reduction mechanisms.
Figure 100B:
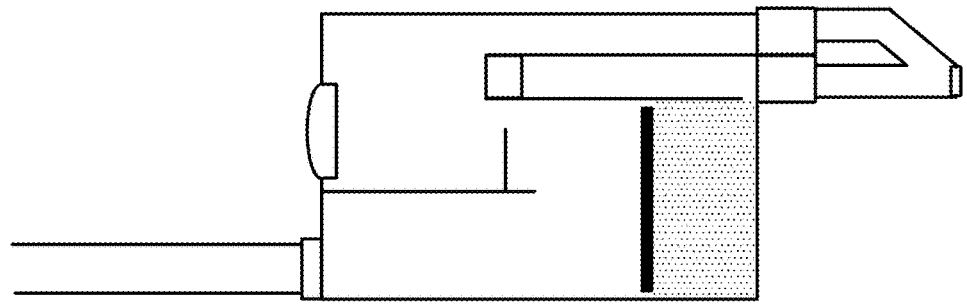
Figure 100A:
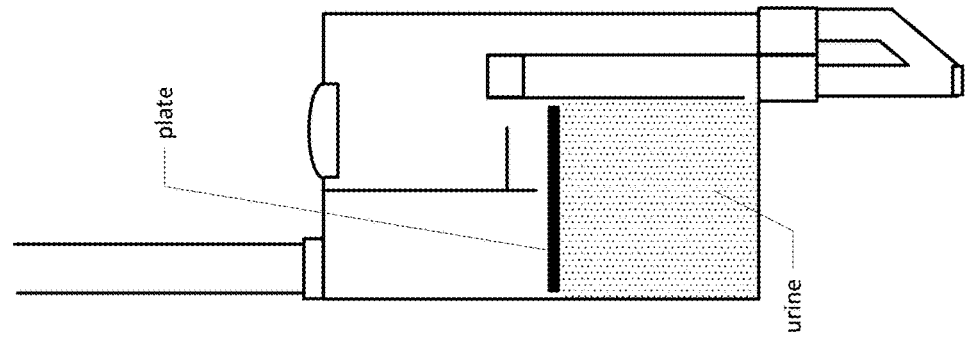

FIGS. 100A-C show embodiments which incorporate a plate, floating or non-floating, to compress or break up the bubbles at or near the surface of the urine in the collection vessel. The plate may simply float on the surface and passively raise and fall with the volume of urine in the vessel, or the plate may be actively moved up and down. The plate may also be fixed in place. The plate may be porous or solid. In embodiments where the plate is on the surface of the fluid, the plate may also be used for urine output measurements. The location of the plate may be identified by ultrasound, visual means (as in a camera), laser or other techniques. The volume of the fluid within the collection vessel can be determined directly from the level of the fluid, which can be determined by the location of the plate.

The interior of the cassette may be rectangular, or shaped otherwise. For example, the sides of the interior of the cassette may taper inward toward the bottom so that there is a larger top surface of urine with respect to the volume of urine in the cassette. This may result in more accurate urine volume measurements at smaller volumes.

Some embodiments may include a volumetric baffle at a set volume mark, for example at 50 ml. This volumetric baffle may be similar to baffle 2302 shown in FIG. 23, except that it will be at a predetermined volume location. When the top surface of the urine volume in the cassette is at or near the volumetric baffle, an ultrasonic signal is stronger than it would be otherwise. For example, the volumetric baffle may be positioned so that when the top surface of the volume of urine is at about 50 ml (or other set volume), the top surface of the urine volume will be at or near the volumetric baffle. As the two surfaces (urine and volumetric baffle) approach each other or touch each other, the ultrasonic signal is strongest.

Figure 101B:
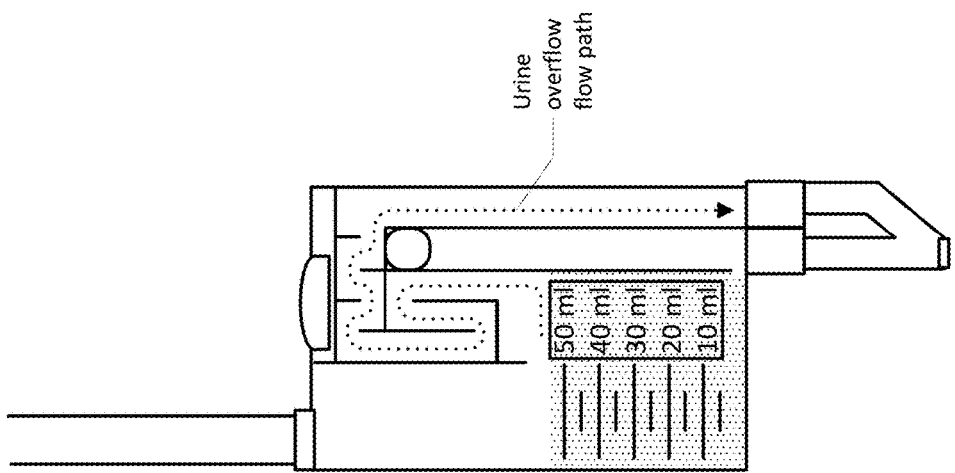
FIGS. 101A and 101B show embodiments of the sensing Foley catheter system with bubble reduction mechanisms.
Figure 101A:
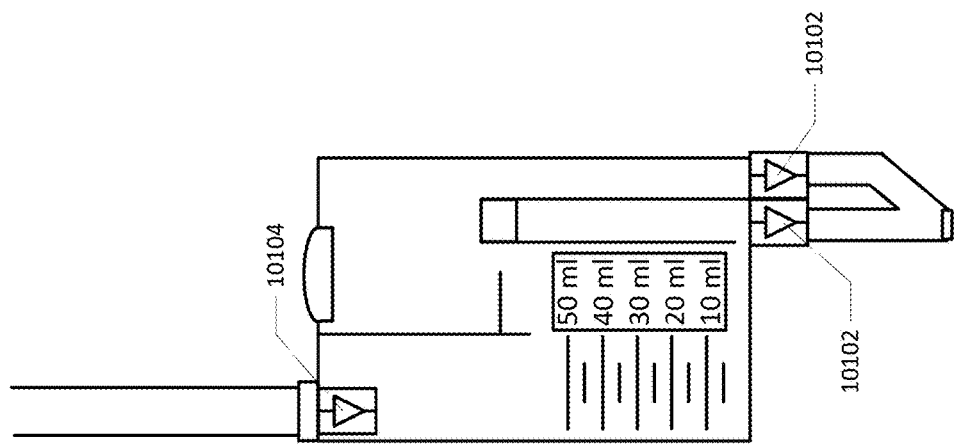

FIG. 101A shows an embodiment of the sensing Foley catheter system which includes valves at both the drainage ports 10102, and at the entry point 10104, where the drainage tubing connects to the collection vessel. This allows the controller to periodically pressurize the collection vessel which may reduce bubbles. This may also result in more accurate measurements of urine output since urine flow into the collection vessel can be stopped by the controller during urine emptying.

FIG. 101B shows an embodiment of the collection vessel where the urine overflow path is made more long and/or convoluted/tortuous and/or narrow. This configuration makes it more difficult for bubbles to flow into the overflow path resulting in inaccurate measurements of urine output. The overflow path may include one or more path angles which are greater than 45 degrees.

Some embodiments include a drainage tube with a small inner lumen diameter. For example, in some embodiments, the inner lumen diameter is about 2 mm. In some embodiments, the inner lumen diameter is about 1 mm. In some embodiments, the inner lumen diameter is about 3 mm. In some embodiments, the inner lumen diameter is less than about 2 mm, in some embodiments the inner lumen diameter is less than about 1 mm. In some embodiments the inner lumen diameter is less than about 3 mm.

In some embodiments, drained urine can be used to "wash" the bubbles within the drainage tube or collection reservoir. Urine can be cycled back into the drainage tube to increase the volume within the drainage tube and help "wash" bubbles in the tubing and/or reservoir. The controller compensates for the recycled urine in calculating the urine output volumes.

In some embodiments, pressurized air may be introduced into the drainage tube and/or the collection vessel. The forced air pops and/or compresses the bubbles and also forces the urine up against the surfaces of the system to decrease bubble formation. The cross sectional area of the drainage tube may decrease, stay the same or increase as the drainage tube transitions into the flattened portion.

Leveling

In embodiments where urine volume is measured within the collection vessel using ultrasound, it is important that the ultrasonic waves have a surface (i.e. the surface of the volume of urine) which is approximately 90 degrees from the ultrasonic sensor. If the system is tilted even a few degrees, the ultrasonic sensor may not be able to sense the surface of the urine and therefore may not obtain accurate measurements of urine volume. To compensate for this, the collection vessel or base/controller may be attached to the bed via a self leveling attachment, for example, an attachment which is on a roller so that gravity automatically levels the base when it is attached.

In some embodiments, slight angles in the system are handled by creating a "rough" surface on the urine volume within the collection reservoir. A "rough" surface provides multiple angles for ultrasonic reflection, some of which will be approximately 90 degrees from the ultrasonic sensor/transducer. Roughness may be created by bubbling the urine using air or other gas, by vibrating the collection reservoir and/or urine. Vibration can be achieved mechanically, ultrasonically etc. A floating plate which floats on the surface of the urine may be used which has a rough lower surface, concave lower surface or convex lower surface. Floating beads may be in the reservoir that are too large in diameter to exit the reservoir when the urine is drained, so that they remain in the reservoir as urine drains. A mesh, narrowing, small diameter opening or other mechanism may be used to prevent the beads from entering the overflow area. In addition, as described above, angled baffles or angle walled or tapered walled cassettes (or urine collection chambers) may also be used to accurately measure urine volumes.

Pressure Balloon Priming

Very small volumes of air or fluid may be necessary to adjust the pressure of the pressure balloon to prime it for optimal pressure sensing measurements. Because of this, an air/gas/fluid restrictor may be utilized between the priming fluid and the pressure balloon. The restrictor allows the priming pump to operate with smaller volumes of air for more precise pressure balloon priming. The restrictor may include a foam insert, a narrowing of the fluid lumen, or any other suitable restrictor.

General Improvements

In some embodiments, a sensor on the bed, patient, within the sensing Foley catheter system or elsewhere senses when the patient is supine or not supine. Pressure measured within the bladder will increase when the patient is not supine and may adversely affect the data for analysis by the controller. As a result, the controller may ignore pressure data collected while the patient is not supine, or stop collecting pressure data during this time. Alternatively, the pressure measurements themselves may be used to sense when a patient is not supine. A sharp increase in pressure or an increase above a certain threshold may indicate that the patient is sitting up, moving, coughing etc. Different pressure profiles may indicate different events. Patient rolling to prevent bed sores may be tracked in this manner.

In some embodiments, an EKG measurement, either obtained through leads attached to the sensing Foley catheter system or obtained independently, are used to sync the heart beats measured via the heart rate in the bladder with the EKG.

In some embodiments, the angle of the bed may be used by the controller as an input parameter to results of calculations such as IAP or APP. For example, increasing the body angle (raising the head level of the patient) will result in increased IAP. This increase may be different for healthier patients than for less healthy patients. As a result, determining the IAP at different bed angles may provide additional information regarding the patient's health. Also, IAP may be lowered by decreasing the head level which may temporarily stabilize a patient with high IAP.

In some embodiments the sensing Foley catheter will have at least one pressure sensor or lumen in fluid communication with an external pressure sensor. This pressure sensor will allow for rapid, or high frequency, sensing of pressure within the lumen (ideally faster than 1 Hz) to allow for monitoring of physiologic signals within the lumen. In some embodiments, the pressure lumen may be manually or automatically pressurized and/or depressurized while pressure is monitored continuously or intermittently. In embodiments where the pressure lumen includes a pressure balloon, the balloon may be inflated and/or deflated while pressure exerted by the body on the pressure balloon is monitored. The pressure lumen is able to transmit the pressure waves from the body lumen, one of which is the cardiac pulsation generated by the inflow of blood to the luminal organ and/or surrounding tissues. The pulsatile pressure from the cardiac pulsation and/or respiratory excursions can be used to determine pulmonary and cardiovascular pressures. In addition, the pressure in the pressure lumen/balloon may be increased above a threshold (i.e. 100 mmHg) and then slowly decreased through the sensing range to determine the origin point of pulse pressure, extinction point of pulse pressure, and/or relative increase/decrease in pressure pulse size. The origin/extinction or relative increase/decrease in the pressure pulsations detected by the pressure sensor can be correlated to the blood pressure, perfusion pressure, mean arterial pressure, stroke volume, stroke volume variability, respiratory effort, pulmonary pressure transmission and other pulmonary, gastrointestinal, renal or cardiovascular parameters. This process may be similar to a blood pressure cuff, where the pressure is increased in the cuff above the blood pressure, and then the pressure in the cuff is slowly decreased until the blood pressure waveforms (heart beat) either appear or disappear.

Figure 102:
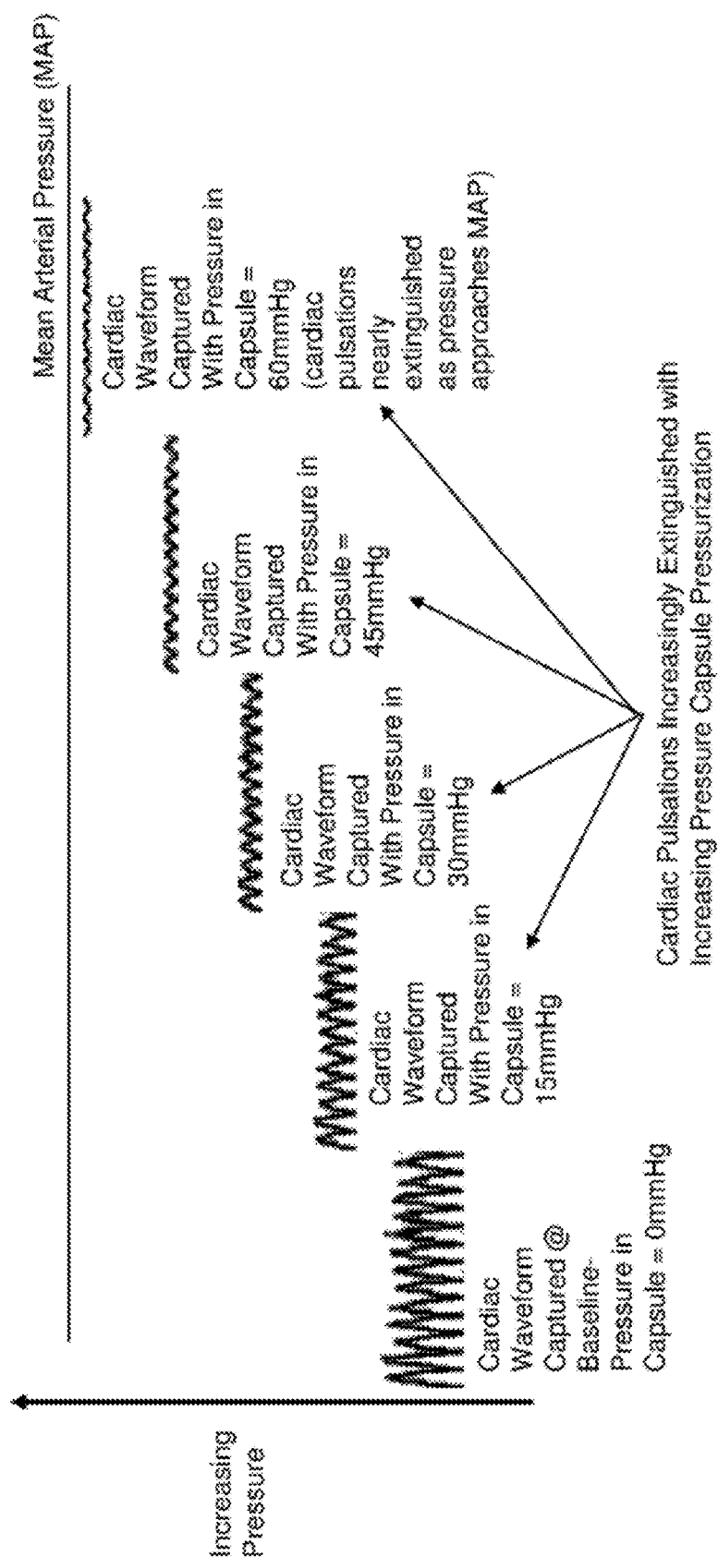
FIG. 102 shows a pressure waveform and its extinction using a pressure balloon.

FIG. 102 illustrates the pressure waveform and its extinction as the pressure balloon inflates. Note that above the mean arterial pressure the cardiac pulsations are diminished and/or extinguished. With enough data to correlate the degree of extinction at relative pressure points to the mean arterial pressure, the mean arterial pressure can be derived from this relative pressure waveform. The same can be used for pulmonary pressures and other pressures that can sensed within the lumens of the body.

In some embodiments the pressure sensor/lumen is a capsule, or balloon, or reservoir, that can be inflated or filled slowly while pressure is being monitored using an external transducer. In some embodiments the pressure sensor is associated with a urinary catheter, such as a Foley catheter. Alternatively the pressure sensor may be associated with a nasogastric, orogastric or rectal tube. In yet further embodiments, the pressure sensor device and associated pressure-increasing device may be fully implantable. In the tissue perfusion embodiment the pressure sensing may be inflated in the urethra or against the luminal surface and pulse oximetry may be performed to detect the blanching and/or perfusion of the luminal tissues at each pressure to determine the tissue perfusion pressure.

In some embodiments the catheter can use multiple measured parameters synergistically in order to improve the quality of data analysis. In one embodiment, the catheter has incorporated sensors for capturing an ECG signal internally, such as via the urethra or bladder, or externally, such as via sensors placed on the legs or hips. Using this signal, the other measured parameters in synchrony with the cardiac cycle (such as stroke volume) can be synced with the electrical signal and noise can be removed by taking the mean or median signal from many individual samples. In another embodiment, the respiratory signal is used to guide which cardiac pressure signals should be used for stroke volume variability analysis, by waiting for a model waveform to appear before performing the analysis.

Figure 103:
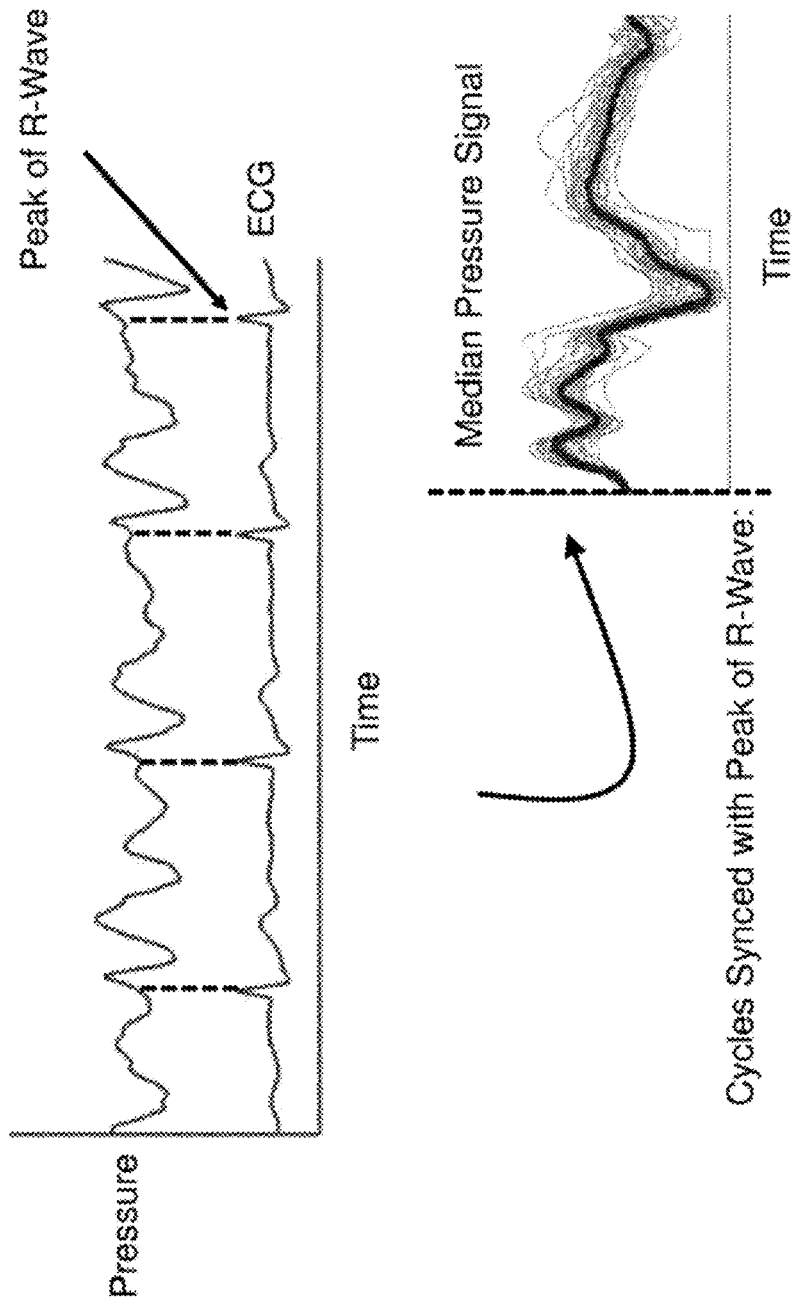
FIG. 103 shows sample clinical data illustrating a method of removing noise from cardiac signals using ECO.

FIG. 103 illustrates a method of syncing cardiogenic signals (such as pressure fluctuations in the bladder caused by the pulse of the nearby abdominal aorta) in order to obtain a clean signal for analysis. When an ECG is captured in synchrony with another cardiac signal of interest, individual samples can be synced using, for example, the R-wave of the ECG. In this figure, multiple pressure samples are captured and then overlaid, using the R-wave of the ECG for alignment. The median signal is then calculated by taking the median value of all pressure samples at the same time during the cardiac cycle. The mean could also be used. In this manner, random noise is filtered out, as an extraneously high value due to noise in one sample will be canceled out by a similarly extraneously low value in another. As more data points are added, the underlying signal becomes stronger and can be used for analysis. For example, in the pressure signal shown, the peak-to-peak amplitude of the signal can be used to derive relative stroke volume.

Figure 104:
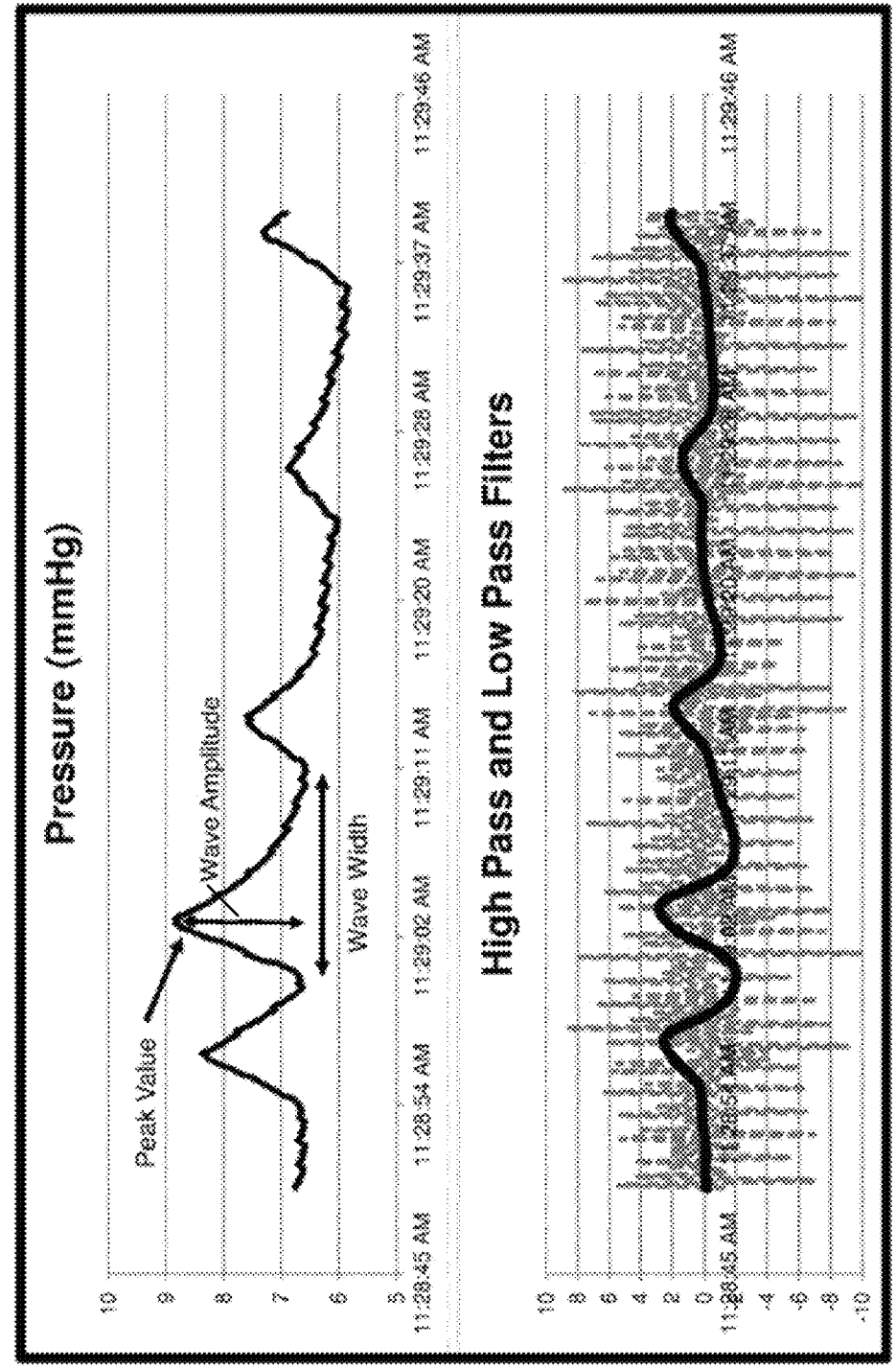
FIG. 104 shows sample clinical data illustrating stroke volume variability analysis using a model waveform.

FIG. 104 illustrates a method of using the respiratory pressure signal to inform the cardiac pressure signal analysis in order to determine stroke volume variability (SVV). This method is particularly valuable in non-ventilated patients, i.e., patients not on a ventilator. Existing techniques for measuring stroke volume, such as thermodilution or pulse contour analysis, are limited in their ability to perform measurements of stroke volume variability (variability of stroke volume between inspiration and exhalation) because they are blind to the respiratory cycle. Using luminal pressure as described herein, such as with a Foley catheter in the bladder, is advantageous in that it allows for simultaneous capture of respiratory and cardiac signals (as well as slower moving intra-abdominal pressure). In this manner, this present device can discriminately choose which respiratory cycles to use for analysis of stroke volume variability, as certain characteristics are more suitable for proper analysis (such as the speed and size of the breath). In this figure, a sample pressure signal captured from the bladder is shown. In the raw pressure signal on top, large fluctuations are due to respirations, and are chosen for analysis based on the width, amplitude, or peak value of the wave, for example. Other characteristics not shown may also be used to define a suitable wave, including slope, area under the curve, shape, frequency, patterns, or repeatability etc. A curve amplitude filter may be used, where curves with an amplitude above a certain value are used, and those below the same, or another certain value are not used in the SVV calculation. The bottom figure shows the same signal after being passed through high- and low-pass filters. The high-pass filter leaves the underlying cardiac signal (dashed), and the low-pass filter leaves the underlying respiratory signal (solid). In this example, the difference in strength of the cardiac signal (such as peak-to-peak value) between the peak and valley of the respiratory signal can be used to calculate stroke volume variability.

Respiratory rate and other parameters may be sensed via the Sensing Foley catheter or may be sensed or obtained by any conventional or non-conventional means. Other parameters that may be collected include tidal volume, spirometry, respiratory flow parameters, data collected via spirometry, expiratory effort, inspiratory effort etc. Any of these parameters may be used to help in calculating stroke volume variability and/or other cardiac parameters.

The filter used to determine which pressure peaks are used in the SVV calculation may be based on any of the pressure curve parameters disclosed here. In addition, the SW calculation itself may be used to determine which pressure curve peaks are used in the calculation. For example, SVV is usually within around 10%. The system disclosed herein may include or exclude pressure curve data based on the resulting SVV calculation being within a certain value range, such as about 10%.

The SVV calculation may also be patient specific. For example, a pressure curve peak filter may be based on amplitude, but the cutoff amplitude may be patient specific and based on the average, mean, or other parameter of the pressure curve for that patient. Alternatively, the filter may be based on multiple patients, or multiple patients within a certain category, such as a certain disease state.

The signals and/or SVV calculation may also filter for patient movements and/or other artifacts, such as coughing, shifting, sneezing etc.

In addition, a calculated result of a very low, or non-existent SVV may be an indication of fluid overload, and appropriate treatment may be indicated.

In some embodiments of the disclosed system, the patient may be prompted to breath in a particular manner. For example, based on the pressure curve shape (peak amplitude, frequency, etc.) the system may prompt the patient to breathe more deeply, breathe more slowly, breathe normally, etc. The resulting respiratory pressure curve can then be factored into the SVV calculation. This type of prompting may be performed by the system when the pressure curve is inadequate to provide a SVV calculation, or for any other reason.

What is claimed is:

1. A drainage assembly configured to prevent negative pressure build-up, comprising:
    an elongate catheter having a first end configured for insertion within a body lumen, the catheter having at least one opening near or at the first end in fluid communication with a catheter lumen defined therethrough;
    a drainage lumen in fluid communication with a second end of the catheter;
    a reservoir in fluid communication with the drainage lumen, wherein the reservoir defines a tortuous path which inhibits bubbles from flowing through the tortuous path;
    an overflow area in fluid communication with the reservoir, wherein the overflow area is configured to drain fluid from the reservoir when excess fluid enters into the reservoir;
    a venting mechanism in fluid communication with the drainage lumen, wherein the venting mechanism includes a vent tube;
    a valve positioned within the venting mechanism and configured to maintain a closed position until a first pressure level within the drainage lumen is dropped to a second pressure level such that the valve moves to an open position;
    a vent positioned in fluid communication with the valve, wherein the venting mechanism is configured to inhibit wetting of the vent from fluid within the drainage lumen; and
    a controller in communication with the reservoir, wherein the controller is configured to apply a negative pressure to the drainage lumen to drop the first pressure level to the second pressure level such that the valve is moved to the open position and wherein the controller is further configured to determine a fluid volume collected within the reservoir.

2. The assembly of claim 1 wherein movement of the valve from the closed position to the open position introduces a gas from the venting mechanism and into the drainage lumen for clearing any obstructions.

3. The assembly of claim 1 further comprising a second valve in fluid communication with the drainage lumen.

4. The assembly of claim 1 wherein the venting mechanism comprises one or more filters which are aligned and in communication with the valve.

5. The assembly of claim 1 wherein the vent is positioned at a remote end of the vent tube.

6. The assembly of claim 5 wherein the vent tube has a length of over 2 cm.

7. The assembly of claim 5 wherein the vent tube defines a tortuous path configured to prevent liquid flow to the vent.

8. The assembly of claim 7 wherein the tortuous path comprises a coil configuration.

9. The assembly of claim 7 wherein the tortuous path comprises tube with baffling.

10. The assembly of claim 5 wherein the vent tube is bendable or deformable.

11. The assembly of claim 5 wherein the vent comprises a filter.

12. The assembly of claim 5 wherein the valve is positioned between an opening of the drainage lumen and the vent.

13. The assembly of claim 5 wherein the valve comprises a passive mechanism.

14. The assembly of claim 5 wherein the vent tube is in fluid communication with atmosphere.

15. The assembly of claim 5 wherein the vent tube has a length of over 4 cm.

16. The assembly of claim 5 wherein the vent tube has a length of over 10 cm.

17. The assembly of claim 1 wherein the vent is positioned in-line with respect to the vent tube such that fluid passes through or across the vent and into the drainage lumen.

18. The assembly of claim 1 wherein the vent defines a surface area greater than about 1 $cm^2$.

19. The assembly of claim 1 wherein the vent is removably securable from the venting mechanism.

20. The assembly of claim 1 further comprising a pump configured to provide a negative pressure in the drainage lumen.

21. The assembly of claim 1 wherein the second pressure level is periodically or continually between about −5 mm Hg to −30 mm Hg.

22. The assembly of claim 1 further comprising a reservoir valve at an entry point of the drainage lumen into the reservoir.

23. The assembly of claim 1 wherein the reservoir defines a tortuous flow path within the reservoir.

24. A drainage assembly configured to prevent negative pressure build-up, comprising:
    an elongate catheter having a first end configured for insertion within a body lumen, the catheter having at least one opening near or at the first end in fluid communication with a catheter lumen defined therethrough;
    a drainage lumen in fluid communication with a second end of the catheter;

a reservoir in fluid communication with the drainage lumen, wherein the reservoir defines a tortuous path which inhibits bubbles from flowing through the tortuous path;

an overflow area in fluid communication with the reservoir, wherein the overflow area is configured to drain fluid from the reservoir when excess fluid enters into the reservoir;

a venting mechanism coupled to the drainage lumen, wherein the venting mechanism includes a vent tube and wherein the venting mechanism is configured to inhibit wetting of a vent from a fluid within the drainage lumen;

a controller in communication with the reservoir, wherein the controller is configured to determine a fluid volume collected within the reservoir; and a valve configurable between a closed position and an open position, wherein the controller is configured to apply a negative pressure to the drainage lumen such that the valve moves from the closed position to the open position when a first pressure level imparted upon the valve is dropped by the controller to a second pressure level.

25. The assembly of claim 1 where the controller is configured to apply the negative pressure periodically.

26. The assembly of claim 25 wherein the controller is configured to apply the negative pressure at least every 60 minutes.

27. The assembly of claim 25 wherein the controller is configured to apply the negative pressure at least every 20 minutes.

28. The assembly of claim 1 wherein the vent tube has a length which extends with the drainage lumen from the venting mechanism.

29. The assembly of claim 24 wherein the second pressure level is periodically or continually between about −5 mm Hg to −30 mm Hg.

30. The assembly of claim 24 further comprising a second valve in fluid communication with the drainage lumen.

31. The assembly of claim 24 wherein the venting mechanism comprises one or more filters which are aligned and in communication with the valve.

32. The assembly of claim 24 wherein the vent is positioned at a remote end of the vent tube.

33. The assembly of claim 32 wherein the vent tube has a length of over 2 cm.

34. The assembly of claim 32 wherein the vent tube defines a tortuous path configured to prevent liquid flow to the vent.

35. The assembly of claim 34 wherein the tortuous path comprises a coil configuration.

36. The assembly of claim 34 wherein the tortuous path comprises tube with baffling.

37. The assembly of claim 32 wherein the vent tube is bendable or deformable.

38. The assembly of claim 32 wherein the vent comprises a filter.

39. The assembly of claim 32 wherein the valve is positioned between an opening of the drainage lumen and the vent.

40. The assembly of claim 32 wherein the valve comprises a passive mechanism.

41. The assembly of claim 32 wherein the vent tube is in fluid communication with atmosphere.

42. The assembly of claim 32 wherein the vent tube has a length of over 4 cm.

43. The assembly of claim 32 wherein the vent tube has a length of over 10 cm.

44. The assembly of claim 24 wherein the vent is positioned in-line with respect to the vent tube such that fluid passes through or across the vent and into the drainage lumen.

45. The assembly of claim 24 wherein the vent which defines a surface area greater than about 1 cm$^2$.

46. The assembly of claim 24 wherein the vent which is removably securable from the venting mechanism.

47. The assembly of claim 24 further comprising a reservoir valve at an entry point of the drainage lumen into the reservoir.

48. The assembly of claim 24 wherein the reservoir defines a tortuous flow path within the reservoir.

49. The assembly of claim 24 further comprising a pump configured to provide a negative pressure within the drainage lumen.

50. The assembly of claim 24 where the controller is configured to apply the negative pressure periodically.

51. The assembly of claim 50 wherein the controller is configured to apply the negative pressure at least every 60 minutes.

52. The assembly of claim 50 wherein the controller is configured to apply the negative pressure at least every 20 minutes.

53. The assembly of claim 24 wherein the vent tube has a length which extends with the drainage lumen from the venting mechanism.

* * * * *